US011666649B2

(12) United States Patent
Strbo et al.

(10) Patent No.: US 11,666,649 B2
(45) Date of Patent: Jun. 6, 2023

(54) VECTORS AND VACCINE CELLS FOR IMMUNITY AGAINST ZIKA VIRUS

(71) Applicant: University of Miami, Miami, FL (US)

(72) Inventors: Natasa Strbo, Miami, FL (US); Laura Romero, Miami, FL (US)

(73) Assignee: University of Miami, Miami, FL (US)

( * ) Notice: Subject to any disclaimer, the term of this patent is extended or adjusted under 35 U.S.C. 154(b) by 511 days.

(21) Appl. No.: 16/334,637

(22) PCT Filed: Oct. 10, 2017

(86) PCT No.: PCT/US2017/055912
§ 371 (c)(1),
(2) Date: Mar. 19, 2019

(87) PCT Pub. No.: WO2018/071405
PCT Pub. Date: Apr. 19, 2018

(65) Prior Publication Data
US 2021/0290750 A1 Sep. 23, 2021

Related U.S. Application Data

(60) Provisional application No. 62/406,506, filed on Oct. 11, 2016.

(51) Int. Cl.
*A61K 39/12* (2006.01)
*A61P 31/14* (2006.01)
*C07K 14/005* (2006.01)
*C12N 15/85* (2006.01)
*A61K 39/00* (2006.01)

(52) U.S. Cl.
CPC .............. *A61K 39/12* (2013.01); *A61P 31/14* (2018.01); *C07K 14/005* (2013.01); *C12N 15/85* (2013.01); *A61K 2039/5156* (2013.01); *A61K 2039/53* (2013.01); *A61K 2039/55* (2013.01); *C07K 2319/30* (2013.01); *C07K 2319/35* (2013.01); *C12N 2770/24134* (2013.01)

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 5,188,964 A | 2/1993 | McGuire et al. | |
| 5,217,891 A | 6/1993 | Brake et al. | |
| 5,232,833 A | 8/1993 | Sanders et al. | |
| 5,348,945 A | 9/1994 | Berberian et al. | |
| 5,719,044 A | 2/1998 | Shoseyov et al. | |
| 5,747,332 A | 5/1998 | Wallen et al. | |
| 5,750,119 A | 5/1998 | Srivastava | |
| 5,830,464 A | 11/1998 | Srivastava | |
| 5,837,251 A | 11/1998 | Srivastava | |
| 5,948,646 A | 9/1999 | Srivastava | |
| 5,961,979 A | 10/1999 | Srivastava | |
| 5,985,270 A | 11/1999 | Srivastava | |
| 5,997,873 A | 12/1999 | Srivastava | |
| 6,007,821 A | 12/1999 | Srivastava et al. | |
| 6,017,540 A | 1/2000 | Srivastava et al. | |
| 6,017,544 A | 1/2000 | Srivastava | |
| 6,030,618 A | 2/2000 | Srivastava | |
| 6,048,530 A | 4/2000 | Srivastava | |
| 6,130,087 A | 10/2000 | Srivastava et al. | |
| 6,136,315 A | 10/2000 | Srivastava | |
| 6,156,302 A | 12/2000 | Srivastava | |
| 6,162,436 A | 12/2000 | Srivastava | |
| 6,168,793 B1 | 1/2001 | Srivastava | |
| 6,322,790 B1 | 11/2001 | Srivastava | |
| 6,328,957 B1 | 12/2001 | Colston et al. | |
| 6,331,299 B1 | 12/2001 | Rothman et al. | |
| 6,383,493 B1 | 5/2002 | Srivastava et al. | |
| 6,383,494 B1 | 5/2002 | Srivastava et al. | |
| 6,387,374 B1 | 5/2002 | Srivastava et al. | |
| 6,399,070 B1 | 6/2002 | Srivastava et al. | |
| 6,403,095 B1 | 6/2002 | Srivastava et al. | |
| 6,406,700 B1 | 6/2002 | Srivastava | |
| 6,410,026 B1 | 6/2002 | Srivastava | |
| 6,410,027 B1 | 6/2002 | Srivastava | |
| 6,410,028 B1 | 6/2002 | Srivastava | |
| 6,436,404 B1 | 8/2002 | Srivastava et al. | |
| 6,447,780 B1 | 9/2002 | Srivastava et al. | |
| 6,447,781 B1 | 9/2002 | Srivastava | |
| 6,451,316 B1 | 9/2002 | Srivastava | |
| 6,455,048 B1 | 9/2002 | Srivastava et al. | |
| 6,455,503 B1 | 9/2002 | Srivastava | |
| 6,461,615 B1 | 10/2002 | Srivastava | |
| 6,468,540 B1 | 10/2002 | Srivastava | |

(Continued)

FOREIGN PATENT DOCUMENTS

| | | | |
|---|---|---|---|
| CA | 2158655 A1 | 9/1994 | |
| DE | 19602985 A1 | 7/1997 | |

(Continued)

OTHER PUBLICATIONS

Pattnaik et al., Vaccines, 2020, 8, 266, 19 pages. (Year: 2020).*
International Search Report & Written Opinion, PCT Appl. No. PCT/US17/55912, dated Jan. 5, 2018, 11 pages.
Ahlen, et al., "In Vivo Electroporation Enhances the Immunogenicity of Hepatitis C Virus Nonstructural ¾A DNA by Increased Local DNA Uptake, Protein Expression, Inflammation, and Infiltration of CD3+ T Cells," The Journal of Immunology, vol. 179, pp. 4741-4753, 2007.
Anderson, et al., "Lag-3, Tim-3, and TIGIT: Co-inhibitory Receptors with Specialized Functions in Immune Regulation", Immunity, vol. 44, pp. 989-1004, 2016.

(Continued)

*Primary Examiner* — Stacy B Chen
(74) *Attorney, Agent, or Firm* — Morgan, Lewis & Bockius LLP

(57) ABSTRACT

The present invention provides an expression vector, host cells, methods and kits for the treatment or prevention of a flavivirus infection in a subject.

12 Claims, 36 Drawing Sheets
Specification includes a Sequence Listing.

(56) References Cited

U.S. PATENT DOCUMENTS

| | | |
|---|---|---|
| 6,475,490 B1 | 11/2002 | Srivastava et al. |
| 6,605,464 B1 | 8/2003 | Rothman et al. |
| 6,610,659 B1 | 8/2003 | Pramod |
| 6,641,812 B2 | 11/2003 | Rothman et al. |
| 6,656,679 B2 | 12/2003 | Rothman et al. |
| 6,663,868 B1 | 12/2003 | Rothman et al. |
| 6,673,348 B2 | 1/2004 | Rothman et al. |
| 6,719,974 B1 | 4/2004 | Rothman et al. |
| 6,761,892 B1 | 7/2004 | Rothman et al. |
| 6,797,480 B1 | 9/2004 | Srivastava |
| 6,984,389 B2 | 1/2006 | Li |
| 7,132,109 B1 | 11/2006 | Srivastava |
| 8,475,785 B2 | 7/2013 | Podack et al. |
| 8,685,384 B2 | 4/2014 | Podack et al. |
| 8,968,720 B2 | 3/2015 | Podack et al. |
| 9,238,064 B2 | 1/2016 | Podack et al. |
| 10,046,047 B2 | 8/2018 | Schreiber et al. |
| 10,279,020 B2 * | 5/2019 | Podack ............... A61K 39/0011 |
| 10,758,611 B2 | 9/2020 | Schreiber et al. |
| 10,780,161 B2 | 9/2020 | Schreiber et al. |
| 10,898,566 B2 * | 1/2021 | Graham ............... C07K 16/1081 |
| 2002/0160496 A1 | 10/2002 | Gewirth et al. |
| 2003/0170756 A1 | 9/2003 | Berd |
| 2004/0009469 A1 | 1/2004 | Apt et al. |
| 2005/0019752 A1 | 1/2005 | Franchini et al. |
| 2005/0221395 A1 | 10/2005 | Zabrecky et al. |
| 2007/0141666 A1 | 6/2007 | Dupraz et al. |
| 2008/0019972 A1 | 1/2008 | Andrieu |
| 2008/0089901 A1 | 4/2008 | Hanke et al. |
| 2009/0047338 A1 | 2/2009 | Swamy et al. |
| 2009/0162404 A1 | 6/2009 | Podack |
| 2010/0136032 A1 | 6/2010 | Weinberg et al. |
| 2010/0247562 A1 | 9/2010 | Gong et al. |
| 2011/0059041 A1 | 3/2011 | Truneh et al. |
| 2011/0086057 A1 | 4/2011 | Soto-Jara et al. |
| 2011/0123552 A1 | 5/2011 | Bakker et al. |
| 2011/0171211 A1 | 7/2011 | Podack et al. |
| 2011/0250229 A1 | 10/2011 | Podack et al. |
| 2011/0312032 A1 | 12/2011 | Choi et al. |
| 2012/0034242 A1 | 2/2012 | Jooss et al. |
| 2012/0093825 A1 | 4/2012 | Renauld et al. |
| 2012/0100173 A1 | 4/2012 | Leclair et al. |
| 2012/0258046 A1 | 10/2012 | Mutzke |
| 2013/0045202 A1 | 2/2013 | Irving et al. |
| 2013/0052160 A1 | 2/2013 | Zitvogel et al. |
| 2013/0121960 A1 | 5/2013 | Sadelain et al. |
| 2013/0195800 A1 | 8/2013 | Roeth et al. |
| 2013/0209511 A1 | 8/2013 | Mebatsion et al. |
| 2014/0030761 A1 | 1/2014 | Panousis et al. |
| 2014/0037682 A1 | 2/2014 | Podack et al. |
| 2014/0107391 A1 | 4/2014 | Srivastava et al. |
| 2014/0127261 A1 | 5/2014 | Yamshchikov |
| 2014/0134650 A1 | 5/2014 | Hawtin et al. |
| 2014/0286991 A1 | 9/2014 | Podack et al. |
| 2014/0335050 A1 | 11/2014 | Haggerty et al. |
| 2014/0335086 A1 | 11/2014 | Podack et al. |
| 2015/0191525 A1 | 7/2015 | Epstein et al. |
| 2015/0368350 A1 | 12/2015 | Tykocinski et al. |
| 2016/0024176 A1 | 1/2016 | Damschroder et al. |
| 2016/0256527 A1 | 9/2016 | Gurney |
| 2016/0286945 A1 | 10/2016 | Tufaro et al. |
| 2017/0182156 A1 | 6/2017 | Khleif |
| 2021/0315987 A1 * | 10/2021 | Weiner ..................... C12N 7/00 |

FOREIGN PATENT DOCUMENTS

| | | |
|---|---|---|
| GB | 2251186 A | 7/1992 |
| WO | WO 198912455 A1 | 12/1989 |
| WO | WO 199002564 A1 | 3/1990 |
| WO | WO 199102077 A1 | 2/1991 |
| WO | WO 199115572 A1 | 10/1991 |
| WO | WO 199201717 A1 | 2/1992 |
| WO | WO 199208484 A1 | 5/1992 |
| WO | WO 199208488 A1 | 5/1992 |
| WO | WO 199314118 A1 | 7/1993 |
| WO | WO 199317712 A1 | 9/1993 |
| WO | WO 199318146 A2 | 9/1993 |
| WO | WO 199318147 A1 | 9/1993 |
| WO | WO 199321529 A1 | 10/1993 |
| WO | WO 199403208 A1 | 2/1994 |
| WO | WO 199403599 A1 | 2/1994 |
| WO | WO 199404676 A1 | 3/1994 |
| WO | WO 199411513 A1 | 5/1994 |
| WO | WO 199504824 A1 | 2/1995 |
| WO | WO 199506725 A1 | 3/1995 |
| WO | WO 199524923 A2 | 9/1995 |
| WO | WO 199601611 A1 | 1/1996 |
| WO | WO 199602143 A1 | 2/1996 |
| WO | WO 199610411 A1 | 4/1996 |
| WO | WO 199610419 A2 | 4/1996 |
| WO | WO 199631613 A1 | 10/1996 |
| WO | WO 199706685 A1 | 2/1997 |
| WO | WO 199706821 A1 | 2/1997 |
| WO | WO 199706828 A1 | 2/1997 |
| WO | WO 199710000 A1 | 3/1997 |
| WO | WO 199710001 A1 | 3/1997 |
| WO | WO 199710002 A1 | 3/1997 |
| WO | WO 199726910 A2 | 7/1997 |
| WO | WO 199735619 A1 | 10/1997 |
| WO | WO 199823735 A1 | 6/1998 |
| WO | WO 199942121 A1 | 8/1999 |
| WO | WO 2001/52791 A2 * | 7/2001 |
| WO | WO 2003005964 A2 | 1/2003 |
| WO | WO 2004032865 A2 | 4/2004 |
| WO | WO 2005030136 A2 | 4/2005 |
| WO | WO 2005058950 A2 | 6/2005 |
| WO | WO 2005092373 A1 | 10/2005 |
| WO | WO 2009114085 A2 | 9/2009 |
| WO | WO 2009114110 A1 | 9/2009 |
| WO | WO 2009117116 A2 | 9/2009 |
| WO | WO 2010060026 A1 | 5/2010 |
| WO | WO 2011146828 A2 | 11/2011 |
| WO | WO 2012116142 A2 | 8/2012 |
| WO | WO 2012166617 A2 | 12/2012 |
| WO | WO 2014140884 A2 | 9/2014 |
| WO | WO 2014140904 A2 | 9/2014 |
| WO | WO 2015/019253 A2 | 2/2015 |
| WO | WO 2015131176 A1 | 9/2015 |
| WO | WO 2016127015 A1 | 8/2016 |
| WO | WO 2018187260 A1 | 10/2018 |
| WO | WO 2019112942 A1 | 6/2019 |

OTHER PUBLICATIONS

Best, et al., "Administration of HPV DNA vaccine via electroporation elicits the strongest CD8+ T cell immune responses compared to intramuscular injection and intradermal gene gun delivery," Vaccine, vol. 27, No. 40, pp. 5450-5459, 2009.

Bloch, et al., "Heat-shock protein peptide complex-96 vaccination for recurrent glioblastoma: a phase II, single-arm trial," Neuro-Oncology, vol. 16, pp. 274-279, 2013.

Brasil, et al., "Zika Virus Infection in Pregnant Women in Rio de Janeiro," New England Journal of Medicine, vol. 375, No. 25, pp. 2321-2334, 2016.

Callahan, et al., "Targeting T Cell Co-receptors for Cancer Therapy", Immunity, vol. 44, pp. 1069-1078, 2016.

Carteaux, et al., "Zika Virus Associated with Meningoencephalitis," New England Journal of Medicine, vol. 374, pp. 1595-1596, 2016.

Curran, et al., "Editorial: Advances in Combination Tumor Immunotherapy", Frontiers in Oncology, vol. 5, No. 198, pp. 1-2, 2015.

Curti, et al., "OX40 Is a Potent Immune-Stimulating Target in Late-Stage Cancer Patients," Cancer Res., vol. 73, No. 24, pp. 7189-7198, 2013.

De Visser, et al., "Paradoxical Roles of the Immune System during Cancer Development", Nature, vol. 6, pp. 24-37, 2006.

Dobaño, et al., "Enhancement of antibody and cellular immune responses to malaria DNA vaccines by in vivo electroporation," Vaccine, vol. 25, No. 36, pp. 6635-6645, 2007.

Guo, et al., "PD-1 Blockade and OX40 Triggering Synergistically Protects against Tumor Growth in a Murine Model of Ovarian Cancer", Plos One, vol. 9, No. 2, pp. 1-10, 2014.

(56) References Cited

OTHER PUBLICATIONS

Hirao, et al., "Combined effects of IL-12 ad electroporation enhances the potency of DNA vaccination in macaques," Vaccine, vol. 26, No. 25, pp. 3112-3120, 2008.
Hirao, et al., "Comparative Analysis of Immune Responses Induced by Vaccination With SIV Antigens by Recombinant Ad5 Vector or Plasmid DNA in Rhesus Macaques," Molecular Therapy, vol. 18, No. 8, pp. 1568-1576, 2010.
Hirao, et al., "Intradermal/subcutaneous immunization by electroporation improves plasmid vaccine delivery and potency in pigs and rhesus macaques," Vaccine, vol. 26, No. 3, pp. 440-448, 2008.
Kanagavelu, et al., "Soluble multi-trimeric TNF superfamily ligand adjuvants enhance immune responses to HIV-1 Gag DNA vaccine," Vaccine, vol. 30, No. 4, pp. 691-702, 2012.
Khalil, et al., "The Future of Cancer Treatment: Immunomodulation, Carsand Combination Immunotherapy", Nature Reviews Clinical Oncology, pp. 1-18, 2016.
Kim, et al., "Increased in vivo immunological potency of HB-110, a novel therapeutic HBV DNA vaccine, by electroporation," Experimental and Molecular Medicine, vol. 40, No. 6, pp. 669-676, 2008.
Laddy, et al., "Electroporation of Synthetic DNA Antigens Offers Protection in Nonhuman Primates Challenged with Highly Pathogenic Avian Influenza Virus," Journal of Virology, vol. 83, No. 9, pp. 4624-4630, 2009.
Laddy, et al., "Heterosubtypic Protection against Pathogenic Human and Avian Influenza Viruses via In Vivo Electroporation of Synthetic Consensus DNA Antigens," PLoS One, vol. vol. 3, No. 6, 8 pages, 2008.
Leblanc, et al., "Markedly Enhanced Immunogenicity of a Pfs25 DNA-Based Malaria Transmission-Blocking Vaccine by In Vivo Electroporation," Vaccine, vol. 26, No. 2, pp. 185-192, 2008.
Ledford, H "The Perfect Blend", Nature, vol. 532, pp. 162-164, 2016.
Linch, et al., "OX40 Agonists and Combination Immunotherapy: Putting the Pedal to the Metal", Frontiers in Oncology, vol. 5, No. 34, pp. 1-14, 2015.
Littel-Van Den Hurk, et al., "Electroporation-based DNA transfer enhances gene expression and immune responses to DNA vaccines in cattle," Vaccine, vol. 26, No. 43, pp. 5503-5509, 2008.
Liu, et al., "Enhancement of Cancer Radiation Therapy by Use of Adenovirus-Mediated Secretable Glucose-Regulated Protein 94/gp96 Expression," Cancer Res., vol. 65, pp. 9126-9131, 2005.
Liu, et al., "Magnitude and Phenotype of Cellular Immune Responses Elicited by Recombinant Adenovirus Vectors and Heterologous Prime-Boost Regimens in Rhesus Monkeys," Journal of Virology, vol. 82, No. 10, pp. 4844-4852, 2008.
Livingston, et al., "Comparative performance of a licensed anthrax vaccine versus electroporation based delivery of a PA encoding DNA vaccine in rhesus macaques," Vaccine, vol. 28, No. 4, pp. 1056-1061, 2010.
Luckay, et al., "Effect of Plasmid DNA Vaccine Design and In Vivo Electroporation on the Resulting Vaccine-Specific Immune Responses in Rhesus Macaques," Journal of Virology, vol. 81, No. 10, pp. 5257-5269, 2007.
Luxembourg, et al., "Immunogenicity in mice and rabbits of DNA vaccines expressing woodchuck hepatitis virus antigens," Vaccine, vol. 26, No. 32, pp. 4025-4033, 2008.
Mahoney, et al., "Combination Cancer Immunotherapy and New Immunomodulatory Targets", Nature Reviews Drug Discovery, vol. 14, pp. 561-584, 2015.
Mellman, et al., "Cancer immunotherapy comes of age", Nature, vol. 480, pp. 480-489, 2010.
Moran, et al., "The TNFRs OX40, 4-1BB, and CD40 as targets for cancer immunotherapy," Current Opinion in Immunology, vol. 25, pp. 230-237, 2013.
Nyström, et al., "Improving on the Ability of Endogenous Hepatitis B Core Antigen to Prime Cytotoxic T Lymphocytes," The Journal of Infectious Diseases, vol. 201, No. 12, pp. 1867-1879, 2010.
Oehler, et al., "Zika virus infection complicated by Guillain-Barré syndrome—case report, French Polynesia, Dec. 2013," Eurosurveillance, vol. 19, No. 9, pp. 4-6, Mar. 2014.
Oizumi, et al., "Molecular and Cellular Requirements for Enhanced Antigen Cross-Presentation to CD8 Cytotoxic T Lymphocytes", The Journal of Immunology, vol. 179, pp. 2310-2317, 2007.
Oizumi, et al., "Surmounting Tumor-induced Immune Suppression by Frequent Vaccination or Immunization in the Absence of B Cells", J Immunother., vol. 31, No. 4, pp. 394-401, 2008.
Pardoll, "The Blockade of Immune Checkpoints in Cancer Immunotherapy" Nature Reviews Cancer, vol. 12, pp. 252-264, 2012.
Raez, et al., "CD8 T Cell Response in A Phase I Study of Therapeutic Vaccination of Advanced NSCLC with Allogeneic Tumor Cells Secreting Endoplasmic Reticulum-Chaperone Gp96-lg-Peptide Complexes" Advances in Lung Cancer, vol. 2, No. 1, pp. 9-18, 2013.
Rosati, et al., "Increased immune responses in rhesus macaques by DNA vaccination combined with electroporation," Vaccine, vol. 26, No. 40, pp. 5223-5229, 2008.
Schildberg, et al., "Coinhibitory Pathways in the B7-CD28 Ligand-Receptor Family", Immunity, vol. 44, pp. 955-972, 2016.
Schreiber, et al., "Tumor-Induced Suppression of CTL Expansion and Subjugation by gp96-lg Vaccination", Cancer Res., vol. 69, No. 5, pp. 2026-2033, 2009.
Schreiber, et al., "Tumor Immunogenicity and Responsiveness to Cancer Vaccine Therapy: The State of the Art", Seminars in Immunology, vol. 22, pp. 105-112, 2010.
Schreiber, et al., "T Cell Costimulation by TNFRSF4 and TNFRSF25 in the Context of Vaccination," J Immunol., vol. 189, No. 7, pp. 3311-3318, 2012.
Seo, et al., "Optimal induction of HPV DNA vaccine-induced $CD8^+T$ cell responses and therapeutic antitumor effect by antigen engineering and electroporation," Vaccine, vol. 27, No. 42, pp. 5906-5912, 2009.
Simon, et al., "Enhanced in vivo transgene expression and immunogenicity from plasmid vectors following electrostimulation in rodents and primates," Vaccine, vol. 26, pp. 5202-5209, 2008.
Strbo, et al., "Cell-secreted Gp96-lg-Peptide Complexes Induce Lamina Propria and Intraepithelial CD8 + Cytotoxic T Lymphocytes in the Intestinal Mucosa", Nature, vol. 3, No. 2, pp. 182-192, 2010.
Tosti, et al., "HSPPC-96 vaccine in metastatic melanoma patients: from the state of the art to a possible future," Expert Rev Vaccines, vol. 8, No. 11, pp. 1513-1526, 2009.
Trollet, et al., "Generation of High-Titer Neutralizing Antibodies against Botulinum Toxins, A, B, and E by DNA Electrotransfer," Infection and Immunity, vol. 77, No. 5, pp. 2221-2229, 2009.
Ward-Kavanagh, et al., "The TNF Receptor Superfamily in Co-stimulating and Co-inhibitory Responses", Immunity, vol. 44, pp. 1005-1019, 2016.
Yamazaki, et al. "Cutting Edge: Tumor Secreted Heat Shock-Fusion Protein Elicits CD8 Cells for Rejection", J Immunol, vol. 163, pp. 5178-5182, 1999.

\* cited by examiner

B45 - 1st cassette hgp96igG1-Fc 2nd cassette NRU SFI SAL

Figure 3 (continued)

```
  1 TCTAGAGAGC TTGGCCCATT GCATACGTTG TATCCATATC ATAATATGTA CATTTATATT GGCTCATGTC
    CAACATTACC GCCATGTTGA CATTGATTAT
101 AGATCTCTCG AACCGGGTAA CGTATGCAAC ATAGGTATAG TATTATACAT GTAAATATAA CCGAGTACAG
    GTTGTAATGG CGGTACAACT GTAACTAATA
201 TGACTAGTTA TTAATAGTAA TCAATTACGG GGTCATTAGT TCATAGCCCA TATATGGAGT TCCGCGTTAC
    ATAACTTACG GTAAATGGCC CGCCTGGCTG
301 ACTGATCAAT AATTATCATT AGTTAATGCC CCAGTAACTA AGTATCGGGT ATATACCTCA AGGCGCAATG
    TATTGAATGC CATTTACCGG GCGGACCGAC
401 ACCGCCCAAC GACCCCGCC CATTGACGTC AATAATGACG TATGTTCCCA TAGTAACGCC AATAGGGACT
    TTCCATTGAC GTCAATGGGT GGAGTATTTA
501 TGGCGGGTTG CTGGGGCGG GTAACTGCAG TTATTACTGC ATACAAGGGT ATCATTGCGG TTATCCCTGA
    AAGGTAAACTG CAGTTACCCA CCTCATAAAT
601 CGGTAAACTG CCCACTTGGC AGTACATCAA GTGTATCATA TGCCAAGTAC GCCCCCTATT GACGTCAATG
    ACGTAAATG GCCCGCCTGG CATTATGCCC
701 GCCATTGAC GGGTGAACCG TCATGTAGTT ACGGTTCATG CACATATAGT ACGGGATAA CTGCAGTTAC
    TGCCATTTAC CGGGCGGACC GTAATACGGG
801 AGTACATGAC CTTATGGGAC TTTCCTACTT GGCAGTACAT CTACGTATTA GTCATCGCTA TTACCATGGT
    GATGCGGTTT TGGCAGTACA TCAATGGGCG
901 TCATGTACTG GAATACCCTG AAAGGATGAA CCGTCATGTA GATGCATAAT CAGTAGCGAT AATGGTACCA
    CTACGCCAAA ACCGTCATGT AGTTACCCGC
    TGGATAGCGG TTTGACTCAC GGGGATTTCC AAGTCTCCAC CCCATTGACG TCAATGGGAG TTTGTTTTGG
    CACCAAAATC AACGGGACTT TCCAAAATGT
    ACCTATCGCC AAACTGAGTG CCCCTAAAGG GGTAACTGC AGTTACCCTC AAACAAAACC
    GTGGTTTTAG TTGCCCTGAA AGTTTTACA
    CGTAACAACT CCGCCCATT GACGCAAATG GGCGGTAGGC GTGTACGGTG GGAGGTCTAT ATAAGCAGAG
    CTCGTTTAGT GAACCGTCAG ATCGCCTGGA
    GCATTGTGA GGCGGGGGTAA CTGCGTTTAC CCGCCATCCG CACATGCCAC CCTCCAGATA TATTCGTCTC
    GAGCAAATCA CTTGGCAGTC TAGCGGACCT
    GACGCCATCC ACGCTGTTTT GACCTCCATA GAAGACACCG GGACCGATCC AGCCTCCGGT CGATCGACCG
    ATCCTGAGAA CTTCAGGGTG AGTTTGGGA
```

Figure 3 (continued)

```
      CTGCGGTAGG TGCGACAAAA CTGGAGGTAT CTTCCTGTGGC CCTGGCTAGG TCGGAGGCCA GCTAGCTGGC
      TAGGACTCTT GAAGTCCCAC TCAAACCCT
 801  CCCTTGATTG TTCTTTCTTT TTGCTATTG TAAAATTCAT GTTATATGGA GGGGGCAAAG TTTTCAGGGT
      GTTGTTTAGA ATGGGAAGAT GTCCCTTGTA
      GGGAACTAAC AAGAAAGAAA AAGCGATAAC ATTTTAAGTA CAATATACCT CCCCCGTTTC AAAAGTCCCA
      CAACAAATCT TACCCTTCTA CAGGGAACAT
 901  TCACCATGGA CCCTCATGAT AATTTTGTTT CTTTCACTTT CTACTCTGTT GACAACCATT GTCTCCCCTT
      ATTTTCTTTT CATTTTCTGT AACTTTTCG
      AGTGGTACCT GGGAGTACTA TTAAAACAAA GAAAGTGAAA GATGAGACAA CTGTTGGTAA CAGAGGAGAA
      TAAAAGAAAA GTAAAAGACA TTGAAAAGC
1001  TTAAACTTTA GCTTGCATTT GTAACGAATT TTTAAAATTCA CTTTTGTTTA TTTGTCAGAT TGTAAGTACT
      TTCTCTAATC ACTTTTTTT CAAGCAATC
      AATTTGAAAT CGAACGTAAA CATTGCTTAA AAATTTAAGT GAAAACAAAT AAACAGTCTA ACATTCATGA
      AAGAGATTAG TGAAAAAAAA GTTCCGTTAG
1101  AGGGTATATT ATATTGTACT TCAGCACAGT TTTAGAGAAC AATTGTTATA ATTAAATGAT AAGGTAGAAT
      ATTTCGCAT ATAAATTCTG GCTGGCGTGG
      TCCCATATAA TATAACATGA AGTCGTGTCA AAATCTCTTG TTAACAATAT TAATTTACTA TTCCATCTTA
      TAAGACGTA TATTTAAGAC CGACCGCACC
1201  AAATATTCTT ATTGGTAGAA ACAACTACAC CCTGGTCATC ATCCCTGCCTT TCTCTTTATG GTTACAATGA
      TATACACTGT TGAGATGAG GATAAAATAC
      TTTATAAGAA TAACCATCTT TGTTGATGTG GGACCAGTAG TAGGACGGAA AGAGAAATAC CAATGTTACT
      ATATGTGACA AACTCTACTC CTATTTTATG
1301  TCTGAGTCCA AACCGGGCCC CTCTGCTAAC CATGTTCATG CCTTCTTCTC TTTCCTACAG CTCCTGGGCA
      ACGTGCTGGT TGTTGTGCTG TCTCATCATT
      AGACTCAGGT TGGCCCGGG GAGACGATTG GTACAAGTAC GGAAGAAGAG AAAGGATGTC GAGGACCCGT
      TGCACGACCA ACAACACGAC AGAGTAGTAA
1401  TTGGCAAAGA ATTCGAAGCC TCGAGATGAT GAAACTTTATC ATCAATTCAT TGTATAAAAA TAAAGAGATT
      TTCCTGAGAG AACTGATTTC AAATGCTTCT
      AACCGTTTCT TAAGCTTCGG AGCTCTACTA CTTTGAATAG TAGTTAAGTA ACATATTTTT ATTTCTTAA
      AAGGACTCTC TTGACTAAAG TTTACGAAGA
```

Figure 3 (continued)

```
1501  GATGCTTTAG ATAAGATAAG GCTAATATCA CTGACTGATG AAAATGCTCT TTCTGGAAAT GAGGAACTAA
      CAGTCAAAAT TAAGTGTGAT AAGGAGAAGA
      CTACGAAATC TATTCTATTC CGATTATAGT GACTGACTAC TTTTACGAGA AAGACCTTTA CTCCTTGATT
      GTCAGTTTTA ATTCACACTA TTCCTCTTCT
1601  ACCTGCTGCA TGTCACAGAC ACCGGTGTAG GAATGACCAG AGAAGAGTTG GTTAAAAACC TTGGTACCAT
      AGCCAAATCT GGGACAAGCG AGTTTTTAAA
      TGGACGACGT ACAGTGTCTG TGGCCACATC CTTACTGGTC TCTTCTCAAC CAATTTTTGG AACCATGGTA
      TCGGTTTAGA CCCTGTTCGC TCAAAAATTT
1701  CAAAATGACT GAAGCACAGG AAGATGGCCA GTCAACTTCT GAATTGATTG GCCAGTTTGG TGTCGGTTTC
      TATTCCGCCT TCCTTGTAGC AGATAAGGTT
      GTTTTACTGA CTTCGTGTCC TTCTACCGGT CAGTTGAAGA CTTAACTAAC CGGTCAAACC ACAGCCAAAG
      ATAAGGCGGA AGGAACATCG TCTATTCCAA
1801  ATTGTCACTT CAAAACACAA CAACGATACC CAGCACACAT CT GGGAGTCTGA CTCCAATGAA TTTTTCGTAA
      TTGCTGACCC AAGAGGAAAC ACTCTAGGAC
      TAACAGTGAA GTTTTGTGTT GTTGCTATGG GTCGTGTAGA CCCTCAGACT GAGGTTACTT AAAAGACATT
      AACGACTGGG TTCTCCTTTG TGAGATCCTG
1901  GGGGAACGAC AATTACCCTT GTCTTAAAAG AAGAAGCATC TGATTACCTT GAATTGGATA CAATTAAAAA
      TCTCGTCAAA AAATATTCAC AGTTCATAAA
      CCCCTTGCTG TTAATGGAA CAGAATTTTC TTCTTCGTAG ACTAATGGAA CTTAACCTAT GTTAATTTTT
      AGAGCAGTTT TTTATAAGTG TCAAGTATTT
2001  CTTTCCTATT TATGTATGGA GCAGCAAGAC TGAAACTGTT GAGGAGCCCA TGGAGGAAGA AGAAGCAGCC
      AAAGAAGATA AAGAAGAATC TGATGATGAA
      GAAAGGATAA ATACATACCT CGTCGTTCTG ACTTTGACAA CTCCCTCGGGT ACCTCCTTCT TCTTCGTCGG
      TTTCTTCTCT TTCTTCTTAG ACTACTACTT
2101  GCTGCAGTAG AGGAAGAAGA AGAAGAAAAG AAACCAAAGA CTAAAAAAGT TGAAAAAACT GTCTGGGACT
      GGGAACTTAT GAATGATATC AAACCAATAT
      CGACGTCATC TCCTTCTTCT TCTTCTTTTC TTTGGTTTCT GATTTTTTCA ACTTTTTTGA CAGACCCTGA
      CCCTTGAATA CTTACTATAG TTTGGTTATA
2201  GGCAGAGACC ATCAAAAGAA GTAGAAGAAG ATGAATACAA AGCTTTCTAC AAATCATTTT CAAAGGAAAG
      TGATGACCCC ATGGCTTATA TTCACTTTAC
```

Figure 3 (continued)

```
       CCGTCTCTGG TAGTTTTCTT CATCTCTCTTC TACTTATGTT TCGAAAGATG TTTAGTAAAA GTTTCCTTTC
       ACTACTGGGG TACCGAATAT AAGTGAAATG
2301   TGCTGAAGGG GAAGTTACCT TCAAATCAAT TTTATTTGTA CCCACATCTG CTCCACGTGG TCTGTTTGAC
       GAATATGGAT CTAAAAAGAG CGATTACATT
       ACGACTTCCC CTTCAATGGA AGTTTAGTTA AAATAAACAT GGGTGTAGAC GAGGTGCACC AGACAAACTG
       CTTATACCTA GATTTTCTC GCTAATGTAA
2401   AAGCTCTATG TGCGCCGTGT ATTCATCACA GACGACTTCC ATGATATGAT GCCTAAATAC CTCAATTTTG
       TCAAGGGTGT GGTGGACTCA GATGATCTCC
       TTCGAGATAC ACGCGGCACA TAAGTAGTGT CTGCCTGAAGG TACTATACTA CGGATTTATG GAGTTAAAAC
       AGTTCCCACA CCACCTGAGT CTACTAGAGG
2501   CCTTGAATGT TTCCCGCGAG ACTCTTCAGC AACATAAAACT GCTTAAGGTG ATTAGGAAGA AGCTTGTTCG
       TAAACGCTG GACATGATCA AGAAGATTGC
       GGAACTTACA AAGGCGCTC TGAGAAGTCG TTGTATTTGA CGAATTCCAC TAATCCTTCT TCGAACAAGC
       ATTTGCGAC CTGTACTAGT TCTTCTAACG
2601   TGATGATAAA TACAATGATA CTTTTTTGGAA AGAATTTGGT ACCAACATCA AGCTTGGTGT GATTGAAGAC
       CACTCGAATC GAACACGTCT TGCTAAACTT
       ACTACTATTT ATGTTACTAT GAAAAAACCTT TCTTAAACCA TGGTTGTAGT TCGAACCACA CTAACTTCTG
       GTGAGCTTAG CTTGTGCAGA ACGATTTGAA
2701   CTTAGGTTCC AGTCTTCTCA TCATCCAACT GACATTACTA GCCTAGACCA GTATGTGGAA AGAATGAAGG
       AAAAACAAGA CAAAATCTAC TTCATGGCTG
       GAATCCAAGG TCAGAAGAGT AGTAGGTTGA CTGTAATGAT CGGATCTGGT CATACACCTT TCTTACTTCC
       TTTTTGTTCT GTTTTAGATG AAGTACCGAC
2801   GGTCAGCAG AAAAGAGGCT GAATCTTCTC CATTTGTTGA GCGACTTCTG AAAAAGGGCT ATGAAGTTAT
       TTACCTCACA GAACCTGTGG ATGAATACTG
       CCAGGTCGTC TTTTCCCGA CTTAGAAGAG GTAAACAACT CGCTGAAGAC TTTTTCCCGA TACTTCAATA
       AATGGAGTGT CTTGGACACC TACTTATGAC
2901   TATTCAGGCC CTTCCGAAT TTGATGGGAA GAGGTTCCAG AATGTTGCCA AGGAAGGAGT GAAGTTCGAT
       GAAAGTGAGA AAACTAAGGA GAGTCGTGAA
       ATAAGTCCGG GAAGGCTTA AACTACCCTT CTCCAAGGTC TTACAACGGT TCCTTCCTCA CTTCAAGCTA
       CTTTCACTCT TTTGATTCCT CTCAGCCACT
```

Figure 3 (continued)

```
3001  GCAGTTGAGA AAGAATTTGA GCCTCTGCTG AATTGGATGA AAGATAAAGC CCTTAAGGAC AAGATTGAAA
      AGGCTGTGGT GTCTCAGCGC CTGACAGAAT
      CGTCAACTCT TTCTTAAACT CGGAGACGAC TTAACCTACT TTCTATTTCG GGAATTCCTG TTCTAACTTT
      TCCGACACCA CAGAGTCGCG GACTGTCTTA
3101  CTCCGTGTGC TTTGGTGGCC AGCCAGTACG GATGGTCTGG CAACATGGAG AGAATCATGA AAGCACAAGC
      GTACCAAACG GGCAAGGACA TCTCTACAAA
      GAGGCACACG AAACCACCGG TCGGTCATGC CTACCAGACC GTTGTACCTC TCTTAGTACT TTCGTGTTCG
      CATGGTTTGC CCGTTCCTGT AGAGATGTTT
3201  TTACTATGCG AGTCAGAAGA AAACATTTGA AATTAATCCC AGACACCCGC TGATCAGAGA CATGCTTCGA
      CGAATTAAGG AAGATGAAGA TGATAAAACA
      AATGATACGC TCAGTCTTCT TTTGTAAACT TTAATTAGGG ACTAGTCTCT GTACGAAGCT
      GCTTAATTCC TTCTACTTCT ACTATTTGT
3301  GTTTTGGATC TTGCTGTGGT TTTGTTTGAA ACAGCAACGC TTCGGTCAGG GTATCTTTTA CCAGACACTA
      AAGCATATGG AGATAGAATA GAAAGAATGC
      CAAAACCTAG AACGACCA AAACAAACTT TGTCCGTTGCG AAGCCAGTCC CATAGAAAAT GGTCTGTGAT
      TTCGTATACC TCTATCTTAT CTTTCTTACG
3401  TTCGCCTCAG TTTGAACATT GACCCTGATG CAAAGGTGGA AGAAGAGCCC GAAGAAGAAC CTGAAGAGAC
      AGCAGAAGAC ACAACAGAAG ACACAGAGCA
      AAGCGGAGTC AAACTTGTAA CTGGACTAC TCTTCCACCT TCTTCTCGGG CTTCTTCTG GACTTCTCTG
      TCGTCTTCTG TGTCTTCTC TGTGTCTCGT
3501  AGACGAAGAT GAAGAAATGG ATGTGGGAAC AGATGAAGAA GAAGAAACAG CAAAGGAATC TACAGCTGAA
      GGATCCTGTG ACAAAACTCA CACATGCCCA
      TCTGCTTCTA CTTCTTTACC TACACCCTTG TCTACTTCTT CTTCTTTGTC GTTTCCTTAG ATGTCGACTT
      CCTAGGACAC TGTTTTGAGT GTGTACGGGT
3601  CCGTGCCCAG CACCTGAACT CCTGGGGGGA CCGTCAGTCT TCCTCTTCCC CCCAAAACCC AAGGACACCC
      TCATGATCTC CCGGACCCCT GAGGTCACAT
      GGCACGGGTC GTGGACTTGA GGACCCCCCT GGCAGTCAGA AGGAGAAGG GGGTTTTGGG TTCCTGTGGG
      AGTACTAGAG GGCCTGGGGA CTCCAGTGTA
3701  GCGTGGTGGT GGACGTGAGC CACGAAGACC CTGAGGTCAA GTTCAACTGG TACGTGGACG GCGTGGAGGT
      GCATAATGCC AAGACAAAGC CGCGGGAGGA
```

Figure 3 (continued)

```
3801  CGCACCACCA CCTGCACTCG GTGCTTCTGG GACTCCAGTT CAAGTTGACC ATGCACCTGC CGCACCTCCA
      CGTATTACGG TTCTGTTTCG GCGCCCTCCT
      GCAGTACAAC AGCACGTACC GTGTGGTCAG CGTCCTCACC GTCCTGCACC AGGACTGGCT GAATGGCAAG
      GAGTACAAGT GCAAGGTCTC CAACAAAGCC
      CGTCATGTTG TCGTGCATGG CACACCAGTC GCAGGAGTGG CAGGACGTGG TCCTGACCGA CTTACCGTTC
      CTCATGTTCA CGTTCCAGAG GTTGTTTCGG
3901  CTCCCAGCCC CCATCGAGAA AACCATCTCC AAAGCCAAAG GGCAGCCCCG AGAACCACAG GTGTACACCC
      TGCCCCCATC CCGGGATGAG CTGACCAAGA
      GAGGGTCGGG GGTAGCTCTT TGGTAGAGG TTTCGGTTTC CCGTCGGGGC TCTTGGTGTC CACATGTGGG
      ACGGGGTAG GGCCCTACTC GACTGGTTCT
4001  ACCAGGTCAG CCTGACCTGC CTGGTCAAAG GCTTCTATCC CAGCGACATC GCCGTGGAGT GGGAGAGCAA
      TGGGCAGCCG GAGAACAACT ACAAGACCAC
      TGGTCCAGTC GGACTGGACG GACCAGTTTC CGAAGATAGG GTCGCTGTAG CGGCACCTCA CCCTCTCGTT
      ACCCGTCGGC CTCTTGTTGA TGTTCTGGTG
4101  GCCTCCCGTG CTGGACTCCG ACGGCTCCTT CTTCCCTCTAC AGCAAGCTCA CCGTGGACAA GAGCAGGTGG
      CAGCAGGGGA ACGTCTTCTC ATGCTCCGTG
      CGGAGGGCAC GACCTGAGGC TGCCGAGGAA GAAGGAGATG TCGTTCGAGT GGCACCTGTT CTCGTCCACC
      GTCGTCCCCT TGCAGAAGAG TACGAGGCAC
4201  ATGCATGAGG CTCTGCACAA CCACTACACG CAGAAGAGCC TCTCCCTGTC TCCGGGTAAA TGACTCGACC
      CAGACTAGTC AAATTAAGCC GAATTCTGCA
      TACGTACTCC GAGACGTGTT GGTGATGTGC GTCTTCTCGG AGAGGGACAG AGGCCCATTT ACTGAGCTGG
      GTCTGATCAG TTTAATTCGG CTTAAGACGT
4301  GATATCCATC ACACTGGCGG CCGCTGGAAT TCACTCCCTCA GGTGCAGGCT GCCTATCAGA AGGTGGTGGC
      TGGTGTGGCC AATGCCCTGG CTCACAAATA
      CTATAGGTAG TGTGACCGCC GGCGACCTTA AGTGAGGAGT CCACGTCCGA CGGATAGTCT TCCACCACCG
      ACCACACCGG TTACGGGACC GAGTGTTTAT
4401  CCACTGAGAT CTTTTTCCCT CTGCCAAAAA TTATGGGGAC ATCATGAAGC CCCTTGAGCA TCTGACTTCT
      GGCTAATAAA GGAAATTTAT TTTCATTGCA
      GGTGACTCTA GAAAAGGGA GACGGTTTTT AATACCCCTG TAGTACTTCG GGAACTCGT AGACTGAAGA
      CCGATTATTT CCTTTAAATA RAAGTAACGT
```

Figure 3 (continued)

```
4501 ATAGTGTGTT GGAATTTTTT GTGTCTCTCA CTCGGAAGGA CATATGGGAG GGCAAATCAT TTAAAACATC
     AGAATGAGTA TTTGGTTTAG AGTTTGGCAA
     TATCACACAA CCTTAAAAAA CACAGAGAGT GAGCCTTCCT GTATACCCTC CCGTTTAGTA AATTTTGTAG
     TCTTACTCAT AAACCAAATC TCAAACCGTT
4601 CATATGCCCA TATGCTGGCT GCCATGAACA AAGGTTGGCT ATAAAGAGGT CATCAGTATA TGAAACAGCC
     CCCTGCTGTC CATTCCTTAT TCCATAGAAA
     GTATACGGGT ATACGACCGA CGGTACTTGT TTCCAACCGA TATTTCTCCA GTAGTCATAT ACTTTGTCGG
     GGGACGACAG GTAAGGAATA AGTTATCTTT
4701 AGCCTTGACT TGAGGTTAGA TTTTTTTTAT ATTTTGTTTT GTGTTATTTT TTTTCTTTAAC ATCCCTAAAA
     TTTTCCTTAC ATGTTTTACT AGCCAGATTT
     TCGGAACTGA ACTCCAATCT AAAAAAAATA TAAAACAAAA CACAATAAAA AAAGAAATTG TAGGGATTTT
     AAAAGGAATG TACAAAATGA TCGGTCTAAA
4801 TTCCTCCTCT CCTGACTACT CCCAGTCATA GCTGTCCCTC TTCTCTTATG GAGATCCCTC GACGGATCCC
     TAGAGTCGAG GCGATCCGGC GCAGCACCAT
     AAGGAGAGA GGACTGATGA GGGTCAGTAT CGACAGGGAG AAGAGAATAC CTCTAGGGAG CTGCCTAGGG
     ATCCAGCTC CGCTACGCCG CGTCGTGGTA
4901 GGCCTGAAAT AACCCTCGAA AGAGGAACTT GGTTAGGTAC CTTGGTTTTT AAAACCAGCC TGGAGTAGAG
     CAGATGGGTT AAGGTGAGTG ACCCCTCAGC
     CCGGACTTTA TTGGAGACTT TCTCCTTGAA CCAATCCATG GAACCAAAAA TTTTGGTCGG ACCTCATCTC
     GTCTACCCAA TTCCACTCAC TGGGGAGTCG
5001 CCTGGACATT CTTAGATGAA CCCCCCCAGG AGTAGAGAAT AATGTTGAGA TGAGTTCTGT TGGCTAAAAT
     AATCAAGGCT AGTCTTTATA AAACTGTCTC
     GGACCTGTAA GAATCTACTC GGGGAGTCC TCATCTCTTA TTACAACTCT ACTCAAGACA ACCGATTTTA
     TTAGTTCCGA TCAGAAATAT TTTGACAGAG
5101 CTCTTCTCCT AGCTTCGATC CAGAGAGAGA CCTGGGCGGA GCTGGTCGCT GCTCAGGAAC TCCAGGAAAG
     GAGAAGCTGA GGTTACCACG CTGCGAATGG
     GAGAAGAGGA TCGAAGCTAG GTCTCTCTCT GGACCCGCCT CGACCAGCGA CGAGTCCTTG AGGTCCTTTC
     CTCTTCGACT CCAATGGTGC GACGCTTACC
5201 GTTTACGGAG ATAGCTGGCT TTCCGGGGTG AGTTCTCGTA AACTCCAGAG CAGCGGATAGG CCGTAATATC
     GGGGAAAGCA CTATAGGGAC ATGATGTTCC
```

Figure 3 (continued)

```
      CAAATGCCTC TATCGACCGA AAGGCCCCAC TCAAGAGCAT TTGAGGTCTC GTCGCTATCC GGCATTATAG
      CCCCTTTCGT GATATCCCTG TACTACAAGG
 5301 ACACGTCACA TGGGTCGTCC TATCCGAGCC AGTCGTGCCA AAGGGGCGGT CCCGCTGTGC ACACTGGCGC
      TCCAGGGAGC TCTGCACTCC GCCCGAAAAG
      TGTGCAGTGT ACCCAGCAGG ATAGGCTCGG TCAGCACGGT TTCCCCGCCA GGGCGACACG TGTGACCGCG
      AGGTCCCCTCG AGACGTGAGG CGGGCTTTTC
 5401 TGCGCTCGGC TCTGCCAGGA CGCGGGGCGC GTGACTATGC GTGGGCTGGA GCAACCGCCT GCTGGGTGCA
      AACCCTTTGC GCCCGGACTC GTCCAACGAC
      ACGCGAGCCG AGACGGTCCT GCGCCCCGCG CACTGATACG CACCCGACCT CGTTGGCGGA CGACCCACGT
      TTGGGAAACG CGGGCCTGAG CAGGTTGCTG
 5501 TATAAAGAGG GCAGGCTGTC CTCTAAGCGT CACCACGACT TCAACGTCCT GAGTACCTTC TCCTCACTTA
      CTCCGTAGCT CCAGCTTCAC CACCAAGCTC
      ATATTTCTCC CGTCCGACAG GAGATTCGCA GTTGCAGGA AGTTGCAGGA CTCATGGAAG AGGAGTGAAT
      GAGGCATCGA GGTCGAAGTG GTGGTTCGAG
                     NruI                                            SalI
                     ~~~~~                                           ~~~~
 5601 CTCGACGTCG ATCGCGAAGC TTTGGCCCCT TTGGCCTTAG CGTCGACCGA TCCTGAGAAC
      TTCAGGGTGA GTTTGGGGAC CCTTGATTGT TCTTTCTTTT
      GAGCTGCAGC TAGCGCTTCG AACCGGGGA AACCGGAATC GCAGCTGGCT AGGACTCTTG AAGTCCCACT
      CAAACCCCTG GGAACTAACA AGAAAGAAAA
 5701 TCGCTATTGT AAAATTCATG TTATATGGAG GGGGCAAAGT TTTCAGGGTG TTGTTTAGAA
      TGGGAAGATG TCCCTTGTAT CACCATGGAC CCTCATGATA
      AGCGATAACA TTTTAAGTAC AATATACCTC CCCGTTTCA AAAGTCCCAC AACAAATCTT ACCCTTCTAC
      AGGGAACATA GTGGTACCTG GGAGTACTAT
 5801 ATTTTGTTTC TTTCACTTTC TACTCTGTTG ACAACCATTG TCTCCTCTTA TTTTCTTTTC
      ATTTTCTGTA ACTTTTTCGT TAAACTTTAG CTTGCATTTG
      TAAACAAAG AAAGTGAAAG ATGAGACAAC TGTTGGTAAC AGAGGAGAAT AAAAGAAAAG TAAAAGACAT
      TGAAAAGCA ATTTGAAATC GAACGTAAAC
 5901 TAACGAATTT TTAAATTCAC TTTTGTTTAT TTGTCAGATT GTAAGTACTT TCTCTAATCA
      CTTTTTTTC AAGGCAATCA GGGTATATTA TATTGTACTT
```

Figure 3 (continued)

```
      ATTGCTTAAA AATTTAAGTG AAAACAAATA AACAGTCTAA CATTCATGAA AGAGATTAGT GAAAAAAAAG
      TTCCGTTAGT CCCATATAAT ATAACATGAA
 6001 CAGCACAGTT TTAGAGAACA ATTGTTATAA TTAAATGATA AGGTAGAATA TTTCTGCATA
      TAAATTCTGG CTGGCGTGGA AATATTCTTA TTGGTAGAAA
      GTCGTGTCAA AATCTCTGT TAACAATATT AATTTACTAT TCCATCTTAT AAAGACGTAT ATTTAAGACC
      GACCGCACCT TTATAAGAAT AACCATCTTT
 6101 CAACTACACC CTGGTCATCA TCCTGCCTTT CTCTTTATGG TTACAATGAT ATACACTGTT
      TGAGATGAGG ATAAAATACT CTGAGTCCAA ACCGGGCCCC
      GTTGATGTGG GACCAGTAGT AGGACGGAAA GAGAAATACC AATGTTACTA TATGTGACAA ACTCTACTCC
      TATTTTATGA GACTCAGGTT TGGCCCGGGG
 6201 TCTGCTAACC ATGTTCATGC CTTCTTCTCT TTCCTACAGC TCCTGGGCAA CGTGCTGGTT
      GTTGCTCTGT CTCATCATTT TGGCAAAGAA TTCCCTCGACC
      AGACGATTGG TACAAGTACG GAAGAAGAGA AGGATGTCG AGGACCCGTT GCACGACCAA CAACACGACA
      GAGTAGTAAA ACCGTTTCTT AAGGAGCTGG
 6301 AGTGCAGGCT GCCTATCAGA AAGTGGTGGC TGGTGTGGCT AATGCCCTGG CCCACAAGTA
      TCACTAAGCT CGCTTCTTG CTGTCCAATT TCTATTAAAG
      TCACGTCCGA CGGATAGTCT TTCACCACCG ACCACACCGA TTACGGGACC GGGTGTTCAT AGTGATTCGA
      GCGAAAGAAC GACAGTTAA AGATAATTTC
 6401 GTTCCTTTGT TCCCTAAGTC CAACTACTAA ACACATTTAT TTTCATTGCA
      TCTGGATTCT GCCTAATAAA AGGGATTCAG GTTGATGATT TGACCCCCTA TAATACTTCC CGGAACTCGT AGACCTAAGA
      CAAGGAAACA AGGGATTCAG GTTGATGATT AAAGTAACGT
      CGGATTATT TTTGTAAATA CTGAATATATT TACTAAAAAG GGAATGTGGG AGGTCAGTGC
 6501 ATGATGTATT TAAATTATTT CTGAATATATT TACTAAAAAG GGAATGTGGG AGGTCAGTGC
      ATTTAAAACA TAAAGAAATG AAGAGCTAGT TCAAACCTTG
      TACTACATAA ATTTAATAAA GACTTATAAA ATGATTTTTC CCTTACACCC TCCAGTCACG TAAATTTGT
      ATTTCTTTAC TTCTCGATCA AGTTTGGAAC
 6601 GGAAAATACA CTATATCTTA AACTCCATGA AAGAAGGTGA GGCTGCAAAC AGCTAATGCA
      CATTGGCAAC AGCCCCTGAT GCCTATGCCT TATTCATCCC
      CCTTTATGT GATATAGAAT TTGAGGTACT TTCTTCCACT CCGACGTTTG TCGATTACGT GTAACCGTTG
      TCGGGGACTA CGGATACGGA ATAAGTAGGG
```

Figure 3 (continued)

```
6701 TCAGAAAAGG ATTCAAGTAG AGGCTTGATT TGGAGGTTAA AGTTTTGCTA TGCTGTATTT
     TACATTACTT ATTGTTTTAG CTGTCCTCAT GAATGTCTTT
     AGTCTTTTCC TAAGTTCATC TCCGAACTAA ACCTCCAATT TCAAAACGAT ACGACATAAA ATGTAATGAA
     TAACAAAATC GACAGGAGTA CTTACAGAAA
6801 TCACTACCCA TTTGCTTATC CTGCATCTCT CAGCCTTGAC TCCACTCAGT TCTCTTGCTT
     AGAGATACCA CCTTTCCCCT GAAGTGTTCC TTCCATGTTT
     AGTGATGGGT AAACGAATAG GACGTAGAGA GTCGGAACTG AGGTGAGTCA AGAGAACGAA TCTCTATGGT
     GGAAAGGGGA CTTCACAAGG AAGGTACAAA
6901 TACGGCGAGA TGGTTTCTCC TCGCCTGGCC ACTCAGCCTT AGTTGTCTCT GTTGTCTTAT
     AGAGGTCTAC TTGAAGAAGG AAAAACAGGG GGCATGGTTT
     ATGCCGCTCT ACCAAGAGAG AGCGGACCGG TGAGTCGGAA TCAACAGAGA CAACAGAATA TCTCCAGATG
     AACTTCTTCC TTTTTGTCCC CCGTACCAAA
7001 GACTGTCTC CGGAACTAC TTCCCTGCCT CACTCTTTCA CAGTGACCCG GAATCTGCAG
     TGCTAGTCTC CCGGAACTAT CACTCTTTCA CAGTCTGCTT
     CTGACAGGAG ACTCGGGAAG AAGGGACGGA GGGGGTGAGT GTCACTGGGC CTTAGACGTC ACGATCAGAG
     GCCTTGATA GTGAGAAAGT GTCAGAAGAA
7101 TGGAAGGACT GGGCTTAGTA TGAAAAGTTA GGACTGAGAA GAATTTGAAA GGGGGCTTTT
     TGTAGCTTGA TATTCACTAC TGTCTTATTA CCCTATCATA
     ACCTTCCTGA CCCGAATCAT ACTTTTCAAT CCTGACTCTT CTTAAACTTT CCCCCGAAAA ACATCGAACT
     ATAAGTGATG ACAGAATAAT GGGATAGTAT
7201 GGCCCACCCC AAATGGAAGT CCCATTCTTC CTCAGGATGT TTAAGATTAG CATTCAGGAA
     GAGATCAGAG GTCTGCTGGC TCCCTTATCA TGTCCCTTAT
     CCGGGTGGGG TTTACCTTCA GGGTAAGAAG GAGTCCTACA AATTCTAATC GTAAGTCCCT TCTCAGTCTC
     CAGACGACCG AGGGAATAGT ACAGGGAATA
7301 GGTGCTTCTG GCTCTCTGCAGT TATTAGCATA GTGTTACCAT CAACCACCTT AACTTCATTT
     TTCTTATTCA ATACCTAGGT AGGTAGATGC TAGATTCTGG
     CCACGAAGAC CGAGACGTCA ATAATCGTAT CACAATGGTA GTTGGTGGAA TTGAAGTAAA AAGAATAAGT
     TATGGATCCA TCCATCTACG ATCTAAGACC
7401 AAATAAAATA TGAGTCTCAA GTGGTCCTTG TCCTCTCTCC CAGTCAAATT CTGAATCTAG
     TTGGCAAGAT TCTGAAATCA AGGCATATAA TCAGTAATAA
```

Figure 3 (continued)

```
      TTTATTTTAT ACTCAGAGTT CACCAGGAAC AGGAGAGAGG GTCAGTTTAA GACTTAGATC AACCGTTCTA
      AGACTTTAGT TCCGTATATT AGTCATTATT
 7501 GTGATGATAG AAGGGTATAT AGAAGAATTT TATTATATGA GAGGGTGAAA TCCCAGCAAT
      TGGGAGGCT GAGGCAGGAG AATCGCTTGA TCCTGGGAGG
      CACTACTATC TTCCCATATA TCTTCTTAAA ATAATATACT CTCCCACTTT AGGGTCGTTA AACCCTCCGA
      CTCCGTCCTC TTAGCGAACT AGGACCCTCC
 7601 CAGAGGTTGC AGTGAGCCAA GATTGTGCCA CTGCATTCCA GCCCAGGTGA CAGCATGAGA
      CTCCGTCACA AAAAAAAAAG AAAAAAAAGG GGGGGGGGG
      GTCTCCAACG TCACTCGGTT CTAACACGGT GACGTAAGGT CGGGTCCACT GTCGTACTCT GAGGCAGTGT
      TTTTTTTTTC TTTTTTTTCC CCCCCCCCCC
 7701 CGGTGGGAGCC AAGATGACCG AATAGGAACA GCTCCAGTAC TATAGCTCCC ATCGTGAGTG
      ACGCAGAAGA CGGGTGATTT CTGCATTTCC AACTGAGGTA
      GCCACCTCGG TTCTACTGGC TTATCCTTGT CGAGGTCATG ATATCGAGGG TAGCACTCAC TGCCGTCTTCT
      GCCCACTAAA GACGTAAAGG TTGACTCCAT
 7801 CCAGGTTCAT CTCACAGGGA AGTGCCAGGC AGTGGGTGCA GGACAGTAGG TGCAGTGCAC
      TGTGCATGAG CCGAAGCAGG GACGAGGCAT CACCTCACCC
      GGTCCAAGTA GAGTGTCCCT TCACGGTCCG TCACCCACGT CCTGTCATCA ACGTCACGTG ACACGTACTC
      GGCTTCGTCC CTGCTCCGTA GTGGAGTGGG
 7901 GGGAAGCACA AGGGGTCAGG GAATTCCCTT TCCTAGTCAA AGAAAAGGGT GACAGATGGC
      ACCTGGAAAA TCGGGTCACT CCCGCCCTAA TACTGCGCTC
      CCCTTCGTGT TCCCCAGTCC CTTAAGGGAA AGGATCAGTT TCTTTTCCCA CTGTCTACCG TGGACCTTTT
      AGCCCAGTGA GGGCGGGATT ATGACGCGAG
 8001 TTCCAACAAG CTTGTCTTTG GAAAATAGAT CAATTCCCT TGGGAAGAAG ATTTTTAGCA
      CAGCAAGGGG CAGGATGTTC AACTGTGAGA AAACGAAGAA
      AAGGTGTTC GAACAGAAAC CTTTTATCTA GTTAAAGGGA ACCCTTCTTC TAAAAATCGT GTCGTTCCCC
      GTCCTACAAG TTGACACTCT TTTGCTTCTT
 8101 TTAGCCAAAA AACTTCCAGT AAGCCTGCAA AAAAAAAAA AAAATAAAAG CTAAGTTTCT
      ATAAATGTTC TGTAAATGTA AAACAGAAGG TAAGTCAACT
      AATCGGTTTT TTGAAGGTCA TTCGGACGTT TTTTTTTTT TTTTATTTTC GATTCAAAGA TATTTACAAG
      ACATTTACAT TTTGTCTTCC ATTCAGTTGA
```

Figure 3 (continued)

```
8201 GCACCTAATA AAAATCACTT AATAGCAATG TGCTGTGTCA GTTGTTTATT GGAACCACAC
     CCGGTACACA TCCTGTCCAG CATTGCAGT GCGTGCATTG
     CGTGGATTAT TTTTAGTGAA TTATCGTTAC ACGACACAGT CAACAAATAA CCTTGGTGTG GGCCATGTGT
     AGGACAGGTC GTAAACGTCA CGCACGTAAC
8301 AATTATTGTG CTGGCTAGAC TTCATGGCGC CTGGCACCGA ATCCTGCCTT CTCAGCGAAA
     ATGAATAATT GCTTTGTTGG CAAGAAACTA AGCATCAATG
     TTAATAACAC GACCGATCTG AAGTACCGCG GACCGTGGCT TAGGACGGAA GAGTCGCTTT TACTTATTAA
     CGAAACAACC GTTCTTTGAT TCGTAGTTAC
8401 GGACGCGTGC AAAGCACCGG CGGCGGTAGA TGCGGGGTAA GTACTGAATT TTAATTCGAC
     CTATCCCGGT AAAGCGAAAG CGACACGCTT TTTTTTCACA
     CCTGCGCACG TTTCGTGGCC GCCGCCATCT ACGCCCCATT CATGACTTAA AATTAAGCTG GATAGGGCCA
     TTTCGCTTTC GCTGTGCGAA AAAAAAGTGT
8501 CATAGCGGGA CCGAACACGT TATAAGTATC GATTAGGTCT ATTTTTGTCT CTCTGTCGGA
     ACCAGAACTG GTAAAAGTTT CCATTGCGTC TGGGCTTGTC
     GTATCGCCCT GGCTTGTGCA ATATTCATAG CTAATCCAGA TAAAAACAGA GAGACAGCCT TGGTCTTTGAC
     CATTTTCAAA GGTAACGCAG ACCGAACACAG
8601 TATCATTGCG TCTCTATGGT TTTTGGAGGA TTAGACGGGG CCACCAGTAA TGGTGCATAG
     CGGATGTCTG TACCGCCCATC GGTGCACCGA TATAGGTTTG
     ATAGTAACGC AGAGATACCA AAAACCTCCT AATCTGCCCC GGTGGTCATT ACCACGTATC GCCTACAGAC
     ATGGCGGTAG CCACGTGGCT ATATCCAAAC
8701 GGGCTCCCCA AGGGACTGCT GGGATGACAG CTTCATATTA TATTGAATGG GCGCATAATC
     AGCTTAATTG GTGAGGACAA GCTACAAGTT GTAACCTGAT
     CCCGAGGGGT TCCCTGACGA CCCTACTGTC GAAGTATAAT ATAACTTACC CGCGTATTAG TCGAATTAAC
     CACTCCCTGT CGATGTTCAA CATTGGACTA
8801 CTCCACAAAG TACGTTGCCG GTCGGGGTCA AACCGTCTTC GGTGCTCGAA ACCGCCTTAA
     ACTACAGACA GGTCCCAGCC AAGTAGGCGG ATCAAAACCT
     GAGGTGTTTC ATGCAACGGC CAGCCCCAGT TGGCAGAAG CCACGAGCTT TGGCGGAATT TGATGTCTGT
     CCAGGGTCGG TTCATCCGCC TAGTTTGGA
8901 CAAAAAGGCG GGAGCCAATC AAAATGCAGC ATTATATTTT AAGCTCACCG AAACCGGTAA
     GTAAGACTA TGTATTTTT CCCAGTGAAT AATTGTGTT
```

Figure 3 (continued)

```
     GTTTTTCCGC CCTCGGTTAG TTTTACGTCG TAATATAAAA TTCGAGTCGG TTTGGCCATT CATTTCTGAT
     ACATAAAAAA GGGTCACTTA TTAACAACAA
9001 AACTATATAA AGCGTCATGG CAAACGATAA AGGTAGCAAT TGGGATTCGG GCTTGGGATG
     CTCATATCTG CTGACTGAGG CAGAATGTGA AAGTGACAAA
     TTGATATTTT TCGCAGTACC GTTTGCTATT TCCATCGTTA ACCCTAAGCC CGAACCCTAC GAGTATAGAC
     GACTGACTCC GTCTTACACT TTCACTGTTT
9101 GAGAATGAGG AACCCGGGGC AGGTGTAGAA CTGTCTGTGG AATCTGATCG GTATGATAGC
     CAGGATGAGG ATTTTGTTGA CAATGCATCA GTCTTTCAGG
     CTCTTACTCC TTGGGCCCG TCCACATCTT GACAGACACC TTAGACTAGC CATACTATCG GTCCTACTCC
     TAAAACAACT GTTACGTAGT CAGAAAGTCC
9201 GAAATCACCT GGAGGTCTTC CAGGCATTAG AGAAAAAGGC GGGTGAGGAG CAGATTTAA
     ATTTGAAAAG AAAAGTATTG GGGAGTTCGC AAAACAGCAG
     CTTAGTGTGA CCCTCAGAAG GTCCGTAATC TCTTTTTCCG CCCACTCCTC GTCTAAAATT TAAACTTTTC
     TTTTCATAAC CCCTCAAGCG TTTTGTCGTC
9301 CGGTTCCGAA GCATCTGAAA CTCCCAGTTAA AAGACGGAAA TCAGGAGCAA AGCGAAGATT
     ATTTGCTAAA AATGAAGCTA ACCGTGTTCT TACGCCCCTC
     GCCAAGGCTT CGTAGACTTT GAGGTCAATT TTCTGCCTTT AGTCCTCGTT TCGCTTCTAA TAAACGACTT
     TTACTTCGAT TGGCACAAGA ATGCGGGGAG
9401 CAGGTACAGG GGGAGGGGGA GGGGAGGCAA GAACTTAATG AGGAGCAGGC AATTAGTCAT
     CTACATCGC AGCTTGTTGA ATCTAAAAAT GCTACAGTTT
     GTCCATGTCC CCCTCCCCCT CCCCTCCGTT CTTGAATTAC TCCTCGTCCG TTAATCAGTA GATGTAGACG
     TCGAACAATT TAGATTTTTA CGATGTCAAA
9501 TTAAGCTGGG GCTCTTTAAA TCTTTGTTCC TTTGTAGCTT CCATGATATT ACGAGGTTGT
     TTAAGAATGA TAAGACCACT AATCAGCAAT GGGTGCTGGC
     AATTCGACCC CGAGAAATTT AGAAACAAGG AAACATCGAA GGTACTATAA TGCTCCAACA AATTCTTACT
     ATTCGGTGA TTAGTCGTTA CCCACGACCG
9601 TGTGTTTGGC CTTGCAGAGG TGTTTTTGA GGCGAGTTTC GAACTCCTAA AGAAGCAGTG
     TAGTTTTCTG CAGATGCAAA AAAGATCTCA TGAAGGAGGA
     ACACAAACCG GAACGTCTCC ACAAAAACT CCGCTCAAAG CTTGAGGATT TCTTCGTCAC ATCAAAGAC
     GTCTACGTTT TTTTCTAGAGT ACTTCCTCCT
```

Figure 3 (continued)

```
 9701 ACTTGTGCAG TTTACTTAAT CTGCTTTAAC ACAGCTAAAA GCAGAGAAAC AGTCCGGAAT
      CTGATGGCAA ACATGCTAAA TGTAAGAGAA GAGTGTTTGA
      TGAACACGTC AAATGAATTA GACGAAATTG TGTCGATTTT CGTCTCTTTG TCAGGCCTTA GACTACCGTT
      TGTACGATTT ACATTCTCTT CTCACAAACT
 9801 TGCTGCAGCC ACCTAAAATT CGAGGACTCA GGGCAGCTCT ATTCTGGTTT AAAAGTAGTT
      TGTCACCCGC TACACTTAAA CATGGTGCTT TACCTGAGTG
      ACGACGTCGG TGGATTTTAA GCTCCTGAGT CGCGTCGAGA TAAGACCAAA TTTTCATCAA ACAGTGGGCG
      ATGTGAATTT GTACCACGAA ATGGACTCAC
 9901 GATACGGGCG CAAACTACTC TGAACGAGAG CTTGCAGACC GAGAAATTCG ACTTCGGAAC
      TATGGTGCAA TGGGCCTATG ATCACAAATA TGCTGAGGAG
      CTATGCCCGC GTTGATGAG ACTTGCTCTC GAACGTCTGG CTCTTTAAGC TGAAGCCTTG ATACCACGTT
      ACCCGGATAC TAGTGTTTAT ACGACTCCTC
10001 TCTAAAATAG CCTATGAATA TGCTTTGGCT GCAGGATCTG AAGGACTGTG
      TTAGCAACTA ACAGCCAAGC TAAGCATGTG AAGGACTGTG
      AGATTTATC GGATACTTAT ACGAAACCGA CGTCCTAGAC TATCGTTACG TGCCCGAAAA AATCGTTGAT
      TGTCGGTTCG ATTCGTACAC TTCCTGACAC
10101 CAACTATGGT AAGACACTAT CTAAGAGCTG AAACACAAGC ATTAAGCATG CCTGCATATA
      TTAAAGCTAG GTGCAAGCTG GCAACTGGGG AAGGAAGCTG
      GTTGATACCA TTCTGTGATA GATTCCTGAC TTTGTGTTCG TAATTCGTAC GGACGTTATAT AATTCCGATC
      CACGTTCGAC CGTTGACCCC TTCCTTCGAC
10201 GAAGTCTATC CTAACTTTTT TTAACTATCA GAATATTGAA TTAATTACCT TTATTAATGC
      TTTAAAGCTC TGGCTAAAAG GAATTCCAAA AAAAAACTGT
      CTTCAGATAG GATTGAAAAA AATTGATAGT CTTATAACTT AATTAATTGA AATAATTACG AAATTTCGAG
      ACCGATTTTC CTTAAGGTTT TTTTTTGACA
10301 TTAGCATTTA TTGGCCCTCC AAACTTTTGT ATCTTTTGCC AAGTCTATGC TCTGCAACTC ATTAATTCAT
      TTTTGGGGTG GTAGTGTTT ATCTTTGCT
      AATCGTAAAT AACCGGGAGG TTGTGTCCG TTCAGATACG AGACGTTGAG TAATTAAGTA AAAAACCCAC
      CATCACAAAA TAGAAAACGG TGGTATTTT
10401 GTCACTTTTG GCTTGCTTCC CTAGCAGATA CTAGAGCTGC TTTAGTAGAT GATGCTACTC
      ATGCTTGCTG GAGGTACTTT GACACATACC TCAGAAATGC
```

Figure 3 (continued)

```
      CAGTGAAAAC CGAACGAAGG GATCGTCTAT GATCTCGACG AAATCATCTA CTACGATGAG TACGAACGAC
      CTCCATGAAA CTGTGTATGG AGTCTTTACG
10501 ATTGGATGGC TACCCTGTCA GTATTGATAG AAAACACAAA GCAGCGGGTTC AAATTAAAGC
      TCCACCCCTC CTGGTAACCA GTAATAATTGA TGTGCAGGCA
      TAACCTACCG ATGGGACAGT CATAACTATC TTTTGTGTTT CGTCGCCAAG TTTAATTTCG AGGTGGGGAG
      GACCATTGGT CATTATAACT ACACGTCCGT
10601 GAGGACAGAT ATTTGTACTT GCATAGTCGG GTGCAAACCT TTCGCTTTGA GCAGCCATGC
      ACAGATGAAT CGGGTGAGCA ACCTTTTAAT ATTACTGATG
      CTCCTGTCTA TAAACATGAA CGTATCAGCC CACGTTGGA AAGCGAAACT CGTCGGTACG TGTCTACTTA
      GCCCACTCGT TGGAAAATTA TAATGACTAC
10701 CAGATTGGAA ATCTTTTTTT GTAAGGTTAT GGGGGCGTTT AGACCTGATT GACGAGGAGG
      AGGATAGTGA AGAGGATGGA GACAGCATGC GAACGTTTAC
      GTCTAACCTT TAGAAAAAAA CATTCCAATA CCCCCGCAAA TCTGGACTAA CTGCCTCCTCC TCCTATCACT
      TCTCCTACCT CTGTCGTACG CTTGCAAATG
10801 ATGCAGCGCA AGAAACACAA ATGCAGTTGA TTGAGAAAAG TAGTGATAAG TTGCAAGATC
      ATATACTGTA CTGGACTGCT GTTAGAACTG AGAACACACT
      TACGTCGGCT TCTTTGTGTT TACGTCAACT AACTCTTTTC ATCACTATTC AACGTTCTAG TATATGACAT
      GACCTGACGA CAATCTTGAC TCTTGTGTGA
10901 GCTTTATGCT GCAAGGAAAA AAGGGGTGAC TGTCCTAGGA CACTGCAGAG TACCACACTC
      TGTAGTTTGT CAAGAGAGA CCAAGCAGGC CAACTTTAC
      CGAAATACGA CGTTCCTTTT TCCCCACTG ACAGGATCCT GTGACGTCTC ATGGGTGTGAG ACATCAAACA
      GTTCTCTCTC GGTTCGTCCG GTAACTTTAC
11001 CAGTTGTCTT TGCAGGAGTT AAGCAAAACT GAGTTGGGGG ATGAACCATG GTCTTTGCTT
      GACACAAGCT GGGACCGATA TATGTCAGAA CCTAAACGGT
      GTCAACAGAA ACGTCCTCAA TTCGTTTGA CTCAAACCCC TACTTGGTAC CAGAAACGAA CTGTGTTGGA
      CCCTGGCTAT ATACAGTCTT GGATTGCCA
11101 GCTTTAAGAA AGGCGCCAGG GTGGTAGAGG TGGAGTTTGA TGGAAATGCA AGCAATACAA
      ACTGGTACAC TGTCTACAGC AATTTGTACA TGCGCACAGA
      CGAATTCTT TCCGGGTCC CACCATCTCC ACCTCAAACT ACCTTTACGT TCGTTATGTT TGACCATGTG
      ACAGATGTCG TTAAACATGT ACGGCGTGTCT
```

Figure 3 (continued)

```
11201 GGACGGCTGG CAGCTTGCGA AGGCTGGGCT GACGGAACTG GGCTCTACTA CTGCACCATG
      GCCGGTGCTG GACGCATTTA CTATTCTGC TTTGGTGACG
      CCTGCCGACC GTCGAACGCT TCCGACCCGA CTGCCTTGAC CCGAGATGAT GACGTGGTAC CGGCCACGAC
      CTGCGTAAAT GATAAGAGCG AAACCACTGC
11301 AGGCAGCCAG ATTTAGTACA ACAGGGCATT ACTCTGTAAG AGATCAGGAC AGAGTGTATG
      CTGGTGTCTC ATCCACCTCT TCTGATTTTA GAGATCGCCC
      TCCGTCGGTC TAAATCATGT TGTCCCGTAA TGAGACATTC TCTAGTCCTG TCTCACATAC GACCACAGAG
      TAGGTGGAGA AGACTAAAAT CTCTAGCGGG
11401 AGACGGAGTC TGGGTCGCAT CCGAAGGACC TGAAGGAGAC CCTGCAGGAA AAGAAGCCGA
      GCCAGCCCAG CCTGTCTCTT CTTTGCTCGG CTCCCCCGCC
      TCTGCCTCAG ACCCAGCGTA GGCTTCCTCC ACTTCCTCTG GGACGTCCTT TTCTTCGGCT CGGTCGGGTC
      GGACAGAGAA GAAACGAGCC GAGGGGCGG
11501 TGCGGTCCCA TCAGAGCAGG CCTCGGTTGG GTACGGGACG GTCCTCGCTC GCACCCCTAC
      AATTTCCTG CAGGCTCGGG GGGCTCTATT CTCCGCTCTT
      ACGCCAGGGT AGTCTCGTCC GGAGCCAACC CATGCCCTGC CAGGAGCCAG CGTGGGGATG TTAAAAGGAC
      GTCCGAGCCC CCCGAGATAA GAGGCGAGAA
11601 CCTCCACCCC GTGCAGGGCA CGGTACCCGGT GGACTTGGCA TCAAGGCAGG AAGAAGAGGA
      GCAGTCGCCC GACTCCACAG AGGAAGAACC AGTGACTCTC
      GGAGGTGGGG CACGTCCCGT GCCATGGCCA CCTGAACCGT AGTTCCGTCC TTCTTCTCCT CGTCAGCGGG
      CTGAGGTGTC TCCTTCTTGG TCACTGAGAG
11701 CCAAGGCGCA CCACCAATGA TGGATTCCAC CTGTTAAAGG CAGGAGGGTC ATGCTTTGCT
      CTAATTTCAG GAACTGCTAA CCAGGTAAAG TGCTATCGCT
      GGTTCCGCGT GGTGGTTACT ACCTAAGGTG GACAATTTCC GTCCCTCCCAG TACGAAACGA GATTAAAGTC
      CTTGACGATT GGTCCATTTC ACGATAGCGA
11801 TTCGGGTGAA AAAGAACCAT AGACAAGGAC AGACATCGCT ACGAGAACTG CACCACCACC TGGTTCACAG
      TTGCTGACAA CGGTGCTGAA AGACAAGGAC AAGCACACAAAT
      AAGCCCACTT TTTCTTGGTA TCTGTAGCGA TGCTCTTGAC GTGGGTGG ACCAAGTGTC AACGACTGTT
      GCCACGACTT TCTGTTCCTG TTCGTGTTTA
11901 ACTGATCACC TTTGGATCGC CAAGTCAAAG GCAAGACTTT CTGAAACATG TACCACTACC
      TCCTGGAATG AACATTTCCG GCTTTACAGC CAGCTTGGAC
```

Figure 3 (continued)

```
      TGACTAGTGG AAACCTAGCG GTTCAGTTTC CGTTCTGAAA GACTTTGTAC ATGGTGATGG AGGACCTTAC
      TTGTAAAGGC CGAAATGTCG GTCGAACCTG
12001 TTCTGATCAC TGCCATTGCC TTTTCTTCAT CTGACTGGTG TACTATGCCA AATCTATGCG
      ACCGCATTAT AAAGCCGAAT TCTGCAGATA TCCATCACAC
      AAGACTAGTG ACGGTAACGG ACGTAACGG AAAAGAAGTA GACTGACCAC ATGATACGGT TTAGATACGC TGGGCGTAATA
      TTTCGGCTTA AGACGTCTAT AGTTAGTGTG
12101 TGGCGGCCAT ATGGCCGCTA TGCGGTGTGA AATACCGCAC AGATGCGTAA GGAGAAAATA
      CCGCATCAGG CGCTCTTCCG CTTCCTCGCT CACTGACTCG
      ACCGCCGGTA TACCGGCGAT ACGCCACACT TTATGGCCGTG TCTACGCATT CCTCTTTTAT GGCGTAGTCC
      GCGAGAAGGC GAAGGAGCGA GTGACTGAGC
12201 CTGCGCGTCGG TCGTTCGGCT GCGGCGAGCG GTATCAGCTC ACTCAAAGGC GGTAATACGG
      TTATCCACAG AATCAGGGGA TAACGCAGGA AAGAACATGT
      GACGGCGAGCC AGCAAGCCGA CGCCGCTCGC CATAGTCGAG TGAGTTTCCG CCATTATGCC AATAGGTGTC
      TTAGTCCCCT ATTGCGTCCT TTCTTGTACA
12301 GAGCAAAAGG CCAGCAAAAG GCCAGGAACC GTAAAAAGGC CGCGTTGCTG GCGTTTTTCC
      ATAGGCTCCG CCCCCCTGAC GAGCATCACA AAAATCGACG
      CTCGTTTTCC GGTCGTTTTC CGGTCCTTGG CATTTTTCCG GCCAACGAC CGCAAAAAGG TATCCGAGGC
      GGGGGACTG CTCGTAGTGT TTTAGCTGC
12401 CTCAAGTCAG AGGTGGCGAA ACCCGACAGG ACTATAAAGA TACCAGGCGT TTCCCCCTGG
      AAGCTCCCTC GTGCGCTCTC CTGTTCCGAC CCTGCCGCTT
      GAGTTCAGTC TCCACCGCTT TGGGCTGTCC TGATATTTCT ATGGTCCGCA AAGGGGGACC TTCGAGGGAG
      CACGCGAGAG GACAAGGCTG GGACGGCGAA
12501 ACCGGATACC TGTCCGCCTT TCTCCCCTTCG GGAAGCGTGG CGCTTTCTCA TAGCTCACGC
      TGTAGGTATC TCAGTTCGGT GTAGGTCGTT CGCTCCAAGC
      TGGCCTATGG ACAGGCGGAA AGAGGGAAGC CCTTCGCACC GCGAAAAGAGT ATCGAGTGCG ACATCCATAG
      AGTCAAGCCA CATCCAGCAA GCGAGGTTCG
12601 TGGGCTGTGT GCACGAACCC CCGTTCAGC CCGACCCGCTG CGCCTTATCC GGTAACTATC
      GTCTTGAGTC CAACCCGGTA AGACACGACT TATCGCCACT
      ACCCGACACA CGTGCTTGGG GGCAAGTCG GGCTGGCGAC GCGGAATAGG CCATTGATAG CAGAACTCAG
      GTTGGGCCAT TCTGTGCTGA ATAGCGGTGA
```

Figure 3 (continued)

```
12701 GGCAGCAGCC ACTGGTAACA GGATTAGCAG AGCGAGGTAT GTAGGCGGTG CTACAGAGTT
      CTTGAAGTGG TGGCCTAACT ACGGCTACAC TAGAAGGACA
      CGGTCGTCGG TGACCATTGT CCTAATCGTC TCGCTCCATA CATCCGCCAC GATGTCTCAA GAACTTCACC
      ACCGGATTGA TGCCGATGTG ATCTTCCTGT
12801 GTATTTGGTA TCTGCGCTCT GCTGAAGCCA GTTACCCTTCG GAAAAAGAGT TGGTAGCTCT
      TGATCCGGCA AACAAACCAC CGCTGGTAGC GGTGGTTTTT
      CATAAACCAT AGACGCGGAGA CGACTTCGGT CAATGGAAGC CTTTTTCTCA ACCATCGAGA ACTAGGCCGT
      TTGTTTGGTG GCGACCATCG CCACCAAAAA
12901 TTGTTTGCAA GCAGCAGATT ACGCGCAGAA AAAAAGGATC TCAAGAAGAT CCTTTGATCT
      TTTCTACGGG GTCTGACGCT CAGTGGAACG AAAACTCACG
      AACAAACGTT CGTCGTCTAA TGCGCGGTCTT TTTTTCCTAG AGTTCTTCTA GGAAACTAGA AAAGATGCCC
      CAGACTGCGA GTCACCTTGC TTTTGAGTGC
13001 TTAAGGGATT TTGGTCATGA GATTATCAAA AAGGATCTTC ACCTAGATCC TTTTAAATTA
      AAAATGAAGT TTTAAATCAA TCTAAAGTAT ATATGAGTAA
      AATTCCCTAA AACCAGTACT CTAATAGTTT TCCTAGAAG TGGATCTAGG AAAATTTAAT TTTTACTTCA
      AAATTAGTT AGATTTCATA TATACTCATT
13101 ACTTGGTCTG ACAGTTACCA ATGCTTAATC AGTGAGGCAC CTATCCTCAGC GATCTGTCTA
      TTTCGTTCAT CCATAGTTGC CTGACTCCCC GTCGTGTAGA
      TGAACCAGAC TGTCAATGGT TACGAATTAG TCACTCCCGTG GATAGAGTCG CTAGACAGAT AAAGCAAGTA
      GGTATCAACG GACTGAGGGG CAGCACATCT
13201 TAACTACGAT ACGGGAGGGC TTACCATCTG GCCCCAGTGC TGCAATGATA CCGCGAGACC
      CACGCTCACC GGCTCCAGAT TTATCAGCAA TAAACCAGCC
      ATTGATGCTA TGCCCTCCCG AATGGTAGAC CGGGTCACG ACGTTACTAT GGCGCTCTGG GTGCGAGTGG
      CCGAGGTCTA AATAGTCGTT ATTTGGTCGG
13301 AGCCGGAAGG GCCGAGCGCA GAAGTGGTCC TGCAACTTTA TCCGCCTCCA TCCAGTCTAT
      TAATTGTTGC CGGGAAGCTA GAGTAAGTAG TTCGCCAGTT
      TCGGCCTTCC CGGCTCGGCGT CTTCACCAGG ACGTTGAAAT AGGCGGAGGT AGGTCAGATA ATTAACAACG
      GCCCTTCGAT CTCATTCATC AAGCGGTCAA
13401 AATAGTTTGC GCAACGTTGT TGCCATTGCT GCAGGCATCG TGGTGTCACG CTCGTCGTTT
      GGTATGGCTT CATTCAGCTC CGGTTCCCAA CGATCAAGGC
```

Figure 3 (continued)

```
      TTATCAAACG CGTTGCAACA ACGGTAACGA CGTCCGTAGC ACCACAGTGC GAGCAGCAAA CCATACCGAA
      GTAAGTCGAG GCCAAGGGTT GCTAGTTCCG
13501 GAGTTACATG ATCCCCCATG TTGTGCAAAA AAGCGGTTAG CTCCTTCGGT CCTCCGATCG
      TTGTCAGAAG TAAGTTGGCC GCAGTGTTAT CACTCATGGT
      CTCAATGTAC TAGGGGGTAC AACACGTTTT TTCGCCAATC GAGGAAGCCA GGAGGCTAGC AACAGTCTTC
      ATTCAACCGG CGTCACAATA GTGAGTACCA
13601 TATGGCAGCA CTGCATAATT CTCTTACTGT CATGCCATCC GTAAGATGCT TTTCTGTGAC
      TGGTGAGTAC TCAACCAAGT CATTCTGAGA ATAGTGTATG
      ATACCGTCGT GACGTATTAA GAGAATGACA GTACGGTAGG CATTCTACGA AAAGACACTG ACCACTCATG
      AGTTGGTTCA GTAAGACTCT TATCACATAC
13701 CGGCGACCGA GTTGCTCTTG CCCGGCGTCA ACACGGGATA ATACCGCGCC ACATAGCAGA
      ACTTTAAAAG TGCTCATCAT TGGAAAACGT TCTTCGGGGC
      GCCGCTGGCT CAACGAGAAC GGGCCGCAGT TGTGCCCTAT TATGGCGCGG TGTATCGTCT TGAAATTTTC
      ACGAGTAGTA ACCTTTTGCA AGAGCCCCG
13801 GAAAACTCTC AAGGATCTTA CCGCTGTTGA GATCCAGTTC GATGTAACCC ACTCGTGCAC
      CCAACTGATC TTCAGCATCT TTTACTTTCA CCAGCGTTTC
      CTTTTGAGAG TTCCTAGAAT GGCGACAACT CTAGGTCAAG CTACATTGGG TGAGCACGTG GGTTGACTAG
      AAGTCGTAGA AAATGAAAGT GGTCGCAAAG
13901 TGGGTGAGCA AAAACAGGAA GGCAAAAATGC CGCAAAAAAG GGAATAAGGG CGACACGGAA
      ATGTTGAATA CTCATATCT TCCTTTTTCA ATATTATTGA
      ACCCACTCGT TTTTGTCCTT CCGTTTTACG GCGTTTTTTC CCTTATTCCC GCTGTGCCTT TACAACTTAT
      GAGTATGAGA AGGAAAAAGT TATAATAACT
14001 AGCATTTATC AGGGTTATTG TCTCATGAGC GGATACATAT TTGAATGTAT TTAGAAAAAT
      AAACAAATAG GGGTTCCGCG CACATTTCCC CGAAAAGTGC
      TCGTAAATAG TCCCAATAAC AGAGTACTCG CCTATGTATA AACTTACATA AATCTTTTTA TTTGTTTATC
      CCCAAGGCGC GTGTAAAGGG GCTTTTCACG
14101 CACCTGACGT CTAAGAAACC ATTATTATCA TGACATTAAC CTATAAAAAT AGGCGTATCA
      CGAGGCCCTT TCGTCTTCAA GAATTCTCAT GTTTGACACG
      GTGGACTGCA GATTCTTTGG TAATAATAGT ACTGTAATTG GATATTTTTA TCCGCATAGT GCTCCGGGAA
      AGCAGAAGTT CTTAAGAGTA CAAACTGTCG
```

Figure 3 (continued)

```
14201 TTATCATCGA TAAGCTTCAC GCTGCCGCAA GCACTCAGGG CGCAAGGGCT GCTAAAGGAA
      GCGGAACACG TAGAAAGCCA GTCCGCAGAA ACGGTGCTGA
      AATAGTAGCT ATTCGAAGTG CGACGGCGTT CGTGAGTCCC GCGTTCCCGA CGATTCCTT CGCCTTGTGC
      ATCTTTCGGT CAGGCGTCTT TGCCACGACT
14301 CCCGGATGA ATGTCAGCTA CTGGGCTATC TGGACAAGGG AAAACGCAAG CGCAAAGAGA
      AAGCAGGTAG CTTGCAGTGG GCTTACATGG CGATAGCTAG
      GGGGCCTACT TACAGTCGAT GACCCGATAG ACCTGTTCCC TTTTGCGTTC GCGTTTCTCT TTCGTCCATC
      GAACGTCACC CGAATGTACC GCTATCGATC
14401 ACTGGGCGGT TTTATGGACA GCAAGCGAAC CGGAATTGCC AGCTGGGGCG CCCTCTGTA
      AGGTTGGGAA GCCCTGCAAA GTAAACTTGA TGGCTTTCTT
      TGACCCGCCA AATACCTGT CGTTCGCTTG GCCTTAACGG TCGACCCCGC GGGAGACCAT TCCAACCCTT
      CGGGACGTTT CATTTGACCT ACCGAAAGAA
14501 GCCGCCAAGG ATCGATGGC GCAGGGGATC AAGATATATTG GACACAAACC CCGCCCAGCG TTCATCCCCG TGGCCCGTTG
      CTCGGGTTTG CTGGCGGTGT CCCCGGAAGA AATATATTTG
      CGGCGGTTCC TAGACTACCG CGTCCCCTAG TTCTAGGACG AAGTAGGGGC ACCGGGCAAC GAGCGCAAAC
      GACCGCCACA GGGGCCTTCT TTATATAAAC
14601 CATGTCTTTA GTTCTATGAT GACACAAACC CCGCCCAGCG TCTTGTCATT GGCGAATTCG
      AACACGCCAGA TGCAGTCGGG GCGGCGCGT CCCAGGTCCA
      GTACAGAAAT CAAGATACTA CTGTGTTTGG GCGGGGTCGC AGAACAGTAA CCGCTTAAGC TTGTGCGTCT
      ACGTCAGCGC CGCCGCGCCA GGGTCCAGGT
14701 CTTCGCATAT TAAGGTGACG CGTGTGGCCT CGAACACCGA GCGACCCTGC AGCGACCCGC
      TTAACAGCGT CAACACGTG CCGCAGATCT GATCAAGAGA
      GAAGCGTATA ATTCCACTGC GCACACCGGA GCTTGTGGCT CGCTGGGACG TGCCTGGGCG AATTGTCGCA
      GTTGTCCGCAC GGCGTCTAGA CTAGTTCTCT
14801 CAGGGTGAGG ATCGTTTCGC ATGATTGAAC AAGATGGATT GCACGCAGGT TCTCCGGCCG
      CTTGGGTGGA GAGGCTATTC GGCTATGACT GGGCACAACA
      GCCCTACTCC TAGCAAAGCG TACTAACTTG TTCTACCTAA CGTGCGTCCA AGAGGCCGGC GAACCCACCT
      CTCCGATAAG CCGATACTGA CCCGTGTTGT
14901 GACAATCGGC TGCTCTGATG CCGGCCGTGT CCGGCTGTCA GCGCAGGGGC GCCCGGTTCT
      TTTGTCAAG ACCGACCTGT CCGGTGCCCT GAATGAACTG
```

Figure 3 (continued)

```
       CTGTTAGCCG ACGAGACTAC GCGGGCACAA GGCCGACAGT CGCGTCCCCG CGGGCCAAGA AAAACAGTTC
       TGGCTGGACA GGCCACGGGA CTTACTTGAC
15001  CAGGACGAGG CAGCGCGGGCT ATCGTGGCTG GCCACGACGG GCGTTCCTTG CGCAGCTGTG
       CTCGACGTTG TCACTGAAGC GGGAAGGGAC TGGCTGCTAT
       GTCCTGCTCC GTCGGCCCGA TAGCACCGAC CGGTGCTGCC CGCAAGGAAC GCGTCGACAC GAGCTGCAAC
       AGTGACTTCG CCCTTCCCTG ACCGACGATA
15101  TGGGCGAAGT GCCGGGGCAG GATCTCCCTGT CATCTCACCT TGCTCCTGCC GAGAAAGTAT
       CCATCATGGC TGATGCAATG CGGGCGGCTGC ATACGCTTGA
       ACCCGCTTCA CGGCCCCGTC CTAGAGGACA GTAGAGTGGA ACGAGGACGG CTCTTTCATA GGTAGTACCG
       ACTACGTTAC GCCGCCGACG TATGCGAACT
15201  TCCGGCTACC TGCCCATTCG ACCACCAAGC GAAACATCGC ATCGAGCGAG CACGTACTCG
       GATGGAAGCC GGTCTTGTCG ATCAGGATGA TCTGGACGAA
       AGGCCGATGG ACGGGTAAGC TGGTGGTTCG CTTTGTAGCG TAGCTCGCTC GTGCATGAGC CTACCTTCGG
       CCAGAACAGC TAGTCCTACT AGACCTGCTT
15301  GAGCATCAGG GGCTCGTCGCG AGCCGAACTG TTCGCCAGGC TCAAGGCGCG CATGCCCGAC
       GGGCGAGGATC TCGTCGTGAC CCATGGCGAT GCCTGCTTGC
       CTCGTAGTCC CCGAGCGCGG TCGGCTTGAC AAGCGGTCCG AGTTCCGCGC GTACGGGGCTG CCGCTCCTAG
       AGCAGCACTG GGTACGCTA CGGACGAACG
15401  CGAATATCAT GGTGGAAAAT GGCCGCTTTT CTGGATTCAT CGACTGTGGC CGGCTGGGTG
       TGGCGGACCG CTATCAGGAC ATAGCGTTGG CTACCCGTGA
       GCTTATAGTA CCACCTTTTA CCGGGCGAAAA GACCTAAGTA GCTGACACCG GCCGACCCAC ACCGCCTGGC
       GATAGTCCTG TATCGCAACC GATGGGCACT
15501  TATTGCTGAA GAGCTTGGCG GCGAATGGGCG TGACCGCTTC CTCGTGCTTT ACGGTATCGC
       CGCTCCCGAT TCGCAGCGCA TCGCCTTCTA TCGCCTTCTT
       ATAACGACTT CTCGAACCGC GCCTTACCCG ACTGGCGAAG GAGCACGAAA TGCCATAGCG GCGAGGGCTA
       AGCGTCGCGT AGCGGAAGAT AGCGGAAGAA
15601  GACGAGTTCT TCTGAGCGGG ACTCTGGGGT TCGAAATGAC CGACCAAGCG ACGCCCAACC
       TGCCATCACG AGATTTCGAT TCCACCGCCG CCTTCTATGA
       CTGCTCAAGA AGACTCGCCC AGACCCCA AGCTTTACTG GCTGGTTCGC TGCGGGTTCG ACGGTAGTGC
       TCTAAAGCTA AGGTGGGCGG GGAAGATACT
```

Figure 3 (continued)

```
15701 AAGGTTGGGC TTCGGAATCG TTTTCCGGGA CGCCGGCTGG ATGATCCTCC AGCGCGGGGA
     TCTCATGCTG GAGTTCTTCG CCCACCCCGG GAGATGGGGG
     TTCCAACCCG AAGCCTTAGC AAAAGGCCCT GCGGCCGACC TACTAGGAGG TCGCGCCCCT AGAGTACGAC
     CTCAAGAAGC GGGTGGGGCC CTCTACCCCC
15801 AGGCTAACTG AAACACGGAA GGAGACAATA CCGGAAGGAA CCCGGCTAT GAACGGCAAT
     AAAAAGACAG AATAAAAACGC ACGGTGTTGG GTCGTTTGTT
     TCCGATTGAC TTTGTGCCTT CCTCTGTTAT GGCCTTCCTT GGGCGCGATA CTTGCCGTTA TTTTTCTGTC
     TTATTTTGCG TGCCACAACC CAGCAAACAA
15901 CATAAACGCG GGGTTCGGTC CCAGGGCTGG CACTCTGTCG ATACCCCACC GAGACCCCAT
     TGGGGCCAAT ACGCCCCGCGT TCTTCCTTT TCCCCACCCC
     GTATTTGCGC CCCAAGCCAG GGTCCCGACC GTGAGACAGC TATGGGGTGG CTCTGGGTA ACCCCGGTTA
     TGCGGGGCGCA AAGAAGGAAA AGGGGTGGGG
16001 ACCCCCCAAG TTCGGGTGAA GGCCCAGGGC TCGCAGCCAA CGTCGGGGCG GCAAGCCCTG
     CCATAGCCAC GGGCCCCGTG GGTTAGGGAC GGCGGATCGC
     TGGGGGGTTC AAGCCCACTT CCGGGTCCCG AGCGTCGGTT GCAGCCCCGC CGTTCGGGAC GGTATCGGGTG
     CCCGGGGCAC CCAATCCCTG CCGCCTAGCG
16101 GGCCC
     CCGGG
```

Gp96-Ig-ZIKVEnv vaccine induces antigen experienced (CD11a+) effector memory CD8 T cells in decidua

FIGURE 14

Gp96-Ig-ZIKVEnv vaccine induced ZIKV-Env-specific CD8+ T lymphocyte responses, as assessed by multiparameter intracellular cytokine staining (ICS) assays

SEQUENCE LISTING

<160> NUMBER OF SEQ ID NOS: 54

<210> SEQ ID NO 1
<211> LENGTH: 2170
<212> TYPE: DNA
<213> ORGANISM: Artificial Sequence
<220> FEATURE:
<223> OTHER INFORMATION: Synthetic Polymer
<220> FEATURE:
<221> NAME/KEY: CDS
<222> LOCATION: (26)..(2170)

<400> SEQUENCE: 1

```
ttggcaaaga attcgaagcc tcgag atg atg aaa ctt atc atc aat tca ttg        52
                            Met Met Lys Leu Ile Ile Asn Ser Leu
                            1               5 tat aaa aat aaa gag att ttc ctg aga gaa ctg att tca aat gct tct       100
Tyr Lys Asn Lys Glu Ile Phe Leu Arg Glu Leu Ile Ser Asn Ala Ser
 10                  15                  20                  25 gat gct tta gat aag ata agg cta ata tca ctg act gat gaa aat gct       148
Asp Ala Leu Asp Lys Ile Arg Leu Ile Ser Leu Thr Asp Glu Asn Ala
                 30                  35                  40 ctt tct gga aat gag gaa cta aca gtc aaa att aag tgt gat aag gag       196
Leu Ser Gly Asn Glu Glu Leu Thr Val Lys Ile Lys Cys Asp Lys Glu
             45                  50                  55 aag aac ctg ctg cat gtc aca gac acc ggt gta gga atg acc aga gaa       244
Lys Asn Leu Leu His Val Thr Asp Thr Gly Val Gly Met Thr Arg Glu
         60                  65                  70 gag ttg gtt aaa aac ctt ggt acc ata gcc aaa tct ggg aca agc gag       292
Glu Leu Val Lys Asn Leu Gly Thr Ile Ala Lys Ser Gly Thr Ser Glu
 75                  80                  85 ttt tta aac aaa atg act gaa gca cag gaa gat ggc cag tca act tct       340
Phe Leu Asn Lys Met Thr Glu Ala Gln Glu Asp Gly Gln Ser Thr Ser
 90                  95                 100                 105 gaa ttg att ggc cag ttt ggt gtc ggt ttc tat tcc gcc ttc ctt gta       388
Glu Leu Ile Gly Gln Phe Gly Val Gly Phe Tyr Ser Ala Phe Leu Val
                110                 115                 120 gca gat aag gtt att gtc act tca aaa cac aac aac gat acc cag cac       436
Ala Asp Lys Val Ile Val Thr Ser Lys His Asn Asn Asp Thr Gln His
            125                 130                 135 atc tgg gag tct gac tcc aat gaa ttt tct gta att gct gac cca aga       484
Ile Trp Glu Ser Asp Ser Asn Glu Phe Ser Val Ile Ala Asp Pro Arg
        140                 145                 150 gga aac act cta gga cgg gga acg aca att acc ctt gtc tta aaa gaa       532
Gly Asn Thr Leu Gly Arg Gly Thr Thr Ile Thr Leu Val Leu Lys Glu
    155                 160                 165 gaa gca tct gat tac ctt gaa ttg gat aca att aaa aat ctc gtc aaa       580
Glu Ala Ser Asp Tyr Leu Glu Leu Asp Thr Ile Lys Asn Leu Val Lys
170                 175                 180                 185 aaa tat tca cag ttc ata aac ttt cct att tat gta tgg agc agc aag       628
Lys Tyr Ser Gln Phe Ile Asn Phe Pro Ile Tyr Val Trp Ser Ser Lys
                190                 195                 200 act gaa act gtt gag gag ccc atg gag gaa gaa gca gcc aaa gaa           676
Thr Glu Thr Val Glu Glu Pro Met Glu Glu Glu Ala Ala Lys Glu
            205                 210                 215 gag aaa gaa gaa tct gat gat gaa gct gca gta gag gaa gaa gaa           724
Glu Lys Glu Glu Ser Asp Asp Glu Ala Ala Val Glu Glu Glu Glu
        220                 225                 230 gaa aag aaa cca aag act aaa aaa gtt gaa aaa act gtc tgg gac tgg       772
Glu Lys Lys Pro Lys Thr Lys Lys Val Glu Lys Thr Val Trp Asp Trp
    235                 240                 245
```

```
gaa ctt atg aat gat atc aaa cca ata tgg cag aga cca tca aaa gaa    820
Glu Leu Met Asn Asp Ile Lys Pro Ile Trp Gln Arg Pro Ser Lys Glu
250             255                 260                 265 gta gaa gaa gat gaa tac aaa gct ttc tac aaa tca ttt tca aag gaa    868
Val Glu Glu Asp Glu Tyr Lys Ala Phe Tyr Lys Ser Phe Ser Lys Glu
                270                 275                 280 agt gat gac ccc atg gct tat att cac ttt act gct gaa ggg gaa gtt    916
Ser Asp Asp Pro Met Ala Tyr Ile His Phe Thr Ala Glu Gly Glu Val
            285                 290                 295 acc ttc aaa tca att tta ttt gta ccc aca tct gct cca cgt ggt ctg    964
Thr Phe Lys Ser Ile Leu Phe Val Pro Thr Ser Ala Pro Arg Gly Leu
        300                 305                 310 ttt gac gaa tat gga tct aaa aag agc gat tac att aag ctc tat gtg   1012
Phe Asp Glu Tyr Gly Ser Lys Lys Ser Asp Tyr Ile Lys Leu Tyr Val
    315                 320                 325 cgc cgt gta ttc atc aca gac gac ttc cat gat atg atg cct aaa tac   1060
Arg Arg Val Phe Ile Thr Asp Asp Phe His Asp Met Met Pro Lys Tyr
330                 335                 340                 345 ctc aat ttt gtc aag ggt gtg gtg gac tca gat gat ctc ccc ttg aat   1108
Leu Asn Phe Val Lys Gly Val Val Asp Ser Asp Asp Leu Pro Leu Asn
                350                 355                 360 gtt tcc cgc gag act ctt cag caa cat aaa ctg ctt aag gtg att agg   1156
Val Ser Arg Glu Thr Leu Gln Gln His Lys Leu Leu Lys Val Ile Arg
            365                 370                 375 aag aag ctt gtt cgt aaa acg ctg gac atg atc aag aag att gct gat   1204
Lys Lys Leu Val Arg Lys Thr Leu Asp Met Ile Lys Lys Ile Ala Asp
        380                 385                 390 gat aaa tac aat gat act ttt tgg aaa gaa ttt ggt acc aac atc aag   1252
Asp Lys Tyr Asn Asp Thr Phe Trp Lys Glu Phe Gly Thr Asn Ile Lys
    395                 400                 405 ctt ggt gtg att gaa gac cac tcg aat cga aca cgt ctt gct aaa ctt   1300
Leu Gly Val Ile Glu Asp His Ser Asn Arg Thr Arg Leu Ala Lys Leu
410                 415                 420                 425 ctt agg ttc cag tct tct cat cat cca act gac att act agc cta gac   1348
Leu Arg Phe Gln Ser Ser His His Pro Thr Asp Ile Thr Ser Leu Asp
                430                 435                 440 cag tat gtg gaa aga atg aag gaa aaa caa gac aaa atc tac ttc atg   1396
Gln Tyr Val Glu Arg Met Lys Glu Lys Gln Asp Lys Ile Tyr Phe Met
            445                 450                 455 gct ggg tcc agc aga aaa gag gct gaa tct tct cca ttt gtt gag cga   1444
Ala Gly Ser Ser Arg Lys Glu Ala Glu Ser Ser Pro Phe Val Glu Arg
        460                 465                 470 ctt ctg aaa aag ggc tat gaa gtt att tac ctc aca gaa cct gtg gat   1492
Leu Leu Lys Lys Gly Tyr Glu Val Ile Tyr Leu Thr Glu Pro Val Asp
    475                 480                 485 gaa tac tgt att cag gcc ctt ccc gaa ttt gat ggg aag agg ttc cag   1540
Glu Tyr Cys Ile Gln Ala Leu Pro Glu Phe Asp Gly Lys Arg Phe Gln
490                 495                 500                 505 aat gtt gcc aag gaa gga gtg aag ttc gat gaa agt gag aaa act aag   1588
Asn Val Ala Lys Glu Gly Val Lys Phe Asp Glu Ser Glu Lys Thr Lys
                510                 515                 520 gag agt cgt gaa gca gtt gag aaa gaa ttt gag cct ctg ctg aat tgg   1636
Glu Ser Arg Glu Ala Val Glu Lys Glu Phe Glu Pro Leu Leu Asn Trp
            525                 530                 535 atg aaa gat aaa gcc ctt aag gac aag att gaa aag gct gtg gtg tct   1684
Met Lys Asp Lys Ala Leu Lys Asp Lys Ile Glu Lys Ala Val Val Ser
        540                 545                 550 cag cgc ctg aca gaa tct ccg tgt gct ttg gtg gcc agc cag tac gga   1732
Gln Arg Leu Thr Glu Ser Pro Cys Ala Leu Val Ala Ser Gln Tyr Gly
    555                 560                 565
```

-continued

```
tgg tct ggc aac atg gag aga atc atg aaa gca caa gcg tac caa acg    1780
Trp Ser Gly Asn Met Glu Arg Ile Met Lys Ala Gln Ala Tyr Gln Thr
570                 575                 580                 585 ggc aag gac atc tct aca aat tac tat gcg agt cag aag aaa aca ttt    1828
Gly Lys Asp Ile Ser Thr Asn Tyr Tyr Ala Ser Gln Lys Lys Thr Phe
                590                 595                 600 gaa att aat ccc aga cac ccg ctg atc aga gac atg ctt cga cga att    1876
Glu Ile Asn Pro Arg His Pro Leu Ile Arg Asp Met Leu Arg Arg Ile
            605                 610                 615 aag gaa gat gaa gat gat aaa aca gtt ttg gat ctt gct gtg gtt ttg    1924
Lys Glu Asp Glu Asp Asp Lys Thr Val Leu Asp Leu Ala Val Val Leu
        620                 625                 630 ttt gaa aca gca acg ctt cgg tca ggg tat ctt tta cca gac act aaa    1972
Phe Glu Thr Ala Thr Leu Arg Ser Gly Tyr Leu Leu Pro Asp Thr Lys
    635                 640                 645 gca tat gga gat aga ata gaa aga atg ctt cgc ctc agt ttg aac att    2020
Ala Tyr Gly Asp Arg Ile Glu Arg Met Leu Arg Leu Ser Leu Asn Ile
650                 655                 660                 665 gac cct gat gca aag gtg gaa gaa gag ccc gaa gaa gaa cct gaa gag    2068
Asp Pro Asp Ala Lys Val Glu Glu Glu Pro Glu Glu Glu Pro Glu Glu
                670                 675                 680 aca gca gaa gac aca aca gaa gac aca gag caa gac gaa gat gaa gaa    2116
Thr Ala Glu Asp Thr Thr Glu Asp Thr Glu Gln Asp Glu Asp Glu Glu
            685                 690                 695 atg gat gtg gga aca gat gaa gaa gaa gaa aca gca aag gaa tct aca    2164
Met Asp Val Gly Thr Asp Glu Glu Glu Glu Thr Ala Lys Glu Ser Thr
        700                 705                 710 gct gaa                                                             2170
Ala Glu
    715
```

<210> SEQ ID NO 2
<211> LENGTH: 715
<212> TYPE: PRT
<213> ORGANISM: Artificial Sequence
<220> FEATURE:
<223> OTHER INFORMATION: Synthetic Construct

<400> SEQUENCE: 2

```
Met Met Lys Leu Ile Ile Asn Ser Leu Tyr Lys Asn Lys Glu Ile Phe
1               5                   10                  15

Leu Arg Glu Leu Ile Ser Asn Ala Ser Asp Ala Leu Asp Lys Ile Arg
                20                  25                  30

Leu Ile Ser Leu Thr Asp Glu Asn Ala Leu Ser Gly Asn Glu Glu Leu
            35                  40                  45

Thr Val Lys Ile Lys Cys Asp Lys Glu Lys Asn Leu Leu His Val Thr
        50                  55                  60

Asp Thr Gly Val Gly Met Thr Arg Glu Glu Leu Val Lys Asn Leu Gly
65              70                  75                  80

Thr Ile Ala Lys Ser Gly Thr Ser Glu Phe Leu Asn Lys Met Thr Glu
                85                  90                  95

Ala Gln Glu Asp Gly Gln Ser Thr Ser Glu Leu Ile Gly Gln Phe Gly
                100                 105                 110

Val Gly Phe Tyr Ser Ala Phe Leu Val Ala Asp Lys Val Ile Val Thr
            115                 120                 125

Ser Lys His Asn Asn Asp Thr Gln His Ile Trp Glu Ser Asp Ser Asn
        130                 135                 140

Glu Phe Ser Val Ile Ala Asp Pro Arg Gly Asn Thr Leu Gly Arg Gly
```

-continued

```
            145                 150                 155                 160
        Thr Thr Ile Thr Leu Val Leu Lys Glu Glu Ala Ser Asp Tyr Leu Glu
                        165                 170                 175
        Leu Asp Thr Ile Lys Asn Leu Val Lys Lys Tyr Ser Gln Phe Ile Asn
                        180                 185                 190
        Phe Pro Ile Tyr Val Trp Ser Ser Lys Thr Glu Thr Val Glu Glu Pro
                        195                 200                 205
        Met Glu Glu Glu Glu Ala Ala Lys Glu Lys Glu Glu Ser Asp Asp
            210                 215                 220
        Glu Ala Ala Val Glu Glu Glu Glu Lys Lys Pro Lys Thr Lys
        225                 230                 235                 240
        Lys Val Glu Lys Thr Val Trp Asp Trp Glu Leu Met Asn Asp Ile Lys
                        245                 250                 255
        Pro Ile Trp Gln Arg Pro Ser Lys Glu Val Glu Glu Asp Glu Tyr Lys
                        260                 265                 270
        Ala Phe Tyr Lys Ser Phe Ser Lys Glu Ser Asp Asp Pro Met Ala Tyr
                        275                 280                 285
        Ile His Phe Thr Ala Glu Gly Glu Val Thr Phe Lys Ser Ile Leu Phe
                        290                 295                 300
        Val Pro Thr Ser Ala Pro Arg Gly Leu Phe Asp Glu Tyr Gly Ser Lys
        305                 310                 315                 320
        Lys Ser Asp Tyr Ile Lys Leu Tyr Val Arg Arg Val Phe Ile Thr Asp
                        325                 330                 335
        Asp Phe His Asp Met Met Pro Lys Tyr Leu Asn Phe Val Lys Gly Val
                        340                 345                 350
        Val Asp Ser Asp Asp Leu Pro Leu Asn Val Ser Arg Glu Thr Leu Gln
                        355                 360                 365
        Gln His Lys Leu Leu Lys Val Ile Arg Lys Lys Leu Val Arg Lys Thr
                        370                 375                 380
        Leu Asp Met Ile Lys Lys Ile Ala Asp Asp Lys Tyr Asn Asp Thr Phe
        385                 390                 395                 400
        Trp Lys Glu Phe Gly Thr Asn Ile Lys Leu Gly Val Ile Glu Asp His
                        405                 410                 415
        Ser Asn Arg Thr Arg Leu Ala Lys Leu Leu Arg Phe Gln Ser Ser His
                        420                 425                 430
        His Pro Thr Asp Ile Thr Ser Leu Asp Gln Tyr Val Glu Arg Met Lys
                        435                 440                 445
        Glu Lys Gln Asp Lys Ile Tyr Phe Met Ala Gly Ser Ser Arg Lys Glu
                        450                 455                 460
        Ala Glu Ser Ser Pro Phe Val Glu Arg Leu Leu Lys Lys Gly Tyr Glu
        465                 470                 475                 480
        Val Ile Tyr Leu Thr Glu Pro Val Asp Glu Tyr Cys Ile Gln Ala Leu
                        485                 490                 495
        Pro Glu Phe Asp Gly Lys Arg Phe Gln Asn Val Ala Lys Glu Gly Val
                        500                 505                 510
        Lys Phe Asp Glu Ser Glu Lys Thr Lys Glu Ser Arg Glu Ala Val Glu
                        515                 520                 525
        Lys Glu Phe Glu Pro Leu Leu Asn Trp Met Lys Asp Lys Ala Leu Lys
                        530                 535                 540
        Asp Lys Ile Glu Lys Ala Val Val Ser Gln Arg Leu Thr Glu Ser Pro
        545                 550                 555                 560
        Cys Ala Leu Val Ala Ser Gln Tyr Gly Trp Ser Gly Asn Met Glu Arg
                        565                 570                 575
```

```
Ile Met Lys Ala Gln Ala Tyr Gln Thr Gly Lys Asp Ile Ser Thr Asn
            580                 585                 590

Tyr Tyr Ala Ser Gln Lys Lys Thr Phe Glu Ile Asn Pro Arg His Pro
        595                 600                 605

Leu Ile Arg Asp Met Leu Arg Arg Ile Lys Asp Glu Asp Lys
610                 615                 620

Thr Val Leu Asp Leu Ala Val Val Leu Phe Glu Thr Ala Thr Leu Arg
625                 630                 635                 640

Ser Gly Tyr Leu Leu Pro Asp Thr Lys Ala Tyr Gly Asp Arg Ile Glu
            645                 650                 655

Arg Met Leu Arg Leu Ser Leu Asn Ile Asp Pro Asp Ala Lys Val Glu
            660                 665                 670

Glu Glu Pro Glu Glu Pro Glu Thr Ala Glu Asp Thr Thr Glu
        675                 680                 685

Asp Thr Glu Gln Asp Glu Asp Glu Met Asp Val Gly Thr Asp Glu
            690                 695                 700

Glu Glu Glu Thr Ala Lys Glu Ser Thr Ala Glu
705                 710                 715
```

<210> SEQ ID NO 3
<211> LENGTH: 2170
<212> TYPE: DNA
<213> ORGANISM: Artificial Sequence
<220> FEATURE:
<223> OTHER INFORMATION: Synthetic Polynucleotide

<400> SEQUENCE: 3

```
aaccgtttct taagcttcgg agctctacta ctttgaatag tagttaagta acatattttt      60
atttctctaa aaggactctc ttgactaaag tttacgaaga ctacgaaatc tattctattc     120
cgattatagt gactgactac ttttacgaga aagaccttta ctccttgatt gtcagtttta     180
attcacacta ttcctcttct tggacgacgt acagtgtctg tggccacatc cttactggtc     240
tcttctcaac caattttggg aaccatggta tcggtttaga ccctgttcgc tcaaaaattt     300
gttttactga cttcgtgtcc ttctaccggt cagttgaaga cttaactaac cggtcaaacc     360
acagccaaag ataaggcgga aggaacatcg tctattccaa taacagtgaa gttttgtgtt     420
gttgctatgg gtcgtgtaga ccctcagact gaggttactt aaaagacatt aacgactggg     480
ttctcctttg tgagatcctg ccccttgctg ttaatgggaa cagaattttc ttcttcgtag     540
actaatggaa cttaacctat gttaattttt agagcagttt tttataagtg tcaagtattt     600
gaaaggataa atacatacct cgtcgttctg actttgacaa ctcctcgggt acctccttct     660
tcttcgtcgg tttcttctct ttcttcttag actactactt cgacgtcatc tccttcttct     720
tcttcttttc tttggtttct gattttttca acttttttga cagaccctga cccttgaata     780
cttactatag tttggttata ccgtctctgg tagttttctt catcttcttc tacttatgtt     840
tcgaaagatg tttagtaaaa gtttcctttc actactgggg taccgaatat aagtgaaatg     900
acgacttccc cttcaatgga agtttagtta aaataaacat gggtgtagac gaggtgcacc     960
agacaaactg cttataccta gatttttctc gctaatgtaa ttcgagatac acgcggcaca    1020
taagtagtgt ctgctgaagg tactatacta cggatttatg gagttaaaac agttcccaca    1080
ccacctgagt ctactagagg ggaacttaca aagggcgctc tgagaagtcg ttgtatttga    1140
cgaattccac taatccttct tcgaacaagc attttgcgac ctgtactagt tcttctaacg    1200
actactattt atgttactat gaaaaacctt tcttaaacca tggttgtagt tcgaaccaca    1260
```

-continued

```
ctaacttctg gtgagcttag cttgtgcaga acgatttgaa gaatccaagg tcagaagagt    1320
agtaggttga ctgtaatgat cggatctggt catacacctt tcttacttcc tttttgttct    1380
gttttagatg aagtaccgac ccaggtcgtc ttttctccga cttagaagag gtaaacaact    1440
cgctgaagac tttttcccga tacttcaata aatggagtgt cttggacacc tacttatgac    1500
ataagtccgg gaagggctta aactacccct ctccaaggtc ttacaacggt tccttcctca    1560
cttcaagcta ctttcactct tttgattcct ctcagcactt cgtcaactct ttcttaaact    1620
cggagacgac ttaacctact ttctatttcg ggaattcctg ttctaacttt tccgacacca    1680
cagagtcgcg gactgtctta gaggcacacg aaaccaccgg tcggtcatgc ctaccagacc    1740
gttgtacctc tcttagtact ttcgtgttcg catggtttgc ccgttcctgt agagatgttt    1800
aatgatacgc tcagtcttct tttgtaaact ttaattaggg tctgtgggcg actagtctct    1860
gtacgaagct gcttaattcc ttctacttct actattttgt caaaacctag aacgacacca    1920
aaacaaactt tgtcgttgcg aagccagtcc catagaaaat ggtctgtgat ttcgtatacc    1980
tctatcttat ctttcttacg aagcggagtc aaacttgtaa ctgggactac gtttccacct    2040
tcttctcggg cttcttcttg gacttctctg tcgtcttctg tgttgtcttc tgtgtctcgt    2100
tctgcttcta cttctttacc tacacccttg tctacttctt cttctttgtc gtttccttag    2160
atgtcgactt                                                          2170

<210> SEQ ID NO 4
<211> LENGTH: 690
<212> TYPE: DNA
<213> ORGANISM: Artificial Sequence
<220> FEATURE:
<223> OTHER INFORMATION: Synthetic Polymer
<220> FEATURE:
<221> NAME/KEY: CDS
<222> LOCATION: (7)..(690)

<400> SEQUENCE: 4 ggatcc gtg ccc agg gat tct ggt tct aag cct tcc ata tct aca gtc      48
       Val Pro Arg Asp Ser Gly Ser Lys Pro Ser Ile Ser Thr Val
       1               5                   10 cca gaa gta tca tct gtc ttc atc ttc ccc cca aag ccc aag gat gtg     96
Pro Glu Val Ser Ser Val Phe Ile Phe Pro Pro Lys Pro Lys Asp Val
15                  20                  25                  30 ctc acc att act ctg act cct aag gtc acg tgt gtt gtg gta gac atc    144
Leu Thr Ile Thr Leu Thr Pro Lys Val Thr Cys Val Val Val Asp Ile
                35                  40                  45 agc aag gat gat ccc gag gtc cag ttc agc tgg ttt gta gat gat gtg    192
Ser Lys Asp Asp Pro Glu Val Gln Phe Ser Trp Phe Val Asp Asp Val
            50                  55                  60 gag gtg cac aca gct cag aca aaa ccc cgg gag gag cag ttc aac agc    240
Glu Val His Thr Ala Gln Thr Lys Pro Arg Glu Glu Gln Phe Asn Ser
65                  70                  75 act ttc cgt tca gtc agt gaa ctt ccc atc atg cac cag gac tgg ctc    288
Thr Phe Arg Ser Val Ser Glu Leu Pro Ile Met His Gln Asp Trp Leu
                80                  85                  90 aat ggc aag gag ttc aaa tgc agg gtc aac agt gca gct ttc cct gcc    336
Asn Gly Lys Glu Phe Lys Cys Arg Val Asn Ser Ala Ala Phe Pro Ala
            95                  100                 110 ccc atc gag aaa acc atc tcc aaa acc aaa ggc aga ccg aag gct cca    384
Pro Ile Glu Lys Thr Ile Ser Lys Thr Lys Gly Arg Pro Lys Ala Pro
                115                 120                 125 cag gtg tac acc att cca cct ccc aag gag cag atg gcc aag gat aaa    432
```

```
             Gln Val Tyr Thr Ile Pro Pro Lys Glu Gln Met Ala Lys Asp Lys
                             130                 135                 140 gtc agt ctg acc tgc atg ata aca gac ttc ttc cct gaa gac att act       480
Val Ser Leu Thr Cys Met Ile Thr Asp Phe Phe Pro Glu Asp Ile Thr
            145                 150                 155 gtg gag tgg cag tgg aat ggg cag cca gcg gag aac tac aag aac act       528
Val Glu Trp Gln Trp Asn Gly Gln Pro Ala Glu Asn Tyr Lys Asn Thr
    160                 165                 170 cag ccc atc atg gac aca gat ggc tct tac ttc gtc tac agc aag ctc       576
Gln Pro Ile Met Asp Thr Asp Gly Ser Tyr Phe Val Tyr Ser Lys Leu
175                 180                 185                 190 aat gtg cag aag agc aac tgg gag gca gga aat act ttc acc tgc tct       624
Asn Val Gln Lys Ser Asn Trp Glu Ala Gly Asn Thr Phe Thr Cys Ser
                195                 200                 205 gtg tta cat gag ggc ctg cac aac cac cat act gag aag agc ctc tcc       672
Val Leu His Glu Gly Leu His Asn His His Thr Glu Lys Ser Leu Ser
            210                 215                 220 cac tct cct ggt aaa tga                                               690
His Ser Pro Gly Lys
            225

<210> SEQ ID NO 5
<211> LENGTH: 227
<212> TYPE: PRT
<213> ORGANISM: Artificial Sequence
<220> FEATURE:
<223> OTHER INFORMATION: Synthetic Construct

<400> SEQUENCE: 5

Val Pro Arg Asp Ser Gly Ser Lys Pro Ser Ile Ser Thr Val Pro Glu
1               5                   10                  15

Val Ser Ser Val Phe Ile Phe Pro Pro Lys Pro Lys Asp Val Leu Thr
                20                  25                  30

Ile Thr Leu Thr Pro Lys Val Thr Cys Val Val Val Asp Ile Ser Lys
            35                  40                  45

Asp Asp Pro Glu Val Gln Phe Ser Trp Phe Val Asp Asp Val Glu Val
        50                  55                  60

His Thr Ala Gln Thr Lys Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Lys Glu Gln Met Ala Lys Asp Lys Val Ser
130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His Thr Glu Lys Ser Leu Ser His Ser
    210                 215                 220
```

Pro Gly Lys
225

```
<210> SEQ ID NO 6
<211> LENGTH: 690
<212> TYPE: DNA
<213> ORGANISM: Artificial Sequence
<220> FEATURE:
<223> OTHER INFORMATION: Synthetic Polynuleotide

<400> SEQUENCE: 6
cctaggcacg ggtccctaag accaagattc ggaaggtata gatgtcaggg tcttcatagt    60
agacagaagt agaaggggg tttcgggttc ctacacgagt ggtaatgaga ctgaggattc   120
cagtgcacac aacaccatct gtagtcgttc ctactagggc tccaggtcaa gtcgaccaaa   180
catctactac acctccacgt gtgtcgagtc tgttttgggg ccctcctcgt caagttgtcg   240
tgaaaggcaa gtcagtcact gaagggtag tacgtggtcc tgaccgagtt accgttcctc   300
aagtttacgt cccagttgtc acgtcgaaag ggacgggggt agctcttttg gtagaggttt   360
tggtttccgt ctggcttccg aggtgtccac atgtggtaag gtggagggtt cctcgtctac   420
cggttcctat ttcagtcaga ctggacgtac tattgtctga agaagggact tctgtaatga   480
cacctcaccg tcaccttacc cgtcggtcgc ctcttgatgt tcttgtgagt cgggtagtac   540
ctgtgtctac cgagaatgaa gcagatgtcg ttcgagttac acgtcttctc gttgaccctc   600
cgtcctttat gaaagtggac gagacacaat gtactcccgg acgtgttggt ggtatgactc   660
ttctcggaga gggtgagagg accatttact                                     690

<210> SEQ ID NO 7
<211> LENGTH: 2900
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (26)..(2857)

<400> SEQUENCE: 7
ttggcaaaga attcgaagcc tcgag atg atg aaa ctt atc atc aat tca ttg      52
                             Met Met Lys Leu Ile Ile Asn Ser Leu
                               1               5 tat aaa aat aaa gag att ttc ctg aga gaa ctg att tca aat gct tct     100
Tyr Lys Asn Lys Glu Ile Phe Leu Arg Glu Leu Ile Ser Asn Ala Ser
 10                  15                  20                  25 gat gct tta gat aag ata agg cta ata tca ctg act gat gaa aat gct     148
Asp Ala Leu Asp Lys Ile Arg Leu Ile Ser Leu Thr Asp Glu Asn Ala
                 30                  35                  40 ctt tct gga aat gag gaa cta aca gtc aaa att aag tgt gat aag gag     196
Leu Ser Gly Asn Glu Glu Leu Thr Val Lys Ile Lys Cys Asp Lys Glu
             45                  50                  55 aag aac ctg ctg cat gtc aca gac acc ggt gta gga atg acc aga gaa     244
Lys Asn Leu Leu His Val Thr Asp Thr Gly Val Gly Met Thr Arg Glu
         60                  65                  70 gag ttg gtt aaa aac ctt ggt acc ata gcc aaa tct ggg aca agc gag     292
Glu Leu Val Lys Asn Leu Gly Thr Ile Ala Lys Ser Gly Thr Ser Glu
 75                  80                  85 ttt tta aac aaa atg act gaa gca cag gaa gat ggc cag tca act tct     340
Phe Leu Asn Lys Met Thr Glu Ala Gln Glu Asp Gly Gln Ser Thr Ser
 90                  95                 100                 105 gaa ttg att ggc cag ttt ggt gtc ggt ttc tat tcc gcc ttc ctt gta     388
```

-continued

| | | | | | | | | | | | | |
|---|---|---|---|---|---|---|---|---|---|---|---|---|
| Glu | Leu | Ile | Gly | Gln | Phe | Gly | Val | Gly | Phe | Tyr | Ser | Ala | Phe | Leu | Val |
| | | 110 | | | | | 115 | | | | | 120 | |

```
gca gat aag gtt att gtc act tca aaa cac aac aac gat acc cag cac      436
Ala Asp Lys Val Ile Val Thr Ser Lys His Asn Asn Asp Thr Gln His
            125                 130                 135 atc tgg gag tct gac tcc aat gaa ttt tct gta att gct gac cca aga      484
Ile Trp Glu Ser Asp Ser Asn Glu Phe Ser Val Ile Ala Asp Pro Arg
        140                 145                 150 gga aac act cta gga cgg gga acg aca att acc ctt gtc tta aaa gaa      532
Gly Asn Thr Leu Gly Arg Gly Thr Thr Ile Thr Leu Val Leu Lys Glu
    155                 160                 165 gaa gca tct gat tac ctt gaa ttg gat aca att aaa aat ctc gtc aaa      580
Glu Ala Ser Asp Tyr Leu Glu Leu Asp Thr Ile Lys Asn Leu Val Lys
170                 175                 180                 185 aaa tat tca cag ttc ata aac ttt cct att tat gta tgg agc agc aag      628
Lys Tyr Ser Gln Phe Ile Asn Phe Pro Ile Tyr Val Trp Ser Ser Lys
                190                 195                 200 act gaa act gtt gag gag ccc atg gag gaa gaa gaa gca gcc aaa gaa      676
Thr Glu Thr Val Glu Glu Pro Met Glu Glu Glu Glu Ala Ala Lys Glu
            205                 210                 215 gag aaa gaa gaa tct gat gat gaa gct gca gta gag gaa gaa gaa gaa      724
Glu Lys Glu Glu Ser Asp Asp Glu Ala Ala Val Glu Glu Glu Glu Glu
        220                 225                 230 gaa aag aaa cca aag act aaa aaa gtt gaa aaa act gtc tgg gac tgg      772
Glu Lys Lys Pro Lys Thr Lys Lys Val Glu Lys Thr Val Trp Asp Trp
    235                 240                 245 gaa ctt atg aat gat atc aaa cca ata tgg cag aga cca tca aaa gaa      820
Glu Leu Met Asn Asp Ile Lys Pro Ile Trp Gln Arg Pro Ser Lys Glu
250                 255                 260                 265 gta gaa gaa gat gaa tac aaa gct ttc tac aaa tca ttt tca aag gaa      868
Val Glu Glu Asp Glu Tyr Lys Ala Phe Tyr Lys Ser Phe Ser Lys Glu
                270                 275                 280 agt gat gac ccc atg gct tat att cac ttt act gct gaa ggg gaa gtt      916
Ser Asp Asp Pro Met Ala Tyr Ile His Phe Thr Ala Glu Gly Glu Val
            285                 290                 295 acc ttc aaa tca att tta ttt gta ccc aca tct gct cca cgt ggt ctg      964
Thr Phe Lys Ser Ile Leu Phe Val Pro Thr Ser Ala Pro Arg Gly Leu
        300                 305                 310 ttt gac gaa tat gga tct aaa aag agc gat tac att aag ctc tat gtg     1012
Phe Asp Glu Tyr Gly Ser Lys Lys Ser Asp Tyr Ile Lys Leu Tyr Val
    315                 320                 325 cgc cgt gta ttc atc aca gac gac ttc cat gat atg atg cct aaa tac     1060
Arg Arg Val Phe Ile Thr Asp Asp Phe His Asp Met Met Pro Lys Tyr
330                 335                 340                 345 ctc aat ttt gtc aag ggt gtg gtg gac tca gat gat ctc ccc ttg aat     1108
Leu Asn Phe Val Lys Gly Val Val Asp Ser Asp Asp Leu Pro Leu Asn
                350                 355                 360 gtt tcc cgc gag act ctt cag caa cat aaa ctg ctt aag gtg att agg     1156
Val Ser Arg Glu Thr Leu Gln Gln His Lys Leu Leu Lys Val Ile Arg
            365                 370                 375 aag aag ctt gtt cgt aaa acg ctg gac atg atc aag aag att gct gat     1204
Lys Lys Leu Val Arg Lys Thr Leu Asp Met Ile Lys Lys Ile Ala Asp
        380                 385                 390 gat aaa tac aat gat act ttt tgg aaa gaa ttt ggt acc aac atc aag     1252
Asp Lys Tyr Asn Asp Thr Phe Trp Lys Glu Phe Gly Thr Asn Ile Lys
    395                 400                 405 ctt ggt gtg att gaa gac cac tcg aat cga aca cgt ctt gct aaa ctt     1300
Leu Gly Val Ile Glu Asp His Ser Asn Arg Thr Arg Leu Ala Lys Leu
410                 415                 420                 425
```

```
ctt agg ttc cag tct tct cat cat cca act gac att act agc cta gac    1348
Leu Arg Phe Gln Ser Ser His His Pro Thr Asp Ile Thr Ser Leu Asp
                430                 435                 440 cag tat gtg gaa aga atg aag gaa aaa caa gac aaa atc tac ttc atg    1396
Gln Tyr Val Glu Arg Met Lys Glu Lys Gln Asp Lys Ile Tyr Phe Met
            445                 450                 455 gct ggg tcc agc aga aaa gag gct gaa tct tct cca ttt gtt gag cga    1444
Ala Gly Ser Ser Arg Lys Glu Ala Glu Ser Ser Pro Phe Val Glu Arg
        460                 465                 470 ctt ctg aaa aag ggc tat gaa gtt att tac ctc aca gaa cct gtg gat    1492
Leu Leu Lys Lys Gly Tyr Glu Val Ile Tyr Leu Thr Glu Pro Val Asp
    475                 480                 485 gaa tac tgt att cag gcc ctt ccc gaa ttt gat ggg aag agg ttc cag    1540
Glu Tyr Cys Ile Gln Ala Leu Pro Glu Phe Asp Gly Lys Arg Phe Gln
490                 495                 500                 505 aat gtt gcc aag gaa gga gtg aag ttc gat gaa agt gag aaa act aag    1588
Asn Val Ala Lys Glu Gly Val Lys Phe Asp Glu Ser Glu Lys Thr Lys
                510                 515                 520 gag agt cgt gaa gca gtt gag aaa gaa ttt gag cct ctg ctg aat tgg    1636
Glu Ser Arg Glu Ala Val Glu Lys Glu Phe Glu Pro Leu Leu Asn Trp
            525                 530                 535 atg aaa gat aaa gcc ctt aag gac aag att gaa aag gct gtg gtg tct    1684
Met Lys Asp Lys Ala Leu Lys Asp Lys Ile Glu Lys Ala Val Val Ser
        540                 545                 550 cag cgc ctg aca gaa tct ccg tgt gct ttg gtg gcc agc cag tac gga    1732
Gln Arg Leu Thr Glu Ser Pro Cys Ala Leu Val Ala Ser Gln Tyr Gly
    555                 560                 565 tgg tct ggc aac atg gag aga atc atg aaa gca caa gcg tac caa acg    1780
Trp Ser Gly Asn Met Glu Arg Ile Met Lys Ala Gln Ala Tyr Gln Thr
570                 575                 580                 585 ggc aag gac atc tct aca aat tac tat gcg agt cag aag aaa aca ttt    1828
Gly Lys Asp Ile Ser Thr Asn Tyr Tyr Ala Ser Gln Lys Lys Thr Phe
                590                 595                 600 gaa att aat ccc aga cac ccg ctg atc aga gac atg ctt cga cga att    1876
Glu Ile Asn Pro Arg His Pro Leu Ile Arg Asp Met Leu Arg Arg Ile
            605                 610                 615 aag gaa gat gaa gat gat aaa aca gtt ttg gat ctt gct gtg gtt ttg    1924
Lys Glu Asp Glu Asp Asp Lys Thr Val Leu Asp Leu Ala Val Val Leu
        620                 625                 630 ttt gaa aca gca acg ctt cgg tca ggg tat ctt tta cca gac act aaa    1972
Phe Glu Thr Ala Thr Leu Arg Ser Gly Tyr Leu Leu Pro Asp Thr Lys
    635                 640                 645 gca tat gga gat aga ata gaa aga atg ctt cgc ctc agt ttg aac att    2020
Ala Tyr Gly Asp Arg Ile Glu Arg Met Leu Arg Leu Ser Leu Asn Ile
650                 655                 660                 665 gac cct gat gca aag gtg gaa gaa gag ccc gaa gaa gaa cct gaa gag    2068
Asp Pro Asp Ala Lys Val Glu Glu Glu Pro Glu Glu Glu Pro Glu Glu
                670                 675                 680 aca gca gaa gac aca aca gaa gac aca gag caa gac gaa gat gaa gaa    2116
Thr Ala Glu Asp Thr Thr Glu Asp Thr Glu Gln Asp Glu Asp Glu Glu
            685                 690                 695 atg gat gtg gga aca gat gaa gaa gaa gaa aca gca aag gaa tct aca    2164
Met Asp Val Gly Thr Asp Glu Glu Glu Glu Thr Ala Lys Glu Ser Thr
        700                 705                 710 gct gaa gga tcc gtg ccc agg gat tct ggt tct aag cct tcc ata tct    2212
Ala Glu Gly Ser Val Pro Arg Asp Ser Gly Ser Lys Pro Ser Ile Ser
    715                 720                 725 aca gtc cca gaa gta tca tct gtc ttc atc ttc ccc cca aag ccc aag    2260
Thr Val Pro Glu Val Ser Ser Val Phe Ile Phe Pro Pro Lys Pro Lys
730                 735                 740                 745
```

```
gat gtg ctc acc att act ctg act cct aag gtc acg tgt gtt gtg gta      2308
Asp Val Leu Thr Ile Thr Leu Thr Pro Lys Val Thr Cys Val Val Val
                750                 755                 760 gac atc agc aag gat gat ccc gag gtc cag ttc agc tgg ttt gta gat      2356
Asp Ile Ser Lys Asp Asp Pro Glu Val Gln Phe Ser Trp Phe Val Asp
            765                 770                 775 gat gtg gag gtg cac aca gct cag aca aaa ccc cgg gag gag cag ttc      2404
Asp Val Glu Val His Thr Ala Gln Thr Lys Pro Arg Glu Glu Gln Phe
        780                 785                 790 aac agc act ttc cgt tca gtc agt gaa ctt ccc atc atg cac cag gac      2452
Asn Ser Thr Phe Arg Ser Val Ser Glu Leu Pro Ile Met His Gln Asp
    795                 800                 805 tgg ctc aat ggc aag gag ttc aaa tgc agg gtc aac agt gca gct ttc      2500
Trp Leu Asn Gly Lys Glu Phe Lys Cys Arg Val Asn Ser Ala Ala Phe
810                 815                 820                 825 cct gcc ccc atc gag aaa acc atc tcc aaa acc aaa ggc aga ccg aag      2548
Pro Ala Pro Ile Glu Lys Thr Ile Ser Lys Thr Lys Gly Arg Pro Lys
                830                 835                 840 gct cca cag gtg tac acc att cca cct ccc aag gag cag atg gcc aag      2596
Ala Pro Gln Val Tyr Thr Ile Pro Pro Pro Lys Glu Gln Met Ala Lys
            845                 850                 855 gat aaa gtc agt ctg acc tgc atg ata aca gac ttc ttc cct gaa gac      2644
Asp Lys Val Ser Leu Thr Cys Met Ile Thr Asp Phe Phe Pro Glu Asp
        860                 865                 870 att act gtg gag tgg cag tgg aat ggg cag cca gcg gag aac tac aag      2692
Ile Thr Val Glu Trp Gln Trp Asn Gly Gln Pro Ala Glu Asn Tyr Lys
    875                 880                 885 aac act cag ccc atc atg gac aca gat ggc tct tac ttc gtc tac agc      2740
Asn Thr Gln Pro Ile Met Asp Thr Asp Gly Ser Tyr Phe Val Tyr Ser
890                 895                 900                 905 aag ctc aat gtg cag aag agc aac tgg gag gca gga aat act ttc acc      2788
Lys Leu Asn Val Gln Lys Ser Asn Trp Glu Ala Gly Asn Thr Phe Thr
                910                 915                 920 tgc tct gtg tta cat gag ggc ctg cac aac cac cat act gag aag agc      2836
Cys Ser Val Leu His Glu Gly Leu His Asn His His Thr Glu Lys Ser
            925                 930                 935 ctc tcc cac tct cct ggt aaa tgactcgacc cagactagtc aaattaagcc         2887
Leu Ser His Ser Pro Gly Lys
            940 gaattctgca gat                                                        2900

<210> SEQ ID NO 8
<211> LENGTH: 944
<212> TYPE: PRT
<213> ORGANISM: Artificial Sequence
<220> FEATURE:
<223> OTHER INFORMATION: Synthetic Construct

<400> SEQUENCE: 8

Met Met Lys Leu Ile Ile Asn Ser Leu Tyr Lys Asn Lys Glu Ile Phe
1               5                   10                  15

Leu Arg Glu Leu Ile Ser Asn Ala Ser Asp Ala Leu Asp Lys Ile Arg
            20                  25                  30

Leu Ile Ser Leu Thr Asp Glu Asn Ala Leu Ser Gly Asn Glu Glu Leu
        35                  40                  45

Thr Val Lys Ile Lys Cys Asp Lys Glu Lys Asn Leu Leu His Val Thr
    50                  55                  60

Asp Thr Gly Val Gly Met Thr Arg Glu Glu Leu Val Lys Asn Leu Gly
65                  70                  75                  80
```

```
Thr Ile Ala Lys Ser Gly Thr Ser Glu Phe Leu Asn Lys Met Thr Glu
                85                  90                  95

Ala Gln Glu Asp Gly Gln Ser Thr Ser Glu Leu Ile Gly Gln Phe Gly
            100                 105                 110

Val Gly Phe Tyr Ser Ala Phe Leu Val Ala Asp Lys Val Ile Val Thr
            115                 120                 125

Ser Lys His Asn Asn Asp Thr Gln His Ile Trp Glu Ser Asp Ser Asn
        130                 135                 140

Glu Phe Ser Val Ile Ala Asp Pro Arg Gly Asn Thr Leu Gly Arg Gly
145                 150                 155                 160

Thr Thr Ile Thr Leu Val Leu Lys Glu Glu Ala Ser Asp Tyr Leu Glu
                165                 170                 175

Leu Asp Thr Ile Lys Asn Leu Val Lys Lys Tyr Ser Gln Phe Ile Asn
                180                 185                 190

Phe Pro Ile Tyr Val Trp Ser Ser Lys Thr Glu Thr Val Glu Glu Pro
            195                 200                 205

Met Glu Glu Glu Ala Ala Lys Glu Glu Lys Glu Glu Ser Asp Asp
        210                 215                 220

Glu Ala Val Glu Glu Glu Glu Glu Lys Lys Pro Lys Thr Lys
225                 230                 235                 240

Lys Val Glu Lys Thr Val Trp Asp Trp Glu Leu Met Asn Asp Ile Lys
                245                 250                 255

Pro Ile Trp Gln Arg Pro Ser Lys Glu Val Glu Glu Asp Glu Tyr Lys
            260                 265                 270

Ala Phe Tyr Lys Ser Phe Ser Lys Glu Ser Asp Asp Pro Met Ala Tyr
            275                 280                 285

Ile His Phe Thr Ala Glu Gly Glu Val Thr Lys Ser Ile Leu Phe
290                 295                 300

Val Pro Thr Ser Ala Pro Arg Gly Leu Phe Asp Glu Tyr Gly Ser Lys
305                 310                 315                 320

Lys Ser Asp Tyr Ile Lys Leu Tyr Val Arg Arg Val Phe Ile Thr Asp
                325                 330                 335

Asp Phe His Asp Met Met Pro Lys Tyr Leu Asn Phe Val Lys Gly Val
            340                 345                 350

Val Asp Ser Asp Asp Leu Pro Leu Asn Val Ser Arg Glu Thr Leu Gln
            355                 360                 365

Gln His Lys Leu Leu Lys Val Ile Arg Lys Lys Leu Val Arg Lys Thr
        370                 375                 380

Leu Asp Met Ile Lys Lys Ile Ala Asp Asp Lys Tyr Asn Asp Thr Phe
385                 390                 395                 400

Trp Lys Glu Phe Gly Thr Asn Ile Lys Leu Gly Val Ile Glu Asp His
            405                 410                 415

Ser Asn Arg Thr Arg Leu Ala Lys Leu Leu Arg Phe Gln Ser Ser His
            420                 425                 430

His Pro Thr Asp Ile Thr Ser Leu Asp Gln Tyr Val Glu Arg Met Lys
        435                 440                 445

Glu Lys Gln Asp Lys Ile Tyr Phe Met Ala Gly Ser Ser Arg Lys Glu
        450                 455                 460

Ala Glu Ser Ser Pro Phe Val Glu Arg Leu Leu Lys Lys Gly Tyr Glu
465                 470                 475                 480

Val Ile Tyr Leu Thr Glu Pro Val Asp Glu Tyr Cys Ile Gln Ala Leu
                485                 490                 495
```

```
Pro Glu Phe Asp Gly Lys Arg Phe Gln Asn Val Ala Lys Glu Gly Val
            500                 505                 510

Lys Phe Asp Glu Ser Glu Lys Thr Lys Glu Ser Arg Glu Ala Val Glu
        515                 520                 525

Lys Glu Phe Glu Pro Leu Leu Asn Trp Met Lys Asp Lys Ala Leu Lys
        530                 535                 540

Asp Lys Ile Glu Lys Ala Val Val Ser Gln Arg Leu Thr Glu Ser Pro
545                 550                 555                 560

Cys Ala Leu Val Ala Ser Gln Tyr Gly Trp Ser Gly Asn Met Glu Arg
                565                 570                 575

Ile Met Lys Ala Gln Ala Tyr Gln Thr Gly Lys Asp Ile Ser Thr Asn
            580                 585                 590

Tyr Tyr Ala Ser Gln Lys Lys Thr Phe Glu Ile Asn Pro Arg His Pro
        595                 600                 605

Leu Ile Arg Asp Met Leu Arg Arg Ile Lys Glu Asp Glu Asp Asp Lys
        610                 615                 620

Thr Val Leu Asp Leu Ala Val Val Leu Phe Glu Thr Ala Thr Leu Arg
625                 630                 635                 640

Ser Gly Tyr Leu Leu Pro Asp Thr Lys Ala Tyr Gly Asp Arg Ile Glu
                645                 650                 655

Arg Met Leu Arg Leu Ser Leu Asn Ile Asp Pro Asp Ala Lys Val Glu
            660                 665                 670

Glu Glu Pro Glu Glu Pro Glu Thr Ala Glu Asp Thr Thr Glu
        675                 680                 685

Asp Thr Glu Gln Asp Glu Asp Glu Glu Met Asp Val Gly Thr Asp Glu
        690                 695                 700

Glu Glu Glu Thr Ala Lys Glu Ser Thr Ala Glu Gly Ser Val Pro Arg
705                 710                 715                 720

Asp Ser Gly Ser Lys Pro Ser Ile Ser Thr Val Pro Glu Val Ser Ser
                725                 730                 735

Val Phe Ile Phe Pro Pro Lys Pro Lys Asp Val Leu Thr Ile Thr Leu
            740                 745                 750

Thr Pro Lys Val Thr Cys Val Val Asp Ile Ser Lys Asp Asp Pro
        755                 760                 765

Glu Val Gln Phe Ser Trp Phe Val Asp Asp Val Glu Val His Thr Ala
        770                 775                 780

Gln Thr Lys Pro Arg Glu Glu Gln Phe Asn Ser Thr Phe Arg Ser Val
785                 790                 795                 800

Ser Glu Leu Pro Ile Met His Gln Asp Trp Leu Asn Gly Lys Glu Phe
                805                 810                 815

Lys Cys Arg Val Asn Ser Ala Ala Phe Pro Ala Pro Ile Glu Lys Thr
            820                 825                 830

Ile Ser Lys Thr Lys Gly Arg Pro Lys Ala Pro Gln Val Tyr Thr Ile
        835                 840                 845

Pro Pro Pro Lys Glu Gln Met Ala Lys Asp Lys Val Ser Leu Thr Cys
        850                 855                 860

Met Ile Thr Asp Phe Phe Pro Glu Asp Ile Thr Val Glu Trp Gln Trp
865                 870                 875                 880

Asn Gly Gln Pro Ala Glu Asn Tyr Lys Asn Thr Gln Pro Ile Met Asp
                885                 890                 895

Thr Asp Gly Ser Tyr Phe Val Tyr Ser Lys Leu Asn Val Gln Lys Ser
            900                 905                 910

Asn Trp Glu Ala Gly Asn Thr Phe Thr Cys Ser Val Leu His Glu Gly
```

```
                915                 920                 925
Leu His Asn His His Thr Glu Lys Ser Leu Ser His Ser Pro Gly Lys
            930                 935                 940
```

<210> SEQ ID NO 9
<211> LENGTH: 2900
<212> TYPE: DNA
<213> ORGANISM: Artificial Sequence
<220> FEATURE:
<223> OTHER INFORMATION: Synthetic Polynucleotide

<400> SEQUENCE: 9

| | | | | | |
|---|---|---|---|---|---|
| aaccgtttct | taagcttcgg | agctctacta | ctttgaatag | tagttaagta | acatattttt | 60 |
| atttctctaa | aaggactctc | ttgactaaag | tttacgaaga | ctacgaaatc | tattctattc | 120 |
| cgattatagt | gactgactac | ttttacgaga | aagaccttta | ctccttgatt | gtcagtttta | 180 |
| attcacacta | ttcctcttct | tggacgacgt | acagtgtctg | tggccacatc | cttactggtc | 240 |
| tcttctcaac | caattttttgg | aaccatggta | tcggtttaga | ccctgttcgc | tcaaaaattt | 300 |
| gttttactga | cttcgtgtcc | ttctaccggt | cagttgaaga | cttaactaac | cggtcaaacc | 360 |
| acagccaaag | ataaggcgga | aggaacatcg | tctattccaa | taacagtgaa | gttttgtgtt | 420 |
| gttgctatgg | gtcgtgtaga | ccctcagact | gaggttactt | aaaagacatt | aacgactggg | 480 |
| ttctcctttg | tgagatcctg | ccccttgctg | ttaatgggaa | cagaatttc | ttcttcgtag | 540 |
| actaatggaa | cttaacctat | gttaattttt | agagcagttt | tttataagtg | tcaagtattt | 600 |
| gaaaggataa | atacatacct | cgtcgttctg | actttgacaa | ctcctcgggt | acctccttct | 660 |
| tcttcgtcgg | tttcttctct | ttcttcttag | actactactt | cgacgtcatc | tccttcttct | 720 |
| tcttcttttc | tttggtttct | gattttttca | acttttttga | cagaccctga | cccttgaata | 780 |
| cttactatag | tttggttata | ccgtctctgg | tagttttctt | catcttcttc | tacttatgtt | 840 |
| tcgaaagatg | tttagtaaaa | gtttcctttc | actactgggg | taccgaatat | aagtgaaatg | 900 |
| acgacttccc | cttcaatgga | agtttagtta | aaataaacat | gggtgtagac | gaggtgcacc | 960 |
| agacaaactg | cttataccta | gattttttctc | gctaatgtaa | ttcgagatac | acgcggcaca | 1020 |
| taagtagtgt | ctgctgaagg | tactatacta | cggatttatg | gagttaaaac | agttcccaca | 1080 |
| ccacctgagt | ctactagagg | ggaacttaca | aagggcgctc | tgagaagtcg | ttgtatttga | 1140 |
| cgaattccac | taatccttct | tcgaacaagc | attttgcgac | ctgtactagt | tcttctaacg | 1200 |
| actactattt | atgttactat | gaaaaacctt | tcttaaacca | tggttgtagt | tcgaaccaca | 1260 |
| ctaacttctg | gtgagcttag | cttgtgcaga | acgatttgaa | gaatccaagg | tcagaagagt | 1320 |
| agtaggttga | ctgtaatgat | cggatctggt | catacacctt | tcttacttcc | tttttgttct | 1380 |
| gttttagatg | aagtaccgac | ccaggtcgtc | ttttctccga | cttagaagag | gtaaacaact | 1440 |
| cgctgaagac | ttttttcccga | tacttcaata | aatggagtgt | cttggacacc | tacttatgac | 1500 |
| ataagtccgg | gaagggctta | aactacccctt | ctccaaggtc | ttacaacggt | tccttcctca | 1560 |
| cttcaagcta | ctttcactct | tttgattcct | ctcagcactt | cgtcaactct | ttcttaaact | 1620 |
| cggagacgac | ttaacctact | ttctatttcg | ggaattcctg | ttctaacttt | tccgacacca | 1680 |
| cagagtcgcg | gactgtctta | gaggcacacg | aaaccaccgg | tcggtcatgc | ctaccagacc | 1740 |
| gttgtacctc | tcttagtact | ttcgtgttcg | catggttttgc | ccgttcctgt | agagatgttt | 1800 |
| aatgatacgc | tcagtcttct | tttgtaaact | ttaattaggg | tctgtgggcg | actagtctct | 1860 |
| gtacgaagct | gcttaattcc | ttctacttct | actattttgt | caaaacctag | aacgacacca | 1920 |

-continued

```
aaacaaactt tgtcgttgcg aagccagtcc catagaaaat ggtctgtgat ttcgtatacc    1980
tctatcttat ctttcttacg aagcggagtc aaacttgtaa ctgggactac gtttccacct    2040
tcttctcggg cttcttcttg gacttctctg tcgtcttctg tgttgtcttc tgtgtctcgt    2100
tctgcttcta cttctttacc tacacccttg tctacttctt cttctttgtc gtttccttag    2160
atgtcgactt cctaggcacg ggtccctaag accaagattc ggaaggtata gatgtcaggg    2220
tcttcatagt agacagaagt agaaggggggg tttcgggttc ctacacgagt ggtaatgaga    2280
ctgaggattc cagtgcacac aacaccatct gtagtcgttc ctactagggc tccaggtcaa    2340
gtcgaccaaa catctactac acctccacgt gtgtcgagtc tgttttgggg ccctcctcgt    2400
caagttgtcg tgaaaggcaa gtcagtcact tgaagggtag tacgtggtcc tgaccgagtt    2460
accgttcctc aagtttacgt cccagttgtc acgtcgaaag ggacgggggt agctcttttg    2520
gtagaggttt tggtttccgt ctggcttccg aggtgtccac atgtggtaag gtggagggtt    2580
cctcgtctac cggttcctat ttcagtcaga ctggacgtac tattgtctga agaagggact    2640
tctgtaatga caccccaccg tcaccttacc cgtcggtcgc ctcttgatgt tcttgtgagt    2700
cgggtagtac ctgtgtctac cgagaatgaa gcagatgtcg ttcgagttac acgtcttctc    2760 gttgacccctc cgtcctttat gaaagtggac gagacacaat gtactcccgg acgtgttggt    2820
ggtatgactc ttctcggaga gggtgagagg accatttact gagctgggtc tgatcagttt    2880
aattcggctt aagacgtcta                                                 2900
```

<210> SEQ ID NO 10
<211> LENGTH: 168
<212> TYPE: PRT
<213> ORGANISM: Flavivirus Zika
<300> PUBLICATION INFORMATION:
<308> DATABASE ACCESSION NUMBER: NCBI / YP_009227197.1
<309> DATABASE ENTRY DATE: 2016-02-08
<313> RELEVANT RESIDUES IN SEQ ID NO: (1)..(168)

<400> SEQUENCE: 10

```
Ala Glu Ile Thr Arg Arg Gly Ser Ala Tyr Tyr Met Tyr Leu Asp Arg
1               5                   10                  15

Ser Asp Ala Gly Lys Ala Ile Ser Phe Ala Thr Thr Leu Gly Val Asn
            20                  25                  30

Lys Cys His Val Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Lys Val Glu Asn Trp
        115                 120                 125

Ile Phe Arg Asn Pro Gly Phe Ala Leu Val Ala Val Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser
                165
```

<210> SEQ ID NO 11
<211> LENGTH: 500
<212> TYPE: PRT
<213> ORGANISM: Flavivirus Zika
<300> PUBLICATION INFORMATION:
<308> DATABASE ACCESSION NUMBER: NCBI / YP_009227198.1
<309> DATABASE ENTRY DATE: 2016-02-08
<313> RELEVANT RESIDUES IN SEQ ID NO: (1)..(500)

<400> SEQUENCE: 11

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
```

355                 360                 365
Lys Met Met Leu Glu Leu Asp Pro Pro Phe Gly Asp Ser Tyr Ile Val
370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
                420                 425                 430

Val Phe Asn Ser Leu Gly Lys Gly Ile His Gln Ile Phe Gly Ala Ala
                435                 440                 445

Phe Lys Ser Leu Phe Gly Gly Met Ser Trp Phe Ser Gln Ile Leu Ile
                450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
                500

<210> SEQ ID NO 12
<211> LENGTH: 352
<212> TYPE: PRT
<213> ORGANISM: Flavivirus Zika
<300> PUBLICATION INFORMATION:
<308> DATABASE ACCESSION NUMBER: NCBI / YP_009227199.1
<309> DATABASE ENTRY DATE: 2016-02-08
<313> RELEVANT RESIDUES IN SEQ ID NO: (1)..(352)

<400> SEQUENCE: 12

Asp Val Gly Cys Ser Val Asp Phe Ser Lys Lys Glu Thr Arg Cys Gly
1               5                   10                  15

Thr Gly Val Phe Ile Tyr Asn Asp Val Glu Ala Trp Arg Asp Arg Tyr
                20                  25                  30

Lys Tyr His Pro Asp Ser Pro Arg Arg Leu Ala Ala Ala Val Lys Gln
                35                  40                  45

Ala Trp Glu Glu Gly Ile Cys Gly Ile Ser Ser Val Ser Arg Met Glu
50                  55                  60

Asn Ile Met Trp Lys Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Glu Leu Pro
                100                 105                 110

His Gly Trp Lys Ala Trp Gly Lys Ser Tyr Phe Val Arg Ala Ala Lys
                115                 120                 125

Thr Asn Asn Ser Phe Val Val Asp Gly Asp Thr Leu Lys Glu Cys Pro
130                 135                 140

Leu Glu His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Arg Glu
                180                 185                 190

Ala Ala His Ser Asp Leu Gly Tyr Trp Ile Glu Ser Glu Lys Asn Asp
                195                 200                 205

```
Thr Trp Arg Leu Lys Arg Ala His Leu Ile Glu Met Lys Thr Cys Glu
            210                 215                 220

Trp Pro Lys Ser His Thr Leu Trp Thr Asp Gly Val Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Val Lys Gly Pro Trp His Ser Glu Glu
            260                 265                 270

Leu Glu Ile Arg Phe Glu Glu Cys Pro Gly Thr Lys Val Tyr Val Glu
        275                 280                 285

Glu Thr Cys Gly Thr Arg Gly Pro Ser Leu Arg Ser Thr Thr Ala Ser
    290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

<210> SEQ ID NO 13
<211> LENGTH: 226
<212> TYPE: PRT
<213> ORGANISM: Flavivirus Zika
<300> PUBLICATION INFORMATION:
<308> DATABASE ACCESSION NUMBER: NCBI / YP_009227200.1
<309> DATABASE ENTRY DATE: 2016-02-08
<313> RELEVANT RESIDUES IN SEQ ID NO: (1)..(226)

<400> SEQUENCE: 13

Gly Ser Thr Asp His Met Asp His Phe Ser Leu Gly Val Leu Val Ile
1               5                   10                  15

Leu Leu Met Val Gln Glu Gly Leu Lys Lys Arg Met Thr Thr Lys Ile
            20                  25                  30

Ile Met Ser Thr Ser Met Ala Val Leu Val Val Met Ile Leu Gly Gly
        35                  40                  45

Phe Ser Met Ser Asp Leu Ala Lys Leu Val Ile Leu Met Gly Ala Thr
50                  55                  60

Phe Ala Glu Met Asn Thr Gly Gly Asp Val Ala His Leu Ala Leu Val
65                  70                  75                  80

Ala Ala Phe Lys Val Arg Pro Ala Leu Leu Val Ser Phe Ile Phe Arg
                85                  90                  95

Ala Asn Trp Thr Pro Arg Glu Ser Met Leu Leu Ala Leu Ala Ser Cys
            100                 105                 110

Leu Leu Gln Thr Ala Ile Ser Ala Leu Glu Gly Asp Leu Met Val Leu
        115                 120                 125

Ile Asn Gly Phe Ala Leu Ala Trp Leu Ala Ile Arg Ala Met Ala Val
130                 135                 140

Pro Arg Thr Asp Asn Ile Ala Leu Pro Ile Leu Ala Ala Leu Thr Pro
145                 150                 155                 160

Leu Ala Arg Gly Thr Leu Leu Val Ala Trp Arg Ala Gly Leu Ala Thr
                165                 170                 175

Cys Gly Gly Ile Met Leu Leu Ser Leu Lys Gly Lys Gly Ser Val Lys
            180                 185                 190

Lys Asn Leu Pro Phe Val Met Ala Leu Gly Leu Thr Ala Val Arg Val
        195                 200                 205
```

-continued

Val Asp Pro Ile Asn Val Val Gly Leu Leu Leu Thr Arg Ser Gly
    210                 215                 220

Lys Arg
225

<210> SEQ ID NO 14
<211> LENGTH: 130
<212> TYPE: PRT
<213> ORGANISM: Flavivirus Zika
<300> PUBLICATION INFORMATION:
<308> DATABASE ACCESSION NUMBER: NCBI / YP_009227201.1
<309> DATABASE ENTRY DATE: 2016-02-08
<313> RELEVANT RESIDUES IN SEQ ID NO: (1)..(130)

<400> SEQUENCE: 14

Ser Trp Pro Pro Ser Glu Val Leu Thr Ala Val Gly Leu Ile Cys Ala
1               5                   10                  15

Leu Ala Gly Gly Phe Ala Lys Ala Asp Ile Glu Met Ala Gly Pro Met
            20                  25                  30

Ala Ala Val Gly Leu Leu Ile Val Ser Tyr Val Val Ser Gly Lys Ser
        35                  40                  45

Val Asp Met Tyr Ile Glu Arg Ala Gly Asp Ile Thr Trp Glu Lys Asp
    50                  55                  60

Ala Glu Val Thr Gly Asn Ser Pro Arg Leu Asp Val Ala Leu Asp Glu
65                  70                  75                  80

Ser Gly Asp Phe Ser Leu Val Glu Glu Asp Gly Pro Pro Met Arg Glu
                85                  90                  95

Ile Ile Leu Lys Val Val Leu Met Ala Ile Cys Gly Met Asn Pro Ile
            100                 105                 110

Ala Ile Pro Phe Ala Ala Gly Ala Trp Tyr Val Tyr Val Lys Thr Gly
        115                 120                 125

Lys Arg
    130

<210> SEQ ID NO 15
<211> LENGTH: 617
<212> TYPE: PRT
<213> ORGANISM: Flavivirus Zika
<300> PUBLICATION INFORMATION:
<308> DATABASE ACCESSION NUMBER: NCBI / YP_009227202.1
<309> DATABASE ENTRY DATE: 2016-02-08
<313> RELEVANT RESIDUES IN SEQ ID NO: (1)..(617)

<400> SEQUENCE: 15

Ser Gly Ala Leu Trp Asp Val Pro Ala Pro Lys Glu Val Lys Lys Gly
1               5                   10                  15

Glu Thr Thr Asp Gly Val Tyr Arg Val Met Thr Arg Arg Leu Leu Gly
            20                  25                  30

Ser Thr Gln Val Gly Val Gly Val Met Gln Glu Gly Val Phe His Thr
        35                  40                  45

Met Trp His Val Thr Lys Gly Ala Ala Leu Arg Ser Gly Glu Gly Arg
    50                  55                  60

Leu Asp Pro Tyr Trp Gly Asp Val Lys Gln Asp Leu Val Ser Tyr Cys
65                  70                  75                  80

Gly Pro Trp Lys Leu Asp Ala Ala Trp Asp Gly Leu Ser Glu Val Gln
                85                  90                  95

Leu Leu Ala Val Pro Pro Gly Glu Arg Ala Arg Asn Ile Gln Thr Leu
            100                 105                 110

Pro Gly Ile Phe Lys Thr Lys Asp Gly Asp Ile Gly Ala Val Ala Leu

```
                    115                 120                 125
Asp Tyr Pro Ala Gly Thr Ser Gly Ser Pro Ile Leu Asp Lys Cys Gly
    130                 135                 140

Arg Val Ile Gly Leu Tyr Gly Asn Gly Val Val Ile Lys Asn Gly Ser
145                 150                 155                 160

Tyr Val Ser Ala Ile Thr Gln Gly Lys Arg Glu Glu Thr Pro Val
                    165                 170                 175

Glu Cys Phe Glu Pro Ser Met Leu Lys Lys Gln Leu Thr Val Leu
                180                 185                 190

Asp Leu His Pro Gly Ala Gly Lys Thr Arg Arg Val Leu Pro Glu Ile
            195                 200                 205

Val Arg Glu Ala Ile Lys Lys Arg Leu Arg Thr Val Ile Leu Ala Pro
    210                 215                 220

Thr Arg Val Val Ala Ala Glu Met Glu Glu Ala Leu Arg Gly Leu Pro
225                 230                 235                 240

Val Arg Tyr Met Thr Thr Ala Val Asn Val Thr His Ser Gly Thr Glu
                    245                 250                 255

Ile Val Asp Leu Met Cys His Ala Thr Phe Thr Ser Arg Leu Leu Gln
                260                 265                 270

Pro Ile Arg Val Pro Asn Tyr Asn Leu Asn Ile Met Asp Glu Ala His
            275                 280                 285

Phe Thr Asp Pro Ser Ser Ile Ala Ala Arg Gly Tyr Ile Ser Thr Arg
    290                 295                 300

Val Glu Met Gly Glu Ala Ala Ala Ile Phe Met Thr Ala Thr Pro Pro
305                 310                 315                 320

Gly Thr Arg Asp Ala Phe Pro Asp Ser Asn Ser Pro Ile Met Asp Thr
                    325                 330                 335

Glu Val Glu Val Pro Glu Arg Ala Trp Ser Ser Gly Phe Asp Trp Val
                340                 345                 350

Thr Asp His Ser Gly Lys Thr Val Trp Phe Val Pro Ser Val Arg Asn
            355                 360                 365

Gly Asn Glu Ile Ala Ala Cys Leu Thr Lys Ala Gly Lys Arg Val Ile
    370                 375                 380

Gln Leu Ser Arg Lys Thr Phe Glu Thr Glu Phe Gln Lys Thr Lys Asn
385                 390                 395                 400

Gln Glu Trp Asp Phe Val Ile Thr Thr Asp Ile Ser Glu Met Gly Ala
                    405                 410                 415

Asn Phe Lys Ala Asp Arg Val Ile Asp Ser Arg Arg Cys Leu Lys Pro
                420                 425                 430

Val Ile Leu Asp Gly Glu Arg Val Ile Leu Ala Gly Pro Met Pro Val
            435                 440                 445

Thr His Ala Ser Ala Ala Gln Arg Arg Gly Arg Ile Gly Arg Asn Pro
    450                 455                 460

Asn Lys Pro Gly Asp Glu Tyr Met Tyr Gly Gly Cys Ala Glu Thr
465                 470                 475                 480

Asp Glu Gly His Ala His Trp Leu Glu Ala Arg Met Leu Leu Asp Asn
                    485                 490                 495

Ile Tyr Leu Gln Asp Gly Leu Ile Ala Ser Leu Tyr Arg Pro Glu Ala
                500                 505                 510

Asp Lys Val Ala Ala Ile Glu Gly Glu Phe Lys Leu Arg Thr Glu Gln
            515                 520                 525

Arg Lys Thr Phe Val Glu Leu Met Lys Arg Gly Asp Leu Pro Val Trp
    530                 535                 540
```

```
Leu Ala Tyr Gln Val Ala Ser Ala Gly Ile Thr Tyr Thr Asp Arg Arg
545                 550                 555                 560

Trp Cys Phe Asp Gly Thr Thr Asn Asn Thr Ile Met Glu Asp Ser Val
                565                 570                 575

Pro Ala Glu Val Trp Thr Lys Tyr Gly Glu Lys Arg Val Leu Lys Pro
            580                 585                 590

Arg Trp Met Asp Ala Arg Val Cys Ser Asp His Ala Ala Leu Lys Ser
        595                 600                 605

Phe Lys Glu Phe Ala Ala Gly Lys Arg
    610                 615

<210> SEQ ID NO 16
<211> LENGTH: 127
<212> TYPE: PRT
<213> ORGANISM: Flavivirus Zika
<300> PUBLICATION INFORMATION:
<308> DATABASE ACCESSION NUMBER: NCBI / YP_009227203.1
<309> DATABASE ENTRY DATE: 2016-02-08
<313> RELEVANT RESIDUES IN SEQ ID NO: (1)..(127)

<400> SEQUENCE: 16

Gly Ala Ala Leu Gly Val Met Glu Ala Leu Gly Thr Leu Pro Gly His
1               5                   10                  15

Met Thr Glu Arg Phe Gln Glu Ala Ile Asp Asn Leu Ala Val Leu Met
            20                  25                  30

Arg Ala Glu Thr Gly Ser Arg Pro Tyr Lys Ala Ala Ala Ala Gln Leu
        35                  40                  45

Pro Glu Thr Leu Glu Thr Ile Met Leu Leu Gly Leu Leu Gly Thr Val
    50                  55                  60

Ser Leu Gly Ile Phe Phe Val Leu Met Arg Asn Lys Gly Ile Gly Lys
65                  70                  75                  80

Met Gly Phe Gly Met Val Thr Leu Gly Ala Ser Ala Trp Leu Met Trp
                85                  90                  95

Leu Ser Glu Ile Glu Pro Ala Arg Ile Ala Cys Val Leu Ile Val Val
            100                 105                 110

Phe Leu Leu Leu Val Val Leu Ile Pro Glu Pro Glu Lys Gln Arg
        115                 120                 125

<210> SEQ ID NO 17
<211> LENGTH: 251
<212> TYPE: PRT
<213> ORGANISM: Flavivirus Zika
<300> PUBLICATION INFORMATION:
<308> DATABASE ACCESSION NUMBER: NCBI / YP_009227204.1
<309> DATABASE ENTRY DATE: 2016-02-08
<313> RELEVANT RESIDUES IN SEQ ID NO: (1)..(251)

<400> SEQUENCE: 17

Asn Glu Leu Gly Trp Leu Glu Arg Thr Lys Asn Asp Ile Ala His Leu
1               5                   10                  15

Met Gly Arg Arg Glu Glu Gly Ala Thr Met Gly Phe Ser Met Asp Ile
            20                  25                  30

Asp Leu Arg Pro Ala Ser Ala Trp Ala Ile Tyr Ala Ala Leu Thr Thr
        35                  40                  45

Leu Ile Thr Pro Ala Val Gln His Ala Val Thr Thr Ser Tyr Asn Asn
    50                  55                  60

Tyr Ser Leu Met Ala Met Ala Thr Gln Ala Gly Val Leu Phe Gly Met
65                  70                  75                  80
```

```
Gly Lys Gly Met Pro Phe Met His Gly Asp Leu Gly Val Pro Leu Leu
             85                  90                  95

Met Met Gly Cys Tyr Ser Gln Leu Thr Pro Leu Thr Leu Ile Val Ala
        100                 105                 110

Ile Ile Leu Leu Val Ala His Tyr Met Tyr Leu Ile Pro Gly Leu Gln
        115                 120                 125

Ala Ala Ala Arg Ala Ala Gln Lys Arg Thr Ala Ala Gly Ile Met
    130                 135                 140

Lys Asn Pro Val Val Asp Gly Ile Val Val Thr Asp Ile Asp Thr Met
145                 150                 155                 160

Thr Ile Asp Pro Gln Val Glu Lys Lys Met Gly Gln Val Leu Leu Ile
                165                 170                 175

Ala Val Ala Ile Ser Ser Ala Val Leu Leu Arg Thr Ala Trp Gly Trp
            180                 185                 190

Gly Glu Ala Gly Ala Leu Ile Thr Ala Ala Thr Ser Thr Leu Trp Glu
        195                 200                 205

Gly Ser Pro Asn Lys Tyr Trp Asn Ser Ser Thr Ala Thr Ser Leu Cys
    210                 215                 220

Asn Ile Phe Arg Gly Ser Tyr Leu Ala Gly Ala Ser Leu Ile Tyr Thr
225                 230                 235                 240

Val Thr Arg Asn Ala Gly Leu Val Lys Arg Arg
                245                 250

<210> SEQ ID NO 18
<211> LENGTH: 1818
<212> TYPE: DNA
<213> ORGANISM: Artificial Sequence
<220> FEATURE:
<223> OTHER INFORMATION: Synthetic Polymer
<220> FEATURE:
<221> NAME/KEY: CDS
<222> LOCATION: (1)..(1818)

<400> SEQUENCE: 18 atg gca aac gat aaa ggt agc aat tgg gat tcg ggc ttg gga tgc tca      48
Met Ala Asn Asp Lys Gly Ser Asn Trp Asp Ser Gly Leu Gly Cys Ser
1               5                   10                  15 tat ctg ctg act gag gca gaa tgt gaa agt gac aaa gag aat gag gaa      96
Tyr Leu Leu Thr Glu Ala Glu Cys Glu Ser Asp Lys Glu Asn Glu Glu
            20                  25                  30 ccc ggg gca ggt gta gaa ctg tct gtg gaa tct gat cgg tat gat agc     144
Pro Gly Ala Gly Val Glu Leu Ser Val Glu Ser Asp Arg Tyr Asp Ser
        35                  40                  45 cag gat gag gat ttt gtt gac aat gca tca gtc ttt cag gga aat cac     192
Gln Asp Glu Asp Phe Val Asp Asn Ala Ser Val Phe Gln Gly Asn His
    50                  55                  60 ctg gag gtc ttc cag gca tta gag aaa aag gcg ggt gag gag cag att     240
Leu Glu Val Phe Gln Ala Leu Glu Lys Lys Ala Gly Glu Glu Gln Ile
65                  70                  75                  80 tta aat ttg aaa aga aaa gta ttg ggg agt tcg caa aac agc agc ggt     288
Leu Asn Leu Lys Arg Lys Val Leu Gly Ser Ser Gln Asn Ser Ser Gly
                85                  90                  95 tcc gaa gca tct gaa act cca gtt aaa aga cgg aaa tca gga gca aag     336
Ser Glu Ala Ser Glu Thr Pro Val Lys Arg Arg Lys Ser Gly Ala Lys
            100                 105                 110 cga aga tta ttt gct gaa aat gaa gct aac cgt gtt ctt acg ccc ctc     384
Arg Arg Leu Phe Ala Glu Asn Glu Ala Asn Arg Val Leu Thr Pro Leu
        115                 120                 125 cag gta cag ggg gag ggg gag ggg agg caa gaa ctt aat gag gag cag     432
```

```
Gln Val Gln Gly Glu Gly Glu Gly Arg Gln Glu Leu Asn Glu Glu Gln
         130                 135                 140 gca att agt cat cta cat ctg cag ctt gtt aaa tct aaa aat gct aca      480
Ala Ile Ser His Leu His Leu Gln Leu Val Lys Ser Lys Asn Ala Thr
145                 150                 155                 160 gtt ttt aag ctg ggg ctc ttt aaa tct ttg ttc ctt tgt agc ttc cat      528
Val Phe Lys Leu Gly Leu Phe Lys Ser Leu Phe Leu Cys Ser Phe His
                165                 170                 175 gat att acg agg ttg ttt aag aat gat aag acc act aat cag caa tgg      576
Asp Ile Thr Arg Leu Phe Lys Asn Asp Lys Thr Thr Asn Gln Gln Trp
            180                 185                 190 gtg ctg gct gtg ttt ggc ctt gca gag gtg ttt ttt gag gcg agt ttc      624
Val Leu Ala Val Phe Gly Leu Ala Glu Val Phe Phe Glu Ala Ser Phe
        195                 200                 205 gaa ctc cta aag aag cag tgt agt ttt ctg cag atg caa aaa aga tct      672
Glu Leu Leu Lys Lys Gln Cys Ser Phe Leu Gln Met Gln Lys Arg Ser
    210                 215                 220 cat gaa gga gga act tgt gca gtt tac tta atc tgc ttt aac aca gct      720
His Glu Gly Gly Thr Cys Ala Val Tyr Leu Ile Cys Phe Asn Thr Ala
225                 230                 235                 240 aaa agc aga gaa aca gtc cgg aat ctg atg gca aac atg cta aat gta      768
Lys Ser Arg Glu Thr Val Arg Asn Leu Met Ala Asn Met Leu Asn Val
                245                 250                 255 aga gaa gag tgt ttg atg ctg cag cca cct aaa att cga gga ctc agc      816
Arg Glu Glu Cys Leu Met Leu Gln Pro Pro Lys Ile Arg Gly Leu Ser
            260                 265                 270 gca gct cta ttc tgg ttt aaa agt agt ttg tca ccc gct aca ctt aaa      864
Ala Ala Leu Phe Trp Phe Lys Ser Ser Leu Ser Pro Ala Thr Leu Lys
        275                 280                 285 cat ggt gct tta cct gag tgg ata cgg gcg caa act act ctg aac gag      912
His Gly Ala Leu Pro Glu Trp Ile Arg Ala Gln Thr Thr Leu Asn Glu
    290                 295                 300 agc ttg cag acc gag aaa ttc gac ttc gga act atg gtg caa tgg gcc      960
Ser Leu Gln Thr Glu Lys Phe Asp Phe Gly Thr Met Val Gln Trp Ala
305                 310                 315                 320 tat gat cac aaa tat gct gag gag tct aaa ata gcc tat gaa tat gct     1008
Tyr Asp His Lys Tyr Ala Glu Glu Ser Lys Ile Ala Tyr Glu Tyr Ala
                325                 330                 335 ttg gct gca gga tct gat agc aat gca cgg gct ttt tta gca act aac     1056
Leu Ala Ala Gly Ser Asp Ser Asn Ala Arg Ala Phe Leu Ala Thr Asn
            340                 345                 350 agc caa gct aag cat gtg aag gac tgt gca act atg gta aga cac tat     1104
Ser Gln Ala Lys His Val Lys Asp Cys Ala Thr Met Val Arg His Tyr
        355                 360                 365 cta aga gct gaa aca caa gca tta agc atg cct gca tat att aaa gct     1152
Leu Arg Ala Glu Thr Gln Ala Leu Ser Met Pro Ala Tyr Ile Lys Ala
    370                 375                 380 agg tgc aag ctg gca act ggg gaa gga agc tgg aag tct atc cta act     1200
Arg Cys Lys Leu Ala Thr Gly Glu Gly Ser Trp Lys Ser Ile Leu Thr
385                 390                 395                 400 ttt ttt aac tat cag aat att gaa tta att acc ttt att aat gct tta     1248
Phe Phe Asn Tyr Gln Asn Ile Glu Leu Ile Thr Phe Ile Asn Ala Leu
                405                 410                 415 aag ctc tgg cta aaa gga att cca aaa aaa aac tgt tta gca ttt att     1296
Lys Leu Trp Leu Lys Gly Ile Pro Lys Lys Asn Cys Leu Ala Phe Ile
            420                 425                 430 ggc cct cca aac aca ggc aag tct atg ctc tgc aac tca tta att cat     1344
Gly Pro Pro Asn Thr Gly Lys Ser Met Leu Cys Asn Ser Leu Ile His
        435                 440                 445
```

```
ttt ttg ggt ggt agt gtt tta tct ttt gcc aac cat aaa agt cac ttt      1392
Phe Leu Gly Gly Ser Val Leu Ser Phe Ala Asn His Lys Ser His Phe
    450                 455                 460 tgg ctt gct tcc cta gca gat act aga gct gct tta gta gat gat gct      1440
Trp Leu Ala Ser Leu Ala Asp Thr Arg Ala Ala Leu Val Asp Asp Ala
465                 470                 475                 480 act cat gct tgc tgg agg tac ttt gac aca tac ctc aga aat gca ttg      1488
Thr His Ala Cys Trp Arg Tyr Phe Asp Thr Tyr Leu Arg Asn Ala Leu
                485                 490                 495 gat ggc tac cct gtc agt att gat aga aaa cac aaa gca gcg gtt caa      1536
Asp Gly Tyr Pro Val Ser Ile Asp Arg Lys His Lys Ala Ala Val Gln
            500                 505                 510 att aaa gct cca ccc ctc ctg gta acc agt aat att gat gtg cag gca      1584
Ile Lys Ala Pro Pro Leu Leu Val Thr Ser Asn Ile Asp Val Gln Ala
        515                 520                 525 gag gac aga tat ttg tac ttg cat agt cgg gtg caa acc ttt cgc ttt      1632
Glu Asp Arg Tyr Leu Tyr Leu His Ser Arg Val Gln Thr Phe Arg Phe
    530                 535                 540 gag cag cca tgc aca gat gaa tcg ggt gag caa cct ttt aat att act      1680
Glu Gln Pro Cys Thr Asp Glu Ser Gly Glu Gln Pro Phe Asn Ile Thr
545                 550                 555                 560 gat gca gat tgg aaa tct ttt ttt gta agg tta tgg ggg cgt tta gac      1728
Asp Ala Asp Trp Lys Ser Phe Phe Val Arg Leu Trp Gly Arg Leu Asp
                565                 570                 575 ctg att gac gag gag gag gat agt gaa gag gat gga gac agc atg cga      1776
Leu Ile Asp Glu Glu Glu Asp Ser Glu Glu Asp Gly Asp Ser Met Arg
            580                 585                 590 acg ttt aca tgc agc gca aga aac aca aat gca gtt gat tga              1818
Thr Phe Thr Cys Ser Ala Arg Asn Thr Asn Ala Val Asp
        595                 600                 605

<210> SEQ ID NO 19
<211> LENGTH: 605
<212> TYPE: PRT
<213> ORGANISM: Artificial Sequence
<220> FEATURE:
<223> OTHER INFORMATION: Synthetic Construct

<400> SEQUENCE: 19

Met Ala Asn Asp Lys Gly Ser Asn Trp Asp Ser Gly Leu Gly Cys Ser
1               5                   10                  15

Tyr Leu Leu Thr Glu Ala Glu Cys Glu Ser Asp Lys Glu Asn Glu Glu
            20                  25                  30

Pro Gly Ala Gly Val Glu Leu Ser Val Glu Ser Asp Arg Tyr Asp Ser
        35                  40                  45

Gln Asp Glu Asp Phe Val Asp Asn Ala Ser Val Phe Gln Gly Asn His
    50                  55                  60

Leu Glu Val Phe Gln Ala Leu Glu Lys Lys Ala Gly Glu Glu Gln Ile
65                  70                  75                  80

Leu Asn Leu Lys Arg Lys Val Leu Gly Ser Ser Gln Asn Ser Ser Gly
                85                  90                  95

Ser Glu Ala Ser Glu Thr Pro Val Lys Arg Arg Lys Ser Gly Ala Lys
            100                 105                 110

Arg Arg Leu Phe Ala Glu Asn Glu Ala Asn Arg Val Leu Thr Pro Leu
        115                 120                 125

Gln Val Gln Gly Glu Gly Glu Gly Arg Gln Glu Leu Asn Glu Glu Gln
    130                 135                 140

Ala Ile Ser His Leu His Leu Gln Leu Val Lys Ser Lys Asn Ala Thr
145                 150                 155                 160
```

```
Val Phe Lys Leu Gly Leu Phe Lys Ser Leu Phe Leu Cys Ser Phe His
                165                 170                 175

Asp Ile Thr Arg Leu Phe Lys Asn Asp Lys Thr Thr Asn Gln Gln Trp
                180                 185                 190

Val Leu Ala Val Phe Gly Leu Ala Glu Val Phe Glu Ala Ser Phe
                195                 200                 205

Glu Leu Leu Lys Lys Gln Cys Ser Phe Leu Gln Met Gln Lys Arg Ser
                210                 215                 220

His Glu Gly Gly Thr Cys Ala Val Tyr Leu Ile Cys Phe Asn Thr Ala
225                 230                 235                 240

Lys Ser Arg Glu Thr Val Arg Asn Leu Met Ala Asn Met Leu Asn Val
                245                 250                 255

Arg Glu Glu Cys Leu Met Leu Gln Pro Pro Lys Ile Arg Gly Leu Ser
                260                 265                 270

Ala Ala Leu Phe Trp Phe Lys Ser Ser Leu Ser Pro Ala Thr Leu Lys
                275                 280                 285

His Gly Ala Leu Pro Glu Trp Ile Arg Ala Gln Thr Thr Leu Asn Glu
                290                 295                 300

Ser Leu Gln Thr Glu Lys Phe Asp Phe Gly Thr Met Val Gln Trp Ala
305                 310                 315                 320

Tyr Asp His Lys Tyr Ala Glu Glu Ser Lys Ile Ala Tyr Glu Tyr Ala
                325                 330                 335

Leu Ala Ala Gly Ser Asp Ser Asn Ala Arg Ala Phe Leu Ala Thr Asn
                340                 345                 350

Ser Gln Ala Lys His Val Lys Asp Cys Ala Thr Met Val Arg His Tyr
                355                 360                 365

Leu Arg Ala Glu Thr Gln Ala Leu Ser Met Pro Ala Tyr Ile Lys Ala
                370                 375                 380

Arg Cys Lys Leu Ala Thr Gly Glu Gly Ser Trp Lys Ser Ile Leu Thr
385                 390                 395                 400

Phe Phe Asn Tyr Gln Asn Ile Glu Leu Ile Thr Phe Ile Asn Ala Leu
                405                 410                 415

Lys Leu Trp Leu Lys Gly Ile Pro Lys Lys Asn Cys Leu Ala Phe Ile
                420                 425                 430

Gly Pro Pro Asn Thr Gly Lys Ser Met Leu Cys Asn Ser Leu Ile His
                435                 440                 445

Phe Leu Gly Gly Ser Val Leu Ser Phe Ala Asn His Lys Ser His Phe
450                 455                 460

Trp Leu Ala Ser Leu Ala Asp Thr Arg Ala Ala Leu Val Asp Asp Ala
465                 470                 475                 480

Thr His Ala Cys Trp Arg Tyr Phe Asp Thr Tyr Leu Arg Asn Ala Leu
                485                 490                 495

Asp Gly Tyr Pro Val Ser Ile Asp Arg Lys His Lys Ala Ala Val Gln
                500                 505                 510

Ile Lys Ala Pro Pro Leu Leu Val Thr Ser Asn Ile Asp Val Gln Ala
                515                 520                 525

Glu Asp Arg Tyr Leu Tyr Leu His Ser Arg Val Gln Thr Phe Arg Phe
                530                 535                 540

Glu Gln Pro Cys Thr Asp Glu Ser Gly Glu Gln Pro Phe Asn Ile Thr
545                 550                 555                 560

Asp Ala Asp Trp Lys Ser Phe Phe Val Arg Leu Trp Gly Arg Leu Asp
                565                 570                 575
```

```
Leu Ile Asp Glu Glu Asp Ser Glu Glu Asp Gly Asp Ser Met Arg
            580                 585                 590

Thr Phe Thr Cys Ser Ala Arg Asn Thr Asn Ala Val Asp
        595                 600                 605

<210> SEQ ID NO 20
<211> LENGTH: 1818
<212> TYPE: DNA
<213> ORGANISM: Artificial Sequence
<220> FEATURE:
<223> OTHER INFORMATION: Synthetic Polynucleotide

<400> SEQUENCE: 20
taccgtttgc tatttccatc gttaaccota agcccgaacc ctacgagtat agacgactga      60
ctccgtctta cactttcact gtttctctta ctccttgggc cccgtccaca tcttgacaga     120
caccttagac tagccatact atcggtccta ctcctaaaac aactgttacg tagtcagaaa     180 gtcccttag tggacctcca gaaggtccgt aatctctttt tccgcccact cctcgtctaa      240
aatttaaact tttcttttca taaccoctca agcgttttgt cgtcgccaag gcttcgtaga     300
ctttgaggtc aattttctgc ctttagtcct cgtttcgctt ctaataaacg acttttactt     360
cgattggcac aagaatgcgg ggaggtccat gtccccctcc ccctccctc cgttcttgaa      420 ttactcctcg tccgttaatc agtagatgta gacgtcgaac aatttagatt tttacgatgt     480
caaaaattcg accccgagaa atttagaaac aaggaaacat cgaaggtact ataatgctcc     540
aacaaattct tactattctg gtgattagtc gttacccacg accgacacaa accggaacgt     600
ctccacaaaa aactccgctc aaagcttgag gatttcttcg tcacatcaaa agacgtctac     660
gttttttcta gagtacttcc tccttgaaca cgtcaaatga attagacgaa attgtgtcga     720
ttttcgtctc tttgtcaggc cttagactac cgtttgtacg atttacattc tcttctcaca     780
aactacgacg tcggtggatt ttaagctcct gagtcgcgtc gagataagac caaattttca     840
tcaaacagtg ggcgatgtga atttgtacca cgaaatggac tcacctatgc ccgcgtttga     900
tgagacttgc tctcgaacgt ctggctcttt aagctgaagc cttgatacca cgttacccgg     960
atactagtgt ttatacgact cctcagattt tatcggatac ttatacgaaa ccgacgtcct    1020
agactatcgt tacgtgcccg aaaaaatcgt tgattgtcgg ttcgattcgt acacttcctg    1080
acacgttgat accattctgt gatagattct cgactttgtg ttcgtaattc gtacggacgt    1140
atataatttc gatccacgtt cgaccgttga ccccttcctt cgaccttcag ataggattga    1200
aaaaaattga tagtcttata acttaattaa tggaaataat tacgaaattt cgagaccgat    1260
tttccttaag gtttttttt gacaaatcgt aaataaccgg gaggtttgtg tccgttcaga    1320
tacgagacgt tgagtaatta agtaaaaaac ccaccatcac aaaatagaaa acggttggta    1380
ttttcagtga aaaccgaacg aagggatcgt ctatgatctc gacgaaatca tctactacga    1440
tgagtacgaa cgacctccat gaaactgtgt atggagtctt tacgtaacct accgatggga    1500
cagtcataac tatcttttgt gtttcgtcgc caagtttaat ttcgaggtgg ggaggaccat    1560
tggtcattat aactacacgt ccgtctcctg tctataaaca tgaacgtatc agcccacgtt    1620
tggaaagcga aactcgtcgg tacgtgtcta cttagcccac tcgttggaaa attataatga    1680
ctacgtctaa cctttagaaa aaaacattcc aatacccocg caaatctgga ctaactgctc    1740
ctcctcctat cacttctcct acctctgtcg tacgcttgca aatgtacgtc gcgttctttg    1800
tgtttacgtc aactaact                                                  1818
```

<210> SEQ ID NO 21
<211> LENGTH: 567
<212> TYPE: DNA
<213> ORGANISM: Artificial Sequence
<220> FEATURE:
<223> OTHER INFORMATION: Synthetic Polymer
<220> FEATURE:
<221> NAME/KEY: CDS
<222> LOCATION: (4)..(567)

<400> SEQUENCE: 21

```
agg atg gag aca gca tgc gaa cgt tta cat gca gcg caa gaa aca caa    48
    Met Glu Thr Ala Cys Glu Arg Leu His Ala Ala Gln Glu Thr Gln
    1               5                   10                  15 atg cag ttg att gag aaa agt agt gat aag ttg caa gat cat ata ctg    96
Met Gln Leu Ile Glu Lys Ser Ser Asp Lys Leu Gln Asp His Ile Leu
                20                  25                  30 tac tgg act gct gtt aga act gag aac aca ctg ctt tat gct gca agg   144
Tyr Trp Thr Ala Val Arg Thr Glu Asn Thr Leu Leu Tyr Ala Ala Arg
            35                  40                  45 aaa aaa ggg gtg act gtc cta gga cac tgc aga gta cca cac tct gta   192
Lys Lys Gly Val Thr Val Leu Gly His Cys Arg Val Pro His Ser Val
        50                  55                  60 gtt tgt caa gag aga gcc aag cag gcc att gaa atg cag ttg tct ttg   240
Val Cys Gln Glu Arg Ala Lys Gln Ala Ile Glu Met Gln Leu Ser Leu
65                  70                  75 cag gag tta agc aaa act gag ttt ggg gat gaa cca tgg tct ttg ctt   288
Gln Glu Leu Ser Lys Thr Glu Phe Gly Asp Glu Pro Trp Ser Leu Leu
80                  85                  90                  95 gac aca agc tgg gac cga tat atg tca gaa cct aaa cgg tgc ttt aag   336
Asp Thr Ser Trp Asp Arg Tyr Met Ser Glu Pro Lys Arg Cys Phe Lys
                100                 105                 110 aaa ggc gcc agg gtg gta gag gtg gag ttt gat gga aat gca agc aat   384
Lys Gly Ala Arg Val Val Glu Val Glu Phe Asp Gly Asn Ala Ser Asn
            115                 120                 125 aca aac tgg tac act gtc tac agc aat ttg tac atg cgc aca gag gac   432
Thr Asn Trp Tyr Thr Val Tyr Ser Asn Leu Tyr Met Arg Thr Glu Asp
        130                 135                 140 ggc tgg cag ctt gcg aag gct ggg ctg acg gaa ctg ggc tct act act   480
Gly Trp Gln Leu Ala Lys Ala Gly Leu Thr Glu Leu Gly Ser Thr Thr
145                 150                 155 gca cca tgg ccg gtg ctg gac gca ttt act att ctc gct ttg gtg acg   528
Ala Pro Trp Pro Val Leu Asp Ala Phe Thr Ile Leu Ala Leu Val Thr
160                 165                 170                 175 agg cag cca gat tta gta caa cag ggc att act ctg taa                567
Arg Gln Pro Asp Leu Val Gln Gln Gly Ile Thr Leu
                180                 185
```

<210> SEQ ID NO 22
<211> LENGTH: 187
<212> TYPE: PRT
<213> ORGANISM: Artificial Sequence
<220> FEATURE:
<223> OTHER INFORMATION: Synthetic Construct

<400> SEQUENCE: 22

```
Met Glu Thr Ala Cys Glu Arg Leu His Ala Ala Gln Glu Thr Gln Met
1               5                   10                  15

Gln Leu Ile Glu Lys Ser Ser Asp Lys Leu Gln Asp His Ile Leu Tyr
            20                  25                  30

Trp Thr Ala Val Arg Thr Glu Asn Thr Leu Leu Tyr Ala Ala Arg Lys
        35                  40                  45
```

```
Lys Gly Val Thr Val Leu Gly His Cys Arg Val Pro His Ser Val Val
    50                  55                  60
Cys Gln Glu Arg Ala Lys Gln Ala Ile Glu Met Gln Leu Ser Leu Gln
 65                  70                  75                  80
Glu Leu Ser Lys Thr Glu Phe Gly Asp Glu Pro Trp Ser Leu Leu Asp
                 85                  90                  95
Thr Ser Trp Asp Arg Tyr Met Ser Glu Pro Lys Arg Cys Phe Lys Lys
            100                 105                 110
Gly Ala Arg Val Val Glu Val Glu Phe Asp Gly Asn Ala Ser Asn Thr
        115                 120                 125
Asn Trp Tyr Thr Val Tyr Ser Asn Leu Tyr Met Arg Thr Glu Asp Gly
130                 135                 140
Trp Gln Leu Ala Lys Ala Gly Leu Thr Glu Leu Gly Ser Thr Thr Ala
145                 150                 155                 160
Pro Trp Pro Val Leu Asp Ala Phe Thr Ile Leu Ala Leu Val Thr Arg
                165                 170                 175
Gln Pro Asp Leu Val Gln Gln Gly Ile Thr Leu
            180                 185

<210> SEQ ID NO 23
<211> LENGTH: 567
<212> TYPE: DNA
<213> ORGANISM: Artificial Sequence
<220> FEATURE:
<223> OTHER INFORMATION: Synthetic Polynucleotide

<400> SEQUENCE: 23
tcctacctct gtcgtacgct tgcaaatgta cgtcgcgttc tttgtgttta cgtcaactaa      60
ctctttcat cactattcaa cgttctagta tatgacatga cctgacgaca atcttgactc     120
ttgtgtgacg aaatacgacg ttcctttttt ccccactgac aggatcctgt gacgtctcat     180
ggtgtgagac atcaaacagt tctctctcgg ttcgtccggt aactttacgt caacagaaac     240
gtcctcaatt cgttttgact caaacccta cttggtacca gaaacgaact gtgttcgacc     300
ctggctatat acagtcttgg atttgccacg aaattcttc gcggtcccca ccatctccac     360
ctcaaactac ctttacgttc gttatgtttg accatgtgac agatgtcgtt aaacatgtac     420
gcgtgtctcc tgccgaccgt cgaacgcttc cgacccgact gccttgaccc gagatgatga     480
cgtggtaccg gccacgacct gcgtaaatga taagagcgaa accactgctc cgtcggtcta     540
aatcatgttg tcccgtaatg agacatt                                         567

<210> SEQ ID NO 24
<211> LENGTH: 16105
<212> TYPE: DNA
<213> ORGANISM: Artificial Sequence
<220> FEATURE:
<223> OTHER INFORMATION: Synthetic Polynucleotide

<400> SEQUENCE: 24
tctagagagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca tagtaacgcc aatagggact ttccattgac gtcaatgggt ggagtattta     300
cggtaaactg cccacttggc agtacatcaa gtgtatcata tgccaagtac gccccctatt     360
```

```
gacgtcaatg acggtaaatg gcccgcctgg cattatgccc agtacatgac cttatgggac    420
tttcctactt ggcagtacat ctacgtatta gtcatcgcta ttaccatggt gatgcggttt    480
tggcagtaca tcaatgggcg tggatagcgg tttgactcac ggggatttcc aagtctccac    540
cccattgacg tcaatgggag tttgttttgg caccaaaatc aacgggactt tccaaaatgt    600
cgtaacaact ccgccccatt gacgcaaatg ggcggtaggc gtgtacggtg ggaggtctat    660
ataagcagag ctcgtttagt gaaccgtcag atcgcctgga gacgccatcc acgctgtttt    720
gacctccata agagacaccg gaccgatcca gcctccggt cgatcgaccg atcctgagaa    780
cttcagggtg agtttgggga cccttgattg ttctttcttt ttcgctattg taaaattcat    840
gttatatgga gggggcaaag ttttcagggt gttgtttaga atgggaagat gtcccttgta    900
tcaccatgga ccctcatgat aattttgttt ctttcacttt ctactctgtt gacaaccatt    960
gtctcctctt attttctttt catttctgt aacttttcg ttaaacttta gcttgcattt   1020
gtaacgaatt tttaaattca cttttgttta tttgtcagat gtaagtact ttctctaatc   1080 actttttttt caaggcaatc agggtatatt atattgtact tcagcacagt tttagagaac   1140
aattgttata attaaatgat aaggtagaat atttctgcat ataaattctg ctggcgtgg   1200 aaatattctt attggtagaa acaactacac cctggtcatc atcctgcctt tctctttatg   1260
gttacaatga tatacactgt ttgagatgag gataaaatac tctgagtcca aaccgggccc   1320
ctctgctaac catgttcatg ccttcttctc tttcctacag ctcctgggca acgtgctggt   1380
tgttgtgctg tctcatcatt ttggcaaaga attcgaagcc tcgagatgat gaaacttatc   1440
atcaattcat tgtataaaaa taagagatt ttcctgagag aactgatttc aaatgcttct   1500
gatgctttag ataagataag gctaatatca ctgactgatg aaaatgctct ttctggaaat   1560
gaggaactaa cagtcaaaat taagtgtgat aaggagaaga acctgctgca tgtcacagac   1620
accggtgtag aatgaccag agaagagttg gttaaaaacc ttggtaccat agccaaatct   1680
gggacaagcg agttttaaa caaaatgact gaagcacagg aagatggcca gtcaacttct   1740
gaattgattg gccagtttgg tgtcggtttc tattccgcct tccttgtagc agataaggtt   1800
attgtcactt caaaacacaa caacgatacc cagcacatct gggagtctga ctccaatgaa   1860
ttttctgtaa ttgctgaccc aagaggaaac actctaggac ggggaacgac aattacccctt   1920 gtcttaaaag aagaagcatc tgattacctt gaattggata caattaaaaa tctcgtcaaa   1980
aaatattcac agttcataaa cttttcctatt tatgtatgga gcagcaagac tgaaactgtt   2040
gaggagccca tggaggaaga agaagcagcc aaagaagaga aagaagaatc tgatgatgaa   2100
gctgcagtag aggaagaaga agaagaaaag aaaccaaaga ctaaaaaagt tgaaaaaact   2160
gtctgggact gggaacttat gaatgatatc aaaccaatat ggcagagacc atcaaaagaa   2220
gtagaagaag atgaatacaa agctttctac aaatcatttt caaggaaag tgatgacccc   2280 atggcttata ttcactttac tgctgaaggg gaagttacct tcaaatcaat tttatttgta   2340
cccacatctg ctccacgtgg tctgtttgac gaatatggat ctaaaagag cgattacatt   2400 aagctctatg tgcgccgtgt attcatcaca gacgacttcc atgatatgat gcctaaatac   2460
ctcaattttg tcaagggtgt ggtggactca atgatctcc ccttgaatgt tcccgcgag   2520 actcttcagc aacataaact gcttaaggtg attaggaaga agcttgttcg taaaacgctg   2580
gacatgatca agaagattgc tgatgataaa tacaatgata ctttttggaa agaatttggt   2640
accaacatca agcttggtgt gattgaagac cactcgaatc gaacacgtct tgctaaactt   2700
cttaggttcc agtcttctca tcatccaact gacattacta gcctagacca gtatgtggaa   2760
```

```
agaatgaagg aaaaacaaga caaaatctac ttcatggctg ggtccagcag aaaagaggct   2820
gaatcttctc catttgttga gcgacttctg aaaaagggct atgaagttat ttacctcaca   2880
gaacctgtgg atgaatactg tattcaggcc cttcccgaat tgatgggaa gaggttccag    2940 aatgttgcca aggaaggagt gaagttcgat gaaagtgaga aaactaagga gagtcgtgaa   3000
gcagttgaga aagaatttga gcctctgctg aattggatga agataaagc ccttaaggac    3060 aagattgaaa aggctgtggt gtctcagcgc ctgacagaat ctccgtgtgc tttggtggcc   3120
agccagtacg gatggtctgg caacatggag agaatcatga agcacaagc gtaccaaacg    3180 ggcaaggaca tctctacaaa ttactatgcg agtcagaaga aaacatttga aattaatccc    3240
agacacccgc tgatcagaga catgcttcga cgaattaagg aagatgaaga tgataaaaca   3300
gttttggatc ttgctgtggt tttgtttgaa acagcaacgc ttcggtcagg gtatctttta    3360
ccagacacta aagcatatgg agatagaata gaaagaatgc ttcgcctcag tttgaacatt    3420
gaccctgatg caaggtggag agaagagccc gaagaagaac ctgaagagac agcagaagac   3480
acaacagaag acacagagca gacgaagat gaagaaatgg atgtgggaac agatgaagaa    3540
gaagaaacag caaaggaatc tacagctgaa ggatcctgtg acaaaactca cacatgccca   3600
ccgtgcccag cacctgaact cctgggggga ccgtcagtct tcctcttccc cccaaaaccc    3660
aaggacaccc tcatgatctc ccggacccct gaggtcacat gcgtggtggt ggacgtgagc   3720
cacgaagacc ctgaggtcaa gttcaactgg tacgtggacg gcgtggaggt gcataatgcc   3780
aagacaaagc cgcgggagga gcagtacaac agcacgtacc gtgtggtcag cgtcctcacc   3840
gtcctgcacc aggactggct gaatggcaag gagtacaagt gcaaggtctc caacaaagcc   3900
ctcccagccc ccatcgagaa aaccatctcc aaagccaaag gcagccccg agaaccacag    3960 gtgtacaccc tgcccccatc ccgggatgag ctgaccaaga accaggtcag cctgacctgc    4020
ctggtcaaag gcttctatcc cagcgacatc gccgtggagt gggagagcaa tgggcagccg    4080
gagaacaact acaagaccac gcctcccgtg ctggactccg acggctcctt cttcctctac    4140
agcaagctca ccgtggacaa gagcaggtgg cagcagggga acgtcttctc atgctccgtg    4200
atgcatgagg ctctgcacaa ccactacacg cagaagagcc tctccctgtc tccgggtaaa   4260
tgactcgacc cagactagtc aaattaagcc gaattctgca gatatccatc acactggcgg    4320
ccgctggaat tcactcctca ggtgcaggct gcctatcaga aggtggtggc tggtgtggcc   4380
aatgccctgg ctcacaaata ccactgagat cttttttccct ctgccaaaaa ttatggggac    4440
atcatgaagc cccttgagca tctgacttct ggctaataaa ggaaatttat tttcattgca    4500
atagtgtgtt ggaattttt gtgtctctca ctcggaagga catatgggag ggcaaatcat     4560
ttaaaacatc agaatgagta tttggttag agtttgcaa catatgccca tatgctggct      4620
gccatgaaca aaggttggct ataaagaggt catcagtata tgaaacagcc ccctgctgtc    4680
cattccttat tccatagaaa agccttgact tgaggttaga tttttttat attttgtttt     4740 gtgttatttt tttctttaac atccctaaaa ttttccttac atgttttact agccagattt    4800
ttcctcctct cctgactact cccagtcata gctgtccctc ttctcttatg gagatccctc   4860
gacggatccc tagagtcgag gcgatgcggc gcagcaccat ggcctgaaat aacctctgaa    4920
agaggaactt ggttaggtac cttggttttt aaaaccagcc tggagtagag cagatgggtt    4980
aaggtgagtg accccctcagc cctggacatt cttagatgag ccccctcagg agtagagaat    5040
aatgttgaga tgagttctgt tggctaaaat aatcaaggct agtctttata aaactgtctc    5100
```

```
ctcttctcct agcttcgatc cagagagaga cctgggcgga gctggtcgct gctcaggaac    5160
tccaggaaag gagaagctga ggttaccacg ctgcgaatgg gtttacggag atagctggct    5220
ttccggggtg agttctcgta aactccagag cagcgatagg ccgtaatatc ggggaaagca    5280
ctatagggac atgatgttcc acacgtcaca tgggtcgtcc tatccgagcc agtcgtgcca    5340
aaggggcggt cccgctgtgc acactggcgc tccagggagc tctgcactcc gcccgaaaag    5400
tgcgctcggc tctgccagga cgcggggcgc gtgactatgc gtgggctgga gcaaccgcct    5460
gctgggtgca aaccctttgc gcccggactc gtccaacgac tataagaggg caggctgtc     5520 ctctaagcgt caccacgact caacgtcct  gagtaccttc tcctcactta ctccgtagct    5580
ccagcttcac caccaagctc ctcgacgtcg atcgcgaagc tttggcccct ttggccttag    5640
cgtcgaccga tcctgagaac ttcagggtga gtttggggac ccttgattgt tctttctttt    5700
tcgctattgt aaaattcatg ttatatggag ggggcaaagt tttcagggtg ttgtttagaa    5760
tgggaagatg tcccttgtat caccatggac cctcatgata attttgtttc tttcactttc    5820
tactctgttg acaaccattg tctcctctta ttttctttto attttctgta acttttcgt     5880 taaactttag cttgcatttg taacgaattt ttaaattcac ttttgtttat ttgtcagatt    5940
gtaagtactt tctctaatca cttttttttc aaggcaatca gggtatatta tattgtactt    6000
cagcacagtt ttagagaaca attgttataa ttaaatgata aggtagaata tttctgcata    6060
taaattctgg ctggcgtgga aatattctta ttggtagaaa caactacacc ctggtcatca    6120
tcctgccttt ctctttatgg ttacaatgat atacactgtt tgagatgagg ataaaatact    6180
ctgagtccaa accgggcccc tctgctaacc atgttcatgc cttcttctct ttcctacagc    6240
tcctgggcaa cgtgctggtt gttgtgctgt ctcatcattt tggcaaagaa ttcctcgacc    6300
agtgcaggct gcctatcaga aagtggtggc tggtgtggct aatgccctgg cccacaagta    6360
tcactaagct cgctttcttg ctgtccaatt tctattaaag gttcctttgt tccctaagtc    6420
caactactaa actgggggat attatgaagg gccttgagca tctggattct gcctaataaa    6480
aaacatttat tttcattgca atgatgtatt taaattattt ctgaatattt tactaaaaag    6540
ggaatgtggg aggtcagtgc atttaaaaca taaagaaatg aagagctagt tcaaaccttg    6600
ggaaaataca ctatatctta aactccatga agaaggtga  ggctgcaaac agctaatgca    6660
cattggcaac agcccctgat gcctatgcct tattcatccc tcagaaaagg attcaagtag    6720
aggcttgatt tggaggttaa agttttgcta tgctgtattt tacattactt attgttttag    6780
ctgtcctcat gaatgtcttt tcactaccca tttgcttatc ctgcatctct cagccttgac    6840
tccactcagt tctcttgctt agagatacca cctttcccct gaagtgttcc ttccatgttt    6900
tacggcgaga tggtttctcc tcgcctggcc actcagcctt agttgtctct gttgtcttat    6960
agaggtctac ttgaagaagg aaaaacaggg ggcatggttt gactgtcctg tgagcccttc    7020
ttccctgcct cccccactca cagtgacccg gaatctgcag tgctagtctc ccggaactat    7080
cactctttca cagtctgctt tggaaggact gggcttagta tgaaaagtta ggactgagaa    7140
gaatttgaaa ggggggcttt tgtagcttga tattcactac tgtcttatta ccctatcata    7200
ggcccacccc aaatgaagt  cccattcttc tcaggatgt  ttaagattag cattcaggaa    7260
gagatcagag gtctgctggc tcccttatca tgtcccttat ggtgcttctg gctctgcagt    7320
tattagcata gtgttaccat caaccacctt aacttcattt ttcttattca atacctaggt    7380
aggtagatgc tagattctgg aaataaaata tgagtctcaa gtggtccttg tcctctctcc    7440
cagtcaaatt ctgaatctag ttggcaagat tctgaaatca aggcatataa tcagtaataa    7500
```

```
gtgatgatag aagggtatat agaagaattt tattatatga gagggtgaaa tcccagcaat   7560
ttgggaggct gaggcaggag aatcgcttga tcctgggagg cagaggttgc agtgagccaa   7620
gattgtgcca ctgcattcca gcccaggtga cagcatgaga ctccgtcaca aaaaaaaaag   7680
aaaaaaaagg gggggggggg cggtggagcc aagatgaccg aataggaaca gctccagtac   7740
tatagctccc atcgtgagtg acgcagaaga cgggtgattt ctgcatttcc aactgaggta   7800
ccaggttcat ctcacaggga agtgccaggc agtgggtgca ggacagtagg tgcagtgcac   7860
tgtgcatgag ccgaagcagg gacgaggcat cacctcaccc gggaagcaca aggggtcagg   7920
gaattccctt tcctagtcaa agaaaagggt gacagatggc acctggaaaa tcgggtcact   7980
cccgccctaa tactgcgctc ttccaacaag cttgtctttg gaaaatagat caatttccct   8040
tgggaagaag attttttagca cagcaagggg caggatgttc aactgtgaga aaacgaagaa   8100
ttagccaaaa aacttccagt aagcctgcaa aaaaaaaaaa aaaataaaag ctaagtttct   8160
ataaatgttc tgtaaatgta aaacagaagg taagtcaact gcacctaata aaaatcactt   8220
aatagcaatg tgctgtgtca gttgtttatt ggaaccacac ccggtacaca tcctgtccag   8280
catttgcagt gcgtgcattg aattattgtg ctggctagac ttcatggcgc ctggcaccga   8340
atcctgcctt ctcagcgaaa atgaataatt gctttgttgg caagaaacta agcatcaatg   8400
ggacgcgtgc aaagcaccgg cggcggtaga tgcggggtaa gtactgaatt ttaattcgac   8460
ctatcccggt aaagcgaaag cgacacgctt ttttttcaca catagcggga ccgaacacgt   8520
tataagtatc gattaggtct attttttgtct ctctgtcgga accagaactg gtaaaagttt   8580
ccattgcgtc tgggcttgtc tatcattgcg tctctatggt ttttggagga ttagacgggg   8640
ccaccagtaa tggtgcatag cggatgtctg taccgccatc ggtgcaccga tataggtttg   8700
gggctcccca agggactgct gggatgacag cttcatatta tattgaatgg gcgcataatc   8760
agcttaattg gtgaggacaa gctacaagtt gtaacctgat ctccacaaag tacgttgccg   8820
gtcggggtca aaccgtcttc ggtgctcgaa accgccttaa actacagaca ggtcccagcc   8880
aagtaggcgg atcaaaacct caaaaaggcg ggagccaatc aaaatgcagc attatatttt   8940
aagctcaccg aaaccggtaa gtaaagacta tgtattttt cccagtgaat aattgttgtt   9000
aactataaaa agcgtcatgg caaacgataa aggtagcaat tgggattcgg gcttgggatg   9060
ctcatatctg ctgactgagg cagaatgtga aagtgacaaa gagaatgagg aacccggggc   9120
aggtgtagaa ctgtctgtgg aatctgatcg gtatgatagc caggatgagg attttgttga   9180
caatgcatca gtctttcagg gaaatcacct ggaggtcttc caggcattag agaaaaaggc   9240
gggtgaggag cagattttaa atttgaaaag aaaagtattg gggagttcgc aaaacagcag   9300
cggttccgaa gcatctgaaa ctccagttaa agacgaaaa tcaggagcaa agcgaagatt   9360
atttgctgaa aatgaagcta accgtgttct tacgcccctc caggtacagg ggagggga    9420 ggggaggcaa gaacttaatg aggagcaggc aattagtcat ctacatctgc agcttgttaa   9480
atctaaaaat gctacagttt ttaagctggg gctctttaaa tctttgttcc tttgtagctt   9540
ccatgatatt acgaggttgt ttaagaatga taagaccact aatcagcaat gggtgctggc   9600
tgtgtttggc cttgcagagg tgttttttga ggcgagtttc gaactcctaa agaagcagtg   9660
tagttttctg cagatgcaaa aaagatctca tgaaggagga acttgtgcag tttacttaat   9720
ctgctttaac acagctaaaa gcagagaaac agtccggaat ctgatggcaa acatgctaaa   9780
tgtaagagaa gagtgtttga tgctgcagcc acctaaaatt cgaggactca gcgcagctct   9840
```

```
attctggttt aaaagtagtt tgtcacccgc tacacttaaa catggtgctt tacctgagtg   9900
gatacgggcg caaactactc tgaacgagag cttgcagacc gagaaattcg acttcggaac   9960
tatggtgcaa tgggcctatg atcacaaata tgctgaggag tctaaaatag cctatgaata  10020
tgctttggct gcaggatctg atagcaatgc acgggctttt ttagcaacta acagccaagc  10080
taagcatgtg aaggactgtg caactatggt aagacactat ctaagagctg aaacacaagc  10140
attaagcatg cctgcatata ttaaagctag gtgcaagctg gcaactgggg aaggaagctg  10200
gaagtctatc ctaactttt ttaactatca gaatattgaa ttaattaccT ttattaatgc   10260
tttaaagctc tggctaaaag gaattccaaa aaaaaactgt ttagcattta ttggccctcc  10320
aaacacaggc aagtctatgc tctgcaactc attaattcat tttttgggtg gtagtgtttt  10380
atcttttgcc aaccataaaa gtcacttttg gcttgcttcc ctagcagata ctagagctgc  10440
tttagtagat gatgctactc atgcttgctg gaggtacttt gacacatacc tcagaaatgc  10500
attggatggc taccctgtca gtattgatag aaaacacaaa gcagcggttc aaattaaagc  10560
tccacccctc ctggtaacca gtaatattga tgtgcaggca gaggacagat atttgtactt  10620
gcatagtcgg gtgcaaacct ttcgctttga gcagccatgc acagatgaat cgggtgagca  10680
accttttaat attactgatg cagattggaa atcttttttt gtaaggttat gggggcgttt  10740
agacctgatt gacgaggagg aggatagtga agaggatgga gacagcatgc gaacgtttac  10800
atgcagcgca agaaacacaa atgcagttga ttgagaaaag tagtgataag ttgcaagatc  10860
atatactgta ctggactgct gttagaactg agaacacact gctttatgct gcaaggaaaa  10920
aaggggtgac tgtcctagga cactgcagag taccacactc tgtagtttgt caagagagag  10980
ccaagcaggc cattgaaatg cagttgtctt tgcaggagtt aagcaaaact gagtttgggg  11040
atgaaccatg gtctttgctt gacacaagct gggaccgata tatgtcagaa cctaaacggt  11100
gctttaagaa aggcgccagg gtggtagagg tggagtttga tggaaatgca agcaatacaa  11160
actggtacac tgtctacagc aatttgtaca tgcgcacaga ggacggctgg cagcttgcga  11220
aggctgggct gacggaactg ggctctacta ctgcaccatg gccggtgctg gacgcattta  11280
ctattctcgc tttggtgacg aggcagccag atttagtaca acagggcatt actctgtaag  11340
agatcaggac agagtgtatg ctggtgtctc atccacctct tctgattta gagatcgccc    11400
agacggagtc tgggtcgcat ccgaaggacc tgaaggagac cctgcaggaa aagaagccga  11460
gccagcccag cctgtctctt ctttgctcgg ctccccgcc tgcggtccca tcagagcagg   11520
cctcggttgg gtacgggacg gtcctcgctc gcacccctac aattttcctg caggctcggg  11580
gggctctatt ctccgctctt cctccacccc gtgcagggca cggtaccggt ggacttggca  11640
tcaaggcagg aagaagagga gcagtcgccc gactccacag aggaagaacc agtgactctc  11700
ccaaggcgca ccaccaatga tggattccac ctgttaaagg caggagggtc atgctttgct  11760
ctaatttcag gaactgctaa ccaggtaaag tgctatcgct ttcgggtgaa aaagaaccat  11820
agacatcgct acgagaactg caccaccacc tggttcacag ttgctgacaa cggtgctgaa  11880
agacaaggac aagcacaaat actgatcacc tttggatcgc caagtcaaag gcaagacttt  11940
ctgaaacatg taccactacc tcctggaatg aacatttccg gctttacagc cagcttggac  12000
ttctgatcac tgccattgcc ttttcttcat ctgactggtg tactatgcca aatctatgcg  12060
accgcattat aaagccgaat tctgcagata tccatcacac tggcggccat atggccgcta  12120
tgcggtgtga aataccgcac agatgcgtaa ggagaaaata ccgcatcagg cgctcttccg  12180
cttcctcgct cactgactcg ctgcgctcgg tcgttcggct gcggcgagcg gtatcagctc  12240
```

```
actcaaaggc ggtaatacgg ttatccacag aatcagggga taacgcagga aagaacatgt   12300
gagcaaaagg ccagcaaaag gccaggaacc gtaaaaaggc cgcgttgctg gcgttttcc    12360 ataggctccg cccccctgac gagcatcaca aaaatcgacg ctcaagtcag aggtggcgaa   12420
acccgacagg actataaaga taccaggcgt ttccccctgg aagctccctc gtgcgctctc   12480
ctgttccgac cctgccgctt accggatacc tgtccgcctt ctcccttcg ggaagcgtgg    12540 cgctttctca tagctcacgc tgtaggtatc tcagttcggt gtaggtcgtt cgctccaagc   12600
tgggctgtgt gcacgaaccc cccgttcagc ccgaccgctg cgccttatcc ggtaactatc   12660
gtcttgagtc caacccggta agacacgact tatcgccact ggcagcagcc actggtaaca   12720
ggattagcag agcgaggtat gtaggcggtg ctacagagtt cttgaagtgg tggcctaact   12780
acggctacac tagaaggaca gtatttggta tctgcgctct gctgaagcca gttaccttcg   12840
gaaaaagagt tggtagctct tgatccggca acaaaccac cgctggtagc ggtggttttt    12900
ttgtttgcaa gcagcagatt acgcgcagaa aaaaaggatc tcaagaagat cctttgatct   12960
tttctacggg gtctgacgct cagtggaacg aaaactcacg ttaagggatt ttggtcatga   13020
gattatcaaa aaggatcttc acctagatcc ttttaaatta aaaatgaagt tttaaatcaa   13080
tctaaagtat atatgagtaa acttggtctg acagttacca atgcttaatc agtgaggcac   13140
ctatctcagc gatctgtcta tttcgttcat ccatagttgc ctgactcccc gtcgtgtaga   13200
taactacgat acgggagggc ttaccatctg gccccagtgc tgcaatgata ccgcgagacc   13260
cacgctcacc ggctccagat ttatcagcaa taaaccagcc agccggaagg gccgagcgca   13320
gaagtggtcc tgcaacttta tccgcctcca tccagtctat taattgttgc cgggaagcta   13380
gagtaagtag ttcgccagtt aatagtttgc gcaacgttgt tgccattgct gcaggcatcg   13440
tggtgtcacg ctcgtcgttt ggtatggctt cattcagctc cggttcccaa cgatcaaggc   13500
gagttacatg atcccccatg ttgtgcaaaa aagcggttag ctccttcggt cctccgatcg   13560
ttgtcagaag taagttggcc gcagtgttat cactcatggt tatggcagca ctgcataatt   13620
ctcttactgt catgccatcc gtaagatgct tttctgtgac tggtgagtac tcaaccaagt   13680
cattctgaga atagtgtatg cggcgaccga gttgctcttg cccggcgtca acacgggata   13740
ataccgcgcc acatagcaga actttaaaag tgctcatcat tggaaaacgt tcttcggggc   13800
gaaaactctc aaggatctta ccgctgttga tccagttc gatgtaaccc actcgtgcac     13860
ccaactgatc ttcagcatct tttactttca ccagcgtttc tgggtgagca aaaacaggaa   13920
ggcaaaatgc cgcaaaaaag gaataagggc gacacggaa atgttgaata ctcatactct    13980 tccttttca atattattga agcatttatc agggttattg tctcatgagc ggatacatat     14040
ttgaatgtat ttagaaaaat aaacaaatag gggttccgcg cacatttccc cgaaaagtgc   14100
cacctgacgt ctaagaaacc attattatca tgacattaac ctataaaaat aggcgtatca   14160
cgaggccctt tcgtcttcaa gaattctcat gtttgacagc ttatcatcga taagcttcac   14220
gctgccgcaa gcactcaggg cgcaagggct gctaaaggaa gcggaacacg tagaaagcca   14280
gtccgcagaa acggtgctga ccccggatga atgtcagcta ctgggctatc tggacaaggg   14340
aaaacgcaag cgcaaagaga aagcaggtag cttgcagtgg gcttacatgg cgatagctag   14400
actgggcggt tttatggaca gcaagcgaac cggaattgcc agctggggcg ccctctggta   14460
aggttgggaa gccctgcaaa gtaaactgga tggctttctt gccgccaagg atctgatggc   14520
gcaggggatc aagatcctgc ttcatccccg tggcccgttg ctcgcgtttg ctggcggtgt   14580
```

| | |
|---|---|
| ccccggaaga aatatatttg catgtcttta gttctatgat gacacaaacc ccgcccagcg | 14640 |
| tcttgtcatt ggcgaattcg aacacgcaga tgcagtcggg gcggcgcggt cccaggtcca | 14700 |
| cttcgcatat taaggtgacg cgtgtggcct cgaacaccga gcgaccctgc agcgacccgc | 14760 |
| ttaacagcgt caacagcgtg ccgcagatct gatcaagaga caggatgagg atcgtttcgc | 14820 |
| atgattgaac aagatggatt gcacgcaggt tctccggccg cttgggtgga gaggctattc | 14880 |
| ggctatgact gggcacaaca gacaatcggc tgctctgatg ccgccgtgtt ccggctgtca | 14940 |
| gcgcaggggc gcccggttct ttttgtcaag accgacctgt ccggtgccct gaatgaactg | 15000 |
| caggacgagg cagcgcggct atcgtggctg gccacgacgg gcgttccttg cgcagctgtg | 15060 |
| ctcgacgttg tcactgaagc gggaagggac tggctgctat tgggcgaagt gccggggcag | 15120 |
| gatctcctgt catctcacct tgctcctgcc gagaaagtat ccatcatggc tgatgcaatg | 15180 |
| cggcggctgc atacgcttga tccggctacc tgcccattcg accaccaagc gaaacatcgc | 15240 |
| atcgagcgag cacgtactcg gatggaagcc ggtcttgtcg atcaggatga tctggacgaa | 15300 |
| gagcatcagg ggctcgcgcc agccgaactg ttcgccaggc tcaaggcgcg catgcccgac | 15360 |
| ggcgaggatc tcgtcgtgac ccatggcgat gcctgcttgc cgaatatcat ggtggaaaat | 15420 |
| ggccgctttt ctggattcat cgactgtggc cggctgggtg tggcggaccg ctatcaggac | 15480 |
| atagcgttgg ctacccgtga tattgctgaa gagcttggcg gcgaatgggc tgaccgcttc | 15540 |
| ctcgtgcttt acggtatcgc cgctcccgat tcgcagcgca tcgccttcta tcgccttctt | 15600 |
| gacgagttct tctgagcggg actctggggt tcgaaatgac cgaccaagcg acgcccaacc | 15660 |
| tgccatcacg agatttcgat tccaccgccg ccttctatga aaggttgggc ttcggaatcg | 15720 |
| ttttccggga cgccggctgg atgatcctcc agcgcgggga tctcatgctg gagttcttcg | 15780 |
| cccaccccgg gagatggggg aggctaactg aaacacggaa ggagacaata ccggaaggaa | 15840 |
| cccgcgctat gaacggcaat aaaaagacag aataaaacgc acggtgttgg gtcgtttgtt | 15900 |
| cataaacgcg gggttcggtc ccagggctgg cactctgtcg ataccccacc gagaccccat | 15960 |
| tggggccaat acgcccgcgt ttcttccttt tccccacccc acccccaag ttcgggtgaa | 16020 |
| ggcccagggc tcgcagccaa cgtcggggcg gcaagccctg ccatagccac gggccccgtg | 16080 |
| ggttagggac ggcggatcgc ggccc | 16105 |

<210> SEQ ID NO 25
<211> LENGTH: 16105
<212> TYPE: DNA
<213> ORGANISM: Artificial Sequence
<220> FEATURE:
<223> OTHER INFORMATION: Synthetic Polynucleotide

<400> SEQUENCE: 25

| | |
|---|---|
| agatctctcg aaccgggtaa cgtatgcaac ataggtatag tattatacat gtaaatataa | 60 |
| ccgagtacag gttgtaatgg cggtacaact gtaactaata actgatcaat aattatcatt | 120 |
| agttaatgcc ccagtaatca agtatcgggt atatacctca aggcgcaatg tattgaatgc | 180 |
| catttaccgg gcggaccgac tggcgggttg ctggggcgg gtaactgcag ttattactgc | 240 |
| atacaagggt atcattgcgg ttatccctga aaggtaactg cagttaccca cctcataaat | 300 |
| gccatttgac gggtgaaccg tcatgtagtt cacatagtat acggttcatg cggggggataa | 360 |
| ctgcagttac tgccatttac cgggcggacc gtaatacggg tcatgtactg aatacctg | 420 |
| aaaggatgaa ccgtcatgta gatgcataat cagtagcgat aatggtacca ctacgccaaa | 480 |
| accgtcatgt agttacccgc acctatcgcc aaactgagtg cccctaaagg ttcagaggtg | 540 |

```
gggtaactgc agttaccctc aaacaaaacc gtggttttag ttgccctgaa aggttttaca        600
gcattgttga ggcggggtaa ctgcgtttac ccgccatccg cacatgccac cctccagata        660
tattcgtctc gagcaaatca cttggcagtc tagcggacct ctgcggtagg tgcgacaaaa        720
ctggaggtat cttctgtggc cctgctaggt cggaggcca gctagctggc taggactctt         780
gaagtcccac tcaaacccct gggaactaac aagaaagaaa aagcgataac atttaagta         840 caatataccct ccccgtttc aaaagtccca caacaaatct taccccttcta cagggaacat       900 agtggtacct gggagtacta ttaaaacaaa gaaagtgaaa gatgagacaa ctgttggtaa        960
cagaggagaa taaagaaaaa gtaaagacta ttgaaaaagc aattttgaaat cgaacgtaaa       1020 cattgcttaa aaatttaagt gaaaacaaat aaacagtcta acattcatga aagagattag        1080
tgaaaaaaaa gttccgttag tcccatataa ataacatga agtcgtgtca aaatctcttg         1140
ttaacaatat taatttacta ttccatctta taaagacgta tatttaagac cgaccgcacc        1200
tttataagaa taaccatctt tgttgatgtg ggaccagtag taggacggaa agagaaatac       1260
caatgttact atatgtgaca aactctactc ctattttatg agactcaggt ttggcccggg        1320
gagacgattg gtacaagtac ggaagaagag aaaggatgtc gaggacccgt tgcacgacca       1380
acaacacgac agagtagtaa aaccgtttct taagcttcgg agctctacta ctttgaatag       1440
tagttaagta acatattttt atttctctaa aaggactctc ttgactaaag tttacgaaga       1500
ctacgaaatc tattctattc cgattatagt gactgactac ttttacgaga aagaccttta      1560
ctccttgatt gtcagttta attcacacta ttcctcttct tggacgacgt acagtgtctg        1620
tggccacatc cttactggtc tcttctcaac caattttttgg aaccatggta tcggtttaga    1680
ccctgttcgc tcaaaaattt gttttactga cttcgtgtcc ttctaccggt cagttgaaga      1740
cttaactaac cggtcaaacc acagccaaag ataaggcgga aggaacatcg tctattccaa       1800
taacagtgaa gttttgtgtt gttgctatgg gtcgtgtaga ccctcagact gaggttactt      1860
aaaagacatt aacgactggg ttctccttttg tgagatcctg cccccttgctg ttaatgggaa   1920 cagaattttc ttcttcgtag actaatggaa cttaaacctat gttaattttt agagcagttt     1980
tttataagtg tcaagtattt gaaaggataa atacatacct cgtcgttctg actttgacaa     2040
ctcctcgggt acctccttct tcttcgtcgg tttcttctct ttcttcttag actactactt        2100
cgacgtcatc tccttcttct tcttctttc tttggtttct gatttttttca acttttttga        2160 cagaccctga cccttgaata cttactatag tttggttata ccgtctctgg tagttttctt     2220
catcttcttc tacttatgtt tcgaaagatg tttagtaaaa gtttcctttc actactgggg      2280
taccgaatat aagtgaaatg acgacttccc cttcaatgga agtttagtta aaataaacat     2340
gggtgtagac gaggtgcacc agacaaactg cttataccta gatttttctc gctaatgtaa       2400
ttcgagatac acgcggcaca taagtagtgt ctgctgaagg tactatacta cggatttatg      2460
gagttaaaac agttcccaca ccacctgagt ctactagagg ggaacttaca aagggcgctc      2520
tgagaagtcg ttgtatttga cgaattccac taatccttct tcgaacaagc attttgcgac     2580
ctgtactagt tcttctaacg actactattt atgttactat gaaaaacctt tcttaaacca      2640
tggttgtagt tcgaaccaca ctaacttctg gtgagcttag cttgtgcaga acgatttgaa      2700
gaatccaagg tcagaagagt agtaggttga ctgtaatgat cggatctggt catacacctt    2760
tcttacttcc ttttttgttct gttttagatg aagtaccgac ccaggtcgtc ttttctccga    2820
cttagaagag gtaaacaact cgctgaagac ttttttcccga tacttcaata aatggagtgt    2880
```

```
cttggacacc tacttatgac ataagtccgg aagggctta aactacccct ctccaaggtc    2940
ttacaacggt tccttcctca cttcaagcta cttcactct tttgattcct ctcagcactt    3000
cgtcaactct ttcttaaact cggagacgac ttaacctact ttctatttcg ggaattcctg    3060
ttctaacttt tccgacacca cagagtcgcg gactgtctta gaggcacacg aaaccaccgg    3120
tcggtcatgc ctaccagacc gttgtacctc tcttagtact ttcgtgttcg catggtttgc    3180
ccgttcctgt agagatgttt aatgatacgc tcagtcttct tttgtaaact ttaattaggg    3240
tctgtgggcg actagtctct gtacgaagct gcttaattcc ttctacttct actattttgt    3300
caaaacctag aacgacacca aaacaaactt tgtcgttgcg aagccagtcc catagaaaat    3360
ggtctgtgat ttcgtatacc tctatcttat ctttcttacg aagcggagtc aaacttgtaa    3420
ctgggactac gtttccacct tcttctcggg cttcttcttg gacttctctg tcgtcttctg    3480
tgttgtcttc tgtgtctcgt tctgcttcta cttctttacc tacacccttg tctacttctt    3540
cttctttgtc gtttccttag atgtcgactt cctaggacac tgttttgagt gtgtacgggt    3600
ggcacgggtc gtggacttga ggaccccct ggcagtcaga aggagaaggg gggtttggg    3660 ttcctgtggg agtactagag ggcctgggga ctccagtgta cgcaccacca cctgcactcg    3720
gtgcttctgg gactccagtt caagttgacc atgcacctgc cgcacctcca cgtattacgg    3780
ttctgtttcg gcgccctcct cgtcatgttg tcgtgcatgg cacaccagtc gcaggagtgg    3840
caggacgtgt tcctgaccga cttaccgttc tcatgttca cgttcagag gttgtttcgg    3900 gagggtcggg ggtagctctt ttggtagagg tttcggtttc ccgtcggggc tcttggtgtc    3960
cacatgtggg acggggtag ggccctactc gactggttct tggtccagtc ggactggacg    4020
gaccagtttc cgaagatagg gtcgctgtag cggcacctca ccctctcgtt acccgtcggc    4080
ctcttgttga tgttctggtg cggagggcac gacctgaggc tgccgaggaa gaggagatg    4140 tcgttcgagt ggcacctgtt ctcgtccacc gtcgtcccct tgcagaagag tacgaggcac    4200
tacgtactcc gagacgtgtt ggtgatgtgc gtcttctcgg agaggggacag aggcccattt    4260 actgagctgg gtctgatcag tttaattcgg cttaagacgt ctataggtag tgtgaccgcc    4320
ggcgacctta agtgaggagt ccacgtccga cggatagtct tccaccaccg accacaccgg    4380
ttacgggacc gagtgttat ggtgactcta gaaaaaggga gacggttttt aatacccctg    4440
tagtacttcg gggaactcgt agactgaaga ccgattattt cctttaaata aaagtaacgt    4500
tatcacacaa ccttaaaaaa cacagagagt gagccttcct gtataccctc ccgtttagta    4560
aattttgtag tcttactcat aaaccaaatc tcaaaccgtt gtatacgggt atacgaccga    4620
cggtacttgt ttccaaccga tatttctcca gtagtcatat actttgtcgg gggacgacag    4680
gtaaggaata aggtatcttt tcggaactga actccaatct aaaaaaaata taaaacaaaa    4740
cacaataaaa aaagaaattg tagggatttt aaaaggaatg tacaaaatga tcggtctaaa    4800
aaggaggaga ggactgatga gggtcagtat cgacagggag aagagaatac ctctagggag    4860
ctgcctaggg atctcagctc cgctacgccg cgtcgtggta ccggacttta ttggagactt    4920
tctccttgaa ccaatccatg gaaccaaaaa ttttggtcgg acctcatctc gtctacccaa    4980
ttccactcac tggggagtcg ggacctgtaa gaatctactc ggggagtcc tcatctctta    5040 ttacaactct actcaagaca accgattta ttagttccga tcagaaatat tttgacagag    5100
gagaagagga tcgaagctag gtctctctct ggacccgcct cgaccagcga cgagtccttg    5160 aggtccttc ctcttcgact ccaatggtgc gacgcttacc caaatgcctc tatcgaccga    5220
aaggccccac tcaagagcat ttgaggtctc gtcgctatcc ggcattatag cccctttcgt    5280
```

```
gatatccctg tactacaagg tgtgcagtgt acccagcagg ataggctcgg tcagcacggt    5340
ttccccgcca gggcgacacg tgtgaccgcg aggtccctcg agacgtgagg cgggcttttc    5400
acgcgagccg agacggtcct gcgccccgcg cactgatacg cacccgacct cgttggcgga    5460
cgacccacgt ttgggaaacg cgggcctgag caggttgctg atatttctcc cgtccgacag    5520
gagattcgca gtggtgctga agttgcagga ctcatggaag aggagtgaat gaggcatcga    5580
ggtcgaagtg gtggttcgag gagctgcagc tagcgcttcg aaaccgggga aaccggaatc    5640
gcagctggct aggactcttg aagtcccact caaacccctg gaactaaca agaaagaaaa    5700 agcgataaca ttttaagtac aatataccctc ccccgtttca aaagtcccac aacaaatctt    5760
acccttctac agggaacata gtggtacctg ggagtactat taaaacaaag aaagtgaaag    5820
atgagacaac tgttggtaac agaggagaat aaaagaaaag taaagacat tgaaaaagca    5880 atttgaaatc gaacgtaaac attgcttaaa aatttaagtg aaaacaaata aacagtctaa    5940
cattcatgaa agagattagt gaaaaaaag ttccgttagt cccatataat ataacatgaa    6000
gtcgtgtcaa aatctcttgt taacaatatt aatttactat tccatcttat aaagacgtat    6060
atttaagacc gaccgcacct ttataagaat aaccatcttt gttgatgtgg gaccagtagt    6120
aggacggaaa gagaaatacc aatgttacta tatgtgacaa actctactcc tattttatga    6180
gactcaggtt tggcccgggg agacgattgg tacaagtacg gaagaagaga aaggatgtcg    6240
aggacccgtt gcacgaccaa caacacgaca gagtagtaaa accgtttctt aaggagctgg    6300
tcacgtccga cggatagtct ttcaccaccg accacaccga ttacgggacc gggtgttcat    6360
agtgattcga gcgaaagaac gacaggttaa agataatttc caaggaaaca agggattcag    6420
gttgatgatt tgaccccta taatacttcc cggaactcgt agacctaaga cggattattt    6480
tttgtaaata aaagtaacgt tactacataa atttaataaa gacttataaa atgatttttc    6540 ccttacacccc tccagtcacg taaattttgt atttctttac ttctcgatca agtttggaac    6600 cctttatgt gatatagaat ttgaggtact ttcttccact ccgacgtttg tcgattacgt    6660
gtaaccgttg tcggggacta cggatacgga ataagtaggg agtcttttcc taagttcatc    6720
tccgaactaa acctccaatt tcaaaacgat acgacataaa atgtaatgaa taacaaaatc    6780
gacaggagta cttacagaaa agtgatgggt aaacgaatag gacgtagaga gtcggaactg    6840
aggtgagtca agagaacgaa tctctatggt ggaaagggga cttcacaagg aaggtacaaa    6900
atgccgctct accaaagagg agcggaccgg tgagtcggaa tcaacagaga caacagaata    6960
tctccagatg aacttcttcc ttttttgtccc ccgtaccaaa ctgacaggac actcgggaag    7020
aagggacgga gggggtgagt gtcactgggc cttagacgtc acgatcagag ggccttgata    7080
gtgagaaagt gtcagacgaa accttcctga cccgaatcat acttttcaat cctgactctt    7140
cttaaacttt cccccgaaaa acatcgaact ataagtgatg acagaataat gggatagtat    7200
ccgggtgggt ttaccttca gggtaagaag gagtcctaca aattctaatc gtaagtcctt    7260
ctctagtctc cagacgaccg agggaatagt acagggaata ccacgaagac cgagacgtca    7320
ataatcgtat cacaatggta gttggtggaa ttgaagtaaa aagaataagt tatggatcca    7380
tccatctacg atctaagacc tttatttat actcagagtt caccaggaac aggagagagg    7440
gtcagtttaa gacttagatc aaccgttcta agactttagt tccgtatatt agtcattatt    7500
cactactatc ttcccatata tcttcttaaa ataatatact ctcccacttt agggtcgtta    7560
aaccctccga ctccgtcctc ttagcgaact aggaccctcc gtctccaacg tcactcggtt    7620
```

```
ctaacacggt gacgtaaggt cgggtccact gtcgtactct gaggcagtgt tttttttttc    7680
ttttttttcc cccccccccc gccacctcgg ttctactggc ttatccttgt cgaggtcatg    7740
atatcgaggg tagcactcac tgcgtcttct gcccactaaa gacgtaaagg ttgactccat    7800
ggtccaagta gagtgtccct tcacggtccg tcacccacgt cctgtcatcc acgtcacgtg    7860
acacgtactc ggcttcgtcc ctgctccgta gtggagtggg cccttcgtgt tccccagtcc    7920
cttaagggaa aggatcagtt tcttttccca ctgtctaccg tggacctttt agcccagtga    7980
gggcgggatt atgacgcgag aaggttgttc gaacagaaac cttttatcta gttaagggaa    8040
acccttcttc taaaaatcgt gtcgttcccc gtcctacaag ttgacactct tttgcttctt    8100
aatcggtttt ttgaaggtca ttcggacgtt tttttttttt tttattttc gattcaaaga    8160
tatttacaag acatttacat tttgtcttcc attcagttga cgtggattat ttttagtgaa    8220
ttatcgttac acgacacagt caacaaataa ccttggtgtg ggccatgtgt aggacaggtc    8280
gtaaacgtca cgcacgtaac ttaataacac gaccgatctg aagtaccgcg gaccgtggct    8340
taggacggaa gagtcgcttt tacttattaa cgaaacaacc gttctttgat tcgtagttac    8400
cctgcgcacg tttcgtggcc gccgccatct acgccccatt catgacttaa aattaagctg    8460
gatagggcca tttcgctttc gctgtgcgaa aaaaaagtgt gtatcgccct ggcttgtgca    8520
atattcatag ctaatccaga taaaaacaga gagacagcct tggtcttgac cattttcaaa    8580
ggtaacgcag acccgaacag atagtaacgc agagatacca aaaacctcct aatctgcccc    8640
ggtggtcatt accacgtatc gcctacagac atggcggtag ccacgtggct atatccaaac    8700
cccgaggggt tccctgacga ccctactgtc gaagtataat ataacttacc cgcgtattag    8760
tcgaattaac cactcctgtt cgatgttcaa cattggacta gaggtgtttc atgcaacggc    8820
cagccccagt ttggcagaag ccacgagctt tggcggaatt tgatgtctgt ccagggtcgg    8880
ttcatccgcc tagttttgga gttttttccgc cctcggttag ttttacgtcg taatataaaa    8940
ttcgagtggc tttggccatt catttctgat acataaaaaa gggtcactta ttaacaacaa    9000
ttgatatttt tcgcagtacc gtttgctatt tccatcgtta accctaagcc cgaaccctac    9060
gagtatagac gactgactcc gtcttacact ttcactgttt ctcttactcc ttgggccccg    9120
tccacatctt gacagacacc ttagactagc catactatcg gtcctactcc taaaacaact    9180
gttacgtagt cagaaagtcc ctttagtgga cctccagaag gtccgtaatc tcttttccg     9240
cccactcctc gtctaaaatt taaactttc ttttcataac ccctcaagcg ttttgtcgtc    9300
gccaaggctt cgtagacttt gaggtcaatt ttctgccttt agtcctcgtt tcgcttctaa    9360
taaacgactt ttacttcgat tggcacaaga atgcggggag gtccatgtcc ccctcccct     9420
ccctccgtt cttgaattac tcctcgtccg ttaatcagta gatgtagacg tcgaacaatt    9480
tagatttta cgatgtcaaa aattcgaccc cgagaaattt agaaacaagg aaacatcgaa    9540
ggtactataa tgctccaaca aattcttact attctggtga ttagtcgtta cccacgaccg    9600
acacaaaccg gaacgtctcc acaaaaaact ccgctcaaag cttgaggatt tcttcgtcac    9660
atcaaaagac gtctacgttt tttctagagt acttcctcct tgaacacgtc aaatgaatta    9720
gacgaaattg tgtcgatttt cgtctctttg tcaggcctta gactaccgtt tgtacgattt    9780
acattctctt ctcacaaact acgacgtcgg tggatttaa gctcctgagt cgcgtcgaga    9840
taagaccaaa ttttcatcaa acagtgggcg atgtgaattt gtaccacgaa atggactcac    9900
ctatgcccgc gtttgatgag acttgctctc gaacgtctgg ctctttaagc tgaagccttg    9960
ataccacgtt acccggatac tagtgtttat acgactcctc agatttatc ggatacttat   10020
```

```
acgaaaccga cgtcctagac tatcgttacg tgcccgaaaa aatcgttgat tgtcggttcg   10080
attcgtacac ttcctgacac gttgatacca ttctgtgata gattctcgac tttgtgttcg   10140
taattcgtac ggacgtatat aatttcgatc cacgttcgac cgttgacccc ttccttcgac   10200
cttcagatag gattgaaaaa aattgatagt cttataactt aattaatgga ataattacg    10260 aaatttcgag accgattttc cttaaggttt ttttttgaca aatcgtaaat aaccgggagg   10320
tttgtgtccg ttcagatacg agacgttgag taattaagta aaaaacccac catcacaaaa   10380
tagaaaacgg ttggtatttt cagtgaaaac cgaacgaagg gatcgtctat gatctcgacg   10440
aaatcatcta ctacgatgag tacgaacgac ctccatgaaa ctgtgtatgg agtctttacg   10500
taacctaccg atgggacagt cataactatc ttttgtgttt cgtcgccaag tttaatttcg   10560
aggtggggag gaccattggt cattataact acacgtccgt ctcctgtcta taaacatgaa   10620
cgtatcagcc cacgtttgga aagcgaaact cgtcggtacg tgtctactta gcccactcgt   10680
tggaaaatta taatgactac gtctaacctt tagaaaaaaa cattccaata cccccgcaaa   10740
tctggactaa ctgctcctcc tcctatcact tctcctacct ctgtcgtacg cttgcaaatg   10800
tacgtcgcgt tctttgtgtt tacgtcaact aactctttc atcactattc aacgttctag    10860
tatatgacat gacctgacga caatcttgac tcttgtgtga cgaaatacga cgttcctttt   10920
ttccccactg acaggatcct gtgacgtctc atggtgtgag acatcaaaca gttctctctc   10980
ggttcgtccg gtaactttac gtcaacagaa acgtcctcaa ttcgttttga ctcaaacccc   11040
tacttggtac cagaaacgaa ctgtgttcga ccctggctat atacagtctt ggatttgcca   11100
cgaaattctt tccgcggtcc caccatctcc acctcaaact acctttacgt tcgttatgtt   11160
tgaccatgtg acagatgtcg ttaaacatgt acgcgtgtct cctgccgacc gtcgaacgct   11220
tccgacccga ctgccttgac ccgagatgat gacgtggtac cggccacgac ctgcgtaaat   11280
gataagagcg aaaccactgc tccgtcggtc taaatcatgt tgtcccgtaa tgagacattc   11340
tctagtcctg tctcacatac gaccacagag taggtggaga agactaaaat ctctagcggg   11400
tctgcctcag acccagcgta ggcttcctgg acttcctctg ggacgtcctt ttcttcggct   11460
cggtcgggtc ggacagagaa gaaacagagc gaggggggcgg acgccagggt agtctcgtcc   11520
ggagccaacc catgccctgc caggagcgag cgtggggatg ttaaaaggac gtccgagccc   11580
cccgagataa gaggcgagaa ggaggtgggg cacgtcccgt gccatggcca cctgaaccgt   11640
agttccgtcc ttcttctcct cgtcagcggg ctgaggtgtc tccttcttgg tcactgagag   11700
ggttccgcgt ggtggttact acctaaggtg gacaatttcc gtcctcccag tacgaaacga   11760
gattaaagtc cttgacgatt ggtccatttc acgatagcga aagcccactt tttcttggta   11820
tctgtagcga tgctcttgac gtggtggtgg accaagtgtc aacgactgtt gccacgactt   11880
tctgttcctg ttcgtgttta tgactagtgg aaacctagcg gttcagtttc cgttctgaaa   11940
gactttgtac atggtgatgg aggaccttac ttgtaaaggc cgaaatgtcg gtcgaacctg   12000
aagactagtg acggtaacgg aaaagaagta gactgaccac atgatacggt ttagatacgc   12060
tggcgtaata tttcggctta agacgtctat aggtagtgtg accgccggta taccggcgat   12120
acgccacact ttatggcgtg tctacgcatt cctcttttat ggcgtagtcc gcgagaaggc   12180
gaaggagcga gtgactgagc gacgcgagcc agcaagccga cgccgctcgc catagtcgag   12240
tgagtttccg ccattatgcc aataggtgtc ttagtcccct attgcgtcct ttcttgtaca   12300 ctcgtttttcc ggtcgttttc cggtccttgg catttttccg gcgcaacgac cgcaaaaagg   12360
```

```
tatccgaggc gggggggactg ctccgtagtgt ttttagctgc gagttcagtc tccaccgctt    12420
tgggctgtcc tgatatttct atggtccgca aaggggggacc ttcgagggag cacgcgagag    12480
gacaaggctg ggacggcgaa tggcctatgg acaggcggaa agagggaagc ccttcgcacc    12540
gcgaaagagt atcgagtgcg acatccatag agtcaagcca catccagcaa gcgaggttcg    12600
acccgacaca cgtgcttggg gggcaagtcg ggctggcgac gcggaatagg ccattgatag    12660
cagaactcag gttgggccat tctgtgctga atagcggtga ccgtcgtcgg tgaccattgt    12720
cctaatcgtc tcgctccata catccgccac gatgtctcaa gaacttcacc accggattga    12780
tgccgatgtg atcttcctgt cataaaccat agacgcgaga cgacttcggt caatggaagc    12840 cttttttctca accatcgaga actaggccgt ttgtttggtg gcgaccatcg ccaccaaaaa    12900
aacaaacgtt cgtcgtctaa tgcgcgtctt ttttttcctag agttcttcta ggaaactaga    12960
aaagatgccc cagactgcga gtcaccttgc ttttgagtgc aattccctaa aaccagtact    13020
ctaatagttt ttcctagaag tggatctagg aaaatttaat ttttacttca aaatttagtt    13080
agatttcata tatactcatt tgaaccagac tgtcaatggt tacgaattag tcactccgtg    13140
gatagagtcg ctagacagat aaagcaagta ggtatcaacg gactgagggg cagcacatct    13200
attgatgcta tgccctcccg aatggtagac cggggtcacg acgttactat ggcgctctgg    13260
gtgcgagtgg ccgaggtcta aatagtcgtt atttggtcgg tcggccttcc cggctcgcgt    13320
cttcaccagg acgttgaaat aggcggaggt aggtcagata attaacaacg gcccttcgat    13380
ctcattcatc aagcggtcaa ttatcaaacg cgttgcaaca acggtaacga cgtccgtagc    13440
accacagtgc gagcagcaaa ccataccgaa gtaagtcgag gccaagggtt gctagttccg    13500
ctcaatgtac taggggggtac aacacgtttt ttcgccaatc gaggaagcca ggaggctagc    13560
aacagtcttc attcaaccgg cgtcacaata gtgagtacca ataccgtcgt gacgtattaa    13620
gagaatgaca gtacggtagg cattctacga aaagacactg accactcatg agttggttca    13680
gtaagactct tatcacatac gccgctggct caacagagaac gggccgcagt tgtgccctat    13740
tatggcgcgg tgtatcgtct tgaaattttc acgagtagta accttttgca agaagccccg    13800
cttttgagag ttcctagaat ggcgacaact ctaggtcaag ctacattggg tgagcacgtg    13860
ggttgactag aagtcgtaga aaatgaaagt ggtcgcaaag acccactcgt ttttgtcctt    13920 ccgtttacg gcgttttttc ccttattccc gctgtgcctt tacaacttat gagtatgaga    13980
aggaaaaagt tataataact tcgtaaatag tcccaataac agagtactcg cctatgtata    14040
aacttacata aatctttta tttgtttatc cccaaggcgc gtgtaaaggg gcttttcacg    14100
gtggactgca gattctttgg taataatagt actgtaattg gatattttta tccgcatagt    14160
gctccgggaa agcagaagtt cttaagagta caaactgtcg aatagtagct attcgaagtg    14220
cgacggcgtt cgtgagtccc gcgttcccga cgatttcctt cgccttgtgc atctttcggt    14280
caggcgtctt tgccacgact gggggcctact tacagtcgat gacccgatag acctgttccc    14340
ttttgcgttc gcgtttctct ttcgtccatc gaacgtcacc cgaatgtacc gctatcgatc    14400
tgacccgcca aaatacctgt cgttcgcttg gccttaacgg tcgacccgcg gggagaccat    14460 tccaacccctt cgggacgttt catttgacct accgaaagaa cggcggttcc tagactaccg    14520
cgtcccctag ttctaggacg aagtagggggc accgggcaac gagcgcaaac gaccgccaca    14580
ggggccttct ttatataaac gtacagaaat caagatacta ctgtgtttgg ggcgggtcgc    14640
agaacagtaa ccgcttaagc ttgtgcgtct acgtcagccc cgccgcgcca gggtccaggt    14700
gaagcgtata attccactgc gcacaccgga gcttgtggct cgctgggacg tcgctgggcg    14760
```

```
aattgtcgca gttgtcgcac ggcgtctaga ctagttctct gtcctactcc tagcaaagcg    14820
tactaacttg ttctacctaa cgtgcgtcca agaggccggc gaacccacct ctccgataag    14880
ccgatactga cccgtgttgt ctgttagccg acgagactac ggcggcacaa ggccgacagt    14940 cgcgtcccg cgggccaaga aaacagttc tggctggaca ggccacggga cttacttgac    15000
gtcctgctcc gtcgcgccga tagcaccgac cggtgctgcc cgcaaggaac gcgtcgacac    15060
gagctgcaac agtgacttcg cccttccctg accgacgata acccgcttca cggcccgtc    15120 ctagaggaca gtagagtgga acgaggacgg ctctttcata ggtagtaccg actacgttac    15180
gccgccgacg tatgcgaact aggccgatgg acgggtaagc tggtggttcg ctttgtagcg    15240
tagctcgctc gtgcatgagc ctaccttcgg ccagaacagc tagtcctact agacctgctt    15300
ctcgtagtcc ccgagcgcgg tcggcttgac aagcggtccg agttccgcgc gtacgggctg    15360
ccgctcctag agcagcactg gtaccgcta cggacgaacg gcttatagta ccacctttta    15420
ccggcgaaaa gacctaagta gctgacaccg gccgacccac accgcctggc gatagtcctg    15480
tatcgcaacc gatgggcact ataacgactt ctcgaaccgc cgcttacccg actggcgaag    15540
gagcacgaaa tgccatagcg gcgagggcta agcgtcgcgt agcggaagat agcggaagaa    15600
ctgctcaaga agactcgccc tgagacccca agctttactg gctggttcgc tgcgggttgg    15660
acggtagtgc tctaaagcta aggtggcggc ggaagatact ttccaaccg aagccttagc    15720 aaaaggccct gcggccgacc tactaggagg tcgcgcccct agagtacgac ctcaagaagc    15780
gggtggggcc ctctacccc tccgattgac tttgtgcctt cctctgttat ggccttcctt    15840
gggcgcgata cttgccgtta tttttctgtc ttattttgcg tgccacaacc cagcaaacaa    15900
gtatttgcgc cccaagccag ggtcccgacc gtgagacagc tatggggtgg ctctggggta    15960
accccggtta tgcgggcgca aagaaggaaa aggggtgggg tgggggggttc aagcccactt    16020 ccgggtcccg agcgtcggtt gcagcccgc cgttcgggac ggtatcggtg cccggggcac    16080
ccaatccctg ccgcctagcg ccggg                                           16105
```

<210> SEQ ID NO 26
<211> LENGTH: 3391
<212> TYPE: PRT
<213> ORGANISM: Dengue virus 2
<300> PUBLICATION INFORMATION:
<308> DATABASE ACCESSION NUMBER: NCBI / NP_056776.2
<309> DATABASE ENTRY DATE: 2015-09-15
<313> RELEVANT RESIDUES IN SEQ ID NO: (1)..(3391)

<400> SEQUENCE: 26

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

```
Met Ala Phe His Leu Thr Thr Arg Asn Gly Glu Pro His Met Ile Val
            115                 120                 125
Ser Arg Gln Glu Lys Gly Lys Ser Leu Leu Phe Lys Thr Glu Asp Gly
130                 135                 140
Val Asn Met Cys Thr Leu Met Ala Met Asp Leu Gly Glu Leu Cys Glu
145                 150                 155                 160
Asp Thr Ile Thr Tyr Lys Cys Pro Leu Leu Arg Gln Asn Glu Pro Glu
                165                 170                 175
Asp Ile Asp Cys Trp Cys Asn Ser Thr Ser Thr Trp Val Thr Tyr Gly
                180                 185                 190
Thr Cys Thr Thr Met Gly Glu His Arg Arg Glu Lys Arg Ser Val Ala
        195                 200                 205
Leu Val Pro His Val Gly Met Gly Leu Glu Thr Arg Thr Glu Thr Trp
210                 215                 220
Met Ser Ser Glu Gly Ala Trp Lys His Val Gln Arg Ile Glu Thr Trp
225                 230                 235                 240
Ile Leu Arg His Pro Gly Phe Thr Met Met Ala Ala Ile Leu Ala Tyr
                245                 250                 255
Thr Ile Gly Thr Thr His Phe Gln Arg Ala Leu Ile Phe Ile Leu Leu
            260                 265                 270
Thr Ala Val Thr Pro Ser Met Thr Met Arg Cys Ile Gly Met Ser Asn
        275                 280                 285
Arg Asp Phe Val Glu Gly Val Ser Gly Gly Ser Trp Val Asp Ile Val
    290                 295                 300
Leu Glu His Gly Ser Cys Val Thr Thr Met Ala Lys Asn Lys Pro Thr
305                 310                 315                 320
Leu Asp Phe Glu Leu Ile Lys Thr Glu Ala Lys Gln Pro Ala Thr Leu
                325                 330                 335
Arg Lys Tyr Cys Ile Glu Ala Lys Leu Thr Asn Thr Thr Thr Glu Ser
                340                 345                 350
Arg Cys Pro Thr Gln Gly Glu Pro Ser Leu Asn Glu Glu Gln Asp Lys
        355                 360                 365
Arg Phe Val Cys Lys His Ser Met Val Asp Arg Gly Trp Gly Asn Gly
370                 375                 380
Cys Gly Leu Phe Gly Lys Gly Ile Val Thr Cys Ala Met Phe Arg
385                 390                 395                 400
Cys Lys Lys Asn Met Glu Gly Lys Val Val Gln Pro Glu Asn Leu Glu
                405                 410                 415
Tyr Thr Ile Val Ile Thr Pro His Ser Gly Glu Glu His Ala Val Gly
                420                 425                 430
Asn Asp Thr Gly Lys His Gly Lys Glu Ile Lys Ile Thr Pro Gln Ser
            435                 440                 445
Ser Ile Thr Glu Ala Glu Leu Thr Gly Tyr Gly Thr Val Thr Met Glu
    450                 455                 460
Cys Ser Pro Arg Thr Gly Leu Asp Phe Asn Glu Met Val Leu Leu Gln
465                 470                 475                 480
Met Glu Asn Lys Ala Trp Leu Val His Arg Gln Trp Phe Leu Asp Leu
                485                 490                 495
Pro Leu Pro Trp Leu Pro Gly Ala Asp Thr Gln Gly Ser Asn Trp Ile
            500                 505                 510
Gln Lys Glu Thr Leu Val Thr Phe Lys Asn Pro His Ala Lys Lys Gln
    515                 520                 525
```

-continued

```
Asp Val Val Leu Gly Ser Gln Glu Gly Ala Met His Thr Ala Leu
530                 535                 540
Thr Gly Ala Thr Glu Ile Gln Met Ser Ser Gly Asn Leu Leu Phe Thr
545                 550                 555                 560
Gly His Leu Lys Cys Arg Leu Arg Met Asp Lys Leu Gln Leu Lys Gly
                565                 570                 575
Met Ser Tyr Ser Met Cys Thr Gly Lys Phe Lys Val Val Lys Glu Ile
            580                 585                 590
Ala Glu Thr Gln His Gly Thr Ile Val Ile Arg Val Gln Tyr Glu Gly
        595                 600                 605
Asp Gly Ser Pro Cys Lys Ile Pro Phe Glu Ile Met Asp Leu Glu Lys
    610                 615                 620
Arg His Val Leu Gly Arg Leu Ile Thr Val Asn Pro Ile Val Thr Glu
625                 630                 635                 640
Lys Asp Ser Pro Val Asn Ile Glu Ala Glu Pro Pro Phe Gly Asp Ser
                645                 650                 655
Tyr Ile Ile Ile Gly Val Glu Pro Gly Gln Leu Lys Leu Asn Trp Phe
            660                 665                 670
Lys Lys Gly Ser Ser Ile Gly Gln Met Phe Glu Thr Thr Met Arg Gly
        675                 680                 685
Ala Lys Arg Met Ala Ile Leu Gly Asp Thr Ala Trp Asp Phe Gly Ser
    690                 695                 700
Leu Gly Gly Val Phe Thr Ser Ile Gly Lys Ala Leu His Gln Val Phe
705                 710                 715                 720
Gly Ala Ile Tyr Gly Ala Ala Phe Ser Gly Val Ser Trp Thr Met Lys
                725                 730                 735
Ile Leu Ile Gly Val Ile Ile Thr Trp Ile Gly Met Asn Ser Arg Ser
            740                 745                 750
Thr Ser Leu Ser Val Thr Leu Val Leu Val Gly Ile Val Thr Leu Tyr
        755                 760                 765
Leu Gly Val Met Val Gln Ala Asp Ser Gly Cys Val Val Ser Trp Lys
    770                 775                 780
Asn Lys Glu Leu Lys Cys Gly Ser Gly Ile Phe Ile Thr Asp Asn Val
785                 790                 795                 800
His Thr Trp Thr Glu Gln Tyr Lys Phe Gln Pro Glu Ser Pro Ser Lys
                805                 810                 815
Leu Ala Ser Ala Ile Gln Lys Ala His Glu Glu Gly Ile Cys Gly Ile
            820                 825                 830
Arg Ser Val Thr Arg Leu Glu Asn Leu Met Trp Lys Gln Ile Thr Pro
        835                 840                 845
Glu Leu Asn His Ile Leu Ser Glu Asn Glu Val Lys Leu Thr Ile Met
    850                 855                 860
Thr Gly Asp Ile Lys Gly Ile Met Gln Ala Gly Lys Arg Ser Leu Arg
865                 870                 875                 880
Pro Gln Pro Thr Glu Leu Lys Tyr Ser Trp Lys Thr Trp Gly Lys Ala
                885                 890                 895
Lys Met Leu Ser Thr Glu Ser His Asn Gln Thr Phe Leu Ile Asp Gly
            900                 905                 910
Pro Glu Thr Ala Glu Cys Pro Asn Thr Asn Arg Ala Trp Asn Ser Leu
        915                 920                 925
Glu Val Glu Asp Tyr Gly Phe Gly Val Phe Thr Thr Asn Ile Trp Leu
    930                 935                 940
Lys Leu Lys Glu Lys Gln Asp Val Phe Cys Asp Ser Lys Leu Met Ser
```

```
              945                 950                 955                 960
        Ala Ala Ile Lys Asp Asn Arg Ala Val His Ala Asp Met Gly Tyr Trp
                      965                 970                 975
        Ile Glu Ser Ala Leu Asn Asp Thr Trp Lys Ile Glu Lys Ala Ser Phe
                            980                 985                 990
        Ile Glu Val Lys Asn Cys His Trp Pro Lys Ser His Thr Leu Trp Ser
                      995                1000                1005
        Asn Gly Val Leu Glu Ser Glu Met Ile Ile Pro Lys Asn Leu Ala
                1010                1015                1020
        Gly Pro Val Ser Gln His Asn Tyr Arg Pro Gly Tyr His Thr Gln
                1025                1030                1035
        Ile Thr Gly Pro Trp His Leu Gly Lys Leu Glu Met Asp Phe Asp
                1040                1045                1050
        Phe Cys Asp Gly Thr Thr Val Val Val Thr Glu Asp Cys Gly Asn
                1055                1060                1065
        Arg Gly Pro Ser Leu Arg Thr Thr Ala Ser Gly Lys Leu Ile
                1070                1075                1080
        Thr Glu Trp Cys Cys Arg Ser Cys Thr Leu Pro Pro Leu Arg Tyr
                1085                1090                1095
        Arg Gly Glu Asp Gly Cys Trp Tyr Gly Met Glu Ile Arg Pro Leu
                1100                1105                1110
        Lys Glu Lys Glu Glu Asn Leu Val Asn Ser Leu Val Thr Ala Gly
                1115                1120                1125
        His Gly Gln Val Asp Asn Phe Ser Leu Gly Val Leu Gly Met Ala
                1130                1135                1140
        Leu Phe Leu Glu Glu Met Leu Arg Thr Arg Val Gly Thr Lys His
                1145                1150                1155
        Ala Ile Leu Leu Val Ala Val Ser Phe Val Thr Leu Ile Thr Gly
                1160                1165                1170
        Asn Met Ser Phe Arg Asp Leu Gly Arg Val Met Val Met Val Gly
                1175                1180                1185
        Ala Thr Met Thr Asp Asp Ile Gly Met Gly Val Thr Tyr Leu Ala
                1190                1195                1200
        Leu Leu Ala Ala Phe Lys Val Arg Pro Thr Phe Ala Ala Gly Leu
                1205                1210                1215
        Leu Leu Arg Lys Leu Thr Ser Lys Glu Leu Met Met Thr Thr Ile
                1220                1225                1230
        Gly Ile Val Leu Leu Ser Gln Ser Thr Ile Pro Glu Thr Ile Leu
                1235                1240                1245
        Glu Leu Thr Asp Ala Leu Ala Leu Gly Met Met Val Leu Lys Met
                1250                1255                1260
        Val Arg Asn Met Glu Lys Tyr Gln Leu Ala Val Thr Ile Met Ala
                1265                1270                1275
        Ile Leu Cys Val Pro Asn Ala Val Ile Leu Gln Asn Ala Trp Lys
                1280                1285                1290
        Val Ser Cys Thr Ile Leu Ala Val Val Ser Val Ser Pro Leu Leu
                1295                1300                1305
        Leu Thr Ser Ser Gln Gln Lys Thr Asp Trp Ile Pro Leu Ala Leu
                1310                1315                1320
        Thr Ile Lys Gly Leu Asn Pro Thr Ala Ile Phe Leu Thr Thr Leu
                1325                1330                1335
        Ser Arg Thr Ser Lys Lys Arg Ser Trp Pro Leu Asn Glu Ala Ile
                1340                1345                1350
```

-continued

```
Met Ala Val Gly Met Val Ser Ile Leu Ala Ser Ser Leu Leu Lys
    1355            1360            1365

Asn Asp Ile Pro Met Thr Gly Pro Leu Val Ala Gly Gly Leu Leu
    1370            1375            1380

Thr Val Cys Tyr Val Leu Thr Gly Arg Ser Ala Asp Leu Glu Leu
    1385            1390            1395

Glu Arg Ala Ala Asp Val Lys Trp Glu Asp Gln Ala Glu Ile Ser
    1400            1405            1410

Gly Ser Ser Pro Ile Leu Ser Ile Thr Ile Ser Glu Asp Gly Ser
    1415            1420            1425

Met Ser Ile Lys Asn Glu Glu Glu Gln Thr Leu Thr Ile Leu
    1430            1435            1440

Ile Arg Thr Gly Leu Leu Val Ile Ser Gly Leu Phe Pro Val Ser
    1445            1450            1455

Ile Pro Ile Thr Ala Ala Ala Trp Tyr Leu Trp Glu Val Lys Lys
    1460            1465            1470

Gln Arg Ala Gly Val Leu Trp Asp Val Pro Ser Pro Pro Pro Met
    1475            1480            1485

Gly Lys Ala Glu Leu Glu Asp Gly Ala Tyr Arg Ile Lys Gln Lys
    1490            1495            1500

Gly Ile Leu Gly Tyr Ser Gln Ile Gly Ala Gly Val Tyr Lys Glu
    1505            1510            1515

Gly Thr Phe His Thr Met Trp His Val Thr Arg Gly Ala Val Leu
    1520            1525            1530

Met His Lys Gly Lys Arg Ile Glu Pro Ser Trp Ala Asp Val Lys
    1535            1540            1545

Lys Asp Leu Ile Ser Tyr Gly Gly Gly Trp Lys Leu Glu Gly Glu
    1550            1555            1560

Trp Lys Glu Gly Glu Glu Val Gln Val Leu Ala Leu Glu Pro Gly
    1565            1570            1575

Lys Asn Pro Arg Ala Val Gln Thr Lys Pro Gly Leu Phe Lys Thr
    1580            1585            1590

Asn Ala Gly Thr Ile Gly Ala Val Ser Leu Asp Phe Ser Pro Gly
    1595            1600            1605

Thr Ser Gly Ser Pro Ile Ile Asp Lys Lys Gly Lys Val Val Gly
    1610            1615            1620

Leu Tyr Gly Asn Gly Val Val Thr Arg Ser Gly Ala Tyr Val Ser
    1625            1630            1635

Ala Ile Ala Gln Thr Glu Lys Ser Ile Glu Asp Asn Pro Glu Ile
    1640            1645            1650

Glu Asp Asp Ile Phe Arg Lys Arg Arg Leu Thr Ile Met Asp Leu
    1655            1660            1665

His Pro Gly Ala Gly Lys Thr Lys Arg Tyr Leu Pro Ala Ile Val
    1670            1675            1680

Arg Glu Ala Ile Lys Arg Gly Leu Arg Thr Leu Ile Leu Ala Pro
    1685            1690            1695

Thr Arg Val Val Ala Ala Glu Met Glu Glu Ala Leu Arg Gly Leu
    1700            1705            1710

Pro Ile Arg Tyr Gln Thr Pro Ala Ile Arg Ala Glu His Thr Gly
    1715            1720            1725

Arg Glu Ile Val Asp Leu Met Cys His Ala Thr Phe Thr Met Arg
    1730            1735            1740
```

| | | | | | | | | | | | |
|---|---|---|---|---|---|---|---|---|---|---|---|
|Leu|Leu|Ser|Pro|Val|Arg|Val|Pro|Asn|Tyr|Asn|Leu|Ile|Ile|Met|
| |1745| | |1750| | | |1755| | | | | | |
|Asp|Glu|Ala|His|Phe|Thr|Asp|Pro|Ala|Ser|Ile|Ala|Ala|Arg|Gly|
| |1760| | |1765| | | |1770| | | | | | |
|Tyr|Ile|Ser|Thr|Arg|Val|Glu|Met|Gly|Glu|Ala|Ala|Gly|Ile|Phe|
| |1775| | |1780| | | |1785| | | | | | |
|Met|Thr|Ala|Thr|Pro|Pro|Gly|Ser|Arg|Asp|Pro|Phe|Pro|Gln|Ser|
| |1790| | |1795| | | |1800| | | | | | |
|Asn|Ala|Pro|Ile|Ile|Asp|Glu|Arg|Glu|Ile|Pro|Glu|Arg|Ser|
| |1805| | |1810| | | |1815| | | | | |
|Trp|Asn|Ser|Gly|His|Glu|Trp|Val|Thr|Asp|Phe|Lys|Gly|Lys|Thr|
| |1820| | |1825| | | |1830| | | | | | |
|Val|Trp|Phe|Val|Pro|Ser|Ile|Lys|Ala|Gly|Asn|Asp|Ile|Ala|Ala|
| |1835| | |1840| | | |1845| | | | | | |
|Cys|Leu|Arg|Lys|Asn|Gly|Lys|Lys|Val|Ile|Gln|Leu|Ser|Arg|Lys|
| |1850| | |1855| | | |1860| | | | | | |
|Thr|Phe|Asp|Ser|Glu|Tyr|Val|Lys|Thr|Arg|Thr|Asn|Asp|Trp|Asp|
| |1865| | |1870| | | |1875| | | | | | |
|Phe|Val|Val|Thr|Thr|Asp|Ile|Ser|Glu|Met|Gly|Ala|Asn|Phe|Lys|
| |1880| | |1885| | | |1890| | | | | | |
|Ala|Glu|Arg|Val|Ile|Asp|Pro|Arg|Arg|Cys|Met|Lys|Pro|Val|Ile|
| |1895| | |1900| | | |1905| | | | | | |
|Leu|Thr|Asp|Gly|Glu|Glu|Arg|Val|Ile|Leu|Ala|Gly|Pro|Met|Pro|
| |1910| | |1915| | | |1920| | | | | | |
|Val|Thr|His|Ser|Ser|Ala|Ala|Gln|Arg|Arg|Gly|Arg|Ile|Gly|Arg|
| |1925| | |1930| | | |1935| | | | | | |
|Asn|Pro|Lys|Asn|Glu|Asn|Asp|Gln|Tyr|Ile|Tyr|Met|Gly|Glu|Pro|
| |1940| | |1945| | | |1950| | | | | | |
|Leu|Glu|Asn|Asp|Glu|Asp|Cys|Ala|His|Trp|Lys|Glu|Ala|Lys|Met|
| |1955| | |1960| | | |1965| | | | | | |
|Leu|Leu|Asp|Asn|Ile|Asn|Thr|Pro|Glu|Gly|Ile|Ile|Pro|Ser|Met|
| |1970| | |1975| | | |1980| | | | | | |
|Phe|Glu|Pro|Glu|Arg|Glu|Lys|Val|Asp|Ala|Ile|Asp|Gly|Glu|Tyr|
| |1985| | |1990| | | |1995| | | | | | |
|Arg|Leu|Arg|Gly|Glu|Ala|Arg|Lys|Thr|Phe|Val|Asp|Leu|Met|Arg|
| |2000| | |2005| | | |2010| | | | | | |
|Arg|Gly|Asp|Leu|Pro|Val|Trp|Leu|Ala|Tyr|Arg|Val|Ala|Ala|Glu|
| |2015| | |2020| | | |2025| | | | | | |
|Gly|Ile|Asn|Tyr|Ala|Asp|Arg|Arg|Trp|Cys|Phe|Asp|Gly|Val|Lys|
| |2030| | |2035| | | |2040| | | | | | |
|Asn|Asn|Gln|Ile|Leu|Glu|Glu|Asn|Val|Glu|Val|Glu|Ile|Trp|Thr|
| |2045| | |2050| | | |2055| | | | | | |
|Lys|Glu|Gly|Glu|Arg|Lys|Lys|Leu|Lys|Pro|Arg|Trp|Leu|Asp|Ala|
| |2060| | |2065| | | |2070| | | | | | |
|Arg|Ile|Tyr|Ser|Asp|Pro|Leu|Ala|Leu|Lys|Glu|Phe|Lys|Glu|Phe|
| |2075| | |2080| | | |2085| | | | | | |
|Ala|Ala|Gly|Arg|Lys|Ser|Leu|Thr|Leu|Asn|Leu|Ile|Thr|Glu|Met|
| |2090| | |2095| | | |2100| | | | | | |
|Gly|Arg|Leu|Pro|Thr|Phe|Met|Thr|Gln|Lys|Ala|Arg|Asp|Ala|Leu|
| |2105| | |2110| | | |2115| | | | | | |
|Asp|Asn|Leu|Ala|Val|Leu|His|Thr|Ala|Glu|Ala|Gly|Gly|Arg|Ala|
| |2120| | |2125| | | |2130| | | | | | |
|Tyr|Asn|His|Ala|Leu|Ser|Glu|Leu|Pro|Glu|Thr|Leu|Glu|Thr|Leu|

```
            2135                2140                2145
Leu Leu Leu Thr Leu Leu Ala Thr Val Thr Gly Gly Ile Phe Leu
        2150                2155                2160
Phe Leu Met Ser Gly Arg Gly Ile Gly Lys Met Thr Leu Gly Met
        2165                2170                2175
Cys Cys Ile Ile Thr Ala Ser Ile Leu Leu Trp Tyr Ala Gln Ile
        2180                2185                2190
Gln Pro His Trp Ile Ala Ala Ser Ile Ile Leu Glu Phe Phe Leu
        2195                2200                2205
Ile Val Leu Leu Ile Pro Glu Pro Glu Lys Gln Arg Thr Pro Gln
        2210                2215                2220
Asp Asn Gln Leu Thr Tyr Val Ile Ala Ile Leu Thr Val Val
        2225                2230                2235
Ala Ala Thr Met Ala Asn Glu Met Gly Phe Leu Glu Lys Thr Lys
        2240                2245                2250
Lys Asp Leu Gly Leu Gly Ser Ile Ala Thr Gln Gln Pro Glu Ser
        2255                2260                2265
Asn Ile Leu Asp Ile Asp Leu Arg Pro Ala Ser Ala Trp Thr Leu
        2270                2275                2280
Tyr Ala Val Ala Thr Thr Phe Val Thr Pro Met Leu Arg His Ser
        2285                2290                2295
Ile Glu Asn Ser Ser Val Asn Val Ser Leu Thr Ala Ile Ala Asn
        2300                2305                2310
Gln Ala Thr Val Leu Met Gly Leu Gly Lys Gly Trp Pro Leu Ser
        2315                2320                2325
Lys Met Asp Ile Gly Val Pro Leu Leu Ala Ile Gly Cys Tyr Ser
        2330                2335                2340
Gln Val Asn Pro Ile Thr Leu Thr Ala Ala Leu Phe Leu Leu Val
        2345                2350                2355
Ala His Tyr Ala Ile Ile Gly Pro Gly Leu Gln Ala Lys Ala Thr
        2360                2365                2370
Arg Glu Ala Gln Lys Arg Ala Ala Ala Gly Ile Met Lys Asn Pro
        2375                2380                2385
Thr Val Asp Gly Ile Thr Val Ile Asp Leu Asp Pro Ile Pro Tyr
        2390                2395                2400
Asp Pro Lys Phe Glu Lys Gln Leu Gly Gln Val Met Leu Leu Val
        2405                2410                2415
Leu Cys Val Thr Gln Val Leu Met Met Arg Thr Thr Trp Ala Leu
        2420                2425                2430
Cys Glu Ala Leu Thr Leu Ala Thr Gly Pro Ile Ser Thr Leu Trp
        2435                2440                2445
Glu Gly Asn Pro Gly Arg Phe Trp Asn Thr Thr Ile Ala Val Ser
        2450                2455                2460
Met Ala Asn Ile Phe Arg Gly Ser Tyr Leu Ala Gly Ala Gly Leu
        2465                2470                2475
Leu Phe Ser Ile Met Lys Asn Thr Thr Asn Thr Arg Arg Gly Thr
        2480                2485                2490
Gly Asn Ile Gly Glu Thr Leu Gly Glu Lys Trp Lys Ser Arg Leu
        2495                2500                2505
Asn Ala Leu Gly Lys Ser Glu Phe Gln Ile Tyr Lys Lys Ser Gly
        2510                2515                2520
Ile Gln Glu Val Asp Arg Thr Leu Ala Lys Glu Gly Ile Lys Arg
        2525                2530                2535
```

-continued

```
Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655

Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925
```

| | | | | | | | | | | |
|---|---|---|---|---|---|---|---|---|---|---|
|Glu|Arg 2930|Asn|Leu|His|Leu 2935|Gly|Lys|Cys|Glu 2940|Thr Cys Val Tyr|
|Asn|Met 2945|Met|Gly|Lys|Arg 2950|Lys|Lys|Leu|Gly 2955|Glu Phe Gly Lys|
|Ala|Lys 2960|Gly|Ser|Arg|Ala 2965|Ile|Trp|Tyr|Met 2970|Trp Leu Gly Ala Arg|
|Phe|Leu 2975|Glu|Phe|Glu|Ala 2980|Leu|Gly|Phe|Leu 2985|Asn Glu Asp His Trp|
|Phe|Ser 2990|Arg|Glu|Asn|Ser 2995|Leu|Ser|Gly|Val 3000|Glu Gly Glu Gly Leu|
|His|Lys 3005|Leu|Gly|Tyr|Ile 3010|Leu|Arg|Asp|Val 3015|Ser Lys Lys Glu Gly|
|Gly|Ala 3020|Met|Tyr|Ala|Asp 3025|Asp|Thr|Ala|Gly 3030|Trp Asp Thr Arg Ile|
|Thr|Leu 3035|Glu|Asp|Leu|Lys 3040|Asn|Glu|Glu|Met 3045|Val Thr Asn His Met|
|Glu|Gly 3050|Glu|His|Lys|Lys 3055|Leu|Ala|Glu|Ala 3060|Ile Phe Lys Leu Thr|
|Tyr|Gln 3065|Asn|Lys|Val|Val 3070|Arg|Val|Gln|Arg 3075|Pro Thr Pro Arg Gly|
|Thr|Val 3080|Met|Asp|Ile|Ile 3085|Ser|Arg|Arg|Asp 3090|Gln Arg Gly Ser Gly|
|Gln|Val 3095|Gly|Thr|Tyr|Gly 3100|Leu|Asn|Thr|Phe 3105|Thr Asn Met Glu Ala|
|Gln|Leu 3110|Ile|Arg|Gln|Met 3115|Glu|Gly|Glu|Gly 3120|Val Phe Lys Ser Ile|
|Gln|His 3125|Leu|Thr|Ile|Thr 3130|Glu|Glu|Ile|Ala 3135|Val Gln Asn Trp Leu|
|Ala|Arg 3140|Val|Gly|Arg|Glu 3145|Arg|Leu|Ser|Arg 3150|Met Ala Ile Ser Gly|
|Asp|Asp 3155|Cys|Val|Val|Lys 3160|Pro|Leu|Asp|Asp 3165|Arg Phe Ala Ser Ala|
|Leu|Thr 3170|Ala|Leu|Asn|Asp 3175|Met|Gly|Lys|Ile 3180|Arg Lys Asp Ile Gln|
|Gln|Trp 3185|Glu|Pro|Ser|Arg 3190|Gly|Trp|Asn|Asp 3195|Trp Thr Gln Val Pro|
|Phe|Cys 3200|Ser|His|His|Phe 3205|His|Glu|Leu|Ile 3210|Met Lys Asp Gly Arg|
|Val|Leu 3215|Val|Val|Pro|Cys 3220|Arg|Asn|Gln|Asp 3225|Glu Leu Ile Gly Arg|
|Ala|Arg 3230|Ile|Ser|Gln|Gly 3235|Ala|Gly|Trp|Ser 3240|Leu Arg Glu Thr Ala|
|Cys|Leu 3245|Gly|Lys|Ser|Tyr 3250|Ala|Gln|Met|Trp 3255|Ser Leu Met Tyr Phe|
|His|Arg 3260|Arg|Asp|Leu|Arg 3265|Leu|Ala|Ala|Asn 3270|Ala Ile Cys Ser Ala|
|Val|Pro 3275|Ser|His|Trp|Val 3280|Pro|Thr|Ser|Arg 3285|Thr Thr Trp Ser Ile|
|His|Ala 3290|Lys|His|Glu|Trp 3295|Met|Thr|Thr|Glu 3300|Asp Met Leu Thr Val|
|Trp|Asn 3305|Arg|Val|Trp|Ile 3310|Gln|Glu|Asn|Pro 3315|Trp Met Glu Asp Lys|
|Thr|Pro|Val|Glu|Ser|Trp|Glu|Glu|Ile|Pro|Tyr Leu Gly Lys Arg|

```
                3320                3325                3330

Glu Asp Gln Trp Cys Gly Ser  Leu Ile Gly Leu Thr  Ser Arg Ala
            3335                3340                3345

Thr Trp Ala Lys Asn Ile Gln  Ala Ala Ile Asn Gln  Val Arg Ser
3350                3355                3360

Leu Ile Gly Asn Glu Glu Tyr  Thr Asp Tyr Met Pro  Ser Met Lys
        3365                3370                3375

Arg Phe Arg Arg Glu Glu Glu  Ala Gly Val Leu  Trp
    3380                3385                3390

<210> SEQ ID NO 27
<211> LENGTH: 3411
<212> TYPE: PRT
<213> ORGANISM: Yellow fever virus
<300> PUBLICATION INFORMATION:
<308> DATABASE ACCESSION NUMBER: NCBI / NP_041726.1
<309> DATABASE ENTRY DATE: 2016-02-10
<313> RELEVANT RESIDUES IN SEQ ID NO: (1)..(3411)

<400> SEQUENCE: 27

Met Ser Gly Arg Lys Ala Gln  Gly Lys Thr Leu Gly  Val Asn Met Val
1               5                   10                  15

Arg Arg Gly Val Arg Ser Leu  Ser Asn Lys Ile Lys  Gln Lys Thr Lys
            20                  25                  30

Gln Ile Gly Asn Arg Pro Gly  Pro Ser Arg Gly Val  Gln Gly Phe Ile
        35                  40                  45

Phe Phe Phe Leu Phe Asn Ile  Leu Thr Gly Lys Lys  Ile Thr Ala His
    50                  55                  60

Leu Lys Arg Leu Trp Lys Met  Leu Asp Pro Arg Gln  Gly Leu Ala Val
65                  70                  75                  80

Leu Arg Lys Val Lys Arg Val  Val Ala Ser Leu Met  Arg Gly Leu Ser
                85                  90                  95

Ser Arg Lys Arg Arg Ser His  Asp Val Leu Thr Val  Gln Phe Leu Ile
            100                 105                 110

Leu Gly Met Leu Leu Met Thr  Gly Gly Val Thr Leu  Val Arg Lys Asn
        115                 120                 125

Arg Trp Leu Leu Leu Asn Val  Thr Ser Glu Asp Leu  Gly Lys Thr Phe
    130                 135                 140

Ser Val Gly Thr Gly Asn Cys  Thr Thr Asn Ile Leu  Glu Ala Lys Tyr
145                 150                 155                 160

Trp Cys Pro Asp Ser Met Glu  Tyr Asn Cys Pro Asn  Leu Ser Pro Arg
                165                 170                 175

Glu Glu Pro Asp Asp Ile Asp  Cys Trp Cys Tyr Gly  Val Glu Asn Val
            180                 185                 190

Arg Val Ala Tyr Gly Lys Cys  Asp Ser Ala Gly Arg  Ser Arg Arg Ser
        195                 200                 205

Arg Arg Ala Ile Asp Leu Pro  Thr His Glu Asn His  Gly Leu Lys Thr
    210                 215                 220

Arg Gln Glu Lys Trp Met Thr  Gly Arg Met Gly Glu  Arg Gln Leu Gln
225                 230                 235                 240

Lys Ile Glu Arg Trp Phe Val  Arg Asn Pro Phe Phe  Ala Val Thr Ala
                245                 250                 255

Leu Thr Ile Ala Tyr Leu Val  Gly Ser Asn Met Thr  Gln Arg Val Val
            260                 265                 270

Ile Ala Leu Leu Val Leu Ala  Val Gly Pro Ala Tyr  Ser Ala His Cys
        275                 280                 285
```

-continued

```
Ile Gly Ile Thr Asp Arg Asp Phe Ile Glu Gly Val His Gly Gly Thr
    290                 295                 300
Trp Val Ser Ala Thr Leu Glu Gln Asp Lys Cys Val Thr Val Met Ala
305                 310                 315                 320
Pro Asp Lys Pro Ser Leu Asp Ile Ser Leu Glu Thr Val Ala Ile Asp
                325                 330                 335
Arg Pro Ala Glu Val Arg Lys Val Cys Tyr Asn Ala Val Leu Thr His
                340                 345                 350
Val Lys Ile Asn Asp Lys Cys Pro Ser Thr Gly Glu Ala His Leu Ala
                355                 360                 365
Glu Glu Asn Glu Gly Asp Asn Ala Cys Lys Arg Thr Tyr Ser Asp Arg
370                 375                 380
Gly Trp Gly Asn Gly Cys Gly Leu Phe Gly Lys Gly Ser Ile Val Ala
385                 390                 395                 400
Cys Ala Lys Phe Thr Cys Ala Lys Ser Met Ser Leu Phe Glu Val Asp
                405                 410                 415
Gln Thr Lys Ile Gln Tyr Val Ile Arg Ala Gln Leu His Val Gly Ala
                420                 425                 430
Lys Gln Glu Asn Trp Asn Thr Asp Ile Lys Thr Leu Lys Phe Asp Ala
                435                 440                 445
Leu Ser Gly Ser Gln Glu Val Glu Phe Ile Gly Tyr Gly Lys Ala Thr
450                 455                 460
Leu Glu Cys Gln Val Gln Thr Ala Val Asp Phe Gly Asn Ser Tyr Ile
465                 470                 475                 480
Ala Glu Met Glu Thr Glu Ser Trp Ile Val Asp Arg Gln Trp Ala Gln
                485                 490                 495
Asp Leu Thr Leu Pro Trp Gln Ser Gly Ser Gly Gly Val Trp Arg Glu
                500                 505                 510
Met His His Leu Val Glu Phe Glu Pro Pro His Ala Ala Thr Ile Arg
                515                 520                 525
Val Leu Ala Leu Gly Asn Gln Glu Gly Ser Leu Lys Thr Ala Leu Thr
530                 535                 540
Gly Ala Met Arg Val Thr Lys Asp Thr Asn Asp Asn Leu Tyr Lys
545                 550                 555                 560
Leu His Gly Gly His Val Ser Cys Arg Val Lys Leu Ser Ala Leu Thr
                565                 570                 575
Leu Lys Gly Thr Ser Tyr Lys Ile Cys Thr Asp Lys Met Phe Phe Val
                580                 585                 590
Lys Asn Pro Thr Asp Thr Gly His Gly Thr Val Val Met Gln Val Lys
                595                 600                 605
Val Ser Lys Gly Ala Pro Cys Arg Ile Pro Val Ile Val Ala Asp Asp
610                 615                 620
Leu Thr Ala Ala Ile Asn Lys Gly Ile Leu Val Thr Val Asn Pro Ile
625                 630                 635                 640
Ala Ser Thr Asn Asp Asp Glu Val Leu Ile Glu Val Asn Pro Pro Phe
                645                 650                 655
Gly Asp Ser Tyr Ile Ile Val Gly Arg Gly Asp Ser Arg Leu Thr Tyr
                660                 665                 670
Gln Trp His Lys Glu Gly Ser Ser Ile Gly Lys Leu Phe Thr Gln Thr
                675                 680                 685
Met Lys Gly Val Glu Arg Leu Ala Val Met Gly Asp Thr Ala Trp Asp
690                 695                 700
```

```
Phe Ser Ser Ala Gly Gly Phe Phe Thr Ser Val Gly Lys Gly Ile His
705                 710                 715                 720

Thr Val Phe Gly Ser Ala Phe Gln Gly Leu Phe Gly Gly Leu Asn Trp
            725                 730                 735

Ile Thr Lys Val Ile Met Gly Ala Val Leu Ile Trp Val Gly Ile Asn
            740                 745                 750

Thr Arg Asn Met Thr Met Ser Met Ser Met Ile Leu Val Gly Val Ile
            755                 760                 765

Met Met Phe Leu Ser Leu Gly Val Gly Ala Asp Gln Gly Cys Ala Ile
770                 775                 780

Asn Phe Gly Lys Arg Glu Leu Lys Cys Gly Asp Gly Ile Phe Ile Phe
785                 790                 795                 800

Arg Asp Ser Asp Asp Trp Leu Asn Lys Tyr Ser Tyr Tyr Pro Glu Asp
            805                 810                 815

Pro Val Lys Leu Ala Ser Ile Val Lys Ala Ser Phe Glu Glu Gly Lys
            820                 825                 830

Cys Gly Leu Asn Ser Val Asp Ser Leu Glu His Glu Met Trp Arg Ser
            835                 840                 845

Arg Ala Asp Glu Ile Asn Ala Ile Phe Glu Glu Asn Glu Val Asp Ile
850                 855                 860

Ser Val Val Gln Asp Pro Lys Asn Val Tyr Gln Arg Gly Thr His
865                 870                 875                 880

Pro Phe Ser Arg Ile Arg Asp Gly Leu Gln Tyr Gly Trp Lys Thr Trp
                885                 890                 895

Gly Lys Asn Leu Val Phe Ser Pro Gly Arg Lys Asn Gly Ser Phe Ile
            900                 905                 910

Ile Asp Gly Lys Ser Arg Lys Glu Cys Pro Phe Ser Asn Arg Val Trp
            915                 920                 925

Asn Ser Phe Gln Ile Glu Glu Phe Gly Thr Gly Val Phe Thr Thr Arg
930                 935                 940

Val Tyr Met Asp Ala Val Phe Glu Tyr Thr Ile Asp Cys Asp Gly Ser
945                 950                 955                 960

Ile Leu Gly Ala Ala Val Asn Gly Lys Lys Ser Ala His Gly Ser Pro
            965                 970                 975

Thr Phe Trp Met Gly Ser His Glu Val Asn Gly Thr Trp Met Ile His
            980                 985                 990

Thr Leu Glu Ala Leu Asp Tyr Lys Glu Cys Glu Trp Pro Leu Thr His
            995                 1000                1005

Thr Ile Gly Thr Ser Val Glu Ser Glu Met Phe Met Pro Arg
    1010                1015                1020

Ser Ile Gly Gly Pro Val Ser Ser His Asn His Ile Pro Gly Tyr
    1025                1030                1035

Lys Val Gln Thr Asn Gly Pro Trp Met Gln Val Pro Leu Glu Val
    1040                1045                1050

Lys Arg Glu Ala Cys Pro Gly Thr Ser Val Ile Ile Asp Gly Asn
    1055                1060                1065

Cys Asp Gly Arg Gly Lys Ser Thr Arg Ser Thr Thr Asp Ser Gly
    1070                1075                1080

Lys Val Ile Pro Glu Trp Cys Cys Arg Ser Cys Thr Met Pro Pro
    1085                1090                1095

Val Ser Phe His Gly Ser Asp Gly Cys Trp Tyr Pro Met Glu Ile
    1100                1105                1110

Arg Pro Arg Lys Thr His Glu Ser His Leu Val Arg Ser Trp Val
```

-continued

```
              1115                1120                1125
Thr Ala Gly Glu Ile His Ala Val Pro Phe Gly Leu Val Ser Met
              1130                1135                1140
Met Ile Ala Met Glu Val Val Leu Arg Lys Arg Gln Gly Pro Lys
              1145                1150                1155
Gln Met Leu Val Gly Gly Val Val Leu Leu Gly Ala Met Leu Val
              1160                1165                1170
Gly Gln Val Thr Leu Leu Asp Leu Leu Lys Leu Thr Val Ala Val
              1175                1180                1185
Gly Leu His Phe His Glu Met Asn Asn Gly Gly Asp Ala Met Tyr
              1190                1195                1200
Met Ala Leu Ile Ala Ala Phe Ser Ile Arg Pro Gly Leu Leu Ile
              1205                1210                1215
Gly Phe Gly Leu Arg Thr Leu Trp Ser Pro Arg Glu Arg Leu Val
              1220                1225                1230
Leu Thr Leu Gly Ala Ala Met Val Glu Ile Ala Leu Gly Gly Val
              1235                1240                1245
Met Gly Gly Leu Trp Lys Tyr Leu Asn Ala Val Ser Leu Cys Ile
              1250                1255                1260
Leu Thr Ile Asn Ala Val Ala Ser Arg Lys Ala Ser Asn Thr Ile
              1265                1270                1275
Leu Pro Leu Met Ala Leu Leu Thr Pro Val Thr Met Ala Glu Val
              1280                1285                1290
Arg Leu Ala Ala Met Phe Phe Cys Ala Val Val Ile Ile Gly Val
              1295                1300                1305
Leu His Gln Asn Phe Lys Asp Thr Ser Met Gln Lys Thr Ile Pro
              1310                1315                1320
Leu Val Ala Leu Thr Leu Thr Ser Tyr Leu Gly Leu Thr Gln Pro
              1325                1330                1335
Phe Leu Gly Leu Cys Ala Phe Leu Ala Thr Arg Ile Phe Gly Arg
              1340                1345                1350
Arg Ser Ile Pro Val Asn Glu Ala Leu Ala Ala Ala Gly Leu Val
              1355                1360                1365
Gly Val Leu Ala Gly Leu Ala Phe Gln Glu Met Glu Asn Phe Leu
              1370                1375                1380
Gly Pro Ile Ala Val Gly Gly Leu Leu Met Met Leu Val Ser Val
              1385                1390                1395
Ala Gly Arg Val Asp Gly Leu Glu Leu Lys Lys Leu Gly Glu Val
              1400                1405                1410
Ser Trp Glu Glu Glu Ala Glu Ile Ser Gly Ser Ala Arg Tyr
              1415                1420                1425
Asp Val Ala Leu Ser Glu Gln Gly Glu Phe Lys Leu Leu Ser Glu
              1430                1435                1440
Glu Lys Val Pro Trp Asp Gln Val Val Met Thr Ser Leu Ala Leu
              1445                1450                1455
Val Gly Ala Ala Leu His Pro Phe Ala Leu Leu Val Leu Ala
              1460                1465                1470
Gly Trp Leu Phe His Val Arg Gly Ala Arg Arg Ser Gly Asp Val
              1475                1480                1485
Leu Trp Asp Ile Pro Thr Pro Lys Ile Ile Glu Glu Cys Glu His
              1490                1495                1500
Leu Glu Asp Gly Ile Tyr Gly Ile Phe Gln Ser Thr Phe Leu Gly
              1505                1510                1515
```

-continued

```
Ala Ser Gln Arg Gly Val Gly Val Ala Gln Gly Gly Val Phe His
    1520            1525            1530

Thr Met Trp His Val Thr Arg Gly Ala Phe Leu Val Arg Asn Gly
    1535            1540            1545

Lys Lys Leu Ile Pro Ser Trp Ala Ser Val Lys Glu Asp Leu Val
    1550            1555            1560

Ala Tyr Gly Gly Ser Trp Lys Leu Glu Gly Arg Trp Asp Gly Glu
    1565            1570            1575

Glu Glu Val Gln Leu Ile Ala Ala Val Pro Gly Lys Asn Val Val
    1580            1585            1590

Asn Val Gln Thr Lys Pro Ser Leu Phe Lys Val Arg Asn Gly Gly
    1595            1600            1605

Glu Ile Gly Ala Val Ala Leu Asp Tyr Pro Ser Gly Thr Ser Gly
    1610            1615            1620

Ser Pro Ile Val Asn Arg Asn Gly Glu Val Ile Gly Leu Tyr Gly
    1625            1630            1635

Asn Gly Ile Leu Val Gly Asp Asn Ser Phe Val Ser Ala Ile Ser
    1640            1645            1650

Gln Thr Glu Val Lys Glu Glu Gly Lys Glu Glu Leu Gln Glu Ile
    1655            1660            1665

Pro Thr Met Leu Lys Lys Gly Met Thr Thr Val Leu Asp Phe His
    1670            1675            1680

Pro Gly Ala Gly Lys Thr Arg Arg Phe Leu Pro Gln Ile Leu Ala
    1685            1690            1695

Glu Cys Ala Arg Arg Arg Leu Arg Thr Leu Val Leu Ala Pro Thr
    1700            1705            1710

Arg Val Val Leu Ser Glu Met Lys Glu Ala Phe His Gly Leu Asp
    1715            1720            1725

Val Lys Phe His Thr Gln Ala Phe Ser Ala His Gly Ser Gly Arg
    1730            1735            1740

Glu Val Ile Asp Ala Met Cys His Ala Thr Leu Thr Tyr Arg Met
    1745            1750            1755

Leu Glu Pro Thr Arg Val Val Asn Trp Glu Val Ile Ile Met Asp
    1760            1765            1770

Glu Ala His Phe Leu Asp Pro Ala Ser Ile Ala Ala Arg Gly Trp
    1775            1780            1785

Ala Ala His Arg Ala Arg Ala Asn Glu Ser Ala Thr Ile Leu Met
    1790            1795            1800

Thr Ala Thr Pro Pro Gly Thr Ser Asp Glu Phe Pro His Ser Asn
    1805            1810            1815

Gly Glu Ile Glu Asp Val Gln Thr Asp Ile Pro Ser Glu Pro Trp
    1820            1825            1830

Asn Thr Gly His Asp Trp Ile Leu Ala Asp Lys Arg Pro Thr Ala
    1835            1840            1845

Trp Phe Leu Pro Ser Ile Arg Ala Ala Asn Val Met Ala Ala Ser
    1850            1855            1860

Leu Arg Lys Ala Gly Lys Ser Val Val Val Leu Asn Arg Lys Thr
    1865            1870            1875

Phe Glu Arg Glu Tyr Pro Thr Ile Lys Gln Lys Lys Pro Asp Phe
    1880            1885            1890

Ile Leu Ala Thr Asp Ile Ala Glu Met Gly Ala Asn Leu Cys Val
    1895            1900            1905
```

-continued

| | | | | | | | | | | | | |
|---|---|---|---|---|---|---|---|---|---|---|---|---|
| Glu | Arg | Val | Leu | Asp | Cys | Arg | Thr | Ala | Phe | Lys | Pro | Val | Leu | Val |
| 1910 | | | | | 1915 | | | | | 1920 | | |

Asp Glu Gly Arg Lys Val Ala Ile Lys Gly Pro Leu Arg Ile Ser
1925                     1930                    1935

Ala Ser Ser Ala Ala Gln Arg Arg Gly Arg Ile Gly Arg Asn Pro
1940                     1945                    1950

Asn Arg Asp Gly Asp Ser Tyr Tyr Tyr Ser Glu Pro Thr Ser Glu
1955                     1960                    1965

Asn Asn Ala His His Val Cys Trp Leu Glu Ala Ser Met Leu Leu
1970                     1975                    1980

Asp Asn Met Glu Val Arg Gly Gly Met Val Ala Pro Leu Tyr Gly
1985                     1990                    1995

Val Glu Gly Thr Lys Thr Pro Val Ser Pro Gly Glu Met Arg Leu
2000                     2005                    2010

Arg Asp Asp Gln Arg Lys Val Phe Arg Glu Leu Val Arg Asn Cys
2015                     2020                    2025

Asp Leu Pro Val Trp Leu Ser Trp Gln Val Ala Lys Ala Gly Leu
2030                     2035                    2040

Lys Thr Asn Asp Arg Lys Trp Cys Phe Glu Gly Pro Glu Glu His
2045                     2050                    2055

Glu Ile Leu Asn Asp Ser Gly Glu Thr Val Lys Cys Arg Ala Pro
2060                     2065                    2070

Gly Gly Ala Lys Lys Pro Leu Arg Pro Arg Trp Cys Asp Glu Arg
2075                     2080                    2085

Val Ser Ser Asp Gln Ser Ala Leu Ser Glu Phe Ile Lys Phe Ala
2090                     2095                    2100

Glu Gly Arg Arg Gly Ala Ala Glu Val Leu Val Val Leu Ser Glu
2105                     2110                    2115

Leu Pro Asp Phe Leu Ala Lys Lys Gly Gly Glu Ala Met Asp Thr
2120                     2125                    2130

Ile Ser Val Phe Leu His Ser Glu Glu Gly Ser Arg Ala Tyr Arg
2135                     2140                    2145

Asn Ala Leu Ser Met Met Pro Glu Ala Met Thr Ile Val Met Leu
2150                     2155                    2160

Phe Ile Leu Ala Gly Leu Leu Thr Ser Gly Met Val Ile Phe Phe
2165                     2170                    2175

Met Ser Pro Lys Gly Ile Ser Arg Met Ser Met Ala Met Gly Thr
2180                     2185                    2190

Met Ala Gly Cys Gly Tyr Leu Met Phe Leu Gly Gly Val Lys Pro
2195                     2200                    2205

Thr His Ile Ser Tyr Val Met Leu Ile Phe Phe Val Leu Met Val
2210                     2215                    2220

Val Val Ile Pro Glu Pro Gly Gln Gln Arg Ser Ile Gln Asp Asn
2225                     2230                    2235

Gln Val Ala Tyr Leu Ile Ile Gly Ile Leu Thr Leu Val Ser Ala
2240                     2245                    2250

Val Ala Ala Asn Glu Leu Gly Met Leu Glu Lys Thr Lys Glu Asp
2255                     2260                    2265

Leu Phe Gly Lys Lys Asn Leu Ile Pro Ser Ser Ala Ser Pro Trp
2270                     2275                    2280

Ser Trp Pro Asp Leu Asp Leu Lys Pro Gly Ala Ala Trp Thr Val
2285                     2290                    2295

Tyr Val Gly Ile Val Thr Met Leu Ser Pro Met Leu His His Trp

```
            2300                2305                2310

Ile Lys Val Glu Tyr Gly Asn Leu Ser Leu Ser Gly Ile Ala Gln
    2315                2320                2325

Ser Ala Ser Val Leu Ser Phe Met Asp Lys Gly Ile Pro Phe Met
    2330                2335                2340

Lys Met Asn Ile Ser Val Ile Met Leu Leu Val Ser Gly Trp Asn
    2345                2350                2355

Ser Ile Thr Val Met Pro Leu Leu Cys Gly Ile Gly Cys Ala Met
    2360                2365                2370

Leu His Trp Ser Leu Ile Leu Pro Gly Ile Lys Ala Gln Gln Ser
    2375                2380                2385

Lys Leu Ala Gln Arg Arg Val Phe His Gly Val Ala Glu Asn Pro
    2390                2395                2400

Val Val Asp Gly Asn Pro Thr Val Asp Ile Glu Glu Ala Pro Glu
    2405                2410                2415

Met Pro Ala Leu Tyr Glu Lys Lys Leu Ala Leu Tyr Leu Leu Leu
    2420                2425                2430

Ala Leu Ser Leu Ala Ser Val Ala Met Cys Arg Thr Pro Phe Ser
    2435                2440                2445

Leu Ala Glu Gly Ile Val Leu Ala Ser Ala Ala Leu Gly Pro Leu
    2450                2455                2460

Ile Glu Gly Asn Thr Ser Leu Leu Trp Asn Gly Pro Met Ala Val
    2465                2470                2475

Ser Met Thr Gly Val Met Arg Gly Asn His Tyr Ala Phe Val Gly
    2480                2485                2490

Val Met Tyr Asn Leu Trp Lys Met Lys Thr Gly Arg Arg Gly Ser
    2495                2500                2505

Ala Asn Gly Lys Thr Leu Gly Glu Val Trp Lys Arg Glu Leu Asn
    2510                2515                2520

Leu Leu Asp Lys Arg Gln Phe Glu Leu Tyr Lys Arg Thr Asp Ile
    2525                2530                2535

Val Glu Val Asp Arg Asp Thr Ala Arg Arg His Leu Ala Glu Gly
    2540                2545                2550

Lys Val Asp Thr Gly Val Ala Val Ser Arg Gly Thr Ala Lys Leu
    2555                2560                2565

Arg Trp Phe His Glu Arg Gly Tyr Val Lys Leu Glu Gly Arg Val
    2570                2575                2580

Ile Asp Leu Gly Cys Gly Arg Gly Gly Trp Cys Tyr Tyr Ala Ala
    2585                2590                2595

Ala Gln Lys Glu Val Ser Gly Val Lys Gly Phe Thr Leu Gly Arg
    2600                2605                2610

Asp Gly His Glu Lys Pro Met Asn Val Gln Ser Leu Gly Trp Asn
    2615                2620                2625

Ile Ile Thr Phe Lys Asp Lys Thr Asp Ile His Arg Leu Glu Pro
    2630                2635                2640

Val Lys Cys Asp Thr Leu Leu Cys Asp Ile Gly Glu Ser Ser Ser
    2645                2650                2655

Ser Ser Val Thr Glu Gly Glu Arg Thr Val Arg Val Leu Asp Thr
    2660                2665                2670

Val Glu Lys Trp Leu Ala Cys Gly Val Asp Asn Phe Cys Val Lys
    2675                2680                2685

Val Leu Ala Pro Tyr Met Pro Asp Val Leu Glu Lys Leu Glu Leu
    2690                2695                2700
```

```
Leu Gln Arg Arg Phe Gly Gly Thr Val Ile Arg Asn Pro Leu Ser
2705                2710                2715

Arg Asn Ser Thr His Glu Met Tyr Tyr Val Ser Gly Ala Arg Ser
2720                2725                2730

Asn Val Thr Phe Thr Val Asn Gln Thr Ser Arg Leu Leu Met Arg
2735                2740                2745

Arg Met Arg Arg Pro Thr Gly Lys Val Thr Leu Glu Ala Asp Val
2750                2755                2760

Ile Leu Pro Ile Gly Thr Arg Ser Val Glu Thr Asp Lys Gly Pro
2765                2770                2775

Leu Asp Lys Glu Ala Ile Glu Glu Arg Val Glu Arg Ile Lys Ser
2780                2785                2790

Glu Tyr Met Thr Ser Trp Phe Tyr Asp Asn Asp Asn Pro Tyr Arg
2795                2800                2805

Thr Trp His Tyr Cys Gly Ser Tyr Val Thr Lys Thr Ser Gly Ser
2810                2815                2820

Ala Ala Ser Met Val Asn Gly Val Ile Lys Ile Leu Thr Tyr Pro
2825                2830                2835

Trp Asp Arg Ile Glu Glu Val Thr Arg Met Ala Met Thr Asp Thr
2840                2845                2850

Thr Pro Phe Gly Gln Gln Arg Val Phe Lys Glu Lys Val Asp Thr
2855                2860                2865

Arg Ala Lys Asp Pro Pro Ala Gly Thr Arg Lys Ile Met Lys Val
2870                2875                2880

Val Asn Arg Trp Leu Phe Arg His Leu Ala Arg Glu Lys Asn Pro
2885                2890                2895

Arg Leu Cys Thr Lys Glu Glu Phe Ile Ala Lys Val Arg Ser His
2900                2905                2910

Ala Ala Ile Gly Ala Tyr Leu Glu Glu Gln Glu Gln Trp Lys Thr
2915                2920                2925

Ala Asn Glu Ala Val Gln Asp Pro Lys Phe Trp Glu Leu Val Asp
2930                2935                2940

Glu Glu Arg Lys Leu His Gln Gln Gly Arg Cys Arg Thr Cys Val
2945                2950                2955

Tyr Asn Met Met Gly Lys Arg Glu Lys Lys Leu Ser Glu Phe Gly
2960                2965                2970

Lys Ala Lys Gly Ser Arg Ala Ile Trp Tyr Met Trp Leu Gly Ala
2975                2980                2985

Arg Tyr Leu Glu Phe Glu Ala Leu Gly Phe Leu Asn Glu Asp His
2990                2995                3000

Trp Ala Ser Arg Glu Asn Ser Gly Gly Gly Val Glu Gly Ile Gly
3005                3010                3015

Leu Gln Tyr Leu Gly Tyr Val Ile Arg Asp Leu Ala Ala Met Asp
3020                3025                3030

Gly Gly Gly Phe Tyr Ala Asp Asp Thr Ala Gly Trp Asp Thr Arg
3035                3040                3045

Ile Thr Glu Ala Asp Leu Asp Asp Glu Gln Glu Ile Leu Asn Tyr
3050                3055                3060

Met Ser Pro His His Lys Lys Leu Ala Gln Ala Val Met Glu Met
3065                3070                3075

Thr Tyr Lys Asn Lys Val Val Lys Val Leu Arg Pro Ala Pro Gly
3080                3085                3090
```

| | | | | | | | | | | | |
|---|---|---|---|---|---|---|---|---|---|---|---|
| Gly | Lys | Ala | Tyr | Met | Asp | Val | Ile | Ser | Arg | Arg | Asp | Gln | Arg | Gly |
| | 3095 | | | | 3100 | | | | | 3105 | | | | |

Gly Lys Ala Tyr Met Asp Val Ile Ser Arg Arg Asp Gln Arg Gly
        3095                3100                    3105

Ser Gly Gln Val Val Thr Tyr Ala Leu Asn Thr Ile Thr Asn Leu
        3110                3115                    3120

Lys Val Gln Leu Ile Arg Met Ala Glu Ala Glu Met Val Ile His
        3125                3130                    3135

His Gln His Val Gln Asp Cys Asp Glu Ser Val Leu Thr Arg Leu
        3140                3145                    3150

Glu Ala Trp Leu Thr Glu His Gly Cys Asp Arg Leu Lys Arg Met
        3155                3160                    3165

Ala Val Ser Gly Asp Asp Cys Val Val Arg Pro Ile Asp Asp Arg
        3170                3175                    3180

Phe Gly Leu Ala Leu Ser His Leu Asn Ala Met Ser Lys Val Arg
        3185                3190                    3195

Lys Asp Ile Ser Glu Trp Gln Pro Ser Lys Gly Trp Asn Asp Trp
        3200                3205                    3210

Glu Asn Val Pro Phe Cys Ser His His Phe His Glu Leu Gln Leu
        3215                3220                    3225

Lys Asp Gly Arg Arg Ile Val Val Pro Cys Arg Glu Gln Asp Glu
        3230                3235                    3240

Leu Ile Gly Arg Gly Arg Val Ser Pro Gly Asn Gly Trp Met Ile
        3245                3250                    3255

Lys Glu Thr Ala Cys Leu Ser Lys Ala Tyr Ala Asn Met Trp Ser
        3260                3265                    3270

Leu Met Tyr Phe His Lys Arg Asp Met Arg Leu Leu Ser Leu Ala
        3275                3280                    3285

Val Ser Ser Ala Val Pro Thr Ser Trp Val Pro Gln Gly Arg Thr
        3290                3295                    3300

Thr Trp Ser Ile His Gly Lys Gly Glu Trp Met Thr Thr Glu Asp
        3305                3310                    3315

Met Leu Glu Val Trp Asn Arg Val Trp Ile Thr Asn Asn Pro His
        3320                3325                    3330

Met Gln Asp Lys Thr Met Val Lys Lys Trp Arg Asp Val Pro Tyr
        3335                3340                    3345

Leu Thr Lys Arg Gln Asp Lys Leu Cys Gly Ser Leu Ile Gly Met
        3350                3355                    3360

Thr Asn Arg Ala Thr Trp Ala Ser His Ile His Leu Val Ile His
        3365                3370                    3375

Arg Ile Arg Thr Leu Ile Gly Gln Glu Lys Tyr Thr Asp Tyr Leu
        3380                3385                    3390

Thr Val Met Asp Arg Tyr Ser Val Asp Ala Asp Leu Gln Leu Gly
        3395                3400                    3405

Glu Leu Ile
        3410

<210> SEQ ID NO 28
<211> LENGTH: 3430
<212> TYPE: PRT
<213> ORGANISM: West Nile virus
<300> PUBLICATION INFORMATION:
<308> DATABASE ACCESSION NUMBER: NCBI / NP_041724.2
<309> DATABASE ENTRY DATE: 2016-08-27
<313> RELEVANT RESIDUES IN SEQ ID NO: (1)..(3430)

<400> SEQUENCE: 28

```
Met Ser Lys Lys Pro Gly Gly Pro Gly Lys Asn Arg Ala Val Asn Met
```

-continued

```
1               5                   10                  15
Leu Lys Arg Gly Met Pro Arg Gly Leu Ser Leu Ile Gly Leu Lys Arg
         20                  25                  30
Ala Met Leu Ser Leu Ile Asp Gly Lys Gly Pro Ile Arg Phe Val Leu
         35                  40                  45
Ala Leu Leu Ala Phe Phe Arg Phe Thr Ala Ile Ala Pro Thr Arg Ala
 50                  55                  60
Val Leu Asp Arg Trp Arg Gly Val Asn Lys Gln Thr Ala Met Lys His
 65                  70                  75                  80
Leu Leu Ser Phe Lys Lys Glu Leu Gly Thr Leu Thr Ser Ala Ile Asn
                 85                  90                  95
Arg Arg Ser Thr Lys Gln Lys Lys Arg Gly Gly Thr Ala Gly Phe Thr
                100                 105                 110
Ile Leu Leu Gly Leu Ile Ala Cys Ala Gly Ala Val Thr Leu Ser Asn
                115                 120                 125
Phe Gln Gly Lys Val Met Met Thr Val Asn Ala Thr Asp Val Thr Asp
         130                 135                 140
Val Ile Thr Ile Pro Thr Ala Ala Gly Lys Asn Leu Cys Ile Val Arg
145                 150                 155                 160
Ala Met Asp Val Gly Tyr Leu Cys Glu Asp Thr Ile Thr Tyr Glu Cys
                        165                 170                 175
Pro Val Leu Ala Ala Gly Asn Asp Pro Glu Asp Ile Asp Cys Trp Cys
                180                 185                 190
Thr Lys Ser Ser Val Tyr Val Arg Tyr Gly Arg Cys Thr Lys Thr Arg
                195                 200                 205
His Ser Arg Arg Ser Arg Arg Ser Leu Thr Val Gln Thr His Gly Glu
        210                 215                 220
Ser Thr Leu Ala Asn Lys Lys Gly Ala Trp Leu Asp Ser Thr Lys Ala
225                 230                 235                 240
Thr Arg Tyr Leu Val Lys Thr Glu Ser Trp Ile Leu Arg Asn Pro Gly
                        245                 250                 255
Tyr Ala Leu Val Ala Ala Val Ile Gly Trp Met Leu Gly Ser Asn Thr
                260                 265                 270
Met Gln Arg Val Val Phe Ala Ile Leu Leu Leu Leu Val Ala Pro Ala
        275                 280                 285
Tyr Ser Phe Asn Cys Leu Gly Met Ser Asn Arg Asp Phe Leu Glu Gly
        290                 295                 300
Val Ser Gly Ala Thr Trp Val Asp Leu Val Leu Glu Gly Asp Ser Cys
305                 310                 315                 320
Val Thr Ile Met Ser Lys Asp Lys Pro Thr Ile Asp Val Lys Met Met
                        325                 330                 335
Asn Met Glu Ala Ala Asn Leu Ala Asp Val Arg Ser Tyr Cys Tyr Leu
                340                 345                 350
Ala Ser Val Ser Asp Leu Ser Thr Arg Ala Ala Cys Pro Thr Met Gly
                355                 360                 365
Glu Ala His Asn Glu Lys Arg Ala Asp Pro Ala Phe Val Cys Lys Gln
        370                 375                 380
Gly Val Val Asp Arg Gly Trp Gly Asn Gly Cys Gly Leu Phe Gly Lys
385                 390                 395                 400
Gly Ser Ile Asp Thr Cys Ala Lys Phe Ala Cys Thr Thr Lys Ala Thr
                        405                 410                 415
Gly Trp Ile Ile Gln Lys Glu Asn Ile Lys Tyr Glu Val Ala Ile Phe
                420                 425                 430
```

```
Val His Gly Pro Thr Thr Val Glu Ser His Gly Lys Ile Gly Ala Thr
            435                 440                 445

Gln Ala Gly Arg Phe Ser Ile Thr Pro Ser Ala Pro Ser Tyr Thr Leu
    450                 455                 460

Lys Leu Gly Glu Tyr Gly Glu Val Thr Val Asp Cys Glu Pro Arg Ser
465                 470                 475                 480

Gly Ile Asp Thr Ser Ala Tyr Tyr Val Met Ser Val Gly Glu Lys Ser
                485                 490                 495

Phe Leu Val His Arg Glu Trp Phe Met Asp Leu Asn Leu Pro Trp Ser
                500                 505                 510

Ser Ala Gly Ser Thr Thr Trp Arg Asn Arg Glu Thr Leu Met Glu Phe
            515                 520                 525

Glu Glu Pro His Ala Thr Lys Gln Ser Val Val Ala Leu Gly Ser Gln
    530                 535                 540

Glu Gly Ala Leu His Gln Ala Leu Ala Gly Ala Ile Pro Val Glu Phe
545                 550                 555                 560

Ser Ser Asn Thr Val Lys Leu Thr Ser Gly His Leu Lys Cys Arg Val
                565                 570                 575

Lys Met Glu Lys Leu Gln Leu Lys Gly Thr Thr Tyr Gly Val Cys Ser
            580                 585                 590

Lys Ala Phe Lys Phe Ala Arg Thr Pro Ala Asp Thr Gly His Gly Thr
    595                 600                 605

Val Val Leu Glu Leu Gln Tyr Thr Gly Thr Asp Gly Pro Cys Lys Val
    610                 615                 620

Pro Ile Ser Ser Val Ala Ser Leu Asn Asp Leu Thr Pro Val Gly Arg
625                 630                 635                 640

Leu Val Thr Val Asn Pro Phe Val Ser Val Ala Thr Ala Asn Ser Lys
                645                 650                 655

Val Leu Ile Glu Leu Glu Pro Pro Phe Gly Asp Ser Tyr Ile Val Val
            660                 665                 670

Gly Arg Gly Glu Gln Gln Ile Asn His His Trp His Lys Ser Gly Ser
    675                 680                 685

Ser Ile Gly Lys Ala Phe Thr Thr Thr Leu Arg Gly Ala Gln Arg Leu
    690                 695                 700

Ala Ala Leu Gly Asp Thr Ala Trp Asp Phe Gly Ser Val Gly Gly Val
705                 710                 715                 720

Phe Thr Ser Val Gly Lys Ala Ile His Gln Val Phe Gly Gly Ala Phe
                725                 730                 735

Arg Ser Leu Phe Gly Gly Met Ser Trp Ile Thr Gln Gly Leu Leu Gly
            740                 745                 750

Ala Leu Leu Leu Trp Met Gly Ile Asn Ala Arg Asp Arg Ser Ile Ala
    755                 760                 765

Met Thr Phe Leu Ala Val Gly Gly Val Leu Leu Phe Leu Ser Val Asn
770                 775                 780

Val His Ala Asp Thr Gly Cys Ala Ile Asp Ile Gly Arg Gln Glu Leu
785                 790                 795                 800

Arg Cys Gly Ser Gly Val Phe Ile His Asn Asp Val Glu Ala Trp Met
                805                 810                 815

Asp Arg Tyr Lys Phe Tyr Pro Glu Thr Pro Gln Gly Leu Ala Lys Ile
            820                 825                 830

Ile Gln Lys Ala His Ala Glu Gly Val Cys Gly Leu Arg Ser Val Ser
    835                 840                 845
```

Arg Leu Glu His Gln Met Trp Glu Ala Ile Lys Asp Glu Leu Asn Thr
850                 855                 860

Leu Leu Lys Glu Asn Gly Val Asp Leu Ser Val Val Glu Lys Gln
865                 870                 875                 880

Asn Gly Met Tyr Lys Ala Ala Pro Lys Arg Leu Ala Ala Thr Thr Glu
                885                 890                 895

Lys Leu Glu Met Gly Trp Lys Ala Trp Gly Lys Ser Ile Ile Phe Ala
                900                 905                 910

Pro Glu Leu Ala Asn Asn Thr Phe Val Ile Asp Gly Pro Glu Thr Glu
                915                 920                 925

Glu Cys Pro Thr Ala Asn Arg Ala Trp Asn Ser Met Glu Val Glu Asp
930                 935                 940

Phe Gly Phe Gly Leu Thr Ser Thr Arg Met Phe Leu Arg Ile Arg Glu
945                 950                 955                 960

Thr Asn Thr Thr Glu Cys Asp Ser Lys Ile Ile Gly Thr Ala Val Lys
                965                 970                 975

Asn Asn Met Ala Val His Ser Asp Leu Ser Tyr Trp Ile Glu Ser Gly
                980                 985                 990

Leu Asn Asp Thr Trp Lys Leu Glu Arg Ala Val Leu Gly Glu Val Lys
                995                 1000                1005

Ser Cys Thr Trp Pro Glu Thr His Thr Leu Trp Gly Asp Gly Val
    1010                1015                1020

Leu Glu Ser Asp Leu Ile Ile Pro Ile Thr Leu Ala Gly Pro Arg
    1025                1030                1035

Ser Asn His Asn Arg Arg Pro Gly Tyr Lys Thr Gln Asn Gln Gly
    1040                1045                1050

Pro Trp Asp Glu Gly Arg Val Glu Ile Asp Phe Asp Tyr Cys Pro
    1055                1060                1065

Gly Thr Thr Val Thr Ile Ser Asp Ser Cys Glu His Arg Gly Pro
    1070                1075                1080

Ala Ala Arg Thr Thr Thr Glu Ser Gly Lys Leu Ile Thr Asp Trp
    1085                1090                1095

Cys Cys Arg Ser Cys Thr Leu Pro Pro Leu Arg Phe Gln Thr Glu
    1100                1105                1110

Asn Gly Cys Trp Tyr Gly Met Glu Ile Arg Pro Thr Arg His Asp
    1115                1120                1125

Glu Lys Thr Leu Val Gln Ser Arg Val Asn Ala Tyr Asn Ala Asp
    1130                1135                1140

Met Ile Asp Pro Phe Gln Leu Gly Leu Met Val Val Phe Leu Ala
    1145                1150                1155

Thr Gln Glu Val Leu Arg Lys Arg Trp Thr Ala Lys Ile Ser Ile
    1160                1165                1170

Pro Ala Ile Met Leu Ala Leu Leu Val Leu Val Phe Gly Gly Ile
    1175                1180                1185

Thr Tyr Thr Asp Val Leu Arg Tyr Val Ile Leu Val Gly Ala Ala
    1190                1195                1200

Phe Ala Glu Ala Asn Ser Gly Gly Asp Val Val His Leu Ala Leu
    1205                1210                1215

Met Ala Thr Phe Lys Ile Gln Pro Val Phe Leu Val Ala Ser Phe
    1220                1225                1230

Leu Lys Ala Arg Trp Thr Asn Gln Glu Ser Ile Leu Leu Met Leu
    1235                1240                1245

Ala Ala Ala Phe Phe Gln Met Ala Tyr Tyr Asp Ala Lys Asn Val

```
                1250                1255                1260

Leu Ser Trp Glu Val Pro Asp Val Leu Asn Ser Leu Ser Val Ala
        1265                1270                1275

Trp Met Ile Leu Arg Ala Ile Ser Phe Thr Asn Thr Ser Asn Val
        1280                1285                1290

Val Val Pro Leu Leu Ala Leu Leu Thr Pro Gly Leu Lys Cys Leu
        1295                1300                1305

Asn Leu Asp Val Tyr Arg Ile Leu Leu Leu Met Val Gly Val Gly
        1310                1315                1320

Ser Leu Ile Lys Glu Lys Arg Ser Ser Ala Ala Lys Lys Lys Gly
        1325                1330                1335

Ala Cys Leu Ile Cys Leu Ala Leu Ala Ser Thr Gly Val Phe Asn
        1340                1345                1350

Pro Met Ile Leu Ala Ala Gly Leu Met Ala Cys Asp Pro Asn Arg
        1355                1360                1365

Lys Arg Gly Trp Pro Ala Thr Glu Val Met Thr Ala Val Gly Leu
        1370                1375                1380

Met Phe Ala Ile Val Gly Gly Leu Ala Glu Leu Asp Ile Asp Ser
        1385                1390                1395

Met Ala Ile Pro Met Thr Ile Ala Gly Leu Met Phe Ala Ala Phe
        1400                1405                1410

Val Ile Ser Gly Lys Ser Thr Asp Met Trp Ile Glu Arg Thr Ala
        1415                1420                1425

Asp Ile Thr Trp Glu Ser Asp Ala Glu Ile Thr Gly Ser Ser Glu
        1430                1435                1440

Arg Val Asp Val Arg Leu Asp Asp Gly Asn Phe Gln Leu Met
        1445                1450                1455

Asn Asp Pro Gly Ala Pro Trp Lys Ile Trp Met Leu Arg Met Ala
        1460                1465                1470

Cys Leu Ala Ile Ser Ala Tyr Thr Pro Trp Ala Ile Leu Pro Ser
        1475                1480                1485

Val Ile Gly Phe Trp Ile Thr Leu Gln Tyr Thr Lys Arg Gly Gly
        1490                1495                1500

Val Leu Trp Asp Thr Pro Ser Pro Lys Glu Tyr Lys Lys Gly Asp
        1505                1510                1515

Thr Thr Thr Gly Val Tyr Arg Ile Met Thr Arg Gly Leu Leu Gly
        1520                1525                1530

Ser Tyr Gln Ala Gly Ala Gly Val Met Val Glu Gly Val Phe His
        1535                1540                1545

Thr Leu Trp His Thr Thr Lys Gly Ala Ala Leu Met Ser Gly Glu
        1550                1555                1560

Gly Arg Leu Asp Pro Tyr Trp Gly Ser Val Lys Glu Asp Arg Leu
        1565                1570                1575

Cys Tyr Gly Gly Pro Trp Lys Leu Gln His Lys Trp Asn Gly His
        1580                1585                1590

Asp Glu Val Gln Met Ile Val Val Glu Pro Gly Lys Asn Val Lys
        1595                1600                1605

Asn Val Gln Thr Lys Pro Gly Val Phe Lys Thr Pro Glu Gly Glu
        1610                1615                1620

Ile Gly Ala Val Thr Leu Asp Tyr Pro Thr Gly Thr Ser Gly Ser
        1625                1630                1635

Pro Ile Val Asp Lys Asn Gly Asp Val Ile Gly Leu Tyr Gly Asn
        1640                1645                1650
```

```
Gly Val Ile Met Pro Asn Gly Ser Tyr Ile Ser Ala Ile Val Gln
    1655                1660                1665

Gly Glu Arg Met Glu Glu Pro Ala Pro Ala Gly Phe Glu Pro Glu
    1670                1675                1680

Met Leu Arg Lys Lys Gln Ile Thr Val Leu Asp Leu His Pro Gly
    1685                1690                1695

Ala Gly Lys Thr Arg Lys Ile Leu Pro Gln Ile Ile Lys Glu Ala
    1700                1705                1710

Ile Asn Lys Arg Leu Arg Thr Ala Val Leu Ala Pro Thr Arg Val
    1715                1720                1725

Val Ala Ala Glu Met Ser Glu Ala Leu Arg Gly Leu Pro Ile Arg
    1730                1735                1740

Tyr Gln Thr Ser Ala Val His Arg Glu His Ser Gly Asn Glu Ile
    1745                1750                1755

Val Asp Val Met Cys His Ala Thr Leu Thr His Arg Leu Met Ser
    1760                1765                1770

Pro His Arg Val Pro Asn Tyr Asn Leu Phe Ile Met Asp Glu Ala
    1775                1780                1785

His Phe Thr Asp Pro Ala Ser Ile Ala Ala Arg Gly Tyr Ile Ala
    1790                1795                1800

Thr Lys Val Glu Leu Gly Glu Ala Ala Ala Ile Phe Met Thr Ala
    1805                1810                1815

Thr Pro Pro Gly Thr Ser Asp Pro Phe Pro Glu Ser Asn Ala Pro
    1820                1825                1830

Ile Ser Asp Met Gln Thr Glu Ile Pro Asp Arg Ala Trp Asn Thr
    1835                1840                1845

Gly Tyr Glu Trp Ile Thr Glu Tyr Val Gly Lys Thr Val Trp Phe
    1850                1855                1860

Val Pro Ser Val Lys Met Gly Asn Glu Ile Ala Leu Cys Leu Gln
    1865                1870                1875

Arg Ala Gly Lys Lys Val Ile Gln Leu Asn Arg Lys Ser Tyr Glu
    1880                1885                1890

Thr Glu Tyr Pro Lys Cys Lys Asn Asp Asp Trp Asp Phe Val Ile
    1895                1900                1905

Thr Thr Asp Ile Ser Glu Met Gly Ala Asn Phe Lys Ala Ser Arg
    1910                1915                1920

Val Ile Asp Ser Arg Lys Ser Val Lys Pro Thr Ile Ile Glu Glu
    1925                1930                1935

Gly Asp Gly Arg Val Ile Leu Gly Glu Pro Ser Ala Ile Thr Ala
    1940                1945                1950

Ala Ser Ala Ala Gln Arg Arg Gly Arg Ile Gly Arg Asn Pro Ser
    1955                1960                1965

Gln Val Gly Asp Glu Tyr Cys Tyr Gly Gly His Thr Asn Glu Asp
    1970                1975                1980

Asp Ser Asn Phe Ala His Trp Thr Glu Ala Arg Ile Met Leu Asp
    1985                1990                1995

Asn Ile Asn Met Pro Asn Gly Leu Val Ala Gln Leu Tyr Gln Pro
    2000                2005                2010

Glu Arg Glu Lys Val Tyr Thr Met Asp Gly Glu Tyr Arg Leu Arg
    2015                2020                2025

Gly Glu Glu Arg Lys Asn Phe Leu Glu Phe Leu Arg Thr Ala Asp
    2030                2035                2040
```

```
Leu Pro Val Trp Leu Ala Tyr Lys Val Ala Ala Gly Ile Ser
    2045                2050            2055

Tyr His Asp Arg Lys Trp Cys Phe Asp Gly Pro Arg Thr Asn Thr
    2060                2065            2070

Ile Leu Glu Asp Asn Asn Glu Val Glu Val Ile Thr Lys Leu Gly
    2075                2080            2085

Glu Arg Lys Ile Leu Arg Pro Arg Trp Ala Asp Ala Arg Val Tyr
    2090                2095            2100

Ser Asp His Gln Ala Leu Lys Ser Phe Lys Asp Phe Ala Ser Gly
    2105                2110            2115

Lys Arg Ser Gln Ile Gly Leu Val Glu Val Leu Gly Arg Met Pro
    2120                2125            2130

Glu His Phe Met Val Lys Thr Trp Glu Ala Leu Asp Thr Met Tyr
    2135                2140            2145

Val Val Ala Thr Ala Glu Lys Gly Gly Arg Ala His Arg Met Ala
    2150                2155            2160

Leu Glu Glu Leu Pro Asp Ala Leu Gln Thr Ile Val Leu Ile Ala
    2165                2170            2175

Leu Leu Ser Val Met Ser Leu Gly Val Phe Phe Leu Leu Met Gln
    2180                2185            2190

Arg Lys Gly Ile Gly Lys Ile Gly Leu Gly Gly Val Ile Leu Gly
    2195                2200            2205

Ala Ala Thr Phe Phe Cys Trp Met Ala Glu Val Pro Gly Thr Lys
    2210                2215            2220

Ile Ala Gly Met Leu Leu Leu Ser Leu Leu Leu Met Ile Val Leu
    2225                2230            2235

Ile Pro Glu Pro Glu Lys Gln Arg Ser Gln Thr Asp Asn Gln Leu
    2240                2245            2250

Ala Val Phe Leu Ile Cys Val Leu Thr Leu Val Gly Ala Val Ala
    2255                2260            2265

Ala Asn Glu Met Gly Trp Leu Asp Lys Thr Lys Asn Asp Ile Gly
    2270                2275            2280

Ser Leu Leu Gly His Arg Pro Glu Ala Arg Glu Thr Thr Leu Gly
    2285                2290            2295

Val Glu Ser Phe Leu Leu Asp Leu Arg Pro Ala Thr Ala Trp Ser
    2300                2305            2310

Leu Tyr Ala Val Thr Thr Ala Val Leu Thr Pro Leu Leu Lys His
    2315                2320            2325

Leu Ile Thr Ser Asp Tyr Ile Asn Thr Ser Leu Thr Ser Ile Asn
    2330                2335            2340

Val Gln Ala Ser Ala Leu Phe Thr Leu Ala Arg Gly Phe Pro Phe
    2345                2350            2355

Val Asp Val Gly Val Ser Ala Leu Leu Leu Ala Val Gly Cys Trp
    2360                2365            2370

Gly Gln Val Thr Leu Thr Val Thr Val Thr Ala Ala Ala Leu Leu
    2375                2380            2385

Phe Cys His Tyr Ala Tyr Met Val Pro Gly Trp Gln Ala Glu Ala
    2390                2395            2400

Met Arg Ser Ala Gln Arg Arg Thr Ala Ala Gly Ile Met Lys Asn
    2405                2410            2415

Val Val Val Asp Gly Ile Val Ala Thr Asp Val Pro Glu Leu Glu
    2420                2425            2430

Arg Thr Thr Pro Val Met Gln Lys Lys Val Gly Gln Ile Ile Leu
```

```
                2435                2440                2445

Ile Leu Val Ser Met Ala Ala Val Val Asn Pro Ser Val Arg
    2450                2455                2460

Thr Val Arg Glu Ala Gly Ile Leu Thr Thr Ala Ala Val Thr
    2465                2470                2475

Leu Trp Glu Asn Gly Ala Ser Ser Val Trp Asn Ala Thr Thr Ala
    2480                2485                2490

Ile Gly Leu Cys His Ile Met Arg Gly Gly Trp Leu Ser Cys Leu
    2495                2500                2505

Ser Ile Met Trp Thr Leu Ile Lys Asn Met Glu Lys Pro Gly Leu
    2510                2515                2520

Lys Arg Gly Gly Ala Lys Gly Arg Thr Leu Gly Glu Val Trp Lys
    2525                2530                2535

Glu Arg Leu Asn His Met Thr Lys Glu Glu Phe Thr Arg Tyr Arg
    2540                2545                2550

Lys Glu Ala Ile Thr Glu Val Asp Arg Ser Ala Ala Lys His Ala
    2555                2560                2565

Arg Arg Glu Gly Asn Ile Thr Gly Gly His Pro Val Ser Arg Gly
    2570                2575                2580

Thr Ala Lys Leu Arg Trp Leu Val Glu Arg Arg Phe Leu Glu Pro
    2585                2590                2595

Val Gly Lys Val Val Asp Leu Gly Cys Gly Arg Gly Gly Trp Cys
    2600                2605                2610

Tyr Tyr Met Ala Thr Gln Lys Arg Val Gln Glu Val Lys Gly Tyr
    2615                2620                2625

Thr Lys Gly Gly Pro Gly His Glu Glu Pro Gln Leu Val Gln Ser
    2630                2635                2640

Tyr Gly Trp Asn Ile Val Thr Met Lys Ser Gly Val Asp Val Phe
    2645                2650                2655

Tyr Arg Pro Ser Glu Ala Ser Asp Thr Leu Leu Cys Asp Ile Gly
    2660                2665                2670

Glu Ser Ser Ser Ser Ala Glu Val Glu Glu His Arg Thr Val Arg
    2675                2680                2685

Val Leu Glu Met Val Glu Asp Trp Leu His Arg Gly Pro Lys Glu
    2690                2695                2700

Phe Cys Ile Lys Val Leu Cys Pro Tyr Met Pro Lys Val Ile Glu
    2705                2710                2715

Lys Met Glu Thr Leu Gln Arg Arg Tyr Gly Gly Gly Leu Ile Arg
    2720                2725                2730

Asn Pro Leu Ser Arg Asn Ser Thr His Glu Met Tyr Trp Val Ser
    2735                2740                2745

His Ala Ser Gly Asn Ile Val His Ser Val Asn Met Thr Ser Gln
    2750                2755                2760

Val Leu Leu Gly Arg Met Glu Lys Lys Thr Trp Lys Gly Pro Gln
    2765                2770                2775

Phe Glu Glu Asp Val Asn Leu Gly Ser Gly Thr Arg Ala Val Gly
    2780                2785                2790

Lys Pro Leu Leu Asn Ser Asp Thr Ser Lys Ile Lys Asn Arg Ile
    2795                2800                2805

Glu Arg Leu Lys Lys Glu Tyr Ser Ser Thr Trp His Gln Asp Ala
    2810                2815                2820

Asn His Pro Tyr Arg Thr Trp Asn Tyr His Gly Ser Tyr Glu Val
    2825                2830                2835
```

```
Lys Pro Thr Gly Ser Ala Ser Ser Leu Val Asn Gly Val Val Arg
2840                2845                2850

Leu Leu Ser Lys Pro Trp Asp Thr Ile Thr Asn Val Thr Thr Met
2855                2860                2865

Ala Met Thr Asp Thr Thr Pro Phe Gly Gln Gln Arg Val Phe Lys
2870                2875                2880

Glu Lys Val Asp Thr Lys Ala Pro Glu Pro Pro Glu Gly Val Lys
2885                2890                2895

Tyr Val Leu Asn Glu Thr Thr Asn Trp Leu Trp Ala Phe Leu Ala
2900                2905                2910

Arg Asp Lys Lys Pro Arg Met Cys Ser Arg Glu Glu Phe Ile Gly
2915                2920                2925

Lys Val Asn Ser Asn Ala Ala Leu Gly Ala Met Phe Glu Glu Gln
2930                2935                2940

Asn Gln Trp Lys Asn Ala Arg Glu Ala Val Glu Asp Pro Lys Phe
2945                2950                2955

Trp Glu Met Val Asp Glu Glu Arg Glu Ala His Leu Arg Gly Glu
2960                2965                2970

Cys Asn Thr Cys Ile Tyr Asn Met Met Gly Lys Arg Glu Lys Lys
2975                2980                2985

Pro Gly Glu Phe Gly Lys Ala Lys Gly Ser Arg Ala Ile Trp Phe
2990                2995                3000

Met Trp Leu Gly Ala Arg Phe Leu Glu Phe Glu Ala Leu Gly Phe
3005                3010                3015

Leu Asn Glu Asp His Trp Leu Gly Arg Lys Asn Ser Gly Gly Gly
3020                3025                3030

Val Glu Gly Leu Gly Leu Gln Lys Leu Gly Tyr Ile Leu Lys Glu
3035                3040                3045

Val Gly Thr Lys Pro Gly Gly Lys Val Tyr Ala Asp Asp Thr Ala
3050                3055                3060

Gly Trp Asp Thr Arg Ile Thr Lys Ala Asp Leu Glu Asn Glu Ala
3065                3070                3075

Lys Val Leu Glu Leu Leu Asp Gly Glu His Arg Arg Leu Ala Arg
3080                3085                3090

Ser Ile Ile Glu Leu Thr Tyr Arg His Lys Val Val Lys Val Met
3095                3100                3105

Arg Pro Ala Ala Asp Gly Lys Thr Val Met Asp Val Ile Ser Arg
3110                3115                3120

Glu Asp Gln Arg Gly Ser Gly Gln Val Val Thr Tyr Ala Leu Asn
3125                3130                3135

Thr Phe Thr Asn Leu Ala Val Gln Leu Val Arg Met Met Glu Gly
3140                3145                3150

Glu Gly Val Ile Gly Pro Asp Asp Val Glu Lys Leu Gly Lys Gly
3155                3160                3165

Lys Gly Pro Lys Val Arg Thr Trp Leu Phe Glu Asn Gly Glu Glu
3170                3175                3180

Arg Leu Ser Arg Met Ala Val Ser Gly Asp Asp Cys Val Val Lys
3185                3190                3195

Pro Leu Asp Asp Arg Phe Ala Thr Ser Leu His Phe Leu Asn Ala
3200                3205                3210

Met Ser Lys Val Arg Lys Asp Ile Gln Glu Trp Lys Pro Ser Thr
3215                3220                3225
```

```
Gly Trp Tyr Asp Trp Gln Gln Val Pro Phe Cys Ser Asn His Phe
    3230                3235                3240

Thr Glu Leu Ile Met Lys Asp Gly Arg Thr Leu Val Val Pro Cys
    3245                3250                3255

Arg Gly Gln Asp Glu Leu Ile Gly Arg Ala Arg Ile Ser Pro Gly
    3260                3265                3270

Ala Gly Trp Asn Val Arg Asp Thr Ala Cys Leu Ala Lys Ser Tyr
    3275                3280                3285

Ala Gln Met Trp Leu Leu Leu Tyr Phe His Arg Arg Asp Leu Arg
    3290                3295                3300

Leu Met Ala Asn Ala Ile Cys Ser Ala Val Pro Ala Asn Trp Val
    3305                3310                3315

Pro Thr Gly Arg Thr Thr Trp Ser Ile His Ala Lys Gly Glu Trp
    3320                3325                3330

Met Thr Thr Glu Asp Met Leu Ala Val Trp Asn Arg Val Trp Ile
    3335                3340                3345

Glu Glu Asn Glu Trp Met Glu Asp Lys Thr Pro Val Glu Arg Trp
    3350                3355                3360

Ser Asp Val Pro Tyr Ser Gly Lys Arg Glu Asp Ile Trp Cys Gly
    3365                3370                3375

Ser Leu Ile Gly Thr Arg Thr Arg Ala Thr Trp Ala Glu Asn Ile
    3380                3385                3390

His Val Ala Ile Asn Gln Val Arg Ser Val Ile Gly Glu Glu Lys
    3395                3400                3405

Tyr Val Asp Tyr Met Ser Ser Leu Arg Arg Tyr Glu Asp Thr Ile
    3410                3415                3420

Val Val Glu Asp Thr Val Leu
    3425                3430

<210> SEQ ID NO 29
<211> LENGTH: 701
<212> TYPE: PRT
<213> ORGANISM: Homo sapiens
<300> PUBLICATION INFORMATION:
<308> DATABASE ACCESSION NUMBER: NCBI / AAA02807.1
<309> DATABASE ENTRY DATE: 1993-05-16
<313> RELEVANT RESIDUES IN SEQ ID NO: (1)..(701)

<400> SEQUENCE: 29

Met Ser Val Val Gly Ile Asp Leu Gly Phe Gln Ser Cys Tyr Val Ala
1               5                   10                  15

Val Ala Arg Ala Gly Gly Ile Glu Thr Ile Ala Asn Glu Tyr Ser Asp
            20                  25                  30

Arg Cys Thr Pro Ala Cys Ile Ser Phe Gly Pro Lys Asn Arg Ser Ile
        35                  40                  45

Gly Ala Ala Ala Lys Ser Gln Val Ile Ser Asn Ala Lys Asn Thr Val
    50                  55                  60

Gln Gly Phe Lys Arg Phe His Gly Arg Ala Phe Ser Asp Pro Phe Val
65                  70                  75                  80

Glu Ala Glu Lys Ser Asn Leu Ala Tyr Asp Ile Val Gln Trp Pro Thr
                85                  90                  95

Gly Leu Thr Gly Ile Lys Val Thr Tyr Met Glu Glu Glu Arg Asn Phe
            100                 105                 110

Thr Thr Glu Gln Val Thr Ala Met Leu Leu Ser Lys Leu Lys Glu Thr
        115                 120                 125

Ala Glu Ser Val Leu Lys Lys Pro Val Val Asp Cys Val Val Ser Val
```

```
              130                 135                 140
Pro Cys Phe Tyr Thr Asp Ala Glu Arg Arg Ser Val Met Asp Ala Thr
145                 150                 155                 160

Gln Ile Ala Gly Leu Asn Cys Leu Arg Leu Met Asn Glu Thr Thr Ala
                165                 170                 175

Val Ala Leu Ala Tyr Gly Ile Tyr Lys Gln Asp Leu Pro Arg Leu Glu
                180                 185                 190

Glu Lys Pro Arg Asn Val Val Phe Val Asp Met Gly His Ser Ala Tyr
                195                 200                 205

Gln Val Ser Val Cys Ala Phe Asn Arg Gly Lys Leu Lys Val Leu Ala
            210                 215                 220

Thr Ala Phe Asp Thr Thr Leu Gly Gly Arg Lys Phe Asp Glu Val Leu
225                 230                 235                 240

Val Asn His Phe Cys Glu Glu Phe Gly Lys Lys Tyr Lys Leu Asp Ile
                245                 250                 255

Lys Ser Lys Ile Arg Ala Leu Leu Arg Leu Ser Gln Glu Cys Glu Lys
                260                 265                 270

Leu Lys Lys Leu Met Ser Ala Asn Ala Ser Asp Leu Pro Leu Ser Ile
            275                 280                 285

Glu Cys Phe Met Asn Asp Val Asp Val Ser Gly Thr Met Asn Arg Gly
            290                 295                 300

Lys Phe Leu Glu Met Cys Asn Asp Leu Leu Ala Arg Val Glu Pro Pro
305                 310                 315                 320

Leu Arg Ser Val Leu Glu Gln Thr Lys Leu Lys Lys Glu Asp Ile Tyr
                325                 330                 335

Ala Val Glu Ile Val Gly Gly Ala Thr Arg Ile Pro Ala Val Lys Glu
            340                 345                 350

Lys Ile Ser Lys Phe Phe Gly Lys Glu Leu Ser Thr Thr Leu Asn Ala
            355                 360                 365

Asp Glu Ala Val Thr Arg Gly Cys Ala Leu Gln Cys Ala Ile Leu Ser
        370                 375                 380

Pro Ala Phe Lys Val Arg Glu Phe Ser Ile Thr Asp Val Val Pro Tyr
385                 390                 395                 400

Pro Ile Ser Leu Arg Trp Asn Ser Pro Ala Glu Glu Gly Ser Ser Asp
                405                 410                 415

Cys Glu Val Phe Ser Lys Asn His Ala Ala Pro Phe Ser Lys Val Leu
            420                 425                 430

Thr Phe Tyr Arg Lys Glu Pro Phe Thr Leu Glu Ala Tyr Tyr Ser Ser
            435                 440                 445

Pro Gln Asp Leu Pro Tyr Pro Asp Pro Ala Ile Ala Gln Phe Ser Val
450                 455                 460

Gln Lys Val Thr Pro Gln Ser Asp Gly Ser Ser Ser Lys Val Lys Val
465                 470                 475                 480

Lys Val Arg Val Asn Val His Gly Ile Phe Ser Val Ser Ser Ala Ser
                485                 490                 495

Leu Val Glu Val His Lys Ser Glu Glu Asn Glu Glu Pro Met Glu Thr
            500                 505                 510

Asp Gln Asn Ala Lys Glu Glu Lys Met Gln Val Asp Gln Glu Glu
            515                 520                 525

Pro His Val Glu Glu Gln Gln Gln Thr Pro Ala Glu Asn Lys Ala
        530                 535                 540

Glu Ser Glu Glu Met Glu Thr Ser Gln Ala Gly Ser Lys Asp Lys Lys
545                 550                 555                 560
```

```
Met Asp Gln Pro Pro Gln Cys Gln Glu Gly Lys Ser Glu Asp Gln Tyr
                565                 570                 575

Cys Gly Pro Ala Asn Arg Glu Ser Ala Ile Trp Gln Ile Asp Arg Glu
            580                 585                 590

Met Leu Asn Leu Tyr Ile Glu Asn Glu Gly Lys Met Ile Met Gln Asp
        595                 600                 605

Lys Leu Glu Lys Glu Arg Asn Asp Ala Lys Asn Ala Val Glu Glu Tyr
    610                 615                 620

Val Tyr Glu Met Arg Asp Lys Leu Ser Gly Glu Tyr Glu Lys Phe Val
625                 630                 635                 640

Ser Glu Asp Asp Arg Asn Ser Phe Thr Leu Lys Leu Glu Asp Thr Glu
                645                 650                 655

Asn Trp Leu Tyr Glu Asp Gly Glu Asp Gln Pro Lys Gln Val Tyr Val
            660                 665                 670

Asp Lys Leu Ala Glu Leu Lys Asn Leu Gly Gln Pro Ile Lys Ile Arg
        675                 680                 685

Phe Gln Glu Ser Glu Glu Arg Pro Asn Tyr Leu Lys Asn
    690                 695                 700

<210> SEQ ID NO 30
<211> LENGTH: 653
<212> TYPE: PRT
<213> ORGANISM: Homo sapiens
<300> PUBLICATION INFORMATION:
<308> DATABASE ACCESSION NUMBER: NCBI / CAA61201.1
<309> DATABASE ENTRY DATE: 2008-10-07
<313> RELEVANT RESIDUES IN SEQ ID NO: (1)..(653)

<400> SEQUENCE: 30

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205
```

```
Tyr Gly Leu Asp Lys Arg Glu Gly Glu Lys Asn Ile Leu Val Phe Asp
    210                 215                 220
Leu Gly Gly Thr Phe Asp Val Ser Leu Leu Thr Ile Asp Asn Gly
225                 230                 235                 240
Val Phe Glu Val Val Ala Thr Asn Gly Asp Thr His Leu Gly Gly Glu
                245                 250                 255
Asp Phe Asp Gln Arg Val Met Glu His Phe Ile Lys Leu Tyr Lys Lys
                260                 265                 270
Lys Thr Gly Lys Asp Val Arg Lys Asp Asn Arg Ala Val Gln Lys Leu
                275                 280                 285
Arg Arg Glu Val Glu Lys Ala Lys Ala Leu Ser Ser Gln His Gln Ala
    290                 295                 300
Arg Ile Glu Ile Glu Ser Phe Tyr Glu Gly Glu Asp Phe Ser Glu Thr
305                 310                 315                 320
Leu Thr Arg Ala Lys Phe Glu Glu Leu Asn Met Asp Leu Phe Arg Ser
                325                 330                 335
Thr Met Lys Pro Val Gln Lys Val Leu Glu Asp Ser Asp Leu Lys Lys
                340                 345                 350
Ser Asp Ile Asp Glu Ile Val Leu Val Gly Gly Ser Thr Arg Ile Pro
                355                 360                 365
Lys Ile Gln Gln Leu Val Lys Glu Phe Phe Asn Gly Lys Glu Pro Ser
    370                 375                 380
Arg Gly Ile Asn Pro Asp Glu Ala Val Ala Tyr Gly Ala Ala Val Gln
385                 390                 395                 400
Ala Gly Val Leu Ser Gly Asp Gln Asp Thr Gly Asp Leu Val Leu Leu
                405                 410                 415
His Val Cys Pro Leu Thr Leu Gly Ile Glu Thr Val Gly Gly Val Met
                420                 425                 430
Thr Lys Leu Ile Pro Ser Asn Thr Val Val Pro Thr Lys Asn Ser Gln
    435                 440                 445
Ile Phe Ser Thr Ala Ser Asp Asn Gln Pro Thr Val Thr Ile Lys Val
    450                 455                 460
Tyr Glu Gly Glu Arg Pro Leu Thr Lys Asp Asn His Leu Leu Gly Thr
465                 470                 475                 480
Phe Asp Leu Thr Gly Ile Pro Pro Ala Pro Arg Gly Val Pro Gln Ile
                485                 490                 495
Glu Val Thr Phe Glu Ile Asp Val Asn Gly Ile Leu Arg Val Thr Ala
                500                 505                 510
Glu Asp Lys Gly Thr Gly Asn Lys Asn Lys Ile Thr Ile Thr Asn Asp
                515                 520                 525
Gln Asn Arg Leu Thr Pro Glu Glu Ile Glu Arg Met Val Asn Asp Ala
    530                 535                 540
Glu Lys Phe Ala Glu Glu Asp Lys Lys Leu Lys Glu Arg Ile Asp Thr
545                 550                 555                 560
Arg Asn Glu Leu Glu Ser Tyr Ala Tyr Ser Leu Lys Asn Gln Ile Gly
                565                 570                 575
Asp Lys Glu Lys Leu Gly Gly Lys Leu Ser Ser Glu Asp Lys Glu Thr
                580                 585                 590
Met Glu Lys Ala Val Glu Glu Lys Ile Glu Trp Leu Glu Ser His Gln
                595                 600                 605
Asp Ala Asp Ile Glu Asp Phe Lys Ala Lys Lys Lys Glu Leu Glu Glu
    610                 615                 620
Ile Val Gln Pro Ile Ile Ser Lys Leu Tyr Gly Ser Ala Gly Pro Pro
```

-continued

```
                625                 630                 635                 640
Pro Thr Gly Glu Glu Asp Thr Ala Glu Lys Asp Glu Leu
                        645                 650

<210> SEQ ID NO 31
<211> LENGTH: 654
<212> TYPE: PRT
<213> ORGANISM: Homo sapiens
<300> PUBLICATION INFORMATION:
<308> DATABASE ACCESSION NUMBER: NCBI / NP_005338.1
<309> DATABASE ENTRY DATE: 2016-02-21
<313> RELEVANT RESIDUES IN SEQ ID NO: (1)..(654)

<400> SEQUENCE: 31

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val
                20                  25                  30

Ile Asp Leu Gly Thr Thr Tyr Ser Cys Val Gly Val Phe Lys Asn
            35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335
```

-continued

```
Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650
```

<210> SEQ ID NO 32
<211> LENGTH: 7945
<212> TYPE: DNA
<213> ORGANISM: Deltapapillomavirus 4
<220> FEATURE:
<221> NAME/KEY: misc_feature
<222> LOCATION: (1205)..(1205)
<223> OTHER INFORMATION: n is a, c, g, or t
<300> PUBLICATION INFORMATION:
<308> DATABASE ACCESSION NUMBER: NCBI / NC_001522.1
<309> DATABASE ENTRY DATE: 2010-03-26
<313> RELEVANT RESIDUES IN SEQ ID NO: (1)..(7945)

<400> SEQUENCE: 32
gttaacaata atcacaccat caccgttttt tcaagcggga aaaatagcc agctaactat      60

```
aaaaagctgc tgacagaccc cggttttcac atggacctga aaccttttgc aagaaccaat    120
ccattctcag ggttggattg tctgtggtgc agagagcctc ttacagaagt tgatgctttt    180
aggtgcatgg tcaaagactt tcatgttgta attcgggaag gctgtagata tggtgcatgt    240
accatttgtc ttgaaaactg tttagctact gaaagaagac tttggcaagg tgttccagta    300
acaggtgagg aagctgaatt attgcatggc aaaacacttg ataggctttg cataagatgc    360
tgctactgtg ggggcaaact aacaaaaaat gaaaaacatc ggcatgtgct ttttaatgag    420
cctttctgca aaaccagagc taacataatt agaggacgct gctacgactg ctgcagacat    480
ggttcaaggt ccaaataccc atagaaactt ggatgattca cctgcaggac cgttgctgat    540
tttaagtcca tgtgcaggca cacctaccag gtctcctgca gcacctgatg cacctgatt    600 cagacttccg tgccatttcg gccgtcctac taggaagcga ggtcccacta cccctccgct    660
ttcctctccc ggaaaactgt gtgcaacagg gccacgtcga gtgtattctg tgactgtctg    720
ctgtggaaac tgcggaaaag agctgacttt tgctgtgaag accagctcga cgtccctgct    780
tggatttgaa caccttttaa actcagattt agacctcttg tgtccacgtt gtgaatctcg    840
cgagcgtcat ggcaaacgat aaaggtagca attgggattc gggcttggga tgctcatatc    900
tgctgactga ggcagaatgt gaaagtgaca agagaatga ggaacccggg gcaggtgtag    960
aactgtctgt ggaatctgat cggtatgata gccaggatga ggattttgtt gacaatgcat   1020 cagtcttca gggaaatcac ctggaggtct tccaggcatt agagaaaaag gcgggtgagg   1080
agcagatttt aaatttgaaa agaaaagtat ggggagttc gcaaaacagc agcggttccg   1140
aagcatctga aactccagtt aaaagacgga atcaggagc aaagcgaaga ttatttgctg   1200
aaaangaagc taaccgtgtt cttacgcccc tccaggtaca gggggagggg gaggggaggc   1260
aagaacttaa tgaggagcag gcaattagtc atctacatct gcagcttgtt aaatctaaaa   1320
atgctacagt ttttaagctg gggctctta aatctttgtt cctttgtagc ttccatgata   1380
ttacgaggtt gtttaagaat gataagacca ctaatcagca atgggtgctg gctgtgtttg   1440
gccttgcaga ggtgttttt gaggcgagtt tcgaactcct aaagaagcag tgtagttttc   1500
tgcagatgca aaaagatct catgaaggag gaacttgtgc agtttactta atctgcttta   1560
acacagctaa aagcagagaa acagtccgga atctgatggc aaacacgcta aatgtaagag   1620
aagagtgttt gatgctgcag ccagctaaaa ttcgaggact cagcgcagct ctattctggt   1680
ttaaaagtag tttgtcaccc gctacactta acatggtgc tttacctgag tggatacggg   1740
cgcaaactac tctgaacgag agcttgcaga ccgagaaatt cgacttcgga actatggtgc   1800
aatgggccta tgatcacaaa tatgctgagg agtctaaaat agcctatgaa tatgctttgg   1860
ctgcaggatc tgatagcaat gcacgggctt ttttagcaac taacagccaa gctaagcatg   1920
tgaaggactg tgcaactatg gtaagacact atctaagagc tgaaacacaa gcattaagca   1980
tgcctgcata tattaaagct aggtgcaagc tggcaactgg ggaaggaagc tggaagtcta   2040
tcctaacttt ttttaactat cagaatattg aattaattac ctttattaat gctttaaagc   2100
tctggctaaa aggaattcca aaaaaaaact gtttagcatt tattggccct ccaaacacag   2160
gcaagtctat gctctgcaac tcattaattc atttttgggg tggtagtgtt ttatctttg   2220 ccaaccataa aagtcacttt tggcttgctt ccctagcaga tactagagct gctttagtag   2280
atgatgctac tcatgcttgc tggaggtact ttgacacata cctcagaaat gcattggatg   2340
gctaccctgt cagtattgat agaaaacaca agcagcggt tcaaattaaa gctccacccc   2400
tcctggtaac cagtaatatt gatgtgcagg cagaggacag atatttgtac ttgcatagtc   2460
```

```
gggtgcaaac ctttcgcttt gagcagccat gcacagatga atcgggtgag caacctttta    2520
atattactga tgcagattgg aaatcttttt ttgtaaggtt atgggggcgt ttagacctga    2580
ttgacgagga ggaggatagt gaagaggatg gagacagcat gcgaacgttt acatgtagcg    2640
caagaaacac aaatgcagtt gattgagaaa agtagtgata agttgcaaga tcatatactg    2700
tactggactg ctgttagaac tgagaacaca ctgctttatg ctgcaaggaa aaaggggtg    2760 actgtcctag gacactgcag agtaccacac tctgtagttt gtcaagagag agccaagcag    2820
gccattgaaa tgcagttgtc tttgcaggag ttaagcaaaa ctgagtttgg ggatgaacca    2880
tggtctttgc ttgacacaag ctgggaccga tatatgtcag aacctaaacg gtgctttaag    2940
aaaggcgcca gggtggtaga ggtggagttt gatggaaatg caagcaatac aaactggtac    3000
actgtctaca gcaatttgta catgcgcaca ggagacggct ggcagcttgc gaaggctggg    3060
gctgacggaa ctgggctcta ctactgcacc atggccggtg ctggacgcat ttactattct    3120
cgctttggtg acgaggcagc cagatttagt acaacagggc attactctgt aagagatcag    3180
gacagagtgt atgctggtgt ctcatccacc tcttctgatt ttagagatcg cccagacgga    3240
gtctgggtcg catccgaagg acctgaagga gaccctgcag gaaaagaagc cgagccagcc    3300
cagcctgtct cttctttgct cggctccccc gcctgcggtc ccatcagagc aggcctcggt    3360
tgggtacggg acggtcctcg ctcgcaccc tacaattttc ctgcaggctc ggggggctct    3420
attctccgct cttcctccac cccgtgcagg gcacggtacc ggtggacttg gcatcaaggc    3480
aggaagaaga ggagcagtcg cccgactcca cagaggaaga accagtgact ctcccaaggc    3540
gcaccaccaa tgatggattc cacctgttaa aggcaggagg gtcatgcttt gctctaattt    3600
caggaactgc taaccaggta aagtgctatc gctttcgggt gaaaaagaac catagacatc    3660
gctacgagaa ctgcaccacc acctggttca cagttgctga caacggtgct gaaagacaag    3720
gacaagcaca aatactgatc acctttggat cgccaagtca aaggcaagac tttctgaaac    3780
atgtaccact acctcctgga atgaacattt ccggctttac agccagcttg gacttctgat    3840
cactgccatt gccttttctt catctgactg gtgtactatg ccaaatctat ggtttctatt    3900
gttcttggga ctagttgctg caatgcaact gctgctatta ctgttcttac tcttgttttt    3960
tcttgtatac tgggatcatt ttgagtgctc ctgtacaggt ctgcccttt aatgccttta    4020 catcactggc tattggctgt gttttttactg ttgtgtggat ttgatttgtt ttatatactg    4080
tatgaagttt tttcatttgt gcttgtattg ctgtttgtaa gttttttact agagtttgta    4140
ttccccctgc tcagattta tatggtttaa gctgcagcaa taaaaatgag tgcacgaaaa    4200
agagtaaaac gtgccagtgc ctatgacctg tacaggacat gcaagcaagc gggcacatgt    4260
ccaccagatg tgataccaaa ggtagaagga gatactatag cagataaaat tttgaaattt    4320
gggggtcttg caatctactt aggagggcta ggaataggaa catggtctac tggaagggtt    4380
gctgcaggtg gatcaccaag gtacacacca ctccgaacag cagggccac atcatcgctt    4440 gcatcaatag gatccagagc tgtaacagca gggacccgcc ccagtatagg tgcgggcatt    4500
cctttagaca ccccttgaaac tcttggggcc ttgcgtccag gggtgtatga ggacactgtg    4560
ctaccagagg ccccctgcaat agtcactcct gatgctgttc ctgcagattc agggcttgat    4620
gccctgtcca taggtacaga ctcgtccacg gagaccctca ttactctgct agagcctgag    4680
ggtcccgagg acatagcggt tcttgagctg caacccctgg accgtccaac ttggcaagta    4740
agcaatgctg ttcatcagtc ctctgcatac cacgcccctc tgcagctgca atcgtccatt    4800
```

```
gcagaaacat ctggtttaga aaatatttt gtaggaggct cgggtttagg ggatacagga    4860
ggagaaaaca ttgaactgac atacttcggg tccccacgaa caagcacgcc ccgcagtatt    4920
gcctctaaat cacgtggcat tttaaactgg ttcagtaaac ggtactacac acaggtgccc    4980
acggaagatc ctgaagtgtt ttcatcccaa acatttgcaa acccactgta tgaagcagaa    5040
ccagctgtgc ttaagggacc tagtggacgt gttggactca gtcaggttta taaacctgat    5100
acacttacaa cacgtagcgg gacagaggtg ggaccacagc tacatgtcag gtactcattg    5160
agtactatac atgaagatgt agaagcaatc ccctacacag ttgatgaaaa tacacaggga    5220
cttgcattcg tacccttgca tgaagagcaa gcaggttttg aggagataga attagatgat    5280
tttagtgaga cacatagact gctacctcag aacacctctt ctacacctgt tggtagtggt    5340
gtacgaagaa gcctcattcc aactcaggaa tttagtgcaa cacggcctac aggtgttgta    5400
acctatggct cacctgacac ttactctgct agcccagtta ctgaccctga ttctacctct    5460
cctagtctag ttatcgatga cactactact acaccaatca ttataattga tgggcacaca    5520
gttgatttgt acagcagtaa ctacaccttg catccctcct tgttgaggaa acgaaaaaaa    5580
cggaaacatg cctaatttt tttgcagatg gcgttgtggc aacaaggcca gaagctgtat    5640
ctccctccaa ccccctgtaag caaggtgctt tgcagtgaaa cctatgtgca agaaaaagc    5700
atttttatc atgcagaaac ggagcgcctg ctaactatag gacatccata ttacccagtg    5760
tctatcgggg ccaaaactgt tcctaaggtc tctgcaaatc agtatagggt atttaaaata    5820
caactacctg atcccaatca atttgcacta cctgacagga ctgttcacaa cccaagtaaa    5880
gagcggctgg tgtgggcagt cataggtgtg caggtgtcca gagggcagcc tcttggaggt    5940
actgtaactg ggcaccccac ttttaatgct ttgcttgatg cagaaaatgt gaatagaaaa    6000
gtcaccaccc aaacaacaga tgacaggaaa caaacaggcc tagatgctaa gcaacaacag    6060
attctgttgc taggctgtac ccctgctgaa ggggaatatt ggacaacagc ccgtccatgt    6120
gttactgatc gtctagaaaa tggcgcctgc cctcctcttg aattaaaaaa caagcacata    6180
gaagatgggg atatgatgga aattgggttt ggtgcagcca acttcaaaga aattaatgca    6240
agtaaatcag atctacctct tgacattcaa aatgagatct gcttgtaccc agactacctc    6300
aaaatggctg aggacgctgc tggtaatagc atgttctttt ttgcaaggaa agaacaggtg    6360
tatgttagac acatctggac cagaggggc tcggagaaag aagccctac acagattt    6420
tatttaaaga ataataaagg ggatgccacc cttaaaatac ccagtgtgca ttttggtagt    6480
cccagtggct cactagtctc aactgataat caaatttta atcggcccta ctggctattc    6540
cgtgcccagg gcatgaacaa tggaattgca tggaataatt tattgttttt aacagtgggg    6600
gacaatacac gtggtactaa tcttaccata agtgtagcct cagatggaac cccactaaca    6660
gagtatgata gctcaaaatt caatgtatac catagacata tggaagaata taagctagcc    6720
tttatattag agctatgctc tgtggaaatc acagctcaaa ctgtgtcaca tctgcaagga    6780
cttatgccct ctgtgcttga aaattgggaa ataggtgtgc agcctcctac ctcatcgata    6840
ttagaggaca cctatcgcta tatagagtct cctgcaacta atgtgcaag caatgtaatt    6900
cctgcaaaag aagacccta tgcagggttt aagttttgga acatagatct taagaaaag    6960
cttctttgg acttagatca atttccttg ggaagaagat ttttagcaca gcaaggggca    7020
ggatgttcaa ctgtgagaaa acgaagaatt agccaaaaaa cttccagtaa gcctgcaaaa    7080
aaaaaaaaaa aataaaagct aagtttctat aaatgttctg taaatgtaaa acagaaggta    7140
agtcaactgc acctaataaa aatcacttaa tagcaatgtg ctgtgtcagt tgtttattgg    7200
```

```
aaccacaccc ggtacacatc ctgtccagca tttgcagtgc gtgcattgaa ttattgtgct    7260
ggctagactt catggcgcct ggcaccgaat cctgccttct cagcgaaaat gaataattgc    7320
tttgttggca agaaactaag catcaatggg acgcgtgcaa agcaccggcg gcggtagatg    7380
cggggtaagt actgaatttt aattcgacct atcccggtaa agcgaaagcg acacgctttt    7440
ttttcacaca tagcgggacc gaacacgtta taagtatcga ttaggtctat ttttgtctct    7500
ctgtcggaac cagaactggt aaaagtttcc attgcgtctg ggcttgtcta tcattgcgtc    7560
tctatggttt ttggaggatt agacggggcc accagtaatg gtgcatagcg gatgtctgta    7620
ccgccatcgg tgcaccgata taggtttggg gctccccaag ggactgctgg gatgacagct    7680
tcatattata ttgaatgggc gcataatcag cttaattggt gaggacaagc tacaagttgt    7740
aacctgatct ccacaaagta cgttgccggt cggggtcaaa ccgtcttcgg tgctcgaaac    7800
cgccttaaac tacagacagg tcccagccaa gtaggcggat caaaacctca aaaaggcggg    7860
agccaatcaa aatgcagcat tatattttaa gctcaccgaa accggtaagt aaagactatg    7920 tatttttttcc cagtgaataa ttgtt                                         7945

<210> SEQ ID NO 33
<211> LENGTH: 7412
<212> TYPE: DNA
<213> ORGANISM: Bos taures papillomavirus 7
<300> PUBLICATION INFORMATION:
<308> DATABASE ACCESSION NUMBER: NCBI / NC_007612.1
<309> DATABASE ENTRY DATE: 2011-03-25
<313> RELEVANT RESIDUES IN SEQ ID NO: (1)..(7412)

<400> SEQUENCE: 33
cgttatagtt gtcaacaaca atcactctgt caagtaatga catgaccggt aggggttata      60
ttaagggacc gctttggggg ttcagcacaa atggctgacg aggacgtgat attcgtggac     120
cgactgcgag ctccgtggtg tatcctttgc atgtgctgta aaagatccct aacaaatgac     180
gagagaaaag attttttaaa taagggttta aaaacttttta agaaatggaa taatgggaag     240
aagcgttcgt ttggctgctg cgagacttgc tgtgtatttt tagcaaatga agaggcagaa     300
aaaactcgcg cagaagagat tcatttagaa gcagatggtg tgcagctttt ttgtggagcc     360
cctttgagag atatttccat gaactgtcgc tattgcttag ctgtgctaac tttttatgac     420
aagtacttaa ataaggagaa cagactgccc ttttgcctac gcaggaaaaa gtggagaggc     480
acttgtgaga agtgcctgaa agacaaaaaa cagtgctgat catgcacgat ccagcattgt     540
tctcgtcctc aggagagcag cctccagaag ggattgtgct tgaattgcac ccacttaata     600
caggcaatca tttagtgact gtacctggga cgacagaggt gacttcgtca cctaggtgtc     660
aagaggaggg gccaaggttg tgcttgtatt atatatgtac tgtatgtgct tggtgtcaga     720
gtcacctgcg cctgagtgtg tcaacgtccg attccagcct tagaaaattt caagagcttt     780
tgtgtggtga cttgacagtc gtttgcacac cctgtgcccg aaatggcaga agataaaggt     840
actaaaggcg gtgggggaat ggtcagtggt tcgtggtatt tggatgtgga agctgaatgt     900
gatgagcctg acaatctttg tgacttagaa gcttgttttg ataagtctga cagtgatgat     960
gatccagaat tcattagtaa ctctgatgtt gaggagggga attcttcgga actcttacac    1020
aataatcata tgctagccaa agatggtgag cagatccaac tgctaaagcg aaagtacatg    1080 tcccccaagcc cagataaaga attaagcccg agattagcat tagtgtcaat ttctgctagc    1140
cactctagta agaggaggct ttttccagag acgaaggaca agcatgaagc tagcaattct    1200
```

-continued

```
tctgggtcgg tttcgtccac gcaggttggt tcaaatagcc agagctataa ttccgaggac    1260
ttgagcattg caattcttaa aagcaaaaat cagaaagcaa cagctttagc tcagtttaaa    1320
gaagcctttg gtgtcagctt tacagatttg actaggtcat ttattagcaa taagacttgc    1380
actcagcact gggttgtagc tgtgtttgga ccgaacagtg acattttaga tggcactggt    1440
acactcttag aaccccactg caccttcttg cttaagtgca catgctttgc agaccgtggg    1500
cctataattc tgcttcttat agaatttaaa gccagtaagt gtcgtgatac agtgcaaaat    1560
ttattgaata atattatgag ggttgagcat catcagatgt tgcttgaacc tccaaaaata    1620
aggagccagc ttacagcttt tttttttttat aaaaagacta tggcaggagg ctgcgacgtg    1680
attggcaagt tgcctgattg gctgactcgc ctcactgtgc tcagtcacca aggcgccaca    1740
gaagcatttg agctttcgag aatggtgcag tgggcttatg acaatgacat gttagaggac    1800
agtgaaatcg cttattatta tgcacagcat gcagacgtgg acagcaatgc agcagcatgg    1860
ctcaaaacta ataaccaggc caaatatgtt agagactgtg gtaacatggt ccggctttat    1920
aagcagcagg aaatgaaaaa cttaaccatg tcagagtata tttacaaaag gtgctgtaaa    1980
gttgaaggct caggcgattg gaagcatatt tttaaattgc taaggtatca ggatgttaat    2040
atgatacagt ttttaacatc ttttagagac ttactaagtt gcaagcctaa aagacagtgt    2100
ctggttatat atgggccacc agacacaggg aaatcatact ttttatactc tttgatttcc    2160
ttcttaaagg gaaaagtcat ttcattcaca acagcaaaaa gccattttg gctgcagcct    2220 ttgcttaatg ccaaagttgc attgctagat gatgccacta agcttgctg gaactatatg    2280 gactgttata tgaggacagc tttagatgga aacgcagtgt ctgtagatag caagtttaag    2340
gcaccagtgc aagtaaggct ccccccttta ttaatctcta caaatgtaga gctcccgtta    2400
ctcgaagaat ataagtattt gcactccaga acgatgtgct attgctttgc aaagccatgt    2460
ttatatgatg acgaaggaaa tcccttattt aacttaactg acagacattg gaaaggcttt    2520
ttcctgcatt tggaacaaca actaggcctc aactttagtg agaaggatga agaagctagc    2580
ggagcattta gatgcatgcc aagaacagat gctggaattg attgagaagg acagtcaaga    2640
attagaggac caaatcgact actgggactt ggtcaaacgt gaaaacttgc tgctgtttgc    2700
agcaaaagag gctggcctgt cacggttagg ctacgagcca gtgccaccca ccaaagtgtc    2760
agaaggcaaa gccaaaaatg caataatgat gagtatcagc ttgcagtccc tgcaaagttc    2820
agaatttggt agagacccct ggacactgcc ccagacaagc cttgaggtgt ttatgtctaa    2880
tccctctaac tgtttttaaaa agaatggaga acatgtggaa gtgttatttg atggggacaa    2940
aaacaaagct gtgatttttg tcaagtgggg tgaagtgtat gtgcaggatt tgttgggtgc    3000
ttggcacaaa tgtcctagcc atgttgtgta cgagggtatt tactataacc accctgacta    3060
cggaagaacc ttttacctca ggtttgagga agaggctgca aagtatggag ctcacaaacc    3120
atggcaggtg atgaccacta acggcaccct tttgcactct cctagtgaat cctcaaactc    3180
cgccgacggg tcggaggagt cagctgcccc ctcccccggc ccctccatcg aagcgccgca    3240
gcggctttcc ttttggggat cgcctgcagg agggcctgaa cggggacgga gaagacggag    3300
tgaaacgccg aggaaacggt cttttggaga ccggaggccc aggcccaaa ctccgttggg    3360 aggactcaga cggaaacgag tccgaagagg aagaggagga ggccttgggg ttaaagagct    3420
tgctgaaaaa gctggaggac gacttgcagg aactcctgga cagactgcag aaggaggtgg    3480
acacacttcc acgcgcgctg gccactatcc tgtcctaatt ggcaaaggaa ggccaaactg    3540
tctgaagtgc tggagaaatc gttttggcgt gagccataaa ggtcttttc tagactgttc    3600
```

```
ttcaactttt tcctggactc agactggggg gggaagaggt gtcgatgggg tcatcctcat   3660
tgtatttgaa acagaacaac agttgcaaac ttttgtagac actgtacaca ggcctacgag   3720
catttcattg cgcagagggg gaactgtttt gcgtgctggc tgcttttagc gggtgcagac   3780
aggggtaggg gtgtattaga tcaggggcga taatcatgag tgcactggct caaagataag   3840
gttaagggcg ggttgtggga ggatatttat tggggaatgc gtgcagaggg tgcttgtgca   3900
ggtgtgctta tttgcagctt gctttgtata gtgggtatgc gcggtccaca catttcaact   3960
gtgttgtcac tgttatgtct gctgcgacaa tgtcacggag tcgggttaaa cgtgcttctg   4020
cagaagattt gtaccgtcaa tgccaacttg gcgctgactg tcctccagat gtcaaaaata   4080
aatttgaaaa caacactgtt gcagaccgca tattgaaatg ggtagctggg ttcttatact   4140
taggcacatt agggattggg actggagggg gcacaggggg gcgaggaggg tatgtgccca   4200
ttggacgggg ccctggcacc acaacagaaa ttggggggcac gcgcacactg aggccagtag   4260
gccctgtaga gcctattgga cctggcacac ccactgtcat agatgcaact cccctgtag   4320 atgtggtaga gactccaata gaccccacac tgactgatgt cagaccaact gacccttctg   4380
tgtttgaacc aggggggggaa gacattgagc tggaaacact gcagcctgag gaagatgtcc   4440
ttgcaggctc taaccctaca actgacctgc caactgtggg agagcccaac atagatttca   4500
ctgaaacctc ctttacagaa gtgaggcccc ctgtctccag aactgctgac atttcagaaa   4560
caaacctaga taatgcagcc tataatgcag ctgtagctga gtttgcaaga aagcaaaacc   4620
aagtatcagt catctttgat gctgaagttg tgggtcagt ggtggggtct gaggaatttg   4680
aattagagga agtcccctta acaagcacac ctgaaaatcc tgcaaggcct gctgggagaa   4740
ggagaaattg gggctctatg tatcataggt ttataaaaca agtacgcctt ggctccacct   4800
catttagcag ggcagatgta ggcggacgat ttgaatttga aaatcccgcc tttgaagggg   4860
atgtaggggt gtcagaggaa atgatgcaaa ccagagactt gggtgaagtt gtcattgcca   4920
aaggacctga ggggagagtc cgtatgagta ggttggcacg aatacctggc atgcacacta   4980
gaagtggact ggagcttggt gagcatgtcc acctattcgc tgacatgagc accatagaag   5040
agctcccatt ggaggaaaca atcgaactca gcactttctc caatcctcaa ggcgtattgg   5100
actctgggcc tgtcataata gagtctgaaa ttggcgccac acagggtgtg gtggtcaatg   5160
agcaaacccc aaacccattt gacaatgcag acctcggcaa cactgtctct gaaactgcag   5220
acttacttga atggggagtt gaggacattg aacttttggc ccaggaagac tataatttca   5280
caggcggacg cctaaggctt ttagatgtag aagaagctcc agatattgat gactggacat   5340
tggagtctcc aagaaaagct tatgctgtag ccacaatcaa taaggacagc aaaagccaaa   5400
taccagttaa atcccagtg catgtagacc cgtcagatgt agtggttatt agctacacag   5460
cagatgttag catttttctct ctgttttgagc ccagcttata taggaaaaga aaatatagct   5520
atctgtattg attttttttgc aggatgtgga acaactccag taaagtttat ctgccaccaa   5580
cgcagcctat tgcaagagta ctgtcaacaa aagaatatgt ccaaaccact ggatactact   5640
accatggtca gagtgaacgg ctcataactg ttggtcatcc attttaccca gtttacaatg   5700
aggaaagaac taaatagta gttccacagg tgtctgcaaa tcagctcaga gcattcagaa   5760
tcaaactgcc agaccctaac aaatttgtgt ttgcagaccc aaactttat aatcctgaaa   5820 cacataggct ggtttggctg ctaaaggcca ttgaaattgg tagaggaggc ccattaggtg   5880
taggatgcac aggccatccc ttttttaaca agattgacac tgaaacccct aataaatatc   5940
```

| | | | |
|---|---|---|---|
| caaagacaga caaggatgat cgcatgcaca catcttttga cccaaagcat tgtcagatgt | 6000 |
| ttgtagtagg ctgcaaaccc tgcataggga gtcactgggg tcttgcaaag tcctgtgtgg | 6060 |
| acgcgcacaa tcctgatatt gatgagcact gccctccaat acaactagtt aattcattta | 6120 |
| ttgaagatgg agatatggga gatataggcc ttggcaatat ggactttctc tcattgcaag | 6180 |
| aagacaggtc ttgtgcacca ttagaaattg tcacaaagaa atgtaaattt cctgactttc | 6240 |
| taaaaatgca ggccgaggcc tctggggact ctatgttttt ttatggcaga aaagagtccc | 6300 |
| tatatgctag gcacatgttt tctagagtgg gaaaaaatgg agaagagtat cctcaccctg | 6360 |
| tagagcccag cgactacatc ttgccaagtg cagacgctga agatatggac agacagtctg | 6420 |
| cagcggcccc cttgtacttt gctactccca gtgggtcttt aaatgcaagt gacagtcagc | 6480 |
| tctttaacag agcttacttt ctcaggaact ctcagggtcc caacaatgga gtgctgtgga | 6540 |
| ataatgaaat gtttgtgaca accatggata attccagaaa cacaaacttt acaatttcca | 6600 |
| ttgctcctaa tcccactgct caatatgatg ccacgagaat caagtattac atgagacatg | 6660 |
| tagaaatcta tgagctgatg tttgttttag aagtgggaaa aattgaatta aatggcacag | 6720 |
| tactagctca tataaatgca atgaatccct ctgtgattga cagttggaat cttgggtttg | 6780 |
| ttccaatgcc cacctcaact actgaggaca catatagatt tttggacagt ttagctacta | 6840 |
| agtgcccagc cgatgtagtg ccagagaaaa aggatccgta tgacggctat agttttttggg | 6900 |
| aggtggattg cacagaaaaa atgaccatgg aacttgacca gtacccccta ggacgtaaat | 6960 |
| ttctagctca gcgctttaca gctcgtcctc gaacgaccct aaagagacca ggtgtgagaa | 7020 |
| aaagcacagc tgcaaagaag cgcaggaaat gagttgtaaa tgtatgcata cttgtcatgc | 7080 |
| tgcagcggtt ccgtatgtaa acttgtgtaa ataaacttat caattcccac cgaattcggt | 7140 |
| ctgttactgc gtgttcttcg actgcaccca cccataagtg gtcgcaccta attcgtttgg | 7200 |
| aatgctagaa tgcaaccgcg cccggttggc agctcctctt aacctgcagg tgcaccagtt | 7260 |
| ccgagccaaa tagcaagatc ggatcagccc gacactaatc cttccagctg cacgaaccc | 7320 |
| tcggacttta atccctgaat caataaagtc ttgtctgcga aagcagtttc ggtgagtacg | 7380 |
| accggtttgg ttctcactaa tcttcattat tc | 7412 |

<210> SEQ ID NO 34
<211> LENGTH: 7412
<212> TYPE: DNA
<213> ORGANISM: Bos taurus papillomavirus 7
<300> PUBLICATION INFORMATION:
<308> DATABASE ACCESSION NUMBER: NCBI / NC_007612.1
<309> DATABASE ENTRY DATE: 2011-03-25
<313> RELEVANT RESIDUES IN SEQ ID NO: (1)..(7412)

<400> SEQUENCE: 34

| | | |
|---|---|---|
| cgttatagtt gtcaacaaca atcactctgt caagtaatga catgaccggt aggggttata | 60 |
| ttaagggacc gctttggggg ttcagcacaa atggctgacg aggacgtgat attcgtggac | 120 |
| cgactgcgag ctccgtggtg tatcctttgc atgtgctgta aagatccct aacaaatgac | 180 |
| gagagaaaag attttttaaa taagggttta aaaactttta agaaatggaa taatgggaag | 240 |
| aagcgttcgt ttggctgctg cgagacttgc tgtgtatttt tagcaaatga agaggcagaa | 300 |
| aaaactcgcg cagaagagat tcatttagaa gcagatggtg tgcagctttt ttgtggagcc | 360 |
| cctttgagag atatttccat gaactgtcgc tattgcttag ctgtgctaac ttttatgac | 420 |
| aagtacttaa ataaggagaa cagactgccc ttttgcctac gcaggaaaaa gtggagaggc | 480 |
| acttgtgaga agtgcctgaa agacaaaaaa cagtgctgat catgcacgat ccagcattgt | 540 |

```
tctcgtcctc aggagagcag cctccagaag ggattgtgct tgaattgcac ccacttaata    600
caggcaatca tttagtgact gtacctggga cgacagaggg gacttcgtca cctaggtgtc    660
aagaggaggg gccaaggttg tgcttgtatt atatatgtac tgtatgtgct tggtgtcaga    720
gtcacctgcg cctgagtgtg tcaacgtccg attccagcct tagaaaattt caagagcttt    780
tgtgtggtga cttgacagtc gtttgcacac cctgtgcccg aaatggcaga agataaaggt    840
actaaaggcg gtgggggaat ggtcagtggt tcgtggtatt tggatgtgga agctgaatgt    900
gatgagcctg acaatctttg tgacttagaa gcttgttttg ataagtctga cagtgatgat    960
gatccagaat tcattagtaa ctctgatgtt gaggagggga attcttcgga actcttacac   1020
aataatcata tgctagccaa agatggtgag cagatccaac tgctaaagcg aaagtacatg   1080
tccccaagcc cagataaaga attaagcccg agattagcat tagtgtcaat ttctgctagc   1140
cactctagta agaggaggct ttttccagag acgaaggaca agcatgaagc tagcaattct   1200
tctgggtcgg tttcgtccac gcaggttggt tcaaatagcc agagctataa ttccgaggac   1260
ttgagcattg caattcttaa aagcaaaaat cagaaagcaa cagctttagc tcagtttaaa   1320
gaagcctttg tgtcagctt tacagatttg actaggtcat ttattagcaa taagacttgc   1380
actcagcact gggttgtagc tgtgtttgga ccgaacagtg acattttaga tggcactggt   1440
acactcttag aaccccactg caccttcttg cttaagtgca catgctttgc agaccgtggg   1500
cctataattc tgcttcttat agaatttaaa gccagtaagt gtcgtgatac agtgcaaaat   1560
ttattgaata atattatgag ggttgagcat catcagatgt tgcttgaacc tccaaaaata   1620
aggagccagc ttacagcttt ttttttttat aaaaagacta tggcaggagg ctgcgacgtg   1680
attggcaagt tgcctgattg gctgactcgc tcactgtgc tcagtcacca aggcgccaca   1740
gaagcatttg agctttcgag aatggtgcag tgggcttatg acaatgacat gttagaggac   1800
agtgaaatcg cttattatta tgcacagcat gcagacgtgg acagcaatgc agcagcatgg   1860
ctcaaaacta ataaccaggc caaatatgtt agagactgtg gtaacatggt ccggctttat   1920
aagcagcagg aaatgaaaaa cttaaccatg tcagagtata tttacaaaag gtgctgtaaa   1980
gttgaaggct caggcgattg gaagcatatt tttaaattgc taaggtatca ggatgttaat   2040
atgatacagt ttttaacatc ttttagagac ttactaagtt gcaagcctaa aagacagtgt   2100
ctggttatat atgggccacc agacacaggg aaatcatact ttttatactc tttgatttcc   2160
ttcttaaagg gaaaagtcat ttcattcaca aacagcaaaa gccattttg gctgcagcct   2220
ttgcttaatg ccaaagttgc attgctagat gatgccacta agcttgctg gaactatatg   2280
gactgttata tgaggacagc tttagatgga aacgcagtgt ctgtagatag caagtttaag   2340
gcaccagtgc aagtaaggct cccccctta ttaatctcta caaatgtaga gctcccgtta   2400
ctcgaagaat ataagtattt gcactccaga acgatgtgct attgctttgc aaagccatgt   2460
ttatatgatg acgaaggaaa tcccttattt aacttaactg acagacattg gaaaggctttt   2520
ttcctgcatt tggaacaaca actaggcctc aactttagtg agaaggatga agaagctagc   2580
ggagcattta gatgcatgcc aagaacagat gctggaattg attgagaagg acagtcaaga   2640
attagaggac caaatcgact actgggactt ggtcaaacgt gaaaacttgc tgctgtttgc   2700
agcaaaagag gctggcctgt cacggttagg ctacgagcca gtgccacccc ccaaagtgtc   2760
agaaggcaaa gccaaaaatg caataatgat gagtatcagc ttgcagtccc tgcaaagttc   2820
agaatttggt agagaccct ggacactgcc ccagacaagc cttgaggtgt ttatgtctaa   2880
```

```
tccctctaac tgttttaaaa agaatggaga acatgtggaa gtgttatttg atggggacaa   2940
aaacaaagct gtgattttg tcaagtgggg tgaagtgtat gtgcaggatt tgttgggtgc    3000
ttggcacaaa tgtcctagcc atgttgtgta cgagggtatt tactataacc ccctgacta   3060 cggaagaacc ttttacctca ggtttgagga agaggctgca aagtatggag ctcacaaacc   3120
atggcaggtg atgaccacta acggcaccct tttgcactct cctagtgaat cctcaaactc   3180
cgccgacggg tcggaggagt cagctgcccc ctcccccggc ccctccatcg aagcgccgca   3240
gcggctttcc ttttggggat cgcctgcagg agggcctgaa cggggacgga gaagacggag   3300
tgaaacgccg aggaaacggt cttttggaga ccggaggccc aggccccaaa ctccgttggg   3360
aggactcaga cggaaacgag tccgaagagg aagaggagga ggccttgggg ttaaagagct   3420
tgctgaaaaa gctggaggac gacttgcagg aactcctgga cagactgcag aaggaggtgg   3480
acacacttcc acggcgcctg ccactatcc tgtcctaatt ggcaaaggaa ggccaaactg    3540
tctgaagtgc tggagaaatc gttttggcgt gagccataaa ggtctttttc tagactgttc   3600
ttcaactttt tcctggactc agactgggg gggaagaggt gtcgatgggg tcatcctcat    3660
tgtatttgaa acagaacaac agttgcaaac ttttgtagac actgtacaca ggcctacgag   3720
catttcattg cgcagagggg gaactgtttt gcgtgctggc tgcttttagc gggtgcagac   3780
aggggtaggg gtgtattaga tcaggggcga taatcatgag tgcactggct caaagataag   3840
gttaagggcg ggttgtggga ggatatttat tgggaatgc gtgcagaggg tgcttgtgca    3900
ggtgtgctta tttgcagctt gctttgtata gtgggtatgc gcggtccaca catttcaact   3960
gtgttgtcac tgttatgtct gctgcgacaa tgtcacggag tcgggttaaa cgtgcttctg   4020
cagaagattt gtaccgtcaa tgccaacttg gcgctgactg tcctccagat gtcaaaaata   4080
aatttgaaaa caacactgtt gcagaccgca tattgaaatg ggtagctggg ttcttatact   4140
taggcacatt agggattggg actgggaggg gcacagggg gcgaggaggg tatgtgccca    4200
ttggacgggg ccctggcacc acaacagaaa ttggggcac gcgcacactg aggccagtag    4260
gccctgtaga gcctattgga cctggcacac ccactgtcat agatgcaact cccctgtag    4320 atgtggtaga gactccaata gaccccacac tgactgatgt cagaccaact gacccttctg   4380
tgtttgaacc aggggggga gacattgagc tggaaacact gcagcctgag gaagatgtcc    4440
ttgcaggctc taaccctaca actgacctgc caactgtggg gagcccaac atagatttca    4500 ctgaaacctc ctttacagaa gtgaggcccc ctgtctccag aactgctgac atttcagaaa   4560
caaacctaga taatgcagcc tataatgcag ctgtagctga gtttgcaaga gaagcaaacc   4620
aagtatcagt catctttgat gctgaagttg gtgggtcagt ggtggggtct gaggaatttg   4680
aattagagga agtccccttta acaagcacac ctgaaaatcc tgcaaggcct gctgggagaa   4740
ggagaaattg gggctctatg tatcataggt ttataaaaca agtacgcctt ggctccacct   4800
catttagcag gcagatgta gcggacgat ttgaatttga aaatcccgcc tttgaagggg     4860 atgtagggt gtcagaggaa atgatgcaaa ccagagactt gggtgaagtt gtcattgcca    4920
aaggacctga ggggagagtc cgtatgagta ggttggcacg aatacctggc atgcacacta   4980
gaagtggact ggagcttggt gagcatgtcc acctattcgc tgacatgagc accatagaag   5040
agctcccatt ggaggaaaca atcgaactca gcactttctc caatcctcaa ggcgtattgg   5100
actctgggcc tgtcataata gagtctgaaa ttggcgccac acagggtgtg gtggtcaatg   5160
agcaaacccc aaacccattt gacaatgcag acctcggcaa cactgtctct gaaactgcag   5220
acttacttga atggggagtt gaggacattg aacttttggc ccaggaagac tataatttca   5280
```

-continued

```
caggcggacg cctaaggctt ttagatgtag aagaagctcc agatattgat gactggacat      5340
tggagtctcc aagaaaagct tatgctgtag ccacaatcaa taaggacagc aaaagccaaa      5400
taccagttaa atcccagtg catgtagacc cgtcagatgt agtggttatt agctacacag       5460
cagatgttag catttttctct ctgtttgagc ccagcttata taggaaaaga aaatatagct     5520
atctgtattg attttttgc aggatgtgga acaactccag taaagtttat ctgccaccaa       5580
cgcagcctat tgcaagagta ctgtcaacaa aagaatatgt ccaaaccact ggatactact      5640
accatggtca gagtgaacgg ctcataactg ttggtcatcc attttaccca gtttacaatg      5700
aggaaagaac taaatagta gttccacagg tgtctgcaaa tcagctcaga gcattcagaa       5760
tcaaactgcc agaccctaac aaatttgtgt ttgcagaccc aaacttttat aatcctgaaa      5820
cacataggct ggtttggctg ctaaaggcca ttgaaattgg tagaggaggc ccattaggtg      5880
taggatgcac aggccatccc ttttttaaca agattgacac tgaaaaccct aataaatatc      5940
caaagacaga caaggatgat cgcatgcaca catcttttga cccaaagcat tgtcagatgt      6000
ttgtagtagg ctgcaaaccc tgcatagga gtcactgggg tcttgcaaag tcctgtgtgg       6060
acgcgcacaa tcctgatatt gatgagcact gccctccaat acaactagtt aattcattta      6120
ttgaagatgg agatatggga gatataggcc ttggcaatat ggactttctc tcattgcaag      6180
aagacaggtc ttgtgcacca ttagaaattg tcacaaagaa atgtaaattt cctgactttc      6240
taaaaatgca ggccgaggcc tctggggact ctatgttttt ttatggcaga aaagagtccc      6300
tatatgctag gcacatgttt tctagagtgg gaaaaaatgg agaagagtat cctcaccctg      6360
tagagcccag cgactacatc ttgccaagtg cagacgctga agatatggac agacagtctg     6420
cagcggcccc cttgtacttt gctactccca gtgggtcttt aaatgcaagt gacagtcagc      6480
tctttaacag agcttacttt ctcaggaact ctcagggtcc caacaatgga gtgctgtgga      6540
ataatgaaat gtttgtgaca accatggata attccagaaa cacaaacttt acaatttcca      6600
ttgctcctaa tcccactgct caatatgatg ccacgagaat caagtattac atgagacatg      6660
tagaaatcta tgagctgatg tttgttttag aagtgggaaa aattgaatta aatggcacag      6720
tactagctca tataaatgca atgaatccct ctgtgattga cagttggaat cttgggtttg      6780
ttccaatgcc cacctcaact actgaggaca catatagatt tttggacagt ttagctacta      6840
agtgcccagc cgatgtagtg ccagagaaaa aggatccgta tgacggctat agttttgg       6900 aggtggattg cacagaaaaa atgaccatgg aacttgacca gtacccccta ggacgtaaat      6960
ttctagctca gcgctttaca gctcgtcctc gaacgaccct aaagagacca ggtgtgagaa      7020
aaagcacagc tgcaaagaag cgcaggaaat gagttgtaaa tgtatgcata cttgtcatgc      7080
tgcagcggtt ccgtatgtaa acttgtgtaa ataaacttat caattcccac cgaattcggt      7140
ctgttactgc gtgttcttcg actgcaccca cccataagtg gtcgcaccta attcgtttgg      7200
aatgctagaa tgcaaccgcg cccggttggc agctcctctt aacctgcagg tgcaccagtt      7260
ccgagccaaa tagcaagatc ggatcagccc gacactaatc cttccagctg gcacgaaccc      7320
tcggacttta atccctgaat caataaagtc ttgtctgcga aagcagtttc ggtgagtacg      7380
accggtttgg ttctcactaa tcttcattat tc                                    7412
```

<210> SEQ ID NO 35
<211> LENGTH: 18115
<212> TYPE: DNA
<213> ORGANISM: Artificial Sequence
<220> FEATURE:

<223> OTHER INFORMATION: Synthetic Polynucleotide

<400> SEQUENCE: 35

```
tctagagagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca tagtaacgcc aatagggact ttccattgac gtcaatgggt ggagtattta     300
cggtaaactg cccacttggc agtacatcaa gtgtatcata tgccaagtac gccccctatt     360
gacgtcaatg acggtaaatg gcccgcctgg cattatgccc agtacatgac cttatgggac     420
tttcctactt ggcagtacat ctacgtatta gtcatcgcta ttaccatggt gatgcggttt     480
tggcagtaca tcaatgggcg tggatagcgg tttgactcac ggggatttcc aagtctccac     540
cccattgacg tcaatgggag tttgttttgg caccaaaatc aacgggactt tccaaaatgt     600
cgtaacaact ccgccccatt gacgcaaatg ggcggtaggc gtgtacggtg ggaggtctat     660
ataagcagag ctcgtttagt gaaccgtcag atcgcctgga gacgccatcc acgctgtttt     720
gacctccata gaagacaccg ggaccgatcc agcctccggt cgatcgaccg atcctgagaa     780
cttcagggtg agtttgggga cccttgattg ttctttcttt ttcgctattg taaaattcat     840
gttatatgga gggggcaaag ttttcagggt gttgtttaga atgggaagat gtcccttgta     900
tcaccatgga ccctcatgat aattttgttt ctttcacttt ctactctgtt gacaaccatt     960
gtctcctctt attttctttt catttctgt aacttttcg ttaaacttta gcttgcattt    1020
gtaacgaatt tttaaattca cttttgttta tttgtcagat tgtaagtact ttctctaatc    1080
acttttttt caaggcaatc agggtatatt atattgtact tcagcacagt tttagagaac    1140
aattgttata attaaatgat aaggtagaat atttctgcat ataaattctg gctggcgtgg    1200
aaatattctt attggtagaa acaactacac cctggtcatc atcctgcctt tctctttatg    1260
gttacaatga tatacactgt ttgagatgag gataaaatac tctgagtcca aaccgggccc    1320
ctctgctaac catgttcatg ccttcttctc tttcctacag ctcctgggca acgtgctggt    1380
tgttgtgctg tctcatcatt ttggcaaaga attcgaagcc tcgagatgat gaaacttatc    1440
atcaattcat tgtataaaaa taaagagatt ttcctgagag aactgatttc aaatgcttct    1500
gatgctttag ataagataag gctaatatca ctgactgatg aaaatgctct ttctggaaat    1560
gaggaactaa cagtcaaaat taagtgtgat aaggagaaga acctgctgca tgtcacagac    1620
accggtgtag gaatgaccag agaagagttg gttaaaaacc ttggtaccat agccaaatct    1680
gggacaagcg agttttttaaa caaatgact gaagcacagg aagatggcca gtcaacttct    1740
gaattgattg gccagtttgg tgtcggtttc tattccgcct ccttgtagc agataaggtt    1800
attgtcactt caaaacacaa caacgatacc cagcacatct gggagtctga ctccaatgaa    1860
ttttctgtaa ttgctgaccc aagaggaaac actctaggac ggggaacgac aattacccttt   1920
gtcttaaaag aagaagcatc tgattacctt gaattggata caattaaaaa tctcgtcaaa    1980
aaatattcac agttcataaa ctttcctatt tatgtatgga gcagcaagac tgaaactgtt    2040
gaggagccca tggaggaaga agaagcagcc aagaagagag aagaagaatc tgatgatgaa    2100
gctgcagtag aggaagaaga agaagaaaag aaaccaaaga ctaaaaaagt tgaaaaaact    2160
gtctgggact gggaacttat gaatgatatc aaaccaatat ggcagagacc atcaaaagaa    2220
gtagaagaag atgaatacaa agctttctac aaaatcatttt caaggaaag tgatgacccc    2280
```

```
atggcttata ttcactttac tgctgaaggg gaagttacct tcaaatcaat tttatttgta    2340
cccacatctg ctccacgtgg tctgtttgac gaatatggat ctaaaagag cgattacatt     2400 aagctctatg tgcgccgtgt attcatcaca gacgacttcc atgatatgat gcctaaatac    2460
ctcaattttg tcaagggtgt ggtggactca gatgatctcc ccttgaatgt ttcccgcgag    2520
actcttcagc aacataaact gcttaaggtg attaggaaga agcttgttcg taaaacgctg    2580
gacatgatca agaagattgc tgatgataaa tacaatgata cttttgggaa agaatttggt    2640
accaacatca agcttggtgt gattgaagac cactcgaatc gaacacgtct tgctaaactt    2700
cttaggttcc agtcttctca tcatccaact gacattacta gcctagacca gtatgtggaa    2760
agaatgaagg aaaaacaaga caaaatctac ttcatggctg ggtccagcag aaaagaggct    2820
gaatcttctc catttgttga gcgacttctg aaaaagggct atgaagttat ttacctcaca    2880
gaacctgtgg atgaatactg tattcaggcc cttcccgaat tgatgggaa gaggttccag     2940 aatgttgcca aggaaggagt gaagttcgat gaaagtgaga aaactaagga gagtcgtgaa    3000
gcagttgaga agaatttga gcctctgctg aattggatga agataaagc ccttaaggac      3060 aagattgaaa aggctgtggt gtctcagcgc ctgacagaat ctccgtgtgc tttggtggcc    3120
agccagtacg atggtctgg caacatggag agaatcatga agcacaagc gtaccaaacg      3180 ggcaaggaca tctctacaaa ttactatgcg agtcagaaga aaacatttga attaatcccc    3240 agacaccccgc tgatcagaga catgcttcga cgaattaagg aagatgaaga tgataaaaca   3300
gttttggatc ttgctgtggt tttgtttgaa acagcaacgc ttcggtcagg gtatctttta    3360
ccagacacta aagcatatgg agatagaata gaaagaatgc ttcgcctcag tttgaacatt    3420
gaccctgatg caaaggtgga agaagagccc gaagaagaac ctgaagagac agcagaagac    3480
acaacagaag acacagagca agacgaagat gaagaaatgg atgtgggaac agatgaagaa    3540
gaagaaacag caaaggaatc tacagctgaa ggatcctgtg acaaaactca cacatgccca    3600
ccgtgcccag cacctgaact cctggggga ccgtcagtct tcctcttccc cccaaaaccc     3660
aaggacaccc tcatgatctc ccggacccct gaggtcacat gcgtggtggt ggacgtgagc    3720
cacgaagacc ctgaggtcaa gttcaactgg tacgtggacg gcgtggaggt gcataatgcc    3780
aagacaaagc cgcgggagga gcagtacaac agcacgtacc gtgtggtcag cgtcctcacc    3840
gtcctgcacc aggactggct gaatggcaag gagtacaagt gcaaggtctc caacaaagcc    3900
ctcccagccc ccatcgagaa aaccatctcc aaagccaaag ggcagccccg agaaccacag    3960
gtgtacaccc tgcccccatc ccgggatgag ctgaccaaga accaggtcag cctgacctgc    4020
ctggtcaaag gcttctatcc cagcgacatc gccgtggagt gggagagcaa tgggcagccg    4080
gagaacaact acaagaccac gcctcccgtg ctggactccg acggctcctt cttcctctac    4140
agcaagctca ccgtggacaa gagcaggtgg cagcagggga acgtcttctc atgctccgtg    4200
atgcatgagg ctctgcacaa ccactacacg cagaagagcc tctccctgtc tccgggtaaa    4260
tgactcgacc cagactagtc aaattaagcc gaattctgca gatatccatc acactggcgg    4320
ccgctggaat tcactcctca ggtgcaggct gcctatcaga aggtggtggc tggtgtggcc    4380
aatgccctgg ctcacaaata ccactgagat cttttttccct ctgccaaaaa ttatggggac    4440
atcatgaagc cccttgagca tctgacttct ggctaataaa ggaaatttat tttcattgca    4500
atagtgtgtt ggaatttttt gtgtctctca ctcggaagga catatgggag gcaaatcat    4560 ttaaaacatc agaatgagta tttggtttag agtttggcaa catatgccca tatgctggct    4620
```

```
gccatgaaca aaggttggct ataaagaggt catcagtata tgaaacagcc ccctgctgtc    4680
cattccttat tccatagaaa agccttgact tgaggttaga ttttttttat attttgtttt    4740
gtgttatttt tttctttaac atccctaaaa ttttccttac atgttttact agccagattt    4800
ttcctcctct cctgactact cccagtcata gctgtccctc ttctcttatg gagatccctc    4860
gacggatccc tagagtcgag gcgatgcggc gcagcaccat ggcctgaaat aacctctgaa    4920
agaggaactt ggttaggtac cttggttttt aaaaccagcc tggagtagag cagatggggtt   4980 aaggtgagtg accccctcagc cctggacatt cttagatgag ccccctcagg agtagagaat   5040
aatgttgaga tgagttctgt tggctaaaat aatcaaggct agtctttata aaactgtctc    5100
ctcttctcct agcttcgatc cagagagaga cctgggcgga gctggtcgct gctcaggaac    5160
tccaggaaag gagaagctga ggttaccacg ctgcgaatgg gtttacggag atagctggct    5220
ttccggggtg agttctcgta aactccagag cagcgatagg ccgtaatatc ggggaaagca    5280
ctatagggac atgatgttcc acacgtcaca tgggtcgtcc tatccgagcc agtcgtgcca    5340
aaggggcggt cccgctgtgc acactggcgc tccaggagc tctgcactcc gcccgaaaag     5400
tgcgctcggc tctgccagga cgcggggcgc gtgactatgc gtgggctgga gcaaccgcct    5460
gctgggtgca aacccttttgc gcccggactc gtccaacgac tataaagagg gcaggctgtc   5520
ctctaagcgt caccacgact tcaacgtcct gagtaccttc tcctcactta ctccgtagct    5580
ccagcttcac caccaagctc ctcgacgtcg atcgcgagcc gccaccatgc gtgggagtgc    5640
atactatatg tacttggaca gaaacgatgc tggggaggcc atatcttttc caaccacatt    5700
ggggatgaat aagtgttata tacagatcat ggatcttgga cacatgtgtg atgccaccat    5760
gagctatgaa tgccctatgc tggatgaggg ggtggaacca gatgacgtcg attgttggtg    5820
caacacgacg tcaacttggg ttgtgtacgg aacctgccat cacaaaaaag gtgaagcacg    5880
gagatctaga agagctgtga cgctcccctc ccattccact aggaagctgc aaacgcggtc    5940
gcaaacctgg ttgaatcaa gagaatacac aaagcacttg attagagtcg aaaattggat     6000
atttaggaac cctggcttcg cgttagcagc agctgccatc gcttggcttt tgggaagctc    6060
aacgagccaa aaagtcatat acttggtcat gatactgctg attgccccgg catacagcat    6120
caggtgcata ggagtcagca atagggactt tgtggaaggt atgtcaggtg ggacctgggt    6180
tgatgttgtc ttggaacatg gaggttgtgt caccgtaatg gcacaggaca aaccgactgt    6240
cgacatagag ctggttacaa caacagtcag caacatggcg gaggtaagat cctactgcta    6300
tgaggcatca atatcagaca tggcttcgga cagccgctgc ccaacacaag gtgaagccta    6360
ccttgacaag caatcagaca ctcaatatgt ctgcaaaaga acgttagtgg acagaggctg    6420
gggaaatgga tgtggacttt ttggcaaagg gagcctggtg acatgcgcta agtttgcatg    6480
ctccaagaaa atgaccggga agagcatcca gccagagaat ctggagtacc ggataatgct    6540
gtcagttcat ggctcccagc acagtgggat gattgttaat gacacaggac atgaaactga    6600
tgagaataga gcgaaagttg agataacgcc caattcacca agagccgaag ccaccctggg    6660
gggttttgga agcctaggac ttgattgtga accgaggaca ggccttgact tttcagattt    6720
gtattacttg actatgaata acaagcactg gttggttcac aaggagtggt tccacgacat    6780
tccattacct tggcacgctg ggcagacac cggaactcca cactggaaca caaagaagc     6840 actggtagag ttcaaggacg cacatgccaa aaggcaaact gtcgtggttc tagggagtca    6900
agaaggagca gttcacacgg cccttgctgg agctctggag gctgagatgg atggtgcaaa    6960
gggaaggctg tcctctggcc acttgaaatg tcgcctgaaa atggataaac ttagattgaa    7020
```

```
gggcgtgtca tactccttgt gtactgcagc gttcacattc accaagatcc cggctgaaac      7080
actgcacggg acagtcacag tggaggtaca gtacgcaggg acagatggac cttgcaaggt      7140
tccagctcag atggcggtgg acatgcaaac tctgacccca gttgggaggt tgataaccgc      7200
taaccccgta atcactgaaa gcactgagaa ctctaagatg atgctggaac ttgatccacc      7260
atttggggac tcttacattg tcataggagt cggggagaag aagatcaccc accactggca      7320
caggagtggc agcaccattg gaaaagcatt tgaagccact gtgagaggtg ccaagagaat      7380
ggcagtcttg ggagacacag cctgggactt tggatcagtt ggaggcgctc tcaactcatt      7440
gggcaagggc atccatcaaa ttttggagc agctttcaaa tcattgtttg gaggaatgtc       7500
ctggttctca caaattctca ttggaacgtt gctgatgtgg ttgggtctga acacaaagaa      7560
tggatctatt tcccttatgt gcttggcctt aggggagtg ttgatcttct tatccacagc       7620
cgtctctgct taaggcccct ttggccttag cgtcgaccga tcctgagaac ttcagggtga      7680
gtttggggac ccttgattgt tctttctttt tcgctattgt aaaattcatg ttatatggag      7740
ggggcaaagt tttcagggtg ttgtttagaa tgggaagatg tcccttgtat caccatggac      7800
cctcatgata atttgtttc tttcactttc tactctgttg acaaccattg tctcctctta       7860 ttttctttc attttctgta actttttcgt taaactttag cttgcatttg taacgaattt       7920
ttaaattcac ttttgtttat ttgtcagatt gtaagtactt tctctaatca cttttttttc      7980
aaggcaatca gggtatatta tattgtactt cagcacagtt ttagagaaca attgttataa      8040
ttaaatgata aggtagaata tttctgcata taaattctgg ctggcgtgga aatattctta      8100
ttggtagaaa caactacacc ctggtcatca tcctgccttt ctctttatgg ttacaatgat      8160
atacactgtt tgagatgagg ataaaatact ctgagtccaa accgggcccc tctgctaacc      8220
atgttcatgc cttcttctct ttcctacagc tcctgggcaa cgtgctggtt gttgtgctgt      8280
ctcatcattt tggcaaagaa ttcctcgacc agtgcaggct gcctatcaga aagtggtggc      8340
tggtgtggct aatgccctgg cccacaagta tcactaagct cgctttcttg ctgtccaatt      8400
tctattaaag gttcctttgt tccctaagtc caactactaa actggggat attatgaagg       8460 gccttgagca tctggattct gcctaataaa aaacattat tttcattgca atgatgtatt       8520
taaattattt ctgaatattt tactaaaaag ggaatgtggg aggtcagtgc atttaaaaca      8580
taaagaaatg aagagctagt tcaaaccttg ggaaaataca ctatatctta aactccatga      8640
aagaaggtga ggctgcaaac agctaatgca cattggcaac agcccctgat gcctatgcct      8700
tattcatccc tcagaaaagg attcaagtag aggcttgatt tggaggttaa agttttgcta      8760
tgctgtattt tacattactt attgttttag ctgtcctcat gaatgtcttt tcactaccca      8820
tttgcttatc ctgcatctct cagccttgac tccactcagt tctcttgctt agagatacca      8880
cctttcccct gaagtgttcc ttccatgttt tacggcgaga tggtttctcc tcgcctggcc      8940
actcagcctt agttgtctct gttgtcttat agaggtctac ttgaagaagg aaaaacaggg      9000
ggcatggttt gactgtcctg tgagcccttc ttccctgcct cccccactca cagtgacccg      9060
gaatctgcag tgctagtctc ccggaactat cactctttca cagtctgctt tggaaggact      9120
gggcttagta tgaaaagtta ggactgagaa gaatttgaaa ggggcttt tgtagcttga       9180 tattcactac tgtcttatta ccctatcata ggcccacccc aaatggaagt cccattcttc      9240
ctcaggatgt ttaagattag cattcaggaa gagatcagag gtctgctggc tcccttatca      9300
tgtcccttat ggtgcttctg gctctgcagt tattagcata gtgttaccat caaccacctt      9360
```

```
aacttcattt tcttattca atacctaggt aggtagatgc tagattctgg aaataaaata   9420
tgagtctcaa gtggtccttg tcctctctcc cagtcaaatt ctgaatctag ttggcaagat   9480
tctgaaatca aggcatataa tcagtaataa gtgatgatag aagggtatat agaagaattt   9540
tattatatga gagggtgaaa tcccagcaat ttgggaggct gaggcaggag aatcgcttga   9600
tcctgggagg cagaggttgc agtgagccaa gattgtgcca ctgcattcca gcccaggtga   9660
cagcatgaga ctccgtcaca aaaaaaaaag aaaaaaaagg ggggggggg cggtggagcc   9720
aagatgaccg aataggaaca gctccagtac tatagctccc atcgtgagtg acgcagaaga   9780
cgggtgattt ctgcatttcc aactgaggta ccaggttcat ctcacaggga agtgccaggc   9840
agtgggtgca ggacagtagg tgcagtgcac tgtgcatgag ccgaagcagg gacgaggcat   9900
cacctcaccc gggaagcaca aggggtcagg gaattccctt tcctagtcaa agaaaagggt   9960
gacagatggc acctggaaaa tcgggtcact cccgccctaa tactgcgctc ttccaacaag  10020
cttgtctttg gaaatagat caatttccct tgggaagaag attttttagca cagcaagggg  10080
caggatgttc aactgtgaga aaacgaagaa ttagccaaaa aacttccagt aagcctgcaa  10140
aaaaaaaaaa aaaataaaag ctaagtttct ataaatgttc tgtaaatgta aaacagaagg  10200
taagtcaact gcacctaata aaaatcactt aatagcaatg tgctgtgtca gttgtttatt  10260
ggaaccacac ccggtacaca tcctgtccag catttgcagt gcgtgcattg aattattgtg  10320
ctggctagac ttcatggcgc ctggcaccga atcctgcctt tcagcgaaa atgaataatt   10380
gctttgttgg caagaaacta agcatcaatg ggacgcgtgc aaagcaccgg cggcggtaga  10440
tgcggggtaa gtactgaatt ttaattcgac ctatcccgt aaagcgaaag cgacacgctt   10500
ttttttcaca catagcggga ccgaacacgt tataagtatc gattaggtct atttttgtct  10560
ctctgtcgga accagaactg gtaaaagttt ccattgcgtc tgggcttgtc tatcattgcg  10620
tctctatggt ttttggagga ttagacgggg ccaccagtaa tggtgcatag cggatgtctg  10680
taccgccatc ggtgcaccga tataggtttg gggctcccca agggactgct gggatgacag  10740
cttcatatta tattgaatgg gcgcataatc agcttaattg gtgaggacaa gctacaagtt  10800
gtaacctgat ctccacaaag tacgttgccg gtcggggtca aaccgtcttc ggtgctcgaa  10860
accgccttaa actacagaca ggtcccagcc aagtaggcgg atcaaaacct caaaaaggcg  10920
ggagccaatc aaaatgcagc attatatttt aagctcaccg aaaccggtaa gtaaagacta  10980
tgtattttt cccagtgaat aattgttgtt aactataaaa agcgtcatgg caaacgataa  11040
aggtagcaat tgggattcgg gcttgggatg ctcatatctg ctgactgagg cagaatgtga  11100
aagtgacaaa gagaatgagg aacccggggc aggtgtagaa ctgtctgtgg aatctgatcg  11160
gtatgatagc caggatgagg attttgttga caatgcatca gtctttcagg gaaatcacct  11220
ggaggtcttc caggcattag agaaaaaggc gggtgaggag cagattttaa atttgaaaag  11280
aaaagtattg gggagttcgc aaaacagcag cggttccgaa gcatctgaaa ctccagttaa  11340
aagacggaaa tcaggagcaa agcgaagatt atttgctgaa aatgaagcta accgtgttct  11400
tacgcccctc caggtacagg gggagggga ggggaggcaa gaacttaatg aggagcaggc   11460
aattagtcat ctcacatctgc agcttgttaa atctaaaaat gctacagttt ttaagctggg  11520
gctcttaaa tctttgttcc tttgtagctt ccatgatatt acgaggttgt ttaagaatga  11580
taagaccact aatcagcaat gggtgctggc tgtgtttggc cttgcagagg tgttttttga  11640
ggcgagtttc gaactcctaa agaagcagtg tagttctctg cagatgcaaa aaagatctca  11700
tgaaggagga acttgtgcag tttacttaat ctgctttaac acagctaaaa gcagagaaac  11760
```

```
agtccggaat ctgatggcaa acatgctaaa tgtaagagaa gagtgtttga tgctgcagcc    11820
acctaaaatt cgaggactca gcgcagctct attctggttt aaaagtagtt tgtcacccgc    11880
tacacttaaa catggtgctt tacctgagtg gatacgggcg caaactactc tgaacgagag    11940
cttgcagacc gagaaattcg acttcggaac tatggtgcaa tgggcctatg atcacaaata    12000
tgctgaggag tctaaaatag cctatgaata tgctttggct gcaggatctg atagcaatgc    12060
acgggctttt ttagcaacta acagccaagc taagcatgtg aaggactgtg caactatggt    12120
aagacactat ctaagagctg aaacacaagc attaagcatg cctgcatata ttaaagctag    12180
gtgcaagctg gcaactgggg aaggaagctg aagtctatc ctaactttt ttaactatca    12240 gaatattgaa ttaattacct ttattaatgc tttaaagctc tggctaaaag gaattccaaa    12300
aaaaaactgt ttagcattta ttggccctcc aaacacaggc aagtctatgc tctgcaactc    12360
attaattcat tttttgggtg gtagtgtttt atcttttgcc aaccataaaa gtcactttg    12420 gcttgcttcc ctagcagata ctagagctgc tttagtagat gatgctactc atgcttgctg    12480
gaggtacttt gacacatacc tcagaaatgc attggatggc taccctgtca gtattgatag    12540
aaaacacaaa gcagcggttc aaattaaagc tccaccctc ctggtaacca gtaatattga    12600
tgtgcaggca gaggacagat atttgtactt gcatagtcgg gtgcaaacct ttcgctttga    12660
gcagccatgc acagatgaat cgggtgagca accttttaat attactgatg cagattggaa    12720 atctttttt gtaaggttat ggggcgtttt agacctgatt gacgaggagg aggatagtga    12780
agaggatgga gacagcatgc gaacgtttac atgcagcgca agaaacacaa atgcagttga    12840
ttgagaaaag tagtgataag ttgcaagatc atatactgta ctggactgct gttagaactg    12900
agaacacact gctttatgct gcaaggaaaa aaggggtgac tgtcctagga cactgcagag    12960
taccacactc tgtagtttgt caagagagag ccaagcaggc cattgaaatg cagttgtctt    13020
tgcaggagtt aagcaaaact gagtttgggg atgaaccatg gtctttgctt gacacaagct    13080
gggaccgata tatgtcagaa cctaaacggt gctttaagaa aggcgccagg gtggtagagg    13140
tggagtttga tggaaatgca agcaatacaa actggtacac tgtctacagc aatttgtaca    13200
tgcgcacaga ggacggctgg cagcttgcga aggctgggct gacggaactg ggctctacta    13260
ctgcaccatg gccggtgctg gacgcattta ctattctcgc tttggtgacg aggcagccag    13320
atttagtaca acagggcatt actctgtaag agatcaggac agagtgtatg ctggtgtctc    13380
atccacctct tctgatttta gagatcgccc agacggagtc tgggtcgcat ccgaaggacc    13440
tgaaggagac cctgcaggaa aagaagccga gccagcccag cctgtctctt ctttgctcgg    13500
ctcccccgcc tgcggtccca tcagagcagg cctcggttgg gtacgggacg gtcctcgctc    13560 gcaccctac aatttcctg caggctcggg gggctctatt ctccgctctt cctccacccc    13620
gtgcagggca cggtaccggt ggacttggca tcaaggcagg aagaagagga gcagtcgccc    13680
gactccacag aggaagaacc agtgactctc ccaaggcgca ccaccaatga tggattccac    13740
ctgttaaagg caggagggtc atgctttgct ctaatttcag gaactgctaa ccaggtaaag    13800
tgctatcgct ttcgggtgaa aaagaaccat agacatcgct acgagaactg caccaccacc    13860
tggttcacag ttgctgacaa cggtgctgaa agacaaggac aagcacaaat actgatcacc    13920
tttggatcgc caagtcaaag gcaagacttt ctgaaacatg taccactacc tcctggaatg    13980
aacatttccg gctttacagc cagccttgac ttctgatcac tgccattgcc ttttcttcat    14040
ctgactggtg tactatgcca aatctatgcg accgcattat aaagccgaat tctgcagata    14100
```

```
tccatcacac tggcggccat atggccgcta tgcggtgtga ataccgcac agatgcgtaa    14160 ggagaaaata ccgcatcagg cgctcttccg cttcctcgct cactgactcg ctgcgctcgg   14220
tcgttcggct gcggcgagcg gtatcagctc actcaaaggc ggtaatacgg ttatccacag   14280
aatcagggga taacgcagga aagaacatgt gagcaaaagg ccagcaaaag gccaggaacc   14340
gtaaaaaggc cgcgttgctg gcgtttttcc ataggctccg ccccctgac gagcatcaca   14400 aaaatcgacg ctcaagtcag aggtggcgaa acccgacagg actataaaga taccaggcgt   14460
ttccccctgg aagctccctc gtgcgctctc ctgttccgac cctgccgctt accggatacc   14520
tgtccgcctt tctcccttcg ggaagcgtgg cgctttctca tagctcacgc tgtaggtatc   14580
tcagttcggt gtaggtcgtt cgctccaagc tgggctgtgt gcacgaaccc cccgttcagc   14640
ccgaccgctg cgccttatcc ggtaactatc gtcttgagtc caacccggta agacacgact   14700
tatcgccact ggcagcagcc actggtaaca ggattagcag agcgaggtat gtaggcggtg   14760
ctacagagtt cttgaagtgg tggcctaact acggctacac tagaaggaca gtatttggta   14820
tctgcgctct gctgaagcca gttaccttcg gaaaaagagt tggtagctct tgatccggca   14880
aacaaaccac cgctggtagc ggtggttttt ttgtttgcaa gcagcagatt acgcgcagaa   14940
aaaaaggatc tcaagaagat cctttgatct tttctacggg gtctgacgct cagtggaacg   15000
aaaactcacg ttaagggatt ttggtcatga gattatcaaa aaggatcttc acctagatcc   15060
ttttaaatta aaaatgaagt tttaaatcaa tctaaagtat atatgagtaa acttggtctg   15120
acagttacca atgcttaatc agtgaggcac ctatctcagc gatctgtcta tttcgttcat   15180
ccatagttgc ctgactcccc gtcgtgtaga taactacgat acgggagggc ttaccatctg   15240
gccccagtgc tgcaatgata ccgcgagacc cacgctcacc ggctccagat ttatcagcaa   15300
taaaccagcc agccggaagg gccgagcgca gaagtggtcc tgcaacttta tccgcctcca   15360
tccagtctat taattgttgc cgggaagcta gagtaagtag ttcgccagtt aatagtttgc   15420
gcaacgttgt tgccattgct gcaggcatcg tggtgtcacg ctcgtcgttt ggtatggctt   15480
cattcagctc cggttcccaa cgatcaaggc gagttacatg atccccatg ttgtgcaaaa   15540 aagcggttag ctccttcggt cctccgatcg ttgtcagaag taagttggcc gcagtgttat   15600
cactcatggt tatggcagca ctgcataatt ctcttactgt catgccatcc gtaagatgct   15660
tttctgtgac tggtgagtac tcaaccaagt cattctgaga atagtgtatg cggcgaccga   15720
gttgctcttg cccggcgtca acacgggata ataccgcgcc acatagcaga actttaaaag   15780
tgctcatcat tggaaaacgt tcttcggggc gaaaactctc aaggatctta ccgctgttga   15840
gatccagttc gatgtaaccc actcgtgcac ccaactgatc ttcagcatct tttactttca   15900
ccagcgtttc tgggtgagca aaaacaggaa ggcaaaatgc cgcaaaaaag ggaataaggg   15960
cgacacggaa atgttgaata ctcatactct tcctttttca atattattga agcatttatc   16020
agggttattg tctcatgagc ggatacatat ttgaatgtat ttagaaaaat aaacaaatag   16080
gggttccgcg cacatttccc cgaaaagtgc cacctgacgt ctaagaaacc attattatca   16140
tgacattaac ctataaaaat aggcgtatca cgaggccctt tcgtcttcaa gaattctcat   16200
gtttgacagc ttatcatcga taagcttcac gctgccgcaa gcactcaggg cgcaagggct   16260
gctaaaggaa gcggaacacg tagaaagcca gtccgcagaa acggtgctga ccccggatga   16320
atgtcagcta ctgggctatc tggacaaggg aaaacgcaag cgcaaagaga aagcaggtag   16380
cttgcagtgg gcttacatgg cgatagctag actgggcggt tttatggaca gcaagcgaac   16440
cggaattgcc agctggggcg ccctctggta aggttgggaa gccctgcaaa gtaaactgga   16500
```

```
tggctttctt gccgccaagg atctgatggc cagggatc aagatcctgc ttcatcccg    16560
tggcccgttg ctcgcgtttg ctggcggtgt ccccggaaga aatatatttg catgtcttta    16620
gttctatgat gacacaaacc ccgcccagcg tcttgtcatt ggcgaattcg aacacgcaga    16680
tgcagtcggg gcggcgcggt cccaggtcca cttcgcatat taaggtgacg cgtgtggcct    16740
cgaacaccga gcgaccctgc agcgacccgc ttaacagcgt caacagcgtg ccgcagatct    16800
gatcaagaga caggatgagg atcgtttcgc atgattgaac aagatggatt gcacgcaggt    16860
tctccggccg cttgggtgga gaggctattc ggctatgact gggcacaaca gacaatcggc    16920
tgctctgatg ccgccgtgtt ccggctgtca gcgcaggggc gcccggttct ttttgtcaag    16980
accgacctgt ccggtgccct gaatgaactg caggacgagg cagcgcggct atcgtggctg    17040
gccacgacgg gcgttccttg cgcagctgtg ctcgacgttg tcactgaagc gggaagggac    17100
tggctgctat tgggcgaagt gccggggcag gatctcctgt catctcacct tgctcctgcc    17160
gagaaagtat ccatcatggc tgatgcaatg cggcggctgc atacgcttga tccggctacc    17220
tgcccattcg accaccaagc gaaacatcgc atcgagcgag cacgtactcg gatggaagcc    17280
ggtcttgtcg atcaggatga tctggacgaa gagcatcagg ggctcgcgcc agccgaactg    17340
ttcgccaggc tcaaggcgcg catgcccgac ggcgaggatc tcgtcgtgac ccatggcgat    17400
gcctgcttgc cgaatatcat ggtggaaaat ggccgctttt ctggattcat cgactgtggc    17460
cggctgggtg tggcggaccg ctatcaggac atagcgttgg ctacccgtga tattgctgaa    17520
gagcttggcg gcgaatgggc tgaccgcttc ctcgtgcttt acggtatcgc cgctcccgat    17580
tcgcagcgca tcgccttcta tcgccttctt gacgagttct tctgagcggg actctggggt    17640
tcgaaatgac cgaccaagcg acgcccaacc tgccatcacg agatttcgat tccaccgccg    17700
ccttctatga aaggttgggc ttcggaatcg ttttccggga cgccggctgg atgatcctcc    17760
agcgcgggga tctcatgctg gagttcttcg cccaccccgg gagatggggg aggctaactg    17820
aaacacggaa ggagacaata ccggaaggaa cccgcgctat gaacggcaat aaaaagacag    17880
aataaaacgc acggtgttgg gtcgtttgtt cataaacgcg gggttcggtc ccagggctgg    17940
cactctgtcg atacccccacc gagacccat tgggccaat acgcccgcgt tcttcctttt    18000
tccccacccc acccccaag ttcgggtgaa ggcccagggc tcgcagccaa cgtcggggcg    18060
gcaagccctg ccatagccac gggccccgtg ggttagggac ggcggatcgc ggccc         18115
```

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Gly Gly Gly Gly Ser
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Gly Gly Gly Gly Ser Gly Gly Gly Gly Ser

```
1               5                   10
```

<210> SEQ ID NO 38
<211> LENGTH: 15
<212> TYPE: PRT
<213> ORGANISM: Artificial Sequence
<220> FEATURE:
<223> OTHER INFORMATION: Synthetic Construct

<400> SEQUENCE: 38

```
Gly Gly Gly Gly Ser Gly Gly Gly Gly Ser Gly Gly Gly Gly Ser
1               5                   10                  15
```

<210> SEQ ID NO 39
<211> LENGTH: 20
<212> TYPE: PRT
<213> ORGANISM: Artificial Sequence
<220> FEATURE:
<223> OTHER INFORMATION: Synthetic Construct

<400> SEQUENCE: 39

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

```
Gly Gly Gly Gly Gly Gly Gly Gly
1               5
```

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

```
Gly Gly Gly Gly Gly Gly
1               5
```

<210> SEQ ID NO 42
<211> LENGTH: 5
<212> TYPE: PRT
<213> ORGANISM: Artificial Sequence
<220> FEATURE:
<223> OTHER INFORMATION: Synthetic Construct

<400> SEQUENCE: 42

```
Glu Ala Ala Ala Lys
1               5
```

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Glu Ala Ala Ala Lys Glu Ala Ala Ala Lys
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Glu Ala Ala Ala Lys Glu Ala Ala Ala Lys Glu Ala Ala Ala Lys
1               5                   10                  15

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct

<400> SEQUENCE: 45

Ala Glu Ala Ala Ala Lys Glu Ala Ala Ala Lys Ala
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Ala Glu Ala Ala Ala Lys Glu Ala Ala Ala Lys Glu Ala Ala Ala Lys
1               5                   10                  15
Ala

<210> SEQ ID NO 47
<211> LENGTH: 22
<212> TYPE: PRT
<213> ORGANISM: Artificial Sequence
<220> FEATURE:
<223> OTHER INFORMATION: Synthetic Construct

<400> SEQUENCE: 47

Ala Glu Ala Ala Ala Lys Glu Ala Ala Ala Lys Glu Ala Ala Ala Lys
1               5                   10                  15
Glu Ala Ala Ala Lys Ala
            20

<210> SEQ ID NO 48
<211> LENGTH: 27
<212> TYPE: PRT
<213> ORGANISM: Artificial Sequence
<220> FEATURE:
<223> OTHER INFORMATION: Synthetic Construct

<400> SEQUENCE: 48

Ala Glu Ala Ala Ala Lys Glu Ala Ala Ala Lys Glu Ala Ala Ala Lys
1               5                   10                  15
Glu Ala Ala Ala Lys Glu Ala Ala Ala Lys Ala
            20                  25

<210> SEQ ID NO 49

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 49

Ala Glu Ala Ala Ala Lys Glu Ala Ala Ala Lys Ala
1               5                   10

<210> SEQ ID NO 50
<211> LENGTH: 46
<212> TYPE: PRT
<213> ORGANISM: Artificial Sequence
<220> FEATURE:
<223> OTHER INFORMATION: Synthetic Construct

<400> SEQUENCE: 50

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45

<210> SEQ ID NO 51
<211> LENGTH: 5
<212> TYPE: PRT
<213> ORGANISM: Artificial Sequence
<220> FEATURE:
<223> OTHER INFORMATION: Synthetic Construct

<400> SEQUENCE: 51

Pro Ala Pro Ala Pro
1               5

<210> SEQ ID NO 52
<211> LENGTH: 18
<212> TYPE: PRT
<213> ORGANISM: Artificial Sequence
<220> FEATURE:
<223> OTHER INFORMATION: Synthetic Construct

<400> SEQUENCE: 52

Lys Glu Ser Gly Ser Val Ser Ser Glu Gln Leu Ala Gln Phe Arg Ser
1               5                   10                  15

Leu Asp

<210> SEQ ID NO 53
<211> LENGTH: 14
<212> TYPE: PRT
<213> ORGANISM: Artificial Sequence
<220> FEATURE:
<223> OTHER INFORMATION: Synthetic Construct

<400> SEQUENCE: 53

Glu Gly Lys Ser Ser Gly Ser Gly Ser Glu Ser Lys Ser Thr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 54

Gly Ser Ala Gly Ser Ala Ala Gly Ser Gly Glu Phe
1               5                   10
```

VECTORS AND VACCINE CELLS FOR IMMUNITY AGAINST ZIKA VIRUS

RELATED APPLICATIONS

This application is a 371 national stage filing of International Application No. PCT/US2017/055912, filed on Oct. 10, 2017, which claims priority to and the benefit of U.S. Provisional Patent Application No. 62/406,506, which was filed on Oct. 11, 2016, the contents of which are incorporated herein by reference in their entirety.

FIELD

The present invention relates, in part, to compositions and methods useful for immune modulation in connection with, for example, infection by the Zika virus.

INCORPORATION BY REFERENCE OF MATERIAL SUBMITTED ELECTRONICALLY

The contents of the text file named "HTB-ZOL-029 SEQUENCE LISTING", which was created on Dec. 12, 2022 and is 297 KB in size, are hereby incorporated herein by reference in their entirety.

BACKGROUND

The Zika virus (ZIKV) is a member of the virus family Flaviviridae. It is spread by, among others daytime-active *Aedes* mosquitoes, such as *A. aegypti* and *A. albopictus*.

Although in most instances ZIKV infection results in a self-limiting febrile illness associated with rash and conjunctivitis, severe neurological phenotypes can occur, including Guillain-Barre syndrome and meningoencephalitis (Carteaux et al. NEJM 374: 1595-1596 (2016); Oehler et al., Eurosurveillance 19(9), 6 Mar. 2014). Infection in pregnant women is of major concern, as it is linked to catastrophic fetal abnormalities including microcephaly, spontaneous abortion, and intrauterine growth restriction (IUGR) due to placental insufficiency (Brasil et al., NEJM doi: 10.1056/NEJMoa1602412 (4 Mar. 2016)). Currently, effective ZIKV vaccines do not exist or target only adults without impacting an existing fetus in a pregnant woman.

Accordingly, there remains an urgent need for ZIKV vaccines that could prevent and/or mitigate ZIKV infections and which will not only protect adults from Zika infection but also pregnant women and their embryos and fetuses.

SUMMARY

Accordingly, in various aspects, the present invention relates to compositions and methods that provide vaccine protection from flavivirus infection, e.g., Zika infection. Importantly, in various aspects, the compositions and methods protect adult subjects, inclusive of pregnant female adult subjects and their fetuses.

In various embodiments, the present compositions and methods protect a fetus from flavivirus infection, e.g., Zika infection, and the catastrophic fetal abnormalities associated therewith, by providing placental protection that is mediated by a chaperone-, e.g. gp96-, based vaccine that induces Zika antigen specific cytotoxic T cell (CTL) responses in the placenta and/or decidua.

In various embodiments, the present invention provides an expression vector system comprising (i) a nucleic acid encoding a fusion protein comprising a chaperone protein and an immunoglobulin, or a fragment thereof, and (ii) a nucleic acid encoding a flavivirus protein, or an antigenic portion thereof, wherein each nucleic acid is operably linked to a promoter. In exemplary embodiments, the flavivirus protein is a Zika virus (ZIKV) protein. Accordingly, the present invention provides an expression vector system comprising (i) a nucleic acid encoding a fusion protein comprising a chaperone protein and an immunoglobulin, or a fragment thereof, (i) a nucleic acid encoding a ZIKV protein, or an antigenic portion thereof, wherein each nucleic acid is operably linked to a promoter. Related host cells comprising the expression vector system of the present invention are provided herein.

The present invention also provides a composition comprising an expression vector system, a host cell, or a population of cells, as presently disclosed herein, and an excipient, carrier, or diluent. In exemplary aspects, the composition is a pharmaceutical composition.

Additionally, provided by the present invention is a kit comprising an expression vector system, a host cell, a population of cells, or a composition, as presently disclosed herein.

The present invention further provides a method of eliciting an immune response against a flavivirus in a subject, comprising administering to the subject the expression vector of the present invention or a population of cells transfected with the expression vector, in an amount effective to elicit an immune response against flavivirus in the subject. In exemplary embodiments, the flavivirus is a Zika virus. Accordingly, the present invention further provides a method of eliciting an immune response against ZIKV in a subject, comprising administering to the subject the expression vector of the present invention or a population of cells transfected with the expression vector, in an amount effective to elicit an immune response against ZIKV in the subject.

The present inventions furthermore provide a method of treating or preventing a flavivirus infection in a subject, comprising administering to the subject the expression vector of the present invention or a population of cells transfected with the expression vector, in an amount effective to treat or prevent the flavivirus infection. In exemplary embodiments, the flavivirus infection is a ZIKV infection. Accordingly, the present inventions furthermore provide a method of treating or preventing a Zika virus (ZIKV) infection in a subject, comprising administering to the subject the expression vector of the present invention or a population of cells transfected with the expression vector, in an amount effective to treat or prevent the ZIKV infection.

BRIEF DESCRIPTION OF THE DRAWINGS

FIG. 8A is a Western blot showing that transfected cells were successfully transfected with ZIKA envelope (lane 2). FIG. 8B shows MBS430270 (MyBiosource) Anti-EnvelopeE (Zika-Virus) Polyclonal antibody primary antibody (1:1000) and HRP-anti-rabbit IgG as a secondary antibody (Jackson Immuno research) (1:5000). FIG. 8C shows ELISA for gp96-Ig for clone 5G4 and FIG. 8D is a western blot for ZIKA env and FIG. 8E shows for clone 5G4.

FIG. 10C is a bar graph showing the total number of live born pups at GD 19-21, form control (CTRL) dams that have received only PBS or dams that received 293-gp96-Ig-ZIKA at GD 7.5. (n=8-12)

FIG. 12A shows the percentage of CD8+ cells with CD3+ cells in control and vaccinated mice. FIG. 12B shows decidua CDR+ T cells in control and vaccinated mice.

FIG. 13A shows the expression in control and FIG. 13B shows the expression in Zika vaccinated.

FIG. 14A-B is a set of bar graphs illustrating Gp96-Ig-ZIKVEnv vaccine induced ZIKV-Env-specific CD8+ T lymphocyte responses, as assessed by multiparameter intracellular cytokine staining (ICS) assays. FIG. 14A shows the percentage of cytokines within CD8+ cells in control and vaccinated mice and FIG. 14B shows the percentage of cytokines within CD8+CD11a+ T cells.

DETAILED DESCRIPTION

Figure 1:
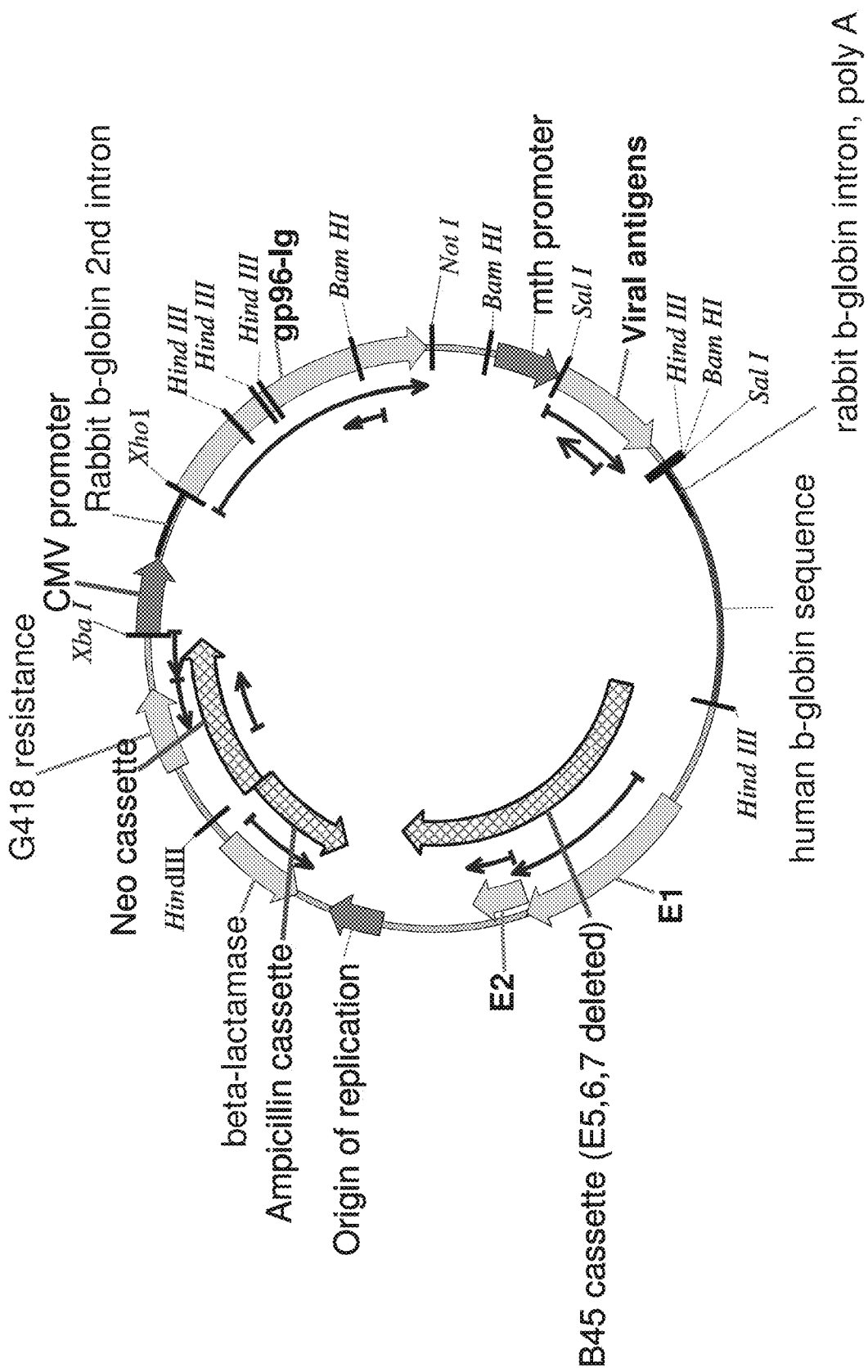
FIG. 1 is a schematic illustration of an exemplary expression vector of the present invention.

The present invention is based, in part, on the surprising discovery that an expression vector system described herein was able to stimulate immune responses in the placenta thereby providing direct protection against ZIKV infection to the unborn fetus.

Expression Vectors and Host Cells

The present invention provides an expression vector system comprising (i) a nucleic acid encoding a fusion protein comprising a chaperone protein and an immunoglobulin, or a fragment thereof, (i) a nucleic acid encoding a flavivirus protein, or an antigenic portion thereof, wherein each nucleic acid is operably linked to a promoter. In exemplary embodiments, the flavivirus protein is a Zika virus (ZIKV) protein. Accordingly, the present invention provides an expression vector system comprising (i) a nucleic acid encoding a fusion protein comprising a chaperone protein and an immunoglobulin, or a fragment thereof, (i) a nucleic acid encoding a Zika virus (ZIKV) protein, or an antigenic portion thereof, wherein each nucleic acid is operably linked to a promoter.

As used herein, the term "expression vector system" refers to one expression vector comprising all components or a set of two or more expression vectors designed to function together. For purposes herein, the term "expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the expression vector is contacted with the cell under conditions sufficient to have the mRNA, protein, polypeptide, or peptide expressed within the cell. The expression vector(s) of the disclosure are not naturally-occurring as a whole. However, parts of the vectors can be naturally-occurring.

The expression vectors of the present invention comprise any type of nucleotides, including, but not limited to DNA and RNA, which may be single-stranded or double-stranded, synthesized or obtained in part from natural sources, and which in exemplary aspects contain natural, non-natural or altered nucleotides. In exemplary aspects, the altered nucleotides or non-naturally occurring internucleotide linkages do not hinder the transcription or replication of the vector. In exemplary aspects, the expression vector system comprises one or more modified or non-natural nucleotides selected from the group consisting of: 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosyl queuosine, inosine, N6-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosyl queuosine, 5'-methoxycarboxymethyluracil, 5-methoxyuracil, 2-methylthio-N6-isopentenyladenine, uracil-5-oxyacetic acid (v), wybutoxosine, pseudouracil, queuosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

The expression vectors disclosed herein in illustrative aspects comprise naturally-occurring or non-naturally-occurring internucleotide linkages, or both types of linkages. In exemplary aspects, the expression vector system comprises one or more modified internucleotide linkages such as phosphoroamidate linkages and phosphorothioate linkages.

The expression vector system of the present invention may comprise any one or more suitable expression vectors, and may include one or more expression vectors used to transform or transfect any suitable host. Suitable expression vectors include those designed for propagation and expansion or for expression or both, such as plasmids and viruses. In various embodiments, the expression vector system in exemplary aspects comprises one or more expression vectors such as those from the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGTIO, λGTI 1, λZapII (Stratagene), λEMBL4, and λNMI 149, also can be used. Examples of plant expression vectors include pBIO1, pBI101.2, pBI101.3, pBI121 and pBIN19 (Clontech). Examples of animal expression vectors include pEUK-C1, pMAM and pMAMneo (Clontech). In exemplary aspects, the expression vector system compnscs a pBCMGSNco expression vector and/or a pBCMGHis expression vector, as described in Yamazaki et al., 1999, supra. In exemplary aspects, the expression vector system comprises a viral vector, e.g., a retroviral vector, an adenovirus vector, an adeno-associated virus (AAV) vector, or a lentivirus vector.

The expression vectors and systems comprising the expression vectors of the present invention can be prepared using standard recombinant DNA techniques described in, for example, Sambrook et al., *Molecular Cloning: A Laboratory Manual*, and Ausubel et al., *Current Protocols in Molecular Biology* (1994). Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The expression vector system may be designed for either transient expression, for stable expression, or for both. In exemplary aspects, the recombinant expression vector system comprises elements necessary for integration into the host genome. Also, the recombinant expression vectors can be made for constitutive expression or for inducible expression. For example, the recombinant expression vector system may comprise one or more suicide genes and/or one or more constitutive or inducible promoters.

In exemplary aspects, the expression vector system comprises regulatory sequences, such as transcription and translation initiation and termination codons, which are specific to the type of host (e.g., bacterium, fungus, or animal) into which the vector is to be introduced, as appropriate and taking into consideration whether the vector is DNA- or RNA-based.

The expression vector system in exemplary aspects comprises a native promoter operably linked to the nucleic acid comprising a nucleotide sequence encoding the fusion protein or the flavivirus (e.g., ZIKV) protein, or an antigenic portion thereof, or the nucleotide sequence which is complementary to or which hybridizes to the nucleotide sequence encoding the fusion protein or the flavivirus (e.g., ZIKV) protein, or an antigenic portion thereof. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, metallothionein (Mth) promoter, or a promoter found in the long-terminal repeat of the murine stem cell virus.

An expression vector also can include transcription enhancer elements, such as those found in SV40 virus, Hepatitis B virus, cytomegalovirus, immunoglobulin genes, metallothionein, and β-actin (see, Bittner et al., Meth Enzymol 1987, 153:516-544; and Gorman, Curr Op Biotechnol 1990, 1:3647). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In exemplary aspects, the nucleic acid encoding the fusion protein is operably linked to the same promoter which is also operably linked to the nucleic acid encoding the flavivirus (e.g., ZIKV) protein or an antigenic portion thereof. In exemplary aspects, the nucleic acid encoding the fusion protein is operably linked to a promoter which is different from the promoter which is operably linked to the nucleic acid encoding the flavivirus (e.g., ZIKV) protein, or an antigenic portion thereof. In exemplary aspects, the nucleic acid encoding the fusion protein is operably linked to a CMV promoter. In exemplary aspects, the nucleic acid encoding the flavivirus (e.g., ZIKV) protein, or an antigenic portion thereof, is operably linked to a Mth promoter In exemplary aspects, the expression vector system of the present invention comprises only one recombinant expression vector. In exemplary aspects, the nucleic acid encoding the fusion protein and the nucleic acid encoding the flavivirus (e.g., ZIKV) protein, or antigenic portion thereof, are present on the same expression vector.

Alternatively, the expression vector system comprises more than one expression vector. In exemplary aspects, the expression vector system comprises one expression vector comprising the nucleic acid encoding the fusion protein and one expression vector per number of different flavivirus (e.g., ZIKV) proteins, or antigenic portion, encoded by the system. In exemplary aspects, the expression vector system comprises a nucleic acid encoding the fusion protein and one or two different flavivirus (e.g., ZIKV) protein, or antigenic portion, and thereby comprises three expression vectors. In exemplary aspects, the recombinant expression vector system comprises two, three, four, five, or more recombinant expression vectors. In exemplary aspects, the expression vector system comprises at least two expression vectors and the nucleic acid encoding the fusion protein is present on an expression vector which is different from the expression vector comprising the nucleic acid encoding the flavivirus (e.g., ZIKV) protein, or antigenic portion thereof.

The expression vector system of the present invention in exemplary aspects comprises additional components. For example, in exemplary aspects, each vector of the recombinant expression vector system comprises a selectable marker. In exemplary aspects, the selectable marker is a gene product which confers resistance to an antibiotic, including but not limited to ampicillin, kanamycin, neomycin/G418, tetracycline, geneticin, triclosan, puromycin, zeocin, and hygromycin. In exemplary aspects, the selectable marker is one or more of kanamycin resistance genes, puromycin resistance genes, zeocin resistance genes, neomycin/G418 resistance genes, hygromycin resistance genes, histidinol resistance genes, tetracycline resistance genes, geneticin resistance genes, triclosan resistance genes, R-fluoroorotic acid resistance genes, 5-fluorouracil resistance genes and ampicillin resistance genes. Combination of any of the selectable markers described herein is contemplated. In exemplary aspects, when the system comprises more than one recombinant expression vector, each vector comprises a selectable marker. In exemplary aspects, each vector has the same selectable marker. Alternatively, each vector within the system comprises a different selectable marker.

In some embodiments, the expression vector system further comprises a nucleic acid encoding a bovine papilloma virus (BPV) protein. The BPV early region encodes nonstructural proteins E1 to E7 E1 and E2 are nonstructural proteins derived from bovine papilloma virus (BPV). E5, E6 and E7 are viral oncoproteins derived from BPV and have the Gene Accession ID Numbers 1489021, 3783667 and 3783668, respectively. In exemplary aspects, the expression vector system further comprises a nucleotide sequence which encodes a BPV E1 and/or a BPV E2. In exemplary aspects, the expression vector system further comprises a nucleic acid encoding an E1 amino acid sequence of SEQ ID NO: 19 and/or an E2 amino acid sequence of SEQ ID NO: 22. In exemplary aspects, the expression vector system does not comprise a nucleic acid encoding a BPV viral oncoprotein. In exemplary aspects, the expression vector system does not comprise a nucleic acid encoding E5. E6, and/or E7. In exemplary aspects, the expression vector system does not comprise nucleotides 3878 to 4012 of GenBank Accession No. NC_001522.1 encoding E5, nucleotides 91 to 519 of GenBank Accession No. NC_007612.1 encoding E6, and/or nucleotides 522 to 836 of GenBank Accession No. NC_007612.1 encoding E7. In exemplary aspects, the expression vector system does not comprise any one of SEQ ID NOs: 32-34.

Figure 3:
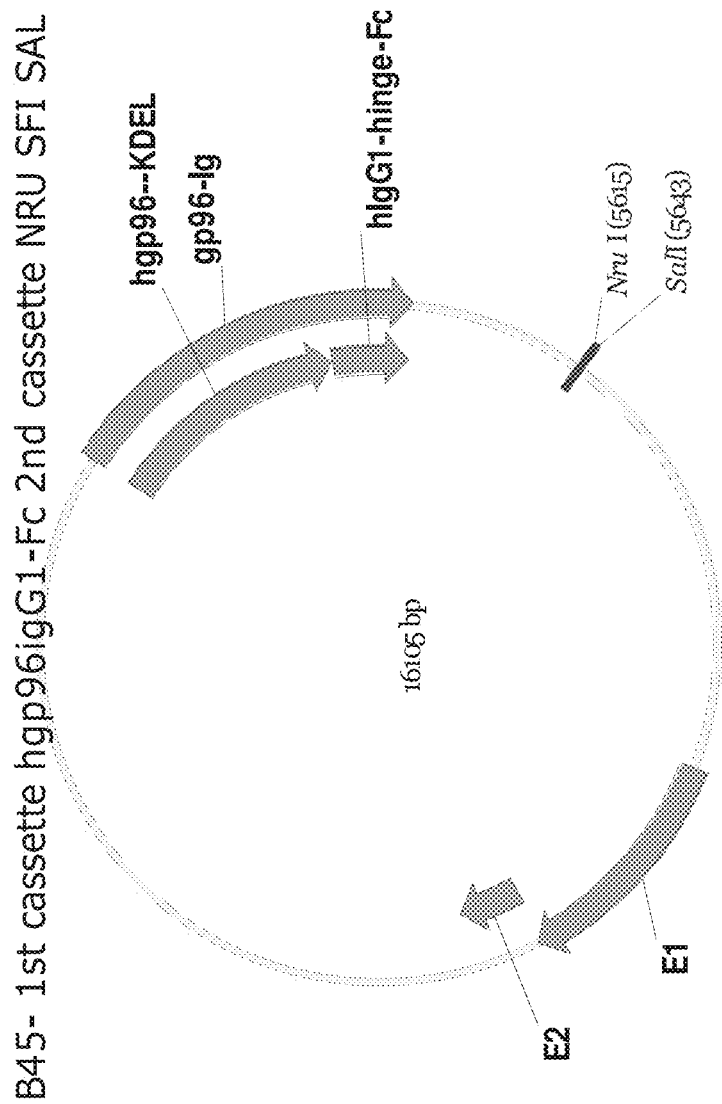
FIG. 3 is a schematic illustration of an exemplary expression vector of the present invention and the sequence thereof and having a sequence of SEQ ID NO: 24. Both forward and reverse nucleotide sequences are shown. The reverse sequence is underlined.

In some embodiments, the expression vector system comprises one or more elements shown in FIG. 1. In some embodiments, the expression vector system comprises the vector shown in FIG. 1 or FIG. 3. In exemplary aspects, the expression vector system of the present invention comprises the sequence of SEQ ID NO: 24 and/or 25.

In various embodiments, the expression vector system of the present invention encodes proteins that can be expressed in prokaryotic and eukaryotic cells. In various embodiments, expression vectors can be introduced into host cells for producing the fusion protein and the ZIKV proteins. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including electroporation, liposomes; natural polymer-based delivery vehicles, such as chitosan and gelatin; viral vectors are also suitable for in vivo transduction.

The present invention further provides a cell (e.g., a host cell) comprising the expression vector system described herein. Cells (e.g., host cells) may be cultured in vitro or genetically engineered, for example. Host cells can be obtained from normal or affected subjects, including healthy humans, patients infected with the ZIKA virus, private laboratory deposits, public culture collections such as the American Type Culture Collection, or from commercial suppliers.

Cells that can be used include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, or granulocytes, various stem or progenitor cells, such as hematopoietic stem or progenitor cells (e.g., as obtained from bone marrow), umbilical cord blood, peripheral blood, fetal liver, etc., and tumor cells (e.g., human tumor cells). The choice of cell type can be determined by one of skill in the art. In various embodiments, the cells are irradiated.

Flavivirus

As used herein, the term "flavivirus" refers to any one of the genus of viruses in the family Flaviviridae, including, but not limited to the West Nile virus, dengue virus, tickborne encephalitis virus, yellow fever virus, Zika virus and several other viruses which may cause encephalitis. The term "flavivirus" also refers to any insect-specific flaviviruses, including, for example, cell fusing agent virus (CFAV), Palm Creek virus (PCV), and Parramatta River virus (PaRV) (McLean et al., Virology 486: 272-283 (2015). In exemplary aspects, the flavivirus is Dengue virus, West Nile virus, or Yellow fever virus.

Flavivirus Proteins

In various embodiments, the expression vector system of the present invention comprises a nucleic acid encoding a flavivirus protein, or an antigenic portion thereof. In some embodiments, the expression vector comprises two or more nucleic acids each encoding a different flavivirus protein, or an antigenic portion thereof. In exemplary aspects, the flavivirus is Dengue virus, West Nile virus, or Yellow fever virus and the flavivirus protein is selected from the group consisting of: flavivirus polyprotein [Dengue virus 2] which is described in the NCBI database as NCBI Reference Sequence: NP_056776.2; polyprotein precursor [Yellow fever virus] which is described in the NCBI database as NCBI Reference Sequence: NP_041726.1; and flavivirus polyprotein [West Nile virus] which is described in the NCBI database as NCBI Reference Sequence: NP_041724.2.

In various embodiments, the flavivirus is ZIKV. In some embodiments, the expression vector system of the present invention comprises a nucleic acid encoding a Zika virus (ZIKV) protein, or an antigenic portion thereof. In exemplary aspects, the expression vector comprises two or more nucleic acids each encoding a different ZIKV protein, or an antigenic portion thereof. The structure of the ZIKV virus is known. See, for example, Kostyuchenko et al (2016) Nature 533:425428, the contents of which are hereby incorporated by reference. In various embodiments, the expression vector system of the invention comprises a nucleic acid encoding any of the known ZIKV protein or an antigenic portion, fragments, or variants thereof. In various embodiments, the ZIKV protein is one or more of membrane glycoprotein precursor M, envelope protein E, nonstructural protein NS1, nonstructural protein NS2A, nonstructural protein NS2B, nonstructural protein NS3, nonstructural protein NS4A, and nonstructural protein NS4B, or antigenic portions, fragments, or variants thereof. In some embodiments, the membrane glycoprotein precursor M comprises the amino acid sequence of SEQ ID NO: 10, the envelope protein E comprises the amino acid sequence of SEQ ID NO: 11, the nonstructural protein NS1 comprises the amino acid sequence of SEQ ID NO: 12, the nonstructural protein NS2A comprises the amino acid sequence of SEQ ID NO: 13, the nonstructural protein NS2B comprises the amino acid sequence of SEQ ID NO: 14, the nonstructural protein NS3 comprises the amino acid sequence of SEQ ID NO: 15, the nonstructural protein NS4A comprises the amino acid sequence of SEQ ID NO: 16, and the nonstructural protein NS4B comprises the amino acid sequence of SEQ ID NO: 17. In some embodiments, the expression vector system comprises a nucleic acid encoding the ZIKV protein membrane glycoprotein precursor M and a nucleic acid encoding the ZIKV protein envelope protein E, or antigenic portions, fragments, or variants thereof. In some embodiments, the expression vector system comprises a nucleic acid encoding the amino acid sequence of SEQ ID NO: 10 and a nucleic acid encoding the amino acid sequence of SEQ ID NO: 11.

Alternatively, in some embodiments, the expression vector system of the present invention may comprise a nucleic acid encoding a ZIKV protein variant that contains one or more substitutions, deletions, or additions as compared to any known wild type amino acid sequence of the ZIKV protein or a ZIKV amino acid sequence disclosed herein.

In various embodiments, the ZIKV protein may comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90°%, or at least about 91%, or at least about 92%, or at least about 93%, or at least about 94%, or at least about 95%, or at least about 96%, or at least about 97%, or at least about 98%, or at least about 99% sequence identity with any known wild type amino acid sequence of the ZIKV protein or a ZIKV amino acid sequence disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

Thus, in some embodiments, the ZIKV protein portion of the nucleic acid can encode an amino acid sequence that differs from any known wild type amino acid sequence of the ZIKV protein or a ZIKV amino acid sequence disclosed herein at one or more amino acid positions, such that it contains one or more conservative substitutions, non-conservative substitutions, splice variants, isoforms, homologues from other species, and polymorphisms.

In some embodiments, present invention provides an expression vector system comprising (i) a nucleic acid encoding the amino acid sequence of SEQ ID NO: 2, optionally lacking the terminal KDEL sequence and (ii) a nucleic acid encoding the amino acid sequence of SEQ ID NO: 11, wherein each nucleic acid is operably linked to a promoter. In some embodiments, present invention provides a method of treating or preventing a flavivirus infection in a subject, comprising administering to the subject this expression.

In some embodiments, present invention provides a biological cell comprising a first recombinant protein having an amino acid sequence of at least about 90%, or at least about 95% or at least about 97%, or at least about 98%, or at least about 99% sequence identity with SEQ ID NO: 2, optionally lacking the terminal KDEL sequence and a second recombinant protein having an amino acid sequence of at least about 90%, or at least about 95% or at least about 97%, or at least about 98%, or at least about 99% sequence identity with SEQ ID NO: 11. In some embodiments, present invention provides a method of treating or preventing a flavivirus infection in a subject, comprising administering to the subject this expression.

As defined herein, a "conservative substitution" denotes the replacement of an amino acid residue by another, biologically similar, residue. Typically, biological similarity, as referred to above, reflects substitutions on the wild type sequence with conserved amino acids. For example, conservative amino acid substitutions would be expected to have little or no effect on biological activity, particularly if they represent less than 10% of the total number of residues in the polypeptide or protein. Conservative substitutions may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. Accordingly, conservative substitutions may be effected by exchanging an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Additional examples of conserved amino acid substitutions, include, without limitation, the substitution of one hydrophobic residue for another, such as isoleucine, valine, leucine, or methionine, or the substitution of one polar residue for another, such as the substitution of arginine for lysine, glutamic for aspartic acid, or glutamine for asparagine, and the like. The term "conservative substitution" also includes the use of a substituted amino acid residue in place of an un-substituted parent amino acid residue, provided that antibodies raised to the substituted polypeptide also immunoreact with the un-substituted polypeptide.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the present ZIKV protein sequence by reference to the genetic code, including taking into account codon degeneracy.

Chaperones/Fusion Proteins

In various embodiments, the expression vector system of the present invention comprises a nucleic acid encoding a fusion protein comprising a chaperone protein and an immunoglobulin, or a fragment thereof. In exemplary aspects, the chaperone protein is any one of: gp96, Heat shock protein 70 (Hsp70), BiP, or Grp78. The amino acid sequences of such chaperone proteins are known in the art and are provided herein as, SEQ ID NOs: 29-31. In exemplary aspects, the chaperone protein is gp96. The coding region of human gp96 is 2,412 bases in length, and encodes an 803 amino acid protein that includes a 21 amino acid signal peptide at the amino terminus, a potential transmembrane region rich in hydrophobic residues, and an ER retention peptide sequence at the carboxyl terminus (GENBANK® Accession No. X15187: see, Maki et al., *Proc Natl Acad Sci USA* 1990, 87:5658-5562). The DNA and protein sequences of human gp96 are provided below:

(SEQ ID NO: 1)
```
atgagggccctgtgggtgctgggcctctgctgcgtcctgctgaccttcgggtcggtcagagctgacgatgaagt
tgatgtggatggtacagtagaagaggatctgggtaaaagtagagaaggatcaaggacggatgatgaagtagta
cagagagaggaagaagctattcagttggatggattaaatgcatcacaaataagagaacttagagagaagtcgg
aaaagtttgccttccaagccgaagttaacagaatgatgaaacttatcatcaattcattgtataaaaataaagagattt
cctgagagaactgatttcaaatgcttctgatgctttagataagataaggctaatatcactgactgatgaaaatgctc
tttctggaaatgaggaactaacagtcaaaattaagtgtgataaggagaagaacctgctgcatgtcacagacacc
ggtgtaggaatgaccagagaagagttggttaaaaaccttggtaccatagccaaatctgggacaagcgagttttta
aacaaaatgactgaagcacaggaagatggccagtcaacttctgaattgattggccagtttggtgtcggtttctattc
cgccttccttgtagcagataaggttattgtcacttcaaaacacaacaacgatacccagcacatctgggagtctgac
tccaatgaatttctgtaattgctgacccaagaggaaacactctaggacggggaacgacaattacccttgtcttaa
agaagaagcatctgattaccttgaattggatacaattaaaaatctcgtcaaaaaatattcacagttcataaactttc
ctatttatgtatggagcagcaagactgaaactgttgaggagcccatggaggaagaagaagcagccaaagaag
agaaagaagaatctgatgatgaagctgcagtagaggaagaagaagaagaaaagaaaccaaagactaaaaaa
gttgaaaaaactgtctgggactgggaacttatgaatgatatcaaaccaatatggcagagaccatcaaaagaagta
gaagaagatgaatacaaagctttctacaaatcattttcaaaggaaagtgatgacccatggcttatattcactttact
gctgaaggggaagttaccttcaaatcaatttttatttgtacccacatctgctccacgtggtctgtttgacgaatatgga
tctaaaaagagcgattacattaagctctatgtgcgccgtgtattcatcacagacgacttccatgatatgatgcctaa
ataccctcaattttgtcaagggtgtggtggactcagatgatctcccccttgaatgtttcccgcgagactcttcagcaac
ataaactgcttaaggtgattaggaagaagcttgttcgtaaaacgctggacatgatcaagaagattgctgatgataa
atacaatgatacttttggaaagaatttggtaccaacatcaagcttggtgtgattgaagaccactcgaatcgaacac
gtcttgctaaacttcttaggttccagtcttctcatcatccaactgacattactagcctagaccagtatgtggaaagaa
tgaaggaaaacaagacaaaatctacttcatggctgggtccagcagaaaagaggctgaatcttctccatttgttg
agcgacttctgaaaaagggctatgaagttatttaccctcacagaacctgtggatgaatactgtattcaggcccttccc
gaatttgatgggaagaggttccagaatgttgccaaggaaggagtgaagttcgatgaaagtgagaaaactaagg
agagtcgtgaagcagttgagaaagaatttgagcctctgctgaattggatgaaagataaagcccttaaggacaag
attgaaaaggctgtggtgtctcagcgcctgacagaatctccgtgtgctttggtggccagccagtacggatggtct
ggcaacatggagagaatcatgaaagcacaagcgtaccaaacgggcaaggacatctctacaaattactatgcga
gtcagaagaaaacatttgaaattaatcccagacacccgctgatcagagacatgcttcgacgaattaaggaagat
gaagatgataaaacagttttggatcttgctgtggttttgtttgaaacagcaacgcttcggtcagggtatcttttacca
gacactaaagcatatggagatagaatagaaagaatgcttcgcctcagtttgaacattgaccctgatgcaaaggtg
gaagaagagcccgaagaagaacctgaagagacagcagaagacacaacagaagacacagagcaagacgaa
gatgaagaaatggatgtgggaacagatgaagaagaagaaacagcaaaggaatctacagctgaaaaagatga
attgtaa
```

(SEQ ID NO: 2)
```
MRALWVLGLCCVLLTFGSVRADDEVDVDGTVEEDLGKSREGSRTDDEVVQREEEAI
QLDGLNASQIRELREKSEKFAFQAEVNRMMKLIINSLYKNKEIFLRELISNASDALDKI
RLISLTDENALSGNEELTVKIKCDKEKNLLHVTDTGVGMTREELVKNLGTIAKSGTSE
FLNKMTEAQEDGQSTSELIGQFGVGFYSAFLVADKVIVTSKHNNDTQHIWESDSNEF
SVIADPRGNTLGRGTTITLVLKEEASDYLELDTIKNLVKKYSQFINFPIYVWSSKTETV
EEPMEEEEAAKEEKEESDDEAAVEEEEEKKPKTKKVEKTVWDWELMNDIKPIWQR
PSKEVEEDEYKAFYKSFSKESDDPMAYIHFTAEGEVTFKSILFVPTSAPRGLFDEYGS
```

-continued

```
KKSDYIKLYVRRVFITDDFHDMMPKYLNFVKGVVDSDDLPLNVSRETLQQHKLLKV

IRKKLVRKTLDMIKKIADDKYNDTFWKEFGTNIKLGVIEDHSNRTRLAKLLRFQSSH

HPTDITSLDQYVERMKEKQDKIYFMAGSSRKEAESSPFVERLLKKGYEVIYLTEPVDE

YCIQALPEFDGKRFQNVAKEGVKFDESEKTKESREAVEKEFEPLLNWMKDKALKDK

IEKAVVSQRLTESPCALVASQYGWSGNMERIMKAQAYQTGKDISTNYYASQKKTFEI

NPRHPLIRDMLRRIKEDEDDKTVLDLAVVLFETATLRSGYLLPDTKAYGDRIERMLR

LSLNIDPDAKVEEEPEEEPEETAEDTTEDTEQDEDEEMDVGTDEEEETAKESTAEKDEL.
```

In exemplary aspects, the gp96 comprises the amino acid sequence of SEQ ID NO: 2. In exemplary aspects, the gp96 comprises the amino acid sequence of SEQ ID NO: 2 but without the terminal KDEL sequence, In various embodiments, the gp96 portion of the fusion protein comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any known wild type amino acid sequences of gp96 or a gp96 amino acid sequence disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77/o, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

Thus, in some embodiments, the gp96 portion of nucleic acid encoding a gp96-Ig fusion polypeptide can encode an amino acid sequence that differs from the wild type gp96 polypeptide at one or more amino acid positions, such that it contains one or more conservative substitutions, non-conservative substitutions, splice variants, isoforms, homologues from other species, and polymorphisms as described previously.

In various embodiments, the expression vector system of the present invention comprises a nucleic acid encoding a fusion protein comprising a chaperone protein and an immunoglobulin, or a fragment thereof having the SEQ ID NO: 35.

(SEQ ID NO: 35)
```
tctagagagcttggcccattgcatacgttgtatccatatcataatatgtacatttatattggctcatgtccaacat taccgccatgttgacattgattattgactagttattaatagtaatcaattacggggtcattagttcatagcccata tatggagttccgcgttacataacttacggtaaatggcccgcctggctgaccgcccaacgaccccgcccat tgacgtcaataatgacgtatgttcccatagtaacgccaatagggactttccattgacgtcaatgggtggagta tttacggtaaactgcccacttggcagtacatcaagtgtatcatatgccaagtacgccccctattgacgtcaat gacggtaaatggcccgcctggcattatgcccagtacatgaccttatgggactttcctacttggcagtacatct acgtattagtcatcgctattaccatggtgatgcggttttggcagtacatcaatgggcgtggatagcggtttga ctcacggggatttccaagtctccacccccattgacgtcaatgggagtttgttttggcaccaaaatcaacggga cttttccaaaattcgtaacaactccgccccattgacgcaaatgggcggtaggcgigtacggtgggaggtct atataagcagagctcgtttagtgaaccgtcagatcgcctggagacgccatccacgctgttttgacctccata gaagacaccgggaccgatccagcctccggtcgatcgaccgatcctgagaacttcagggtgagtttgggg acccttgattgttctttcttttttcgctattgtaaaattcatgttatatggaggggggcaaagttttcagggtgttgttt agaatgggaagatgtcccttgtatcaccatggaccctcatgataattttgtttctttcactttctactctgttgaca accattgtctcctcttatttttcttttcattttctgtaacttttttcgttaaactttagcttgcatttgtaacgaatttttaaat tcactttttgttttatttgtcagattgtaagtactttctctaatcacttttttttcaaggcaatcagggtatattatattgta cttcagcacagttttagagaacaattgttataattaaatgataaggtagaatatttctgcatataaattctggctg
```

-continued gcgtggaaatattcttattggtagaaacaactacaccctggtcatcatcctgcctttctctttatggttacaatg atatacactgtttgagatgaggataaaatactctgagtccaaacgggcccctctgctaaccatgttcatgcc ttcttctctttcctacagctcctgggcaacgtgctggttgttgtgctgtctcatcattttggcaagaattcgaag cctcgagatgatgaaacttatcatcaattcattgtataaaaataaagagattttcctgagagaactgatttcaaa tgcttctgatgctttagataagataaggctaatatcactgactgatgaaaatgctctttctggaaatgaggaac taacagtcaaaattaagtgtgataaggagaagaacctgctgcatgtcacagacaccggtgtaggaatgac cagagaagagttggttaaaaaccttggtaccatagccaaatctgggacaagcgagttttttaaacaaaatga ctgaagcacaggaagatggccagtcaacttctgaattgattggccagtttggtgtcggtttctattccgccttc cttgtagcagataaggttattgtcacttcaaaacacaacaacgatacccagcacatctgggagtctgactcc aatgaatttctgtaattgctgacccaagaggaaacactctaggacggggaacgacaattacccttgtcttaa aagaagaagcatctgattaccttgaattggatacaattaaaaatctgtcaaaaaatattcacagttcataaac tttcctatttatgtatggagcagcaagactgaaactgttgaggagcccatggaggaagaagaagcagcca aagaagagaaagaagaatctgatgatgaagctgcagtagaggaagaagaagaagaaaagaaaccaaa gactaaaaaagttgaaaaaactgtctgggactgggaacttatgaatgatatcaaaccaatatggcagagac catcaaaagaagtagaagaagatgaatacaaagctttctacaaatcattttcaaaggaaagtgatgacccc atggcttatattcactttactgctgaaggggaagttaccttcaaatcaattttatttgtacccacatctgctccac gtggtctgtttgacgaatatggatctaaaaagagcgattacattaagctctatgtgcgccgtgtattcatcaca gacgacttccatgatatgatgcctaaatacctcaattttgtcaagggtgtggtggactcagatgatctcccctt gaatgtttcccgcgagactcttcagcaacataaactgcttaaggtgattaggaagaagcttgttcgtaaaac gctggacatgataagaagattgctgatgataaatacaaigaiacttttttggaaagaatttggtaccaacatc aagcttggtgtgattgaagaccactcgaatcgaacacgtcttgctaaacttcttaggttccagtcttctcatcat ccaactgacattactagcctagaccagtatgtggaaagaatgaaggaaaaacaagacaaaatctacttcat ggctgggtccagcagaaaagaggctgaatcttctccatttgttgagcgacttctgaaaaagggctatgaag ttatttacctcacagaacctgtggatgaatactgtattcaggcccttcccgaatttgatgggaagaggttcca gaatgttgccaaggaaggagtgaagttcgatgaaagtgagaaaactaaggagagtcgtgaagcagttga gaaagaatttgagcctctgctgaattggatgaaagataaagcccttaaggacaagattgaaaaggctgtgg tgtctcagcgcctgacagaatctccgtgtgctttggtggccagccagtacggatggtctggcaacatggag agaatcatgaaagcacaagcgtaccaaacgggcaaggacatctctacaaattactatgcgagtcagaaga aaacatttgaaattaatcccagacacccgctgatcagagacatgcttcgacgaattaaggaagatgaagat gataaaacagttttggatcttgctgtggttttgtttgaaacagcaacgcttcggtcagggtatcttttaccagac actaaagcatatggagatagaatagaaagaatgcttcgcctcagtttgaacattgaccctgatgcaaaggtg gaagaagagcccgaagaagaacctgaagagacagcagaagacacaacagaagacacagagcaaga cgaagatgaagaaatggatgtgggaacagatgaagaagaagaaacagcaaaggaatctacagctgaag gatcctgtgacaaaactcacacatgcccaccgtgcccagcacctgaactcctgggggaccgtcagtctt cctcttccccccaaaacccaaggacaccctcatgatctcccggacccctgaggtcacatgcgtggtggtg gacgtgagccacgaagaccctgaggtcaagttcaactggtacgtggacggcgtggaggtgcataatgcc aagacaaagccgcgggaggagcagtacaacagcacgtaccgtgtggtcagcgtcctcaccgtcctgca ccaggactggctgaatggcaaggagtacaagtgcaaggtctccaacaaagccctcccagcccccatcga gaaaaccatctccaaagccaaagggcagccccgagaaccacaggtgtacaccctgcccccatcccggg atgagctgaccaagaaccaggtcagcctgacctgcctggtcaaaggcttctatcccagcgacatcgccgt ggagtgggagagcaatgggcagccggagaacaactacaagaccacgcctcccgtgctggactccgac -continued

```
ggctccttcttcctctacagcaagctcaccgtggacaagagcaggtggcagcagggaacgtcttctcat gctccgtgatgcatgaggctctgcacaa.ccactacacgcagaagagcctctccctgtctccgggtaaatg actcgacccagactagtcaaattaagccgaattctgcagatatccatcacactggcggccgctggaattca ctcctcaggtgcaggctgcctatcagaaggtggtggctggtgtggccaatgccctggctcacaaatacca ctgagatcttttcctctgccaaaaattatggggacatcatgaagcccttgagcatctgacttctggctaat aaaggaaatttattttcattgcaatagtgtgttggaattttttgtgtctctcactcggaaggacatatgggaggg caaatcatttaaaacatcagaatgagtatttggtttagagtttggcaacatatgcccatatgctggctgccatg aacaaaggttggctataaagaggtcatcagtatatgaaacagcccctgctgtccattccttattccatagaa aagccttgacttgaggttagattttttttatattttgttttgtgttattttttctttaacatccctaaaattttccttacat gttttactagccagattttcctcctctcctgactactcccagtcatagctgtccctcttctcttatggagatccct cgacggatccctagagtcgaggcgatgcggcgcagcaccatggcctgaaataacctctgaaagaggaa cttggttaggtaccttggttttaaaaccagcctggagtagagcagatgggttaaggtgagtgacccctcag ccctggacattcttagatgagccccctcaggagtagagaataatgttgagatgagttctgttggctaaaataa tcaaggctagtctttataaaactgtctcctcttctcctagcttcgatccagagagagacctgggcggagctgg tcgctgctcaggaactccaggaaaggagaagctgaggttaccacgctgcgaatgggtttacggagatag ctggcttccggggtgagttctcgtaaactccagagcagcgataggccgtaatatcggggaaagcactata gggacatgatgttccacacgtcacatgggtcgtcctatccgagccagtcgtgccaaaggggcggtcccg ctgtgcacactggcgctccagggagctctgcactccgcccgaaaagtgcgctcggctctgccaggacgc ggggcgcgtgactatgcgtgggctggagcaaccgcctgctgggtgcaaacccttttgcgcccggactcgt ccaacgactataaagagggcaggctgtcctctaagcgtcaccacgacttcaacgtcctgagtaccttctcct cacttactccgtagctccagcttcaccaccaagctcctcgacgtcgatcgcgagccgccaccatgcgtgg gagtgcatactatatgta.cttggacagaaacgatgctggggaggccatatcttttccaaccacattggggat gaataagtgttatatacagatcatggatcttggacacatgtgtgatgccaccatgagctatgaatgccctatg ctggatgagggggtggaaccagatgacgtcgattgttggtgcaacacgacgtcaacttgggttgtgtacg gaacctgccatcacaaaaaggtgaagcacggagatctagaagagctgtgacgctcccctcccattccac taggaagctgcaaacgcggtcgcaaacctggttggaatcaagagaatacacaaagcacttgattagagtc gaaaattggatatttaggaaccctggcttcgcgttagcagcagctgccatcgcttggcttttgggaagctca acgagccaaaaagtcatatacttggtcatgatactgctgattgccccggcatacagcatcaggtgcatagg agtcagcaatagggactttgtggaaggtatgtcaggtgggacctgggttgatgttgtcttggaacatggag gttgtgtcaccgtaatggcacaggacaaaccgactgtcgacatagagctggttacaacaacagtcagcaa catggcggaggtaagatcctactgctatgaggcatcaatatcagacatggcttcggacagccgctgccca acacaaggtgaagcctaccttgacaagcaatcagacactcaatatgtctgcaaaagaacgttagtggaca gaggctggggaaatggatgtggactttttggcaaaggagcctggtgacatgcgctaagtttgcatgctcc aagaaaatgaccgggaagagcatccagccagagaatctggagtaccggataatgctgtcagttcatggct cccagcacagtgggatgattgttaatgacacaggacatgaaactgatgagaatagagcgaaagttgagat aacgcccaattcaccaagagccgaagccaccctggggggttttggaagcctaggacttgattgtgaaccg acgacaggccttgacttttcagatttgtattacttgactatgaataacaagcactggttggttcacaaggagtg gttccacgacattccattaccttggcacgctggggcagacaccggaactccacactggaacaacaaagaa gcactggtagagttcaaggacgcacatgccaaaaggcaaactgtcgtggttctagggagtcaagaagga gcagttcacacggcccttgctggagctctggaggctgagatggatggtgcaaagggaaggctgtcctctg
```

-continued

```
gccacttgaaatgtcgcctgaaaatggataaacttagattgaagggcgtgtcatactccttgtgtactgcagc gttcacattcaccaagatcccggctgaaacactgcacgggacagtcacagtggaggtacagtacgcagg gacagatggaccttgcaaggttccagctcagatggcggtggacatgcaaactctgaccccagttgggag gttgataaccgctaaccccgtaatcactgaaagcactgagaactctaagatgatgctggaacttgatccacc atttggggactcttacattgtcataggagtcggggagaagaagatcacccaccactggcacaggagtggc agcaccattggaaaagcatttgaagccactgtgagaggtgccaagagaatggcagtcttgggagacaca gcctgggactttggatcagttggaggcgctctcaactcattgggcaagggcatccatcaaattttttggagca gctttcaaatcattgtttggaggaatgtcctggttctcacaaattctcattggaacgttgctgatgtggttgggt ctgaacacaaagaatggatctatttcccttatgtgcttggccttagggggagtgttgatcttcttatccacagc cgtctctgcttaaggccccttttggccttagcgtcgaccgatcctgagaacttcagggtgagtttggggaccc ttgattgttctttcttttttcgctattgtaaaattcatgttatatggaggggggcaaagttttcagggtgttgtttagaa tgggaagatgtcccttgtatcaccatggaccctcatgataattttgtttctttcactttctactctgttgacaacca ttgtctcctcttattttcttttcatttctgtaacttttttcgttaaactttagcttgcatttgtaacgaattttttaaattcac ttttgtttatttgtcagattgtaagtactttctctaatcacttttttttcaaggcaatcagggtatattatattgtacttc agcacagttttagagaacaattgttataattaaatgataaggtagaatatttctgcatataaattctggctggcg tggaaatattcttattggtagaaacaactacaccctggtcatcatcctgcctttctctttatggttacaatgatat acactgtttgagatgaggataaaaatactctgagtccaaaccgggcccctctgctaaccatgttcatgccttct tctctttcctacagctcctgggcaacgtgctggttgttgtgctgtctcatcattttggcaaagaattcctcgacc agtgcaggctgcctatcagaaagtggtggctggtgtggctaatgccctggcccacaagtatcactaagctc gctttcttgctgtccaatttctattaaaggttcctttgtt.ccctaagtccaactactaaactgggggatattatgaa gggccttgagcatctggattctgcctaataaaaaacatttattttcattgcaatgatgtatttaaattatttctgaa tattttactaaaaagggaatgtgggaggtcagtgcatttaaaacataaagaaatgaagagctagttcaaacc ttgggaaaatacactatatcttaaactccatgaaagaaggtgaggctgcaaacagctaatgcacattggca acagcccctgatgcctatgccttattcatccctcagaaaaggattcaagtagaggcttgatttggaggttaaa gttttgctatgctgtattttacattacttattgttttagctgtcctcatgaatgtcttttcactacccatttgcttatcct gcatctctcagccttgactccactcagttctcttgcttagagataccacctttccctgaagtgttccttccatgt tttacggcgagatggtttctcctcgcctggccactcagccttagttgtctctgttgtcttatagaggtctacttga agaaggaaaacaggggcatggtttgactgtcctgtgagcccttcttccctgcctcccccactcacagtg acccggaatctgcagtgctagtctcccggaactatcactcttttcacagtctgctttggaaggactgggcttag tatgaaaagttaggactgagaagaatttgaaaggggggcttttttgtagcttgatattcactactgtcttattaccc tatcataggcccaccccaaatggaagtcccattcttcctcaggatgtttaagattagcattcaggaagagatc agaggtctgctggctcccttatcatgtcccttatggtgcttctggctctgcagttattagcatagtgttaccatc aaccaccttaacttcatttttcttattcaataccaggtaggtagatgctagattctggaaataaaatatgagtct caagtggtccttgtcctctctcccagtcaaattctgaatctagttggcaagattctgaaatcaaggcatataat cagtaataagtgatgatagaagggtatatagaagaatttttattatatgagagggtgaaatcccagcaatttgg gaggctgaggcaggagaatcgcttgatcctgggaggcagaggttgcagtgagccaagattgtgccactg cattccagcccaggtgacagcatgagactccgtcacaaaaaaaagaaaaaaaagggggggggg cggtggagccaagatgaccgaataggaacagctccagtactatagctcccatcgtgagtgacgcagaag acgggtgatttctgcatttccaactgaggtaccaggttcatctcacagggaagtgccaggcagtgggtgca ggacagtaggtgcagtgcactgtgcatgagccgaagcagggacgaggcatcacctcacccgggaagc acaaggggtcagggaattccctttcctagtcaaagaaaagggtgacagatggcacctggaaaatcgggtc
```

-continued

```
actcccgccctaatactgcgctcttccaacaagcttgtctttggaaaatagatcaatttcccttgggaagaag attttagcacagcaaggggcaggatgttcaactgtgagaaaacgaagaattagccaaaaaacttccagta agcctgcaaaaaaaaaaaaaaatataaaagctaagtttctataaatgttctgtaaatgtaaaacagaaggtaa gtcaactgcacctaataaaaatcacttaatagcaatgtgctgtgtcagttgtttattggaaccacacccggtac acatctgtccagcatttgcagtgcgtgcattgaattattgtgctggctagacttcatggcgcctggcaccga atcctgccttctcagcgaaaatgaataattgctttgttggcaagaaactaagcatcaatgggacgcgtgcaa agcaccggcggcggtagatgcggggtaagtactgaattttaattcgacctatcccggtaaagcgaaagcg acacgcttttttcacacatagcgggaccgaacacgttataagtatcgattaggtctattttttgtctctctgtcg gaaccagaactggtaaaagtttccattgcgtctgggcttgtctatcattgcgtctctatggttttttggaggatta gacggggccaccagtaatggtgcatagcggatgtctgtaccgccatcggtgcaccgatataggtttgggg ctccccaagggactgctgggatgacagcttcatattatattgaatgggcgcataatcacgttaattggtgag ctccccaagggactgctgggatgacagcttcatattatattgaatgggcgcataatcagcttaattggtgag gacaagctacaagttgtaacctgatctccacaaagtacgttgccggtcggggtcaaaccgtcttcggtgct cgaaaccgccttaaactacagacaggtcccagccaagtaggcggatcaaaacctcaaaaaggcgggag ccaatcaaaatgcagcattatatttttaagctcaccgaaaccggtaagtaaagactatgtatttttttcccagtga ataattgttgttaactataaaaagcgtcatggcaaacgataaaagtagcaattgggattcgggcttgggatg ctcatatctgctgactgaggcagaatgtgaaagtgacaaagagaatgaggaacccggggcaggtgtaga actgtctgtggaatctgatcggtatgatagccaggatgaggattttgttgacaatgcatcagtctttcaggga aatcacctggaggtcttccaggcattagagaaaaggcgggtgaggagcagattttaaattgaaaagaa aagtattggggagttcgcaaaacagcagcggttccgaagcatctgaaactccagttaaaagacggaaatc aggagcaaagcgaagattatttgctgaaaatgaagctaaccgtgttcttacgcccctccaggtacagggg gaggggagggaggcaagaacttaatgaggagcaggcaattagtcatctacatctgcagcttgttaaat ctaaaaatgctacagttttaagctggggctctttaaatctttgttcctttgtagcttccatgatattacgaggttg tttaagaatgataagaccactaatcagcaatgggtgctggctgtgtttggccttgcagaggtgttttttgaggc gagtttcgaactcctaaagaagcagtgtagttttctgcagatgcaaaaaagatctcatgaaggaggaacttg tgcagtttacttaatctgctttaacacagctaaaagcagagaaacagtccggaatctgatggcaaacatgct aaatgtaagagaagagtgtttgatgctgcagccacctaaaattcgaggactcagcgcagctctattctggttt aaaagtagtttgtcacccgctacacttaaacatggtgctttacctgagtggatacgggcgcaaactactctg aacgagagcttgcagaccgagaaattcgacttcggaactatggtgcaatgggcctatgatcacaaatatgc tgaggagtctaaaatagcctatgaatatgctttggctgcaggatctgatagcaatgcacgggcttttttagca actaacagccaagctaagcatgtgaaggactgtgcaactatggtaagacactatctaagagctgaaacac aagcattaagcatgcctgcatatattaaagctaggtgcaagctggcaactggggaaggaagctggaagtc tatcctaacttttttttaactatcagaatattgaattaattacctttattaatgctttaaagctctggctaaaaggaatt ccaaaaaaaaactgtttagcatttattggccctccaaacacaggcaagtctatgctctgcaactcattaattca ttttttgggtggtagtgttttatcttttgccaaccataaaagtcacttttggcttgcttccctagcagatactagag ctgctttagtagatgatgctactcatgcttgctggaggtactttgacacatacctcagaaatgcattggatggc taccctgtcagtattgatagaaaacacaaagcagcggttcaaattaaagctccacccctcctggtaaccagt aatattgatgtgcaggcagaggacagatatttgtacttgcatagtcgggtgcaaacctttcgctttgagcagc catgcacagatgaatcgggtgagcaaccttttaatattactgatgcagattggaaatctttttttgtaaggttat gggggcgtttagacctgattgacgaggaggaggatagtgaagaggatggagacagcatgcgaacgttta
```

-continued

```
catgcagcgcaagaaacacaaatgcagttgattgagaaaagtagtgataagttgcaagatcatatactgta
ctggactgctgttagaactgagaacacactgctttatgctgcaaggaaaaaggggtgactgtcctaggac
actgcagagtaccacactctgtagtttgtcaagagagagccaagcaggccattgaaatgcagttgtctttgc
aggagttaagcaaaactgagtttggggatgaaccatggtctttgcttgacacaagctgggaccgatatatgt
cagaacctaaacggtgctttaagaaaggcgccagggtggtagaggtggagtttgatggaaatgcaagca
atacaaactggtacactgtctacagcaatttgtacatgcgcacagaggacggctggcagcttgcgaaggct
gggctgacggaactgggctctactactgcaccafggccggtgctggacgcatttactattctcgctttggtg
acgaggcagccagatttagtacaacagggcattactctgtaagagatcaggacagagtgtatgctggtgtc
tcatccacctcttctgattttagagatcgcccagacggagtctgggtcgcatccgaaggacctgaaggaga
ccctgcaggaaaagaagccgagccagcccagcctgtctcttctttgctcggctccccgcctgcggtccc
atcagagcaggcctcggttgggtacgggacggtcctcgctcgcacccctacaattttcctgcaggctcgg
ggggctctattctccgctcttcctccaccccgtgcagggcacggtaccggtggacttggcatcaaggcag
gaagaagaggagcagtcgcccgactccacagaggaagaaccagtgactctcccaaggcgcaccacca
atgatggattccacctgttaaaggcaggagggtcatgctttgctctaatttcaggaactgctaaccaggtaaa
gtgctatcgctttcgggtgaaaaagaaccatagacatcgctacgagaactgcaccaccacctggttcacag
ttgctgacaacggtgctgaaagacaaggacaagcacaaatactgatcacctttggatcgccaagtcaaag
gcaagactttctgaaacatgtaccactacctcctggaatgaacatttccggctttacagccagcttggacttct
gatcactgccattgccttttcttcatctgactggtgtactatgccaaatctatgcgaccgcattataaagccga
attctgcagatatccatcacactggcggccatatggccgctatgcggtgtgaaataccgcacagatgcgta
aggagaaaataccgcatcaggcgctcttccgcttcctcgctcactgactcgctgcgctcggtcgttcggct
gcggcgagcggtatcagctcactcaaaggcggtaatacggttatccacagaatcaggggataacgcagg
aaagaacatgtgagcaaaaggccagcaaaaggccaggaaccgtaaaaaggccgcgttgctggcgttttt
ccataggctccgcccccctgacgagcatcacaaaaatcgacgctcaagtcagaggtggcgaaacccga
caggactataaagataccaggcgtttccccctggaagctccctcgtgcgctctcctgttccgaccctgccg
cttaccggatacctgtccgcctttctcccttcgggaagcgtggcgctttctcatagctcacgctgtaggtatct
cagttcggtgtaggtcgttcgctccaagctgggctgtgtgcacgaaccccccgttcagcccgaccgctgc
gccttatccggtaactatcgtcttgagtccaacccggtaagacacgacttatcgccactggcagcagccac
tggtaacaggattagcagagcgaggtatgtaggcggtgctacagagttcttgaagtggtggcctaactacg
gctacactagaaggacagtatttggtatctgcgctctgctgaagccagttaccttcggaaaaagagttggta
gctcttgatccggcaaacaaaccaccgctggtagcggtggtttttttgtttgcaagcagcagattacgcgca
gaaaaaaggatctcaagaagatcctttgatcttttctacggggtctgacgctcagtggaacgaaaactcac
gttaagggattttggtcatgagattatcaaaaaggatcttcacctagatcctttaaattaaaaatgaagttttaa
atcaatctaaagtatatatgagtaaacttggtctgacagttaccaatgcttaatcagtgaggcacctatctcag
cgatctgtctatttcgttcatccatagttgcctgactccccgtcgtgtagataactacgatacgggagggctta
ccatctggccccagtgctgcaatgataccgcgagacccacgctcaccggctccagatttatcagcaataa
accagccagccggaagggccgagcgcagaagtggtcctgcaactttatccgcctccatccagtctattaa
ttgttgccgggaagctagagtaagtagttcgccagttaatagtttgcgcaacgttgttgccattgctgcaggc
atcgtggtgtcacgctcgtcgtttggtatggcttcattcagctccggttcccaacgatcaaggcgagttacat
gatccccatgttgtgcaaaaaagcggttagctccttcggtcctccgatcgttgtcagaagtaagttggccg
cagtgttatcactcatggttatggcagcactgcataattctcttactgtcatgccatccgtaagatgcttttctgt
gactggtgagtactcaaccaagtcattctgagaatagtgtatgcggcgaccgagttgctcttgcccggcgt
```

```
caacacgggataataccgcgccacatagcagaactttaaaagtgctcatcattggaaaacgttcttcggg g
cgaaaactctcaaggatcttaccgctgttgagatccagttcgatgtaacccactcgtgcacccaactgatctt
cagcatcttttactttcaccagcgtttctgggtgagcaaaaacaggaaggcaaaatgccgcaaaaaggg
aataagggcgacacggaaatgttgaatactcatactcttccttttcaatattattgaagcatttatcagggttat
tgtctcatgagcggatacatatttgaatgtatttagaaaaataaacaatagggggttccgcgcacatttcccc
gaaaagtgccacctgacgtctaagaaaccattattatcatgacattaacctataaaaataggcgtatcacga
ggccctttcgtcttcaagaattctcatgtttgacagcttatcatcgataagcttcacgctgccgcaagcactca
gggcgcaagggctgctaaaggaagcggaacacgtagaaagccagtccgcagaaacggtgctgacccc
ggatgaatgtcagctactgggctatctggacaagggaaaacgcaagcgcaaagagaaagcaggtagctt
gcagtgggcttacatggcgatagctagactgggcggttttatggacagcaagcgaaccggaattgccagc
tggggcgccctctggtaaggttgggaagccctgcaaagtaaactggatggctttcttgccgccaaggatct
gatgcgcaggggatcaagatcctgcttcatccccgtggcccgttgctcgcgtttgctggcggtgtccccg
gaagaaatatatttgcatgtctttagttctatgatgacacaaacccgcccagcgtcttgtcattggcgaattc
gaacacgcagatgcagtcggggcggcgcggtcccaggtccacttcgcatattaaggtgacgcgtgtggc
ctcgaacaccgagcgaccctgcagcgacccgcttaacagcgtcaacagcgtgccgcagatctgatcaag
agacaggatgaggatcgtttcgcatgattgaacaagatggattgcacgcaggttctccggccgcttgggtg
gagaggctattcggctatgactgggcacaacagacaatcggctgctctgatgccgccgtgttccggctgtc
agcgcaggggcgcccggttctttttgtcaagaccgacctgtccggtgccctgaatgaactgcaggacgag
gcagcgcggctatcgtggctggccacgacgggcgttccttgcgcagctgtgctcgacgttgtcactgaag
cgggaagggactggctgctattgggcgaagtgccggggcaggatctcctgtcatctccttgctcctgc
cgagaaagtatccatcatggctgatgcaatgcggcggctgcatacgcttgatccggctacctgcccattcg
accaccaagcgaaacatcgcatcgagcgagcacgtactcggatggaagccggtcttgtcgatcaggatg
atctggacgaagagcatcaggggctcgcgccagccgaactgttcgccaggctcaaggcgcgcatgccc
gacggcgaggatctcgtcgtgacccatggcgatgcctgcttgccgaatatcatggtggaaaatggccgct.
tttctggattcatcgactgtggccggctgggtgtggcggaccgctatcaggacatagcgttggctacccgt
gatattgctgaagagcttggcggcgaatgggctgaccgcttcctcgtgctttacggtatcgccgctcccgat
tcgcagcgcatcgccttctatcgccttcttgacgagttcttctgagcgggactctggggttcgaaatgaccg
accaagcgacgcccaacctgccatcacgagatttcgattccaccgccgccttctatgaaaggttgggcttc
ggaatcgttttccgggacgccggctggatgatcctccagcgcggggatctcatgctggagttcttcgccca
ccccgggagatggggggaggctaactgaaacacggaaggagacaataccggaaggaacccgcgctatg
aacggcaataaaagacagaataaaacgcacggtgttgggtcgtttgttcataaacgcggggttcggtcc
cagggctggcactctgtcgatacccaccgagacccattggggccaatacgcccgcgtttcttccttttcc
ccaccccaccccccaagttcggtgaaggcccagggctcgcagccaacgtcggggcggcaagccctg
ccatagccacgggcccgtgggttagggacggcggatcgcggccc.
```

In various embodiments, the expression vector system comprises a nucleotide sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 35 (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity with SEQ ID NO: 35).

Mutations may also be made to the nucleotide sequences of the present fusion proteins by reference to the genetic code, including taking into account codon degeneracy.

In some embodiments, the chaperone protein may be a heat shock protein. In various embodiments, the heat shock protein is one or more of hsp40, hsp60, hsp70, hsp90, and hsp110 family members, inclusive of fragments, variants, mutants, derivatives or combinations thereof (Hickey, et al., 1989, *Mol. Cell. Biol.* 9:2615-2626: Jindal, 1989, *Mol. Cell. Biol.* 9:2279-2283).

In various aspects, the fusion protein comprises an immunoglobulin or antibody. The antibody may be any type of antibody, i.e., immunoglobulin, known in the art. In illustrative embodiments, the antibody is an antibody of class or isotype IgA, IgD, IgE, IgG, or IgM. In illustrative embodiments, the antibody described herein comprises one or more alpha, delta, epsilon, gamma, and/or mu heavy chains. In illustrative embodiments, the antibody described herein comprises one or more kappa or light chains. In illustrative aspects, the antibody is an IgG antibody and optionally is one of the four human subclasses: IgG1, IgG2, IgG3 and IgG4. Also, the antibody in some embodiments is a monoclonal antibody. In other embodiments, the antibody is a polyclonal antibody. In some embodiments, the antibody is structurally similar to or derived from a naturally-occurring antibody, e.g., an antibody isolated and/or purified from a mammal, e.g., mouse, rabbit, goat, horse, chicken, hamster, human, and the like. In this regard, the antibody may be considered as a mammalian antibody, e.g., a mouse antibody, rabbit antibody, goat antibody, horse antibody, chicken antibody, hamster antibody, human antibody, and the like. In illustrative aspects, the antibody comprises sequence of only mammalian antibodies.

In illustrative aspects, the fusion protein comprises a fragment of an immunoglobulin or antibody. Antibody fragments include, but are not limited to, the F(ab')$_2$ fragment which may be produced by pepsin digestion of the antibody molecule; the Fab' fragments which may be generated by reducing the disulfide bridges of the F(ab')$_2$ fragment, and the two Fab' fragments which may be generated by treating the antibody molecule with papain and a reducing agent. In exemplary aspects, the fusion protein comprises an Fc fragment of an antibody.

DNAs encoding immunoglobulin light or heavy chain constant regions are known or readily available from cDNA libraries. See, for example, Adams et al., *Biochemistry* 1980, 19:2711-2719; Gough et al., *Biochemistry* 1980 19:2702-2710; Dolby et al., *Proc Natl Acad Sci USA* 1980, 77:6027-6031; Rice et al. *Proc Nod Acad Sci USA* 1982, 79:7862-7865; Falkner et al., *Nature* 1982, 298:286-288; and Morrison et al., *Ann Rev Immunol* 1984, 2:239-256.

In some embodiments, a gp96 peptide can be fused to the hinge, CH2 and CH3 domains of murine IgG1 (Bowen et al., *J Immunol* 1996, 156:442-449). This region of the IgG1 molecule contains three cysteine residues that normally are involved in disulfide bonding with other cysteines in the Ig molecule. Since none of the cysteines are required for the peptide to function as a tag, one or more of these cysteine residues can be substituted by another amino acid residue, such as, for example, serine.

In illustrative aspects, the fusion protein comprises an Fc fragment of an IgG1 antibody. In illustrative aspects, the Fc fragment comprises the amino acid sequence of SEQ ID NO: 5.

In exemplary aspects, the fusion protein comprises a gp96 chaperone protein fused to a Fc fragment of an IgG1 antibody. In illustrative aspects, the fusion protein comprises the amino acid sequence of SEQ ID NO: 8.

A nucleic acid encoding a gp96-Ig fusion sequence can be produced using the methods described in U.S. Pat. No. 8,685,384, which is incorporated herein by reference in its entirety. In some embodiments, the gp96 portion of a gp96-Ig fusion protein can contain all or a portion of a wild type gp96 sequence (e.g., the human sequence set forth herein). For example, a secretable gp96-Ig fusion protein can include the first 799 amino acids of the human gp96 sequence provided herein, such that it lacks the C-terminal KDEL sequence. Alternatively, the gp96 portion of the fusion protein can have an amino acid sequence that contains one or more substitutions, deletions, or additions as compared to any known wild type amino acid sequences of gp96 or a gp96 amino acid sequence disclosed herein.

In various embodiments, the gp96-Ig fusion protein and/or the flavivirus protein or an antigenic portion thereof, further comprises a linker. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et, al., (2000). Protein Eng. 13(5):309-312, the entire contents of which are hereby incorporated by reference. In some embodiments, the linker is a synthetic linker such as PEG. In other embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid. In various embodiments, the linker is substantially comprised of glycine and serine residues (e.g. about 30%, or about 40%, or about 50%, or about 60%, or about 70%, or about 80%, or about 90%, or about 95%, or about 97% glycines and serines).

In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively faraway from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

Additional illustrative linkers include, but are not limited to, linkers having the sequence LE, GGGGS, (SEQ ID NO: 36), (GGGGS)n (n=1-4) (SEQ ID NO: 36-39), (Gly)$_8$ (SEQ ID NO: 40), (Gly)$_6$ (SEQ ID NO: 41), (EAAAK)n (n=1-3) (SEQ ID NO: 42-44), A(EAAAK)nA (n=2-5) (SEQ ID NO: 45-48), AEAAAKEAAAKA (SEQ ID NO: 49), A(EAAAK)$_4$ALEA(EAAAK)$_4$A (SEQ ID NO: 50), PAPAP (SEQ ID NO: 51), KESGSVSSEQLAQFRSLD (SEQ ID NO: 52), EGKSSGSGSESKST (SEQ ID NO: 53), GSAGSAAGSGEF (SEQ ID NO: 54), and (XP)n, with X designating any amino acid, e.g., Ala, Lys, or Glu.

In various embodiments, the linker may be functional. For example, without limitation, the linker may function to improve the folding and/or stability, improve the expression, improve the pharmacokinetics, and/or improve the bioactivity of the present compositions. In another example, the linker may function to target the compositions to a particular cell type or location.

Host Cells

Also provided by the present invention is a host cell comprising any one of the expression vector systems described herein. As used herein, the term "host cell" refers to any type of cell that can contain the inventive expression vector system. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. In illustrative aspects, the host cell is a mammalian host cell. In illustrative aspects, the host cell is a human host cell. In illustrative aspects, the human host cell is an NIH 3T3 cell or an HEK 293 cell. The presently disclosed host cells are not limited to just these two types of cells, however, and may be any cell type described herein. For example, the cells that can be used include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, or granulocytes, various stem or progenitor cells, such as hematopoietic stem or progenitor cells (e.g., as obtained from bone marrow), umbilical cord blood, peripheral blood, fetal liver, etc., and tumor cells (e.g., human tumor cells). The choice of cell type can be determined by one of skill in the art. In various embodiments, the cells are irradiated.

Also provided by the present invention is a population of cells comprising at least one host cell described herein. The population of cells can be a heterogeneous population comprising the host cell comprising any of the recombinant expression vectors described, in addition to at least one other cell. Alternatively, the population of cells can be a substantially homogeneous population, in which the population comprises mainly host cells (e.g., consisting essentially of) comprising the expression vector(s). The population also can be a clonal population of cells, in which all cells of the population are clones of a single host cell comprising the recombinant expression vector(s), such that all cells of the population comprise the recombinant expression vector(s). In one embodiment of the invention, the population of cells is a clonal population comprising host cells comprising the expression vector(s) as described herein. In illustrative aspects, the cell population of the present invention is one wherein at least 50% of the cells are host cells as described herein. In illustrative aspects, the cell population of the present invention is one wherein at least 60%, at least 70%, at least 80% or at least 90% or more of the cells are host cells as described herein.

Compositions

The present invention also provides a composition comprising an expression vector system or a host cell or a population of cells, as described herein, and an excipient, carrier, or diluent. In exemplary aspects, the composition is a pharmaceutical composition. In illustrative aspects, the composition may comprise virus particles containing the vector expression system In illustrative aspects, the composition is a sterile composition and optionally is suitable for administration to a human. In illustrative aspects, the composition is ready for use. In illustrative aspects, the composition comprises a unit dose of host cells. In illustrative aspects, the unit dose is about $10^5$, about $10^6$, about $10^7$, about $10^8$, about $10^9$, about $10^{10}$, about $10^{11}$, about $10^{12}$, about $10^{13}$, about $10^{14}$, about $10^{15}$, or more host cells transfected with the expression vector system.

The pharmaceutical composition can comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration, for example between 4 and 7, or 4.5 and 5.5. In illustrative embodiments, the pharmaceutical compositions may comprise buffering agents to achieve a physiological compatible pH. The buffering agents may include any compounds capable of buffering at the desired pH such as, for example, phosphate buffers (e.g., PBS), triethanolamine, Tris, tricine, TAPS, tricine, HEPES, TES, MOPS, PIPES, cacodylate, MES, acetate, citrate, succinate, histidine or other pharmaceutically acceptable buffers.

The present invention therefore provides compositions including pharmaceutical compositions containing an expression vector system or a cell containing the expression vector system as described herein, in combination with a physiologically and pharmaceutically acceptable carrier. In various embodiments, the physiologically and pharmaceutically acceptable carrier can include any of the well-known components useful for immunization. The carrier can facilitate or enhance an immune response to an antigen administered in a vaccine. The cell formulations can contain buffers to maintain a preferred pH range, salts or other components that present an antigen to an individual in a composition that stimulates an immune response to the antigen. The physiologically acceptable carrier also can contain one or more adjuvants that enhance the immune response to an antigen. Pharmaceutically acceptable carriers include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water, saline solution, binding agents (e.g., polyvinylpyrrolidone or hydroxypropyl methylcellulose): fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Compositions can be formulated for subcutaneous, intramuscular, or intradermal administration, or in any manner acceptable for administration.

An adjuvant refers to a substance which, when added to an immunogenic agent such as a cell containing the expression vector system of the invention, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, *mycobacterium* cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al., Nature 1990, 344:873-875. For veterinary use and for production of antibodies in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, CRC Critical Reviews in Immunology 1988, 8:83; and Allison and Byars, in Vaccines: New Approaches to Immunological Problems, 1992, Ellis, ed., Butterworth-Heinemann, Boston). Additional adjuvants include, for example, bacille Calmett-Guerin (BCG), DETOX (containing cell wall skeleton of *Mycobacterium phlei* (CWS) and monophosphoryl lipid A from *Salmonella minnesota* (MPL)), and the like (see, for example. Hoover et al., J Clin Oncol 1993, 11:390; and Woodlock et al., J Immunother 1999, 22:251-259).

Routes of Administration

Methods of administering cells to a subject are well-known, and include, but not limited to perfusions, infusions and injections. See, e.g., Burch et al., *Clin Cancer Res* 6(6): 2175-2182 (2000). Dudley et al., *J Clin Oncol* 26(32): 5233-5239 (2008); Khan et al., *Cell Transplant* 19:409-418 (2010); Gridelli et al., *Liver Transpl* 18:226-237 (2012)).

Methods of Use

Without being bound to a particular theory, the methods of the present invention advantageously rely on the chaperone function of the secreted fusion protein. The fusion protein chaperones the one or more ZIKV proteins or antigen portions thereof, which are efficiently taken up by activated antigen presenting cells (APCs). The APCs act to cross-present the ZIKV proteins or antigen portions thereof via MHC I to CD8+ CTLs, whereupon an avid, antigen specific, cytotoxic CD8+ T cell response is stimulated. Without being bound to a particular theory, the expression vector systems of the present invention are advantageously capable of initiating both an innate immune response (including, e.g., activation of APCs, pro-inflammatory cytokine release, activation of NK cells), and an adaptive immune response (including, e.g., priming, activation and proliferation of antigen specific CTLs). Such dual-activation leads to successful clearance of the antigen/pathogen.

Accordingly, in various embodiments, the present invention provides a method of eliciting an immune response against a flavivirus, e.g., Zika virus (ZIKV), in a subject. In illustrative embodiments, the method comprises administering to the subject the expression vector as disclosed herein, or a population of cells transfected with the expression vector. If the subject is a pregnant female, the immune response is detected in the placenta and/or decidua in various embodiments. For example, in various instances, the method inhibits or reduces the severity of infection in a fetus and/or inhibits or reduces the severity of the biological effects of ZIKV infection of the fetus. In some embodiments, methods of the invention induce immune responses in the placenta and prevent flavivirus (e.g., ZIKV) infection to the embryo or fetus. In some embodiments, methods of the invention induce virus-specific T cell response (e.g., CD8 T cells or cytotoxic T lymphocytes) in the placenta and/or the decidua resulting in clearance of the virus (for example, before it reaches the embryo or fetus).

In various embodiments, the present methods stimulate an immune response, e.g. against a flavivirus, e.g., Zika virus, in various structures within the placenta and/or the decidua, where the flavivirus, e.g., Zika virus, is transmitted and/or infects the placenta, without wishing to be bound by theory, via the blood-syncytiotrophoblast interface and/or the uterus trophoblast interface.

The present invention also provides a method of treating or preventing a Zika virus infection in a subject, comprising administering to the subject the expression vector as disclosed herein, or a population of cells transfected with the expression vector. In various embodiments, the subject is an embryo or fetus.

The present invention also provides a method of treating or preventing one or more birth defects in an embryo or fetus, including fetal brain defects (such as microcephaly), eye defects, hearing loss, and impaired growth, fever, rash, joint pain, or conjunctivitis (red eyes). The present invention also provides a method of treating or preventing one or more symptoms/associated diseases of Zika infection including without limitation Guillain-Barre syndrome, muscle pain, headache, fever, rash, joint pain, and conjunctivitis.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating a ZIKV infection of the present invention can provide any amount or any level of treatment. Furthermore, the treatment provided by the method of the present invention may include treatment of one or more conditions or symptoms or signs of the infection, being treated. Also, the treatment provided by the methods of the present invention may encompass slowing the progression of the infection. For example, the methods can treat the infection by virtue of eliciting an immune response against ZIKV, stimulating or activating CD8+ T cells specific for ZIKV to proliferate, and the like.

As used herein, the term "prevent" and words stemming therefrom encompasses inhibiting or otherwise blocking infection by ZIKV. As used herein, the term "inhibit" and words stemming therefrom may not be a 100% or complete inhibition or abrogation. Rather, there are varying degrees of inhibition of which one of ordinary skill in the art recognizes as having a potential benefit or therapeutic effect. In this respect, the presently disclosed expression vector systems or host cells may inhibit ZIKV infection to any amount or level. In illustrative embodiments, the inhibition provided by the methods of the present invention is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition).

In various embodiments, methods of the invention prevent, alleviate, and/or treat one or more symptoms associated with ZIKV infection. Illustrative symptoms that may be treated include, but are not limited to fever, rash (e.g., skin rash), muscle and/or joint pain, swollen joints, malaise, headache, conjunctivitis (red eyes), post-infection asthenia, digestive problems including abdominal pain, diarrhea, constipation, mucous membrane ulcerations (aphthae), pruritus, meningoencephalitis, and Guillain-Barre syndrome.

In various embodiments, methods of the invention may prevent, alleviate, and/or treat one or more symptoms associated with ZIKV infection in pregnant women including those symptoms described above. Additionally, methods of the invention may prevent spontaneous abortions in pregnant women.

Without wishing to be bound by theory, it is believed that the present invention enhances placental functions against ZIKV infection. In various embodiments, administration of the expression vector system of the invention or the cell including the expression vector system prevents and/or reduces pathological changes in the placenta induced by ZIKV infection.

Without wishing to be bound by theory, it is believed that methods of the invention prevent the placenta from conveying the ZIKV to the embryo or fetus. For example, methods of the invention may prevent the ZIKV from reaching the fetal brain by transplacental passage, leakage through the trophoblastic plugs, and/or diffusion into the amniotic and yolk sac during embryogenesis. In some embodiments, methods of the invention may prevent the transmission of ZIKV to the placenta through the blood-syncytiotrophoblast interface where the placenta is bathed in maternal blood. In another embodiment, methods of the invention may prevent the transmission of ZIKV to the placenta through the uterus-trophoblast interface where the extra villous trophoblast in humans invade the uterine epithelium and come in contact with maternal immune cells. Alternatively, or additionally, methods of the invention may prevent the placenta from mounting an abnormal response against the ZIKV thus causing defects in the embryo or the fetus. In some embodiments, methods of the invention prevent the ZIKV in semen from reaching the embryo or fetus.

Accordingly, in various embodiments, methods of the invention prevent, alleviate, and/or treat one or more symptoms associated with ZIKV infection in an embryo or a fetus including an unborn embryo or fetus. In some embodiments, the expression vector system of the invention stimulates immune responses in the placenta and prevent the embryo or fetus from developing congenital abnormalities including microcephaly and other fetal brain defects. Additionally, methods of the invention may prevent the embryo or fetus from developing other health issues including, but not limited to, eye defects, hearing loss, and impaired growth.

The present expression vector system and cells comprising the same may be administered by any route considered appropriate by a medical practitioner. Illustrative routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, by electroporation, or topically. Administration can be local or systemic.

In illustrative aspects, the method comprises intramuscular (IM) administration of the expression vector. In illustrative aspects, the method comprises electroporation or electroporation following the IM administration of expression vector. In various embodiments, electroporation is used to help deliver vectors (genes) into the cell by applying short and intense electric pulses that transiently permeabilize the cell membrane, thus allowing transport of molecules otherwise not transported through a cellular membrane. Methods for electroporating a nucleic acid construct into cells and electroporation devices for such delivery are known. Sec, for example, Flanagan et al. Cancer Gene Ther (2012) 18:579-586, WO 2014/066655, U.S. Pat. No. 9,020,605, the entire contents are incorporated by reference.

In exemplary aspects, DNA (50 µg) containing expression vector that contains gp96-Ig and ZIKV antigens in 50 µL of saline is injected in the tibialis anterior muscle of anesthetized wild-type C57BL/6 mice. A two-needle array electrode pair is inserted into muscle immediately after DNA delivery and the injection site is electroporated with field strength of 50 V/cm (constant) and six electric pulses of 50 ms each by using the AgilePulse in Vivo System (BTX, Harvard Apparatus).

In illustrative aspects, the method comprises subcutaneously administering the population of cells. In illustrative aspects, the method comprises subcutaneously administering the population of cells to an arm or leg of the subject.

In various embodiments, the vector or the cell can be administered to a subject one or more times (e.g., once, twice, two to four times, three to five times, five to eight times, six to ten times, eight to 12 times, or more than 12 times). A vector or a cell as provided herein can be administered one or more times per day, one or more times per week, every other week, one or more times per month, once every two to three months, once every three to six months, or once every six to 12 months. A vector or a cell can be administered over any suitable period of time, such as a period from about 1 day to about 12 months. In some embodiments, for example, the period of administration can be from about 1 day to 90 days; from about 1 day to 60 days; from about 1 day to 30 days; from about 1 day to 20 days; from about 1 day to 10 days; from about 1 day to 7 days. In some embodiments, the period of administration can be from about 1 week to 50 weeks; from about 1 week to 50 weeks; from about 1 week to 40 weeks; from about 1 week to 30 weeks; from about 1 week to 24 weeks; from about 1 week to 20 weeks; from about 1 week to 16 weeks; from about 1 week to 12 weeks: from about 1 week to 8 weeks; from about 1 week to 4 weeks; from about 1 week to 3 weeks; from about 1 week to 2 weeks; from about 2 weeks to 3 weeks; from about 2 weeks to 4 weeks; from about 2 weeks to 6 weeks; from about 2 weeks to 8 weeks; from about 3 weeks to 8 weeks; from about 3 weeks to 12 weeks; or from about 4 weeks to 20 weeks.

Embodiments that relate to methods of treatment are also envisioned to apply to medical uses and uses in manufacture of medicaments.

Combination Therapy

In various embodiments, the composition of the present invention is co-administered in conjunction with additional therapeutic agent(s). Co-administration can be simultaneous or sequential.

In some embodiments, the additional therapeutic agent is an agent that is used to provide relief to symptoms of ZIKV infections. Such agents include anti-inflammatory agents such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolide, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunsolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin.

In an embodiment, the additional therapeutic agent is chloroquine, including chloroquine phosphate.

In an embodiment, the additional therapeutic agent is a composition comprising all-natural herbal ingredients as disclosed in US 2016/0250181, the contents of which are hereby incorporated by reference. In some embodiments, the composition comprises a combination of one or more artemisinin, berberine, capsaicin and *Tinospora cordifolia*.

In various embodiments, the additional therapeutic agent is a Zika vaccine (e.g. which allows use of two vaccines in a subject for possible improved response), including GLS-5700 (Inovio Pharmaceuticals) and VRC-ZKADNA085-00-VP (NIAID). For instance, in various embodiments, the present vaccines in combination with known Zika vaccines allows for stimulation of both humoral- and T cell-based immunity.

Subjects

In illustrative embodiments, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes).

In various embodiments, the mammal is a human. In some embodiments, the human is an adult aged 18 years or older. In some embodiments, the human is a child aged 17 years or less. In an embodiment, the subject is male, e.g., a male human. In another embodiment, the subject is a female subject. In illustrative embodiments, the subject is a female subject, e.g., a female human, aged from about 16 years to about 50 years. In illustrative embodiments, the female human is capable of giving birth. In illustrative embodiments, the subject is a pregnant female. In illustrative embodiments, the human pregnant female is in the first trimester, second trimester, or third trimester of pregnancy. In illustrative embodiments, the subject is a female and the population of cells is administered prior to pregnancy. In illustrative embodiments, the subject is not pregnant. In various embodiments, the subject is an embryo or a fetus including an unborn embryo or fetus. As referred to herein, an embryo is developed from the time of fertilization until the end of the eighth week of gestation, at which time it is referred to as a fetus.

Kits

Kits comprising host cells (or a cell population comprising the same) or expression vector systems or a composition comprising any one of the foregoing of the present invention are also provided. In illustrative aspects, the kits comprise a unit dose of cells comprising the expression vector systems of the present invention. In illustrative aspects, the kit comprises a sterile, GMP-grade unit dose of the cells. In illustrative aspects, a unit dose of cells comprises $10^5$, $10^6$, $10^7$, $10^8$, $10^9$, $10^{10}$, $10^{11}$, $10^{12}$ $10^{13}$, or more than $10^{15}$ cells comprising the expression vector system of the present invention.

In illustrative aspects, the unit dose of cells are packaged in an intravenous bag. In illustrative aspects, the unit dose of coils are provided in a cryogenic form. In illustrative aspects, the unit dose of cells are ready to use. In illustrative aspects, the unit dose of cells are provided in a tube, a flask, a dish, or like container.

In illustrative aspects, the cells are cryopreserved. In illustrative aspects, the cells are not frozen.

The following examples are given merely to illustrate the present invention and not in any way to limit its scope.

EXAMPLES

Example 1

This example demonstrates, inter alia, a method of constructing an expression vector encoding a gp96-Ig fusion protein.

An expression vector comprising a nucleic acid encoding a gp96-IgFc fusion protein and one or more ZIKV antigens is constructed. The expression vector is shown in FIG. 1. For reference, Yamazaki et al., *The Journal of Immunology* 163: 5178-5182 (1999) describes the construction of a similar expression vector comprising a nucleic acid encoding gp96-Ig fusion protein and the transfection of the expression vector into cells. Briefly, Yamazaki et al., 1999, supra, teaches that the KDEL sequence was deleted and replaced with the hinge, CH2 and CH3 domains of murine IgG1 (see, References 16-23 of Yamazaki et al., 1999, supra); double-stranded cDNA was prepared from Jurkat DNA (see, Reference 24 of Yamazaki et al., 1999, supra) with the GeneAmp RNA PCR Kit (Perkin-Elmer Cetus, Norwalk, Conn.) and amplified by PCR. The PCR primers were 5'-ATTACTCGAGGGCCGCACGC CATGAGGG-3' and 5'-GCCCGGATCCTTCAGCTGTAGATTCCTT TGC-3' (Maki et al., *PNAS USA* 87: 5658(1990); Maki et al., *Somat Cell Mol Genet* 19:73 (1993)). The PCR primers included an XhoI site (forward primer) and a BamHI site (reverse primer). The hinge, CH2 and CH3 domains of murine IgG1, was amplified by using murine IgG1 cDNA as a template and mutating the three cysteines of the hinge portion to serines (see, References 21, 25 of Yamazaki et al., 1999, supra). The PCR primers were 5'-GCGAG-GATCCGTGCCCAGGGATTCTGGTT CTAAG-3' and 5'-CTAAGCGGCCGCAAGGACACTGGGATCATIT ACCAGG-3'. The PCR primers included a BamHI site (forward primer) and NolI site (reverse primer). Gp96 was inserted into XhoI and BamHI sites of the eukaryotic expression vector, pBCMGSNeo and pBCMGHis (see References 26-29 of Yamazaki et al., 1999, supra) and transfected into SCLC-2, SCLC-7. B16F10, MC57, LLC NIH3T3, EL4, E.G7, and P815. Transfected cells were selected with 1 mg/ml of G418 or 2.5-10 mM of L-Histidinol (Sigma, St. Louis, Mo.). A second expression vector encoding chicken ovalbumin (OVA) named apc-NEO-OVA was co-transfected into the cells that were transfected with pBCMGSneo expressing gp96-Ig. The production of the gp96-IG fusion protein by transfected cells and the secretion of the fusion protein into the culture medium was assayed via ELISA. Transfected cells were administered to mice and shown to enhance the CD8 T cell immune response.

Example 2

This example demonstrates the induction of antigen specific CTL responses in placenta and decidua of pregnant B6 mice by secreted gp96$^{OVA}$-Ig.

The placenta acts as a barrier against infections, due to multiple unique structural, cellular, and immune properties. The detrimental effects of congenital viruses on pregnancy and fetal outcomes occur in part because of impaired placental function and profound pathological changes in ZIKV-infected placentas have been observed. Induction of appropriate immune responses in placenta are key to successful prevention of viral infections from developing fetus. Induction of virus-specific CD8 T cells responses in the placenta is hypothesized to lead to clearance of the pathogen/virus.

Figure 4:
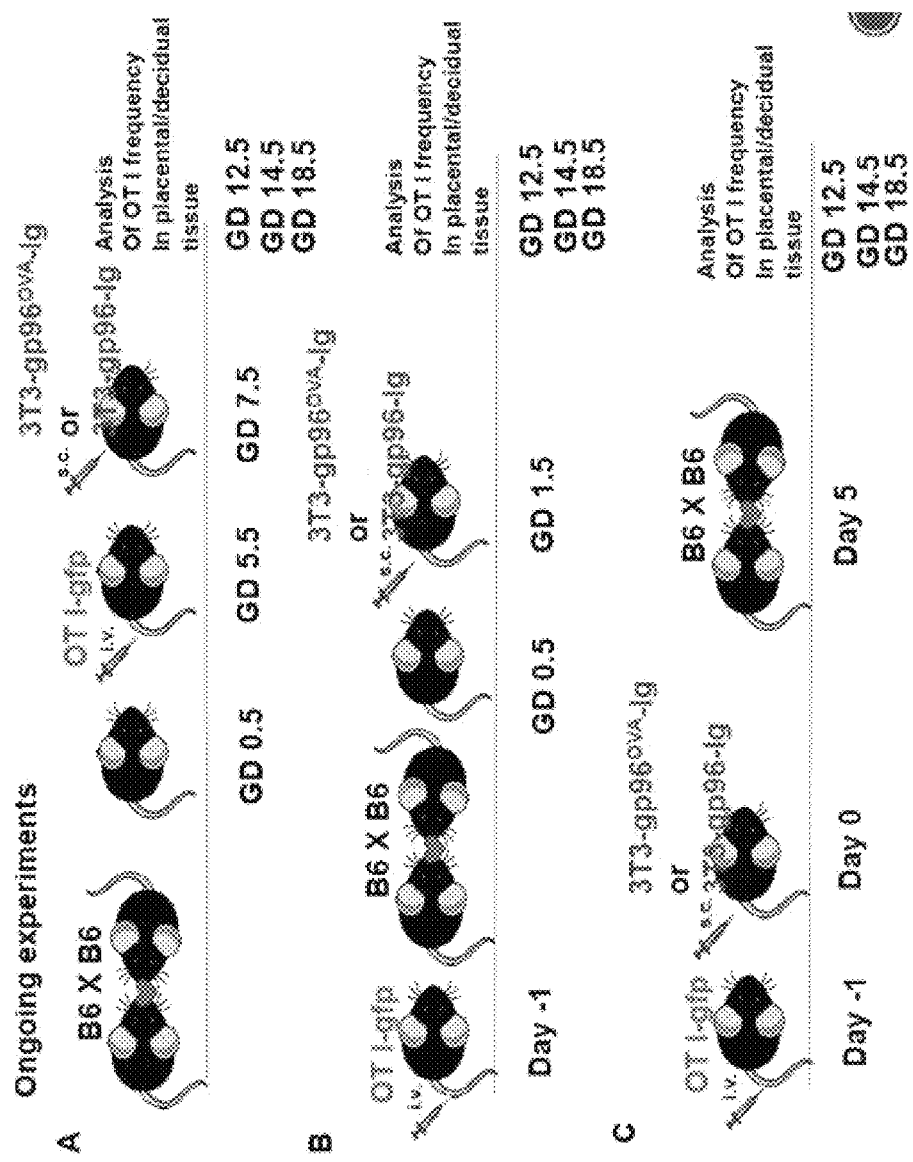
FIGS. 4 and 5 provide a schematic of the experiment described in Example 2 and additional experimental schematics.
Figure 5:
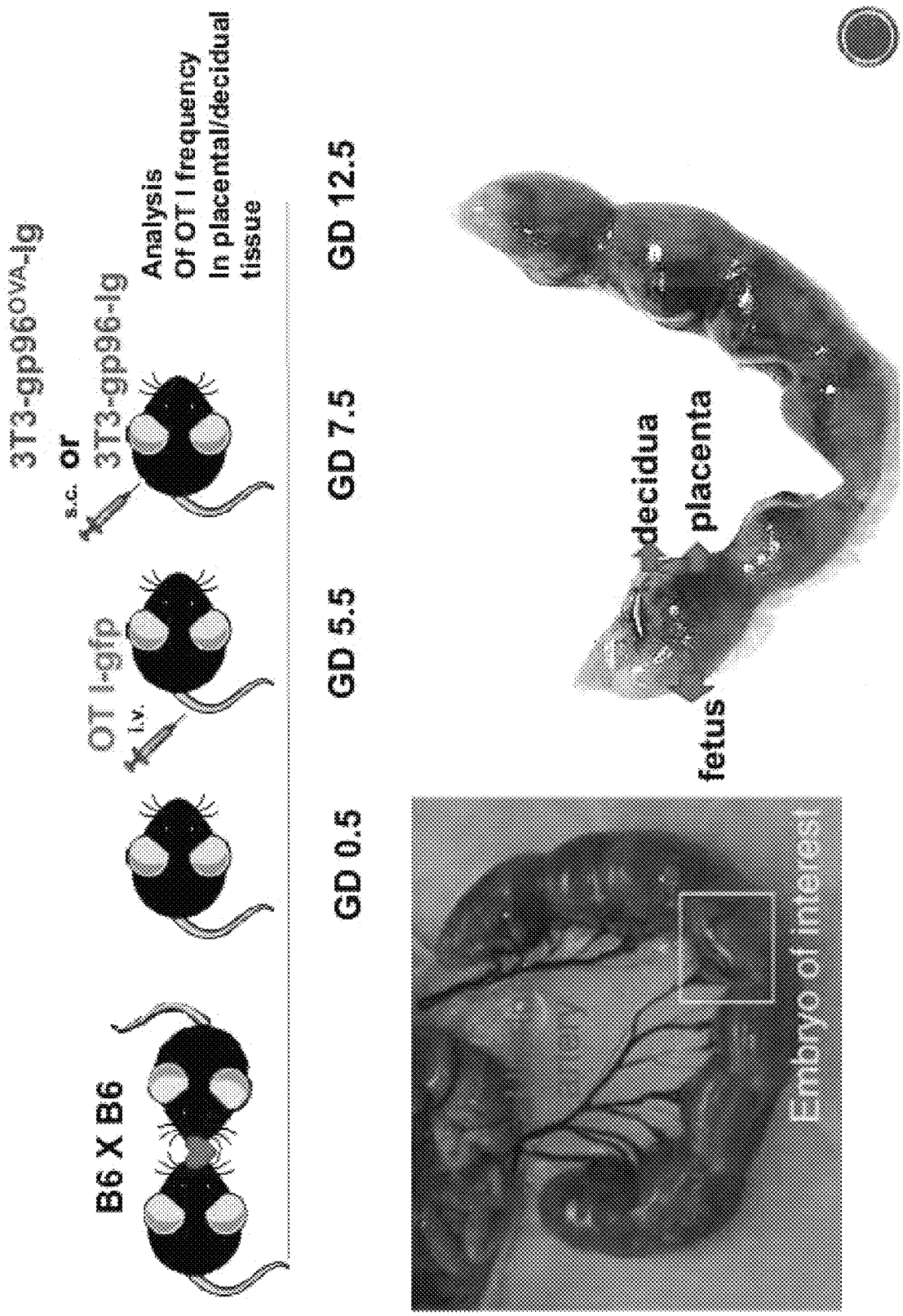
Figure 6:
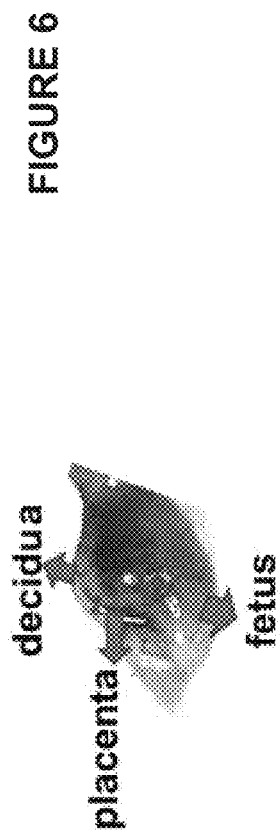
FIG. 6 provides a photo of tissue and anatomical drawings of a pregnant mouse from Erlebacher, Nature Reviews Immunology 13: 23-33 (2013).
Figure 6:
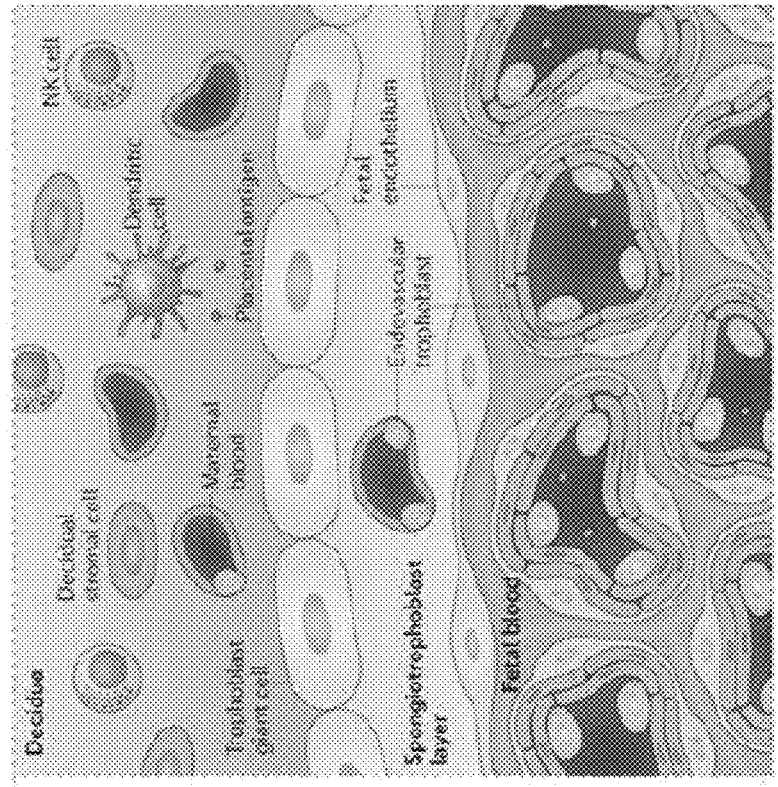
Figure 7:
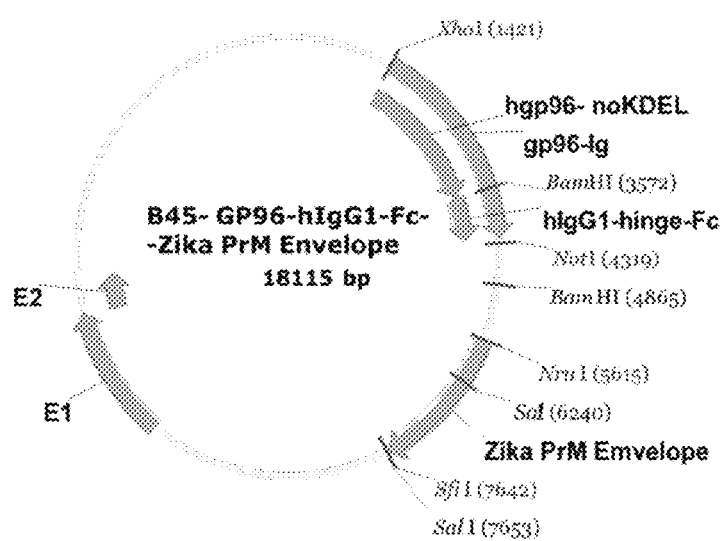
FIG. 7 is a schematic illustration of an exemplary expression B45 vector expressing Gp96-Ig and ZIKA Pre-Membrane and Envelope protein of the present invention and the sequence thereof and having a sequence of SEQ ID NO: 35. Gp96-Ig construct was cloned in the first expression cassette and ZIKA Pre-membrane Envelope construct was cloned in the second expression cassette.

To test the ability of vaccine cells to stimulate CD8 T cells in the placenta and decidua, NIH3T3 cells were co-transfected with a gp96-Ig expression vector were made as described in Example 1 and Yamazaki et al., 1999, supra, and a second expression vector encoding chicken ovalbumin (OVA) named apc-NEO-OVA. Such cells are referred to as 3T3-gp96-OVA-Ig cells. An illustrative schematic of the experiment is depicted in FIG. 4.

Figure 2:
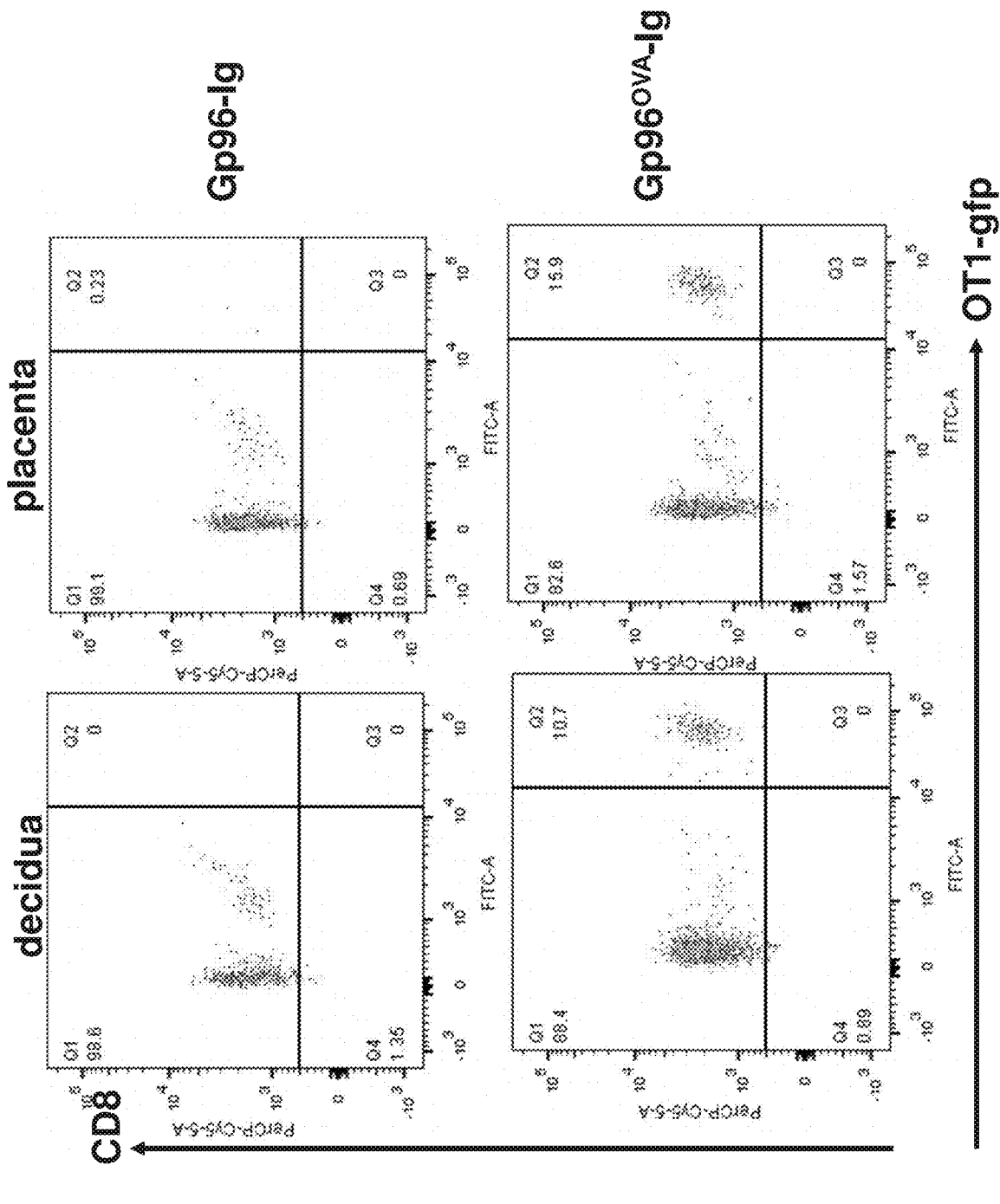
FIG. 2 is a set of representative dot plots of gated CD3+CD8+ T cells in placenta and decidua and the frequency of OT1 positive cells.

B6 females were mated with B6 mice and gestation day (GD) 0.5 was determined by the presence of vaginal plug. At GD 5.5, 1 million of OT1 cells (T cells comprising T cell receptors specific for the OVA antigen) were injected in the tail vein. Two days' post-injection. 2.5 million 3T3-gp96-OVA-Ig or 3T3-gp96-Ig cells were injected subcutaneously. Five days later, mice were euthanized. Pregnant uteri were collected and from individual fetal/placental units (FPU) placental disk was separated form decidua (maternal endometrium). Placental and decidual single cells suspension was obtained by collagenase D digestion. Cells were labeled with antiCD8 antibody and frequency of OT1 cells was determent by flow cytometry. Representative dot plots of gated CD3+CD8+ T cells in the placenta and decidua and the frequency of OT1 positive cells are shown in FIG. 2.

After subcutaneous injection of vaccine cells (3T3-OVA-gp96-Ig) into pregnant B6 mice. OVA specific CD8 T cells (OT1) were detected in high frequencies in placenta and decidua (10-15% of all CD8 T cells in placenta and decidua were OVA specific T cells) (FIG. 2) without damaging maternal-fetal interface and preserving healthy fetus.

These data support that complexes of gp96-Ig fusion protein chaperoning the OVA antigens are recognized by antigen presenting cells (APCs) local to the site of SC injection. The APCs prime or activate the innate and adaptive arms of the immune system, and activate CD8-specific T cells having T cell receptors that specifically bind and recognize the OVA antigen chaperoned by the gp96-Ig fusion protein, thereby causing proliferation of these T cells and priming of these T cells. Primed cells circulate in the blood and make their way into the placenta through means of normal circulation.

This example provides proof-of-principle that the administration of cells expressing gp96-Ig fusion protein and an antigen of interest can lead to stimulation of antigen-specific CD8 T cells located in the placenta and decidua of pregnant subjects.

Example 3

This example demonstrates a method of administering cells comprising an illustrative expression vector of the present invention.

An expression vector encoding the gp96-Ig fusion protein and ZIKV antigens was constructed. A map of the expression vector made is shown in FIG. 1. HEK293 cells were then transfected with the gp96-Ig-ZIKV antigen expression vector.

Transfected HEK293 cells are first irradiated (12,000 rads) and then suspended in freezing medium containing 10% DMSO, 25% human serum albumin, sodium bicarbonate 8.4% and sodium chloride 0.9% and subcutaneously administered to the upper outer arm or thigh of a human female. The number of cells that are injected depends on the amount of secreted gp96-Ig: equivalent number of cells that produce 10-20 micrograms of gp96-Ig in in vitro established assay. Based on previous experiments (e.g., J Immunol. 2013 Mar. 15; 190(6):2495-9. doi: 10.4049/jimmunol.1202655. Epub 2013 Feb. 11. PMID: 23401588; Vaccine. 2011 Mar. 21; 29(14):2619-25. doi: 10.1016/j.vaccine.2011.01.044. Epub 2011 Jan. 28. PMID:21277409; Mucosal Immunol. 2010 March; 3(2):182-92. doi: 10.1038/mi.2009.127. Epub 2009 Nov. 18. PMID: 19924120: J Immunol. 2007 Aug. 15; 179(4):2310-7. PMID:17675492), the complexes of gp96-Ig chaperoning the ZIKV antigens are recognized by APCs local to the injection site. The APCs prime or activate the innate and adaptive arms of the immune system, and activate CD8-specific T cells having T cell receptors that specifically bind and recognize the ZIKV antigens chaperoned by the gp96-Ig fusion protein, thereby causing proliferation of these T cells and priming of these T cells. Primed T cells circulate in the blood and make their way into the placenta through means of normal circulation. In this experiment, the number of cells injected depends on the amount of secreted gp96-Ig, i.e., equivalent number of cells are used that produces 10-20 micrograms of gp96-Ig in in vitro established assays.

Example 4

This example demonstrates a method of administering illustrative expression vectors of the present invention.

The expression vector of FIG. 1 is generated and formulated into a sterile composition. The composition is injected into the muscle of the upper outer arm or thigh of a human female subject. Subsequently, electroporation (EP) pulses are delivered, a slow resealing of the membrane occurs on the second to minutes' time scale. The end result of the process is that upwards of 100-1000-fold enhancement of vector delivery and increased expression of the encoded ZIKV antigens and gp96-Ig fusion protein, which in turn, leads to elevated immune responses relative to delivery of DNA alone without electroporation. See, e.g., Luckay et al., J Virol 81.5257-5269 (2007); Liu et al., J Virol 82: 4844-4852 (2008); Hirao et al., Vaccine 26:3112-3120 (2008); Rosati et al., Vaccine 26: 5223-5229 (2008); Simon et al., Vaccine 26:5202-5209 (2008): Hirao et al., Mol Ther 18:1568-1576 (2010); Dobano et al., Vaccine 25: 6635-6645 (2007), LeBlanc et al., Vaccine 26:185-192 (2008); Ahlen et al., J Immunol 179:4741-4753 (2007); Luxembourg et al., Vaccine 26: 4025-4033 (2008): van Drunen Littel-van den Hurk et al., Vaccine 26: 5503-5509 (2008); Kim et al., Exp Mol Med 40: 669-676 (2008); Nystrom et al., J Infect Dis 201: 1867-1879 (2010). Trollet et al., Infect Immun 77:2221-2229 (2009): Best et al., Vaccine 27: 5450-5459 (2009); Seo et al., Vaccine 27: 5906-5912 (2009); Livingston et al., Vaccine 28: 1056-1061 (2010); Laddy et al., J Virol 83: 4624-4630 (2009): Laddy et al., PLoS One 3:e2517 (2008): and Hirao et al., Vaccine 26: 440-448 (2008).

Experiments are also performed in mice. Specifically, 50 micrograms of DNA containing expression vector that contains gp96-Ig and ZIKV antigens in 50 micro liters of saline was injected in the tibialis anterior muscle of anesthetized wild-type C57BL16 mice. A two-needle array electrode pair was inserted into muscle immediately after DNA delivery and the injection site was electroporated with field strength of 50 V/cm (constant) and six electric pulses of 50 ms each by using the AgilePulse In Vivo System (BTX, Harvard Apparatus).

Example 5

This example demonstrates the generation of gp96-Ig and ZIKA envelope vaccine and induction of ZIKV-Env-specific CD8+ T lymphocyte responses.

Figure 8:
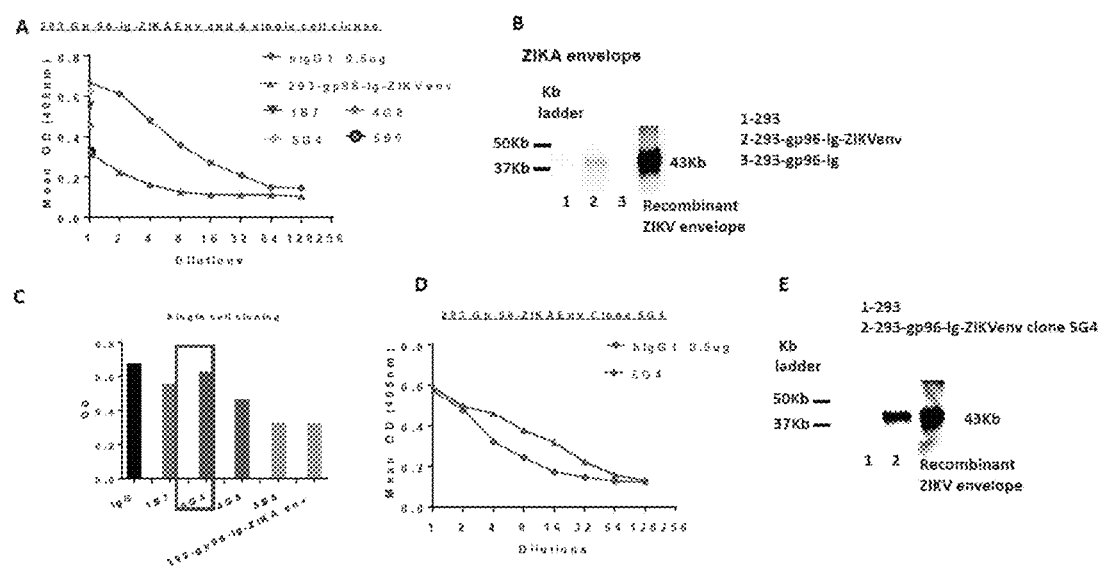
FIG. 8A-E illustrate single cell cloning of vaccine 293 cells expressing gp96-Ig and ZIKA envelope.

HEK-293-gp96-Ig was transfected with the B45 vector expressing gp9-Ig and ZIKV-envelope. The cells were transfected using Effectin-based transfection protocol and subsequently selected in the presence of selection marker (geneticin, G418), a stable transfection of HEK-293 cells that co express gp96-Ig and ZIKV-envelope as shown in the figure below was established (FIG. 8A). Production of gp96-Ig was confirmed by ELISA using human IgG1 as a standard. Western blotting was also used to confirm that cells express ZIKA envelope (FIG. 8B, lane 2). MBS430270 (MyBiosource) Anti-Envelope E (ZikaVirus) Polyclonal antibody as a primary antibody (1:1000) and HRP-anti-rabbit IgG as a secondary antibody (Jackson Immunoresearch) (1:5000) were used to confirm (FIG. 8B). The expression of gp96-Ig production was improved in an already established cell line, 293-gp96-Ig-ZIKVenv (FIG. 8A. C) by performing single cell cloning. Data showed several highly gp96-Ig-expressing cell clones (FIG. 8C). Clone 5G4 was further expanded, high production of gp96-Ig confirmed by ELISA (FIG. 8D) and ZIKA envelope expression confirmed by Western blotting (FIG. 8E). Vaccine cells were irradiated and stored in freezing media at concentration $10^6/500$ ul at $-135°$ C. and used for in vivo experiments.

Data shows that continuous cell secretion of gp96-Ig in vivo is more effective for CD8 CTL induction than injection of purified gp96-Ig. This increased efficiency is attributed to continuous secretion and stimulation of the immune system, similar to attenuated viral vaccines. However, DNA vaccines are more attractive due to their safety and ease of engineering and manufacturing compared to cell-based vaccine approach.

Figure 9:
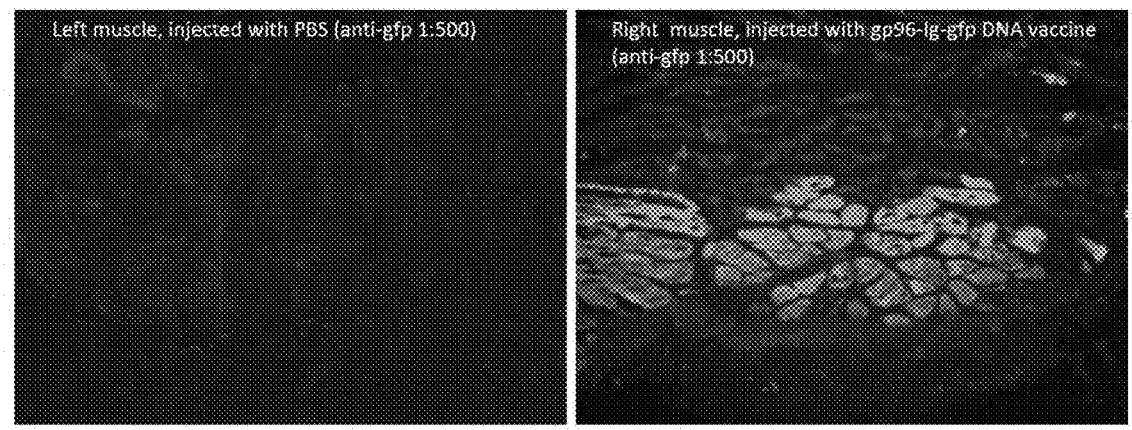
FIG. 9 is a confocal microscopy image illustrating the expression of DNA vaccination with in vivo electroporation (EP) of Gp96-Ig-gfp DNA vaccine.

In order to confirm efficacy of DNA vaccine delivery, transfection efficiency of B45 plasmid entry into target (muscle) cells after in vivo electroporation (EP) by fluorescent microscopy was measured. B45 plasmid containing secreted gp96-Ig (in the 1st expression cassette) and EGFP (in the 2nd expression cassette) was injected into muscle (tibialis anterior) (50 micrograms) followed by a brief electric field pulse that induces temporary and reversible pores in the muscle cell membrane. B45 plasmid (prepared using Endotoxin-free DNA purification kit, Qiagen, CA) at previously determined dose of 50 micrograms was used. In vivo electroporation was applied after injection of the plasmid(s) into muscles using AgilePulse IM in Vivo gene delivery system (BTX Harvard Apparatus). Left muscle was injected with PBS. Expression of EGFP protein was analyzed in longitudinal sections of the tibialis anterior muscle 48 h after injection (FIG. 9). Frozen tissue samples were cut in 10 micron sections, stained with anti-gfp-AF488 antibody and examined under the fluorescent microscope. Nuclei were stained with DAPI (blue). Results indicated very high level of expression of gp96-Ig-gfp in the injected site. This results confirms that in vivo transfection of gp96-Ig is successful and that immunization protocols can begin with gp96-Ig-ZIKV DNA and electroporation.

Figure 10:
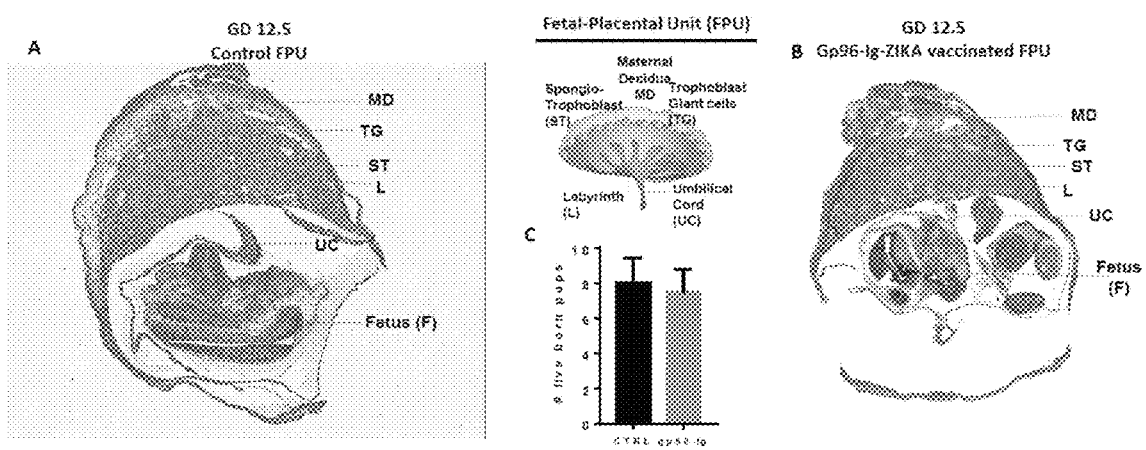
FIG. 10A-C is a histological staining and a bar graph illustrating that secreted gp96-Ig vaccination during mouse pregnancy is safe. Pregnant Wildtype (WT) mice were injected s.c. with PBS control (FIG. 10A) or with 293-gp96-Ig-ZIKAEnv (FIG. 10B) at GD 7.5.

Without wishing to be bound by theory, a critical issue for protective ZIKV vaccines is induction of protective immune responses at maternal/fetal interface. In order to develop ZIKV protective vaccine, immunogenicity and efficacy was tested in a pregnant mouse model to measure immunogenicity of secreted gp96-Ig vaccine (FIGS. 10A-C and FIG. 11). First, to confirm preliminary data that vaccination with gp96-Ig during pregnancy is safe, female mice were first evaluated for the stage of the estrous cycle by visual observation for 2 weeks. Females in the proestrus cycle were put with one male for 24 h. Appearance of a vaginal plug was marked as day 0.5 of pregnancy, gestation day (GD) 0.5 at which time male mice were removed. Pregnant mice at GD 7.5 were vaccinated with established vaccine cells (293-gp96-Ig-ZIKVenv) or with mock control (PBS) Mice were followed up until the end of pregnancy (GD 19.5-21.5) or humanely euthanized 5 days after vaccination (GD 12.5) (FIG. 10). Results indicated that vaccinated mice have the same number of live-born pups as control mice (n=12). In addition, histological findings confirm that there was no difference among fetal-placental units from control vs vaccinated dams with an overall conclusion that gp96-Ig vaccination during pregnancy does not induce pathological changes in placenta or in fetus. (FIGS. 10A, B and C).

Figure 11:
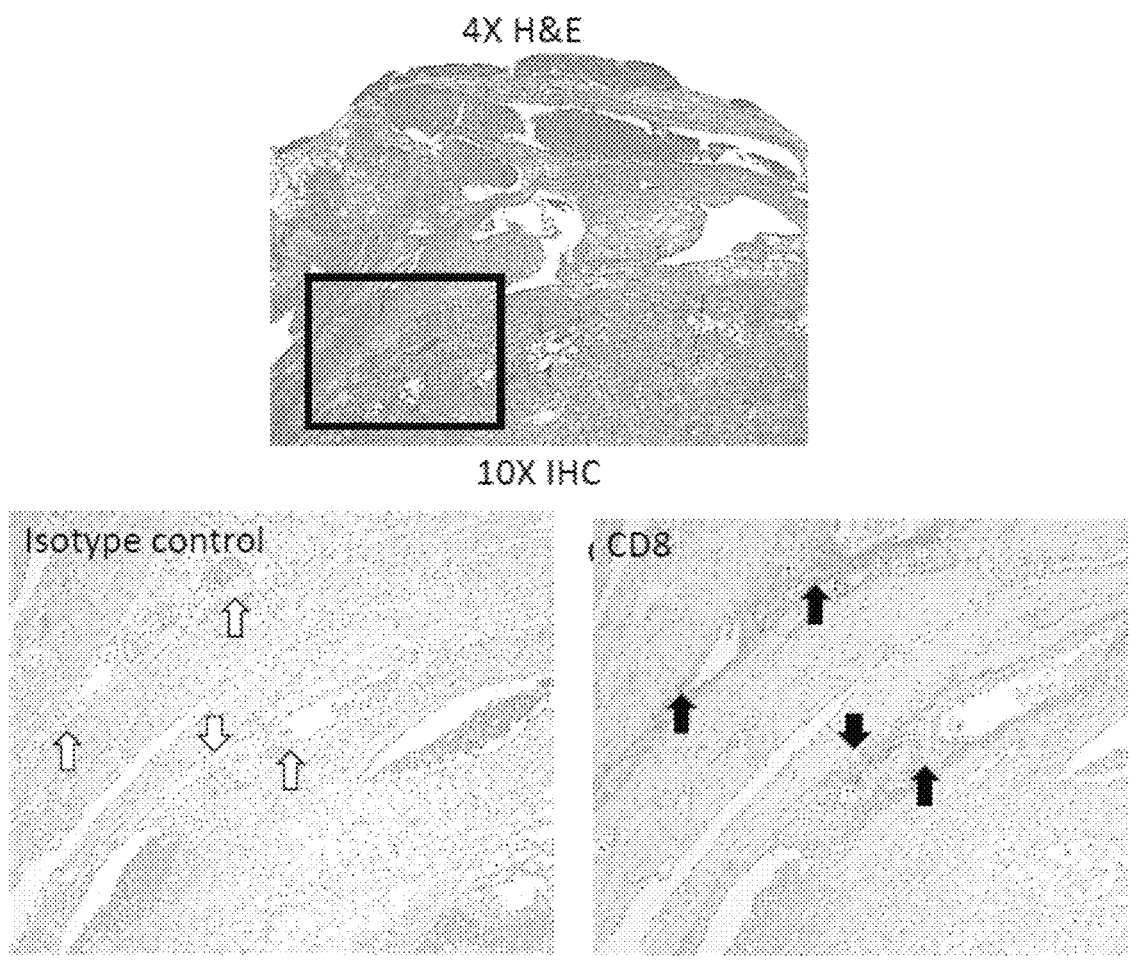
FIG. 11 is a histological staining showing accumulation of CD8 T cells in the maternal decidua after secreted Gp96ZIKAEnv-Ig vaccination.

To confirmation of preliminary data showing that gp96-Ig vaccination induces CD8 T cell responses in placenta. Pregnant WT mice were injected s.c with 293-gp96-Ig-ZIKAEnv at GD 7.5. Individual Fetal-Placental Unit at GD 12.5 was fixed in 10% neutral buffered formalin solution and embedded in paraffin. Deparaffinized sections were fixed in acetone and staining was performed using primary antibody against CD8 (clone YTS169) followed by incubation with secondary goat-anti-rabbit antibody and peroxidase-linked avidin (Dako). 3 Amino-9 ethylcarbazole (Sigma-Aldrich) was used as the chromogen resulting in the brown staining. Serial section incubated with an Ab of the same isotype were used for control staining. White arrows correspond to the same section area of black arrows (FIG. 11). Results showed that dams vaccinated s.c. with 293-gp96-Ig-ZIKVenv (0.2× $10^6$) at GD 7.5, accumulate CD8 specific cells in the maternal decidua (FIG. 11). This is the first finding that confirms the presence of gp96-Ig-ZIKVenv-induced CD8 T cells around arteries and larger blood vessels in the maternal decidua.

Figure 12:
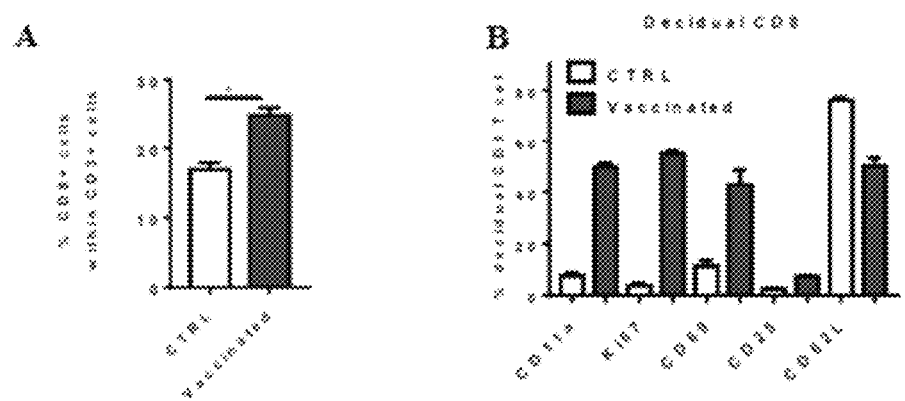
FIG. 12A-B is a set of bar graphs illustrating that Gp96-Ig-ZIKVEnv vaccine induces antigen experienced (CD11a+) effector memory CD8 T cells in decidua.

CD8 T cells in decidua was evaluated by flow cytometry (FIG. 12). Pregnant WT mice were injected s.c with 293-gp96-Ig-ZIKAEnv or PBS (CTRL) at GD 7.5. Individual Fetal-Placental Unit at GD 12.5 were collected and decidua was dissected form the placental tissue. Decidual single cell suspension was prepared by physical dissociation, cells were passed through the mesh and stained for following cell surface markers: live/dead marker, CD45, CD3, CD11a, CD69, CD25, CD62L. After surface staining cells were fixed/permeabilized and stained for Ki67. Cells were analyzed on Fortessa (BD) flow cytometer. Live, CD45+CD3+ lymphocytes were analyzed for expression of CD8 and frequency of CD8+ T cells is shown (n=6+/−SEM, p=0.05). Gated CD8 T cells were analyzed for the expression of following markers: CD11a, Ki67, CD69, CD25 and CD62L. Results indicated that frequency of decidual CD8 T cells was significantly increased in vaccinated vs control (PBS treated) pregnant mice. Phenotype of decidual CD8 T cells revealed that in vaccinated dams CD8 T cells were highly proliferating cells (high Ki67 expression), activated (high CD69 and CD25 expression) effector memory CDR T cells (high CD11a and lower CD62L expression) compared to non-vaccinated controls (FIG. 12). Increased expression of integrin molecule CD11a on CD8 T cells after various types of infections and/or antigen stimulations can distinguish naïve from antigen-experienced effector and memory CD8 T cells in both lymphoid and non-lymphoid tissues. Thus, CD11a marker can be used to determine the magnitude and kinetics of most, if not all, antigen-specific polyclonal CD8 T cell responses.

Figure 13:
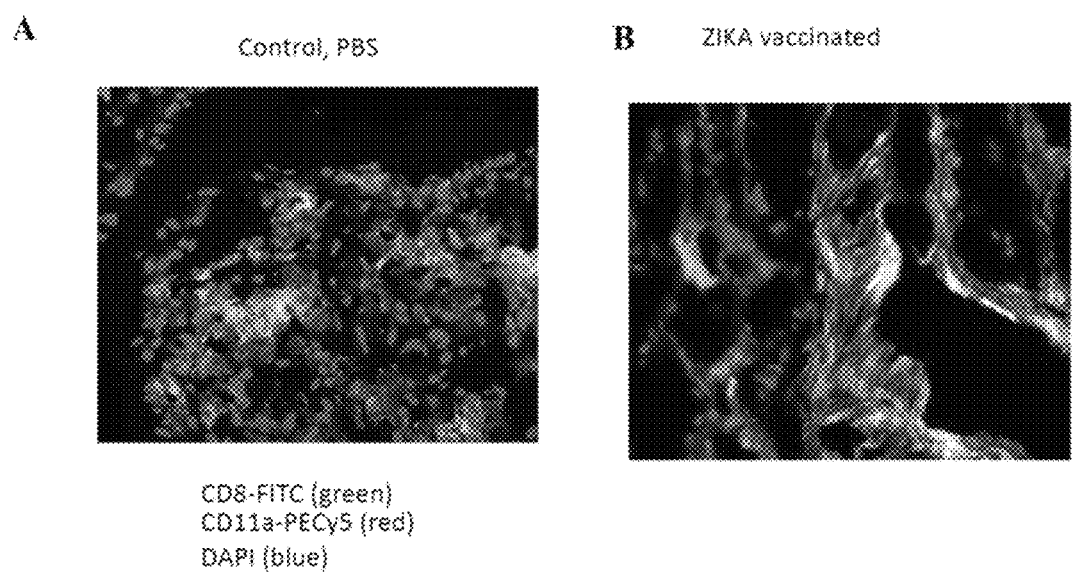
FIG. 13A-B is a confocal microscopy image illustrating the Co-expression of CD11a and CD8 in placenta of Gp96-Ig-ZIKVenv vaccinated mice.

CD11a marker was confirmed by immunofluorescence (IF) staining of frozen placental tissue, predominant distribution of CD11a marker (red) on CD8 (green) positive cells (shown as orange overlay) (FIG. 13) in placenta from vaccinated pregnant animals. Briefly, pregnant WT mice were injected s.c with 293-gp96-Ig-ZIKAEnv or PBS (CTRL) at GD 7.5. Individual Fetal-Placental Unit at GD 12.5 were collected and total placental tissue dissected and frozen in OCT medium. 7 um tissue sections were fixed with paraformaldehyde, permeabilized with 0.3% Triton X-100 in PBS and blocked with 5% serum for 1 hour at 24° C. Samples were incubated with primary antibodies anti-CD8-FITC and anti-CD11a-PECy5 for 3 hours at RT. Tissues were stained with DAPI (DNA stain) for 1 min. Representative samples for vaccinated and control PBS placenta are shown.

Decidua CD8 T cells ZIKV specificity was confirmed by stimulation of isolated decidual cells with overlapping ZIKV envelope peptide library and intracellular cytokine staining assay (ICS) (FIG. 14). Pregnant WT mice were injected s.c with 293-gp96-Ig-ZIKAEnv or PBS (CTRL) at GD 7.5. Individual Fetal-Placental Unit at GD 12.5 were collected and decidua was dissected form the placental tissue. ZIKV-specific CD8+ T lymphocyte responses were assessed using decidual cells and analyzed by flow cytometry. Cells were stimulated for 6 h at 37° C., with 2 μg/ml of overlapping 15-amino-acid peptides covering the prM or Env proteins (JPT, Berlin. Germany). Following 4 h incubation, brefeldin-A and monensin (BioLegend, CA. USA) were added, and samples were incubated for total of 6 h at 37° C. Cells were then washed, stained, permeabilized with Cytofix/Cytoperm (BD Biosciences, CA, USA). Data was acquired using an Fortessa flow cytometer (BD Biosciences, CA. USA) and analyzed using FlowJo v.10.2 (Treestar, OR, USA). Monoclonal antibodies included: CD45, CD3, CD8a, CD11a, IL-2, IFN-γ and TNFa. Antibodies were purchased from BD Biosciences, eBioscience, or BioLegend, CA, USA. Vital dye exclusion (LIVE/DEAD) was purchased from Life Technologies. CA. USA. (n=4). The Gp96-Ig-ZIKAenv vaccine induced ZIKAEnv-specific CD8+ lymphocyte that produce IFN-γ, TNFa and IL-2 after ZIKA envelope peptide stimulation. In addition, 50% of all CD11a+ CD8+ T cells represent ZIKA-specific CD8 T cells (FIG. 14).

Overall the results indicate, inter alia, success in generating a B45 plasmid that expresses gp96-Ig and ZIKV envelope protein and also confirms that vaccination with cell based secreted gp96-Ig-ZIKA is safe and induces CD8 T cell responses in maternal decidua. Additionally, in vitro stimulation with Zika peptide activates CD8+ specific antigen, indicating an antigen specific effect. This T-cell specific response is beneficial as it improves over existing methods directed to antibody protection only. Vaccination with gp96 provides a unique T-cell mediated response that is protective in the placenta.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or illustrative language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

As used herein, all headings are simply for organization and are not intended to limit the disclosure in any manner. The content of any individual section may be equally applicable to all sections.

REFERENCES

1. Luckay A, Sidhu M K, Kjeken R, Megati S, Chong S Y, Roopchand V, Garcia-Hand D, Abdullah R. Braun R. Montefiori D C, et al. Effect of plasmid DNA vaccine design and in vivo electroporation on the resulting vaccine-specific immune responses in rhesus macaques. J Virol. 2007; 81:5257-5269.
2. Liu J, Ewald B A, Lynch D M, Denholtz M. Abbink P, Lemekert A A, Carville A, Mansfield K G, Havenga M J, Goudsmit J, et al. Magnitude and phenotype of cellular immune responses elicited by recombinant adenovirus vectors and heterologous prime-boost regimens in rhesus monkeys. J Virol. 2008; 82:4844-4852.
3. Hirao L A, Wu L, Khan A S, Hokey D A, Yan J, Dai A, Betts M R, Draghia-Akli R, Weiner D B. Combined effects of IL-12 and electroporation enhances the potency of DNA vaccination in macaques. Vaccine. 2008:26:3112-3120.
4. Rosati M, Valentin A, Jalah R, Patel V, von Gegerfelt A, Bergamaschi C, Alicea C, Weiss D. Treece J, Pal R, et al. Increased immune responses in rhesus macaques by DNA vaccination combined with electroporation. Vaccine. 2008; 26:5223-5229.
5. Simon A J, Casimiro D R, Finnefrock A C, Davies M E, Tang A, Chen M, Chastain M, Kath G S, Chen L. Shiver J W. Enhanced in vivo transgene expression and immunogenicity from plasmid vectors following electrostimulation in rodents and primates. Vaccine. 2008; 26:5202-5209.
6. Hirao L A, Wu L. Satishehandran A. Khan A S, Draghia-Akli R. Finnefrock A C. Bett A J, Betts M R, Casimiro D R, Sardesai N Y, et al. Comparative analysis of immune responses induced by vaccination with SIV antigens by recombinant Ad5 vector or plasmid DNA in rhesus macaques. Mol Ther. 2010; 18:1568-1576.
7. Dobano C, Widera G. Rabussay D, Doolan D L. Enhancement of antibody and cellular immune responses to malaria DNA vaccines by in vivo electroporation. Vaccine. 2007; 25:6635-6645.
8. LeBlanc R, Vasquez Y, Hannaman D. Kumar N. Markedly enhanced immunogenicity of a Pfs25 DNA-based malaria transmission-blocking vaccine by in vivo electroporation. Vaccine. 2008; 26:185-192.
9. Ahlen G, Soderholm J, Tjelle T, Kjeken R, Frelin L, Hoglund U, Blomberg P, Fons M, Mathiesen I, Sallberg M. In vivo electroporation enhances the immunogenicity of hepatitis C virus nonstructural 3/4A DNA by increased local DNA uptake, protein expression, inflammation, and infiltration of CD3+ T cells. J Immunol. 2007:179:4741-4753.
10. Luxembourg A, Hannaman D, Wills K, Bernard R, Tennant B C, Menne S, Cote P J. Immunogenicity in mice and rabbits of DNA vaccines expressing woodchuck hepatitis virus antigens. Vaccine. 2008:26:4025-4033.
11. van Drunen Littel-van den Hurk S, Luxembourg A, Ellefsen B, Wilson D, Ubach A, Hannaman D, van den Hurk I V. Electroporation-based DNA transfer enhances gene expression and immune responses to DNA vaccines in cattle. Vaccine. 2008; 26:5503-5509.
12. Kim C Y, Kang E S, Kim S B, Kim H E, Choi J H, Lee D S, Im S J, Yang S H, Sung Y C, Kim B M, et al. Increased in vivo immunological potency of 1113-110, a novel therapeutic HBV DNA vaccine, by electroporation. Exp Mol Med. 2008; 40:669-676.
13. Nystrom J, Chen A, Frelin L, Ahlen G, Koh S, Brass A, Peterson D L. Fons M, Milich D R, Hultgren C, et al. Improving on the ability of endogenous hepatitis B core antigen to prime cytotoxic T lymphocytes. J Infect Dis. 2010:201:1867-1879.
14. Trollet C. Pereira Y, Burgain A, Litzler E, Mezrahi M, Seguin J, Manich M, Popoff M R, Scherman D. Bigey P. Generation of high-titer neutralizing antibodies against botulinum toxins A, B, and E by DNA electrotransfer. Infect Immun. 2009:77:2221-2229.
15. Best S R, Peng S. Juang C M, Hung C F, Hannaman D, Saunders J R, Wu T C, Pai S I. Administration of HPV DNA vaccine via electroporation elicits the strongest CD8+ T cell immune responses compared to intramuscular injection and intradermal gene gun delivery. Vaccine. 2009; 27:5450-5459.
16. Seo S H Jin H T. Park S H, Youn J I. Sung Y C. Optimal induction of HPV DNA vaccine-induced CD8+ T cell responses and therapeutic antitumor effect by antigen engineering and electroporation. Vaccine. 2009:27:5906-5912.
17. Livingston B D, Little S F, Luxembourg A, Ellefsen B, Hannaman D. Comparative performance of a licensed anthrax vaccine versus electroporation based delivery of a PA encoding DNA vaccine in rhesus macaques. Vaccine 2010:28:1056-1061.
18. Laddy D J. Yan J. Khan A S. Andersen H, Cohn A. Greenhouse J, Lewis M, Manischewitz J, King L R, Golding H, et al. Electroporation of synthetic DNA antigens offers protection in nonhuman primates challenged with highly pathogenic avian influenza virus. J Virol. 2009; 83:4624-4630.
19. Laddy D J, Yan J, Kutzler M, Kobasa D, Kobinger G P, Khan A S, Greenhouse J. Sardcsai N Y, Draghia-Akli R. Weiner D B. Heterosubtypic protection against pathogenic human and avian influenza viruses via in vivo electroporation of synthetic consensus DNA antigens. PLoS One. 2008; 3:e2517.
20. Hirao L A, Wu L, Khan A S, Satishehandran A, Draghia-Akli R, Weiner D B. Intradermal/subcutaneous immunization by electroporation improves plasmid vaccine delivery and potency in pigs and rhesus macaques. Vaccine. 2008; 26:440-448.

What is claimed is:

1. An expression vector system comprising:
   (i) a nucleic acid encoding a fusion protein comprising a chaperone protein and an Fc fragment of an IgG immunoglobulin, wherein the fusion protein comprises the amino acid sequence of SEQ ID NO: 8, and
   (ii) a nucleic acid encoding a flavivirus protein, or an antigenic portion thereof, wherein the flavivirus protein is a Zika virus protein,
   wherein each nucleic acid is operably linked to a promoter.

2. The expression vector system of claim 1, wherein the nucleic acid encoding the fusion protein is operably linked to a promoter which is different from the promoter which is operably linked to the nucleic acid encoding the Zika virus protein, or an antigenic portion thereof.

3. The expression vector system of claim 2, wherein the nucleic acid encoding the fusion protein is operably linked to a CMV promoter or an Mth promoter.

4. The expression vector system of claim 1, wherein the nucleic acid encoding the fusion protein and the nucleic acid encoding the Zika virus protein, or antigenic portion thereof, are present on the same expression vector or wherein the nucleic acid encoding the fusion protein is present on an expression vector which is different from the expression vector comprising the nucleic acid encoding the Zika virus protein, or antigenic portion thereof.

5. The expression vector system of claim 1, comprising a nucleic acid encoding the ZIKV protein membrane glycoprotein precursor M and/or a nucleic acid encoding the ZIKV protein envelope protein E.

6. The expression vector system of claim 1, comprising a nucleic acid encoding the amino acid sequence of SEQ ID NO: 10 and/or a nucleic acid encoding the amino acid sequence of SEQ ID NO: 11.

7. The expression vector system of claim 1, further comprising a nucleic acid encoding a bovine papillomavirus (BPV) E1 protein and/or a BPV E2 protein.

8. The expression vector system of claim 7, further comprising a nucleic acid encoding a BPV E1 protein of SEQ ID NO: 19 and/or a BPV E2 protein of SEQ ID NO: 22.

9. The expression vector system of claim 1, which does not comprise a nucleic acid encoding an E5 sequence (SEQ ID NO: 32), E6 sequence (SEQ ID NO: 33), and E7 sequence (SEQ ID NO: 34).

10. An isolated mammalian host cell comprising the expression vector system of claim 1.

11. A method of eliciting an immune response against Zika virus in a subject, comprising administering to the subject the expression vector of claim 1, or a population of cells transfected with the expression vector.

12. A method of inhibiting a Zika virus infection in a subject, comprising administering to the subject an expression vector comprising a sequence having at least 95% identity with SEQ ID NO: 35 or a population of cells transfected an expression vector comprising a sequence having at least 95% identity with SEQ ID NO: 35.

* * * * *